(12) United States Patent
Lee et al.

(10) Patent No.: US 9,320,826 B2
(45) Date of Patent: Apr. 26, 2016

(54) ADHESIVE COMPOUNDS AND METHODS USE FOR HERNIA REPAIR

(75) Inventors: Bruce P. Lee, Madison, WI (US);
Jeffrey L. Dalsin, Verona, WI (US);
John L. Murphy, Verona, WI (US);
Laura Vollenweider, Lodi, WI (US);
Arinne N. Lyman, Fitchburg, WI (US);
Fangmin Xu, Sudbury, MA (US);
Jediah White, Madison, WI (US);
William D. Lew, Mendota Heights, MN (US); Michael Brodie, Belleville, WI (US)

(73) Assignee: KENSEY NASH CORPORATION, Exton, PA (US)

(*) Notice: Subject to any disclaimer, the term of this patent is extended or adjusted under 35 U.S.C. 154(b) by 440 days.

(21) Appl. No.: 13/292,527

(22) Filed: Nov. 9, 2011

(65) Prior Publication Data

US 2012/0116424 A1    May 10, 2012

Related U.S. Application Data

(60) Provisional application No. 61/411,747, filed on Nov. 9, 2010, provisional application No. 61/415,743, filed on Nov. 19, 2010.

(51) Int. Cl.
*A61F 2/02* (2006.01)
*A61L 24/04* (2006.01)
*A61L 24/00* (2006.01)

(52) U.S. Cl.
CPC ........... *A61L 24/046* (2013.01); *A61L 24/0005* (2013.01); *A61L 24/001* (2013.01)

(58) Field of Classification Search
USPC .............. 623/11.11, 23.57, 23.72–23.76; 606/151, 213, 214; 602/41, 42, 54; 424/423, 426
See application file for complete search history.

(56) References Cited

U.S. PATENT DOCUMENTS

| | | | |
|---|---|---|---|
| 4,339,561 A | 7/1982 | Jacquet et al. | |
| 4,496,397 A | 1/1985 | Waite | |
| 4,585,585 A | 4/1986 | Waite | |
| 4,615,697 A | 10/1986 | Robinson | |
| 4,687,740 A | 8/1987 | Waite | |
| 4,795,436 A | 1/1989 | Robinson | |
| 4,808,702 A | 2/1989 | Waite | |
| 4,908,404 A | 3/1990 | Benedict et al. | |
| 4,978,336 A | 12/1990 | Capozzi et al. | |
| 4,983,392 A | 1/1991 | Robinson | |

(Continued)

FOREIGN PATENT DOCUMENTS

| | | |
|---|---|---|
| DE | 19643007 A1 | 4/1998 |
| JP | 03-294292 | 12/1991 |

(Continued)

OTHER PUBLICATIONS

Yu et al., Adhesion of Coagulase-Negative *Staphylococci* and Adsorption of Plasma-Proteins to Heparinized Polymer Surfaces. Biomaterials 1994,15, (10),805-814.

(Continued)

*Primary Examiner* — Robert Lynch
(74) *Attorney, Agent, or Firm* — Kirk J. Hogan; Casimir Jones, S.C.

(57) ABSTRACT

The invention describes new synthetic medical adhesives and films which exploit the key components of natural marine mussel adhesive proteins.

22 Claims, 279 Drawing Sheets

(56) References Cited

U.S. PATENT DOCUMENTS

| | | |
|---|---|---|
| 5,015,677 A | 5/1991 | Benedict et al. |
| 5,024,933 A | 6/1991 | Yang et al. |
| 5,030,230 A | 7/1991 | White |
| 5,049,504 A | 9/1991 | Maugh et al. |
| 5,098,999 A | 3/1992 | Yamamoto et al. |
| 5,108,923 A | 4/1992 | Benedict et al. |
| 5,116,315 A | 5/1992 | Capozzi et al. |
| 5,156,956 A | 10/1992 | Motoki et al. |
| 5,192,316 A | 3/1993 | Ting |
| 5,197,973 A | 3/1993 | Pang et al. |
| 5,202,236 A | 4/1993 | Maugh et al. |
| 5,202,256 A | 4/1993 | Maugh et al. |
| 5,225,196 A | 7/1993 | Robinson |
| 5,242,808 A | 9/1993 | Maugh et al. |
| 5,260,194 A | 11/1993 | Olson |
| 5,374,431 A | 12/1994 | Pang et al. |
| 5,410,023 A | 4/1995 | Burzio |
| 5,428,014 A | 6/1995 | Labroo et al. |
| 5,487,739 A | 1/1996 | Aebischer et al. |
| 5,490,980 A | 2/1996 | Richardson et al. |
| 5,520,727 A | 5/1996 | Vreeland et al. |
| 5,525,336 A | 6/1996 | Green et al. |
| 5,549,904 A | 8/1996 | Juergensen et al. |
| 5,563,047 A | 10/1996 | Petersen |
| 5,574,134 A | 11/1996 | Waite |
| 5,580,697 A | 12/1996 | Keana et al. |
| 5,582,955 A | 12/1996 | Keana et al. |
| 5,605,938 A | 2/1997 | Roufa et al. |
| 5,618,551 A | 4/1997 | Tardy et al. |
| 5,628,793 A | 5/1997 | Zirm |
| 5,705,177 A | 1/1998 | Roufa et al. |
| 5,705,178 A | 1/1998 | Roufa et al. |
| 5,736,132 A | 4/1998 | Juergensen et al. |
| 5,776,747 A | 7/1998 | Schinstine et al. |
| 5,800,828 A | 9/1998 | Dionne et al. |
| 5,817,470 A | 10/1998 | Burzio et al. |
| 5,830,539 A | 11/1998 | Yan et al. |
| 5,834,232 A | 11/1998 | Bishop et al. |
| 5,858,747 A | 1/1999 | Schinstine et al. |
| 5,935,849 A | 8/1999 | Schinstine et al. |
| 5,939,385 A | 8/1999 | Labroo et al. |
| 5,955,096 A | 9/1999 | Santos et al. |
| 5,968,568 A | 10/1999 | Kuraishi et al. |
| 5,985,312 A | 11/1999 | Jacob et al. |
| 5,994,325 A | 11/1999 | Roufa et al. |
| 6,010,871 A | 1/2000 | Takahara et al. |
| 6,020,326 A | 2/2000 | Roufa et al. |
| 6,022,597 A | 2/2000 | Yan et al. |
| 6,083,930 A | 7/2000 | Roufa et al. |
| 6,093,686 A | 7/2000 | Nakada et al. |
| 6,126,903 A | 10/2000 | Preston et al. |
| 6,129,761 A | 10/2000 | Hubbell |
| 6,150,461 A | 11/2000 | Takei et al. |
| 6,156,348 A | 12/2000 | Santos et al. |
| 6,162,903 A | 12/2000 | Trowern et al. |
| 6,235,313 B1 | 5/2001 | Mathiowitz et al. |
| 6,267,957 B1 | 7/2001 | Green et al. |
| 6,284,267 B1 | 9/2001 | Aneja |
| 6,294,187 B1 | 9/2001 | Boyce et al. |
| 6,306,993 B1 | 10/2001 | Rothbard et al. |
| 6,309,669 B1 | 10/2001 | Setterstrom et al. |
| 6,322,996 B1 | 11/2001 | Sato et al. |
| 6,325,951 B1 | 12/2001 | Soper et al. |
| 6,331,422 B1 | 12/2001 | Hubbell et al. |
| 6,335,430 B1 | 1/2002 | Qvist |
| 6,365,187 B2 | 4/2002 | Mathiowitz et al. |
| 6,368,586 B1 | 4/2002 | Jacob et al. |
| 6,417,173 B1 | 7/2002 | Roufa et al. |
| 6,486,213 B1 | 11/2002 | Chen et al. |
| 6,491,903 B1 | 12/2002 | Forster et al. |
| 6,497,729 B1 | 12/2002 | Moussy et al. |
| 6,506,577 B1 | 1/2003 | Deming et al. |
| 6,555,103 B2 | 4/2003 | Leukel et al. |
| 6,565,960 B2 | 5/2003 | Koob et al. |
| 6,566,074 B1 | 5/2003 | Goetinck |
| 6,566,406 B1 | 5/2003 | Pathak et al. |
| 6,635,274 B1 | 10/2003 | Masiz et al. |
| 6,663,883 B1 | 12/2003 | Akiyama et al. |
| 6,821,530 B2 | 11/2004 | Koob et al. |
| 6,833,408 B2 | 12/2004 | Sehl et al. |
| 6,887,845 B2 | 5/2005 | Barron et al. |
| 7,009,034 B2 | 3/2006 | Pathak et al. |
| 7,208,171 B2 | 4/2007 | Messersmith et al. |
| 7,300,991 B2 | 11/2007 | Nishimura et al. |
| 7,303,759 B2 | 12/2007 | Mershon |
| 7,622,533 B2 | 11/2009 | Lee |
| 7,732,539 B2 | 6/2010 | Shull et al. |
| 7,988,673 B2 * | 8/2011 | Wright et al. ............... 604/174 |
| 8,030,413 B2 | 10/2011 | Lee |
| 2001/0043940 A1 | 11/2001 | Boyce et al. |
| 2001/0049400 A1 | 12/2001 | Alli et al. |
| 2002/0022013 A1 | 2/2002 | Leukel et al. |
| 2002/0049290 A1 | 4/2002 | Vanderbilt |
| 2002/0182633 A1 | 12/2002 | Chen et al. |
| 2003/0008011 A1 | 1/2003 | Mershon |
| 2003/0009235 A1 | 1/2003 | Manrique et al. |
| 2003/0012734 A1 | 1/2003 | Pathak et al. |
| 2003/0039676 A1 | 2/2003 | Boyce et al. |
| 2003/0065060 A1 | 4/2003 | Qvist et al. |
| 2003/0069205 A1 | 4/2003 | Roufa et al. |
| 2003/0087338 A1 | 5/2003 | Messersmith et al. |
| 2003/0099682 A1 | 5/2003 | Moussy et al. |
| 2003/0109587 A1 | 6/2003 | Mori |
| 2003/0119985 A1 | 6/2003 | Sehl et al. |
| 2003/0194610 A1 | 10/2003 | Nishimura et al. |
| 2003/0208888 A1 | 11/2003 | Fearing et al. |
| 2004/0005421 A1 | 1/2004 | Gervase et al. |
| 2004/0028646 A1 | 2/2004 | Gross et al. |
| 2004/0049187 A1 | 3/2004 | Burnett et al. |
| 2005/0032929 A1 | 2/2005 | Greener |
| 2005/0155937 A1 | 7/2005 | Zawada et al. |
| 2005/0208091 A1 | 9/2005 | Pacetti |
| 2005/0288398 A1 | 12/2005 | Messersmith et al. |
| 2006/0009550 A1 | 1/2006 | Messersmith et al. |
| 2007/0031498 A1 | 2/2007 | Zong et al. |
| 2007/0208141 A1 | 9/2007 | Shull et al. |
| 2008/0171836 A1 | 7/2008 | Lee et al. |
| 2008/0247984 A1 | 10/2008 | Messersmith |
| 2008/0286326 A1 | 11/2008 | Benco |
| 2008/0286329 A1 | 11/2008 | Campbell et al. |
| 2009/0076241 A1 * | 3/2009 | Lee ............................. 528/184 |
| 2010/0137902 A1 | 6/2010 | Lee et al. |
| 2010/0197868 A1 | 8/2010 | Lee |
| 2010/0305589 A1 * | 12/2010 | Solecki ..................... 606/151 |
| 2011/0015760 A1 * | 1/2011 | Kullas ..................... 623/23.72 |

FOREIGN PATENT DOCUMENTS

| | | |
|---|---|---|
| JP | 2000-281699 | 10/2000 |
| WO | 88/03953 | 6/1988 |
| WO | 92/10567 | 6/1992 |
| WO | 94/28937 | 12/1994 |
| WO | 97/34016 | 9/1997 |
| WO | 98/07076 | 2/1998 |
| WO | 01/44401 | 6/2001 |
| WO | 02/34764 | 5/2002 |
| WO | 03/008376 | 1/2003 |
| WO | 03/080137 | 10/2003 |
| WO | 2004/042068 | 5/2004 |
| WO | 2005/033198 | 4/2005 |
| WO | 2005/056708 | 6/2005 |
| WO | 2005/070866 | 8/2005 |
| WO | 2005/118831 | 12/2005 |
| WO | 2007/127225 | 11/2007 |
| WO | 2008/019352 | 2/2008 |
| WO | 2009/015124 | 1/2009 |
| WO | 2010/037044 | 4/2010 |
| WO | 2010/091298 | 8/2010 |
| WO | 2010/091300 | 8/2010 |

(56) References Cited

FOREIGN PATENT DOCUMENTS

OTHER PUBLICATIONS

Yu, et al., "Micellisation and Gelation of Triblock Copoly(oxyethylene/oxypropylene/oxyethylene), F127," J. Chem. Soc., Faraday Trans., vol. 88, No. 17 (1992), pp. 2537-2544.
Yu, et al., "Role of L-3,4-Dihydroxyphenylalanine in Mussel Adhesive Proteins," J. Am. Chem. Soc., vol. 121 (1999), pp. 5825-5826.
Yu, et al., "Synthetic Polypeptide Mimics of Marine Adhesives," Macromolecules, vol. 31 (1998), po. 4739-4745.
Yurdumakan, et al., "Synthetic gecko foot-hairs from multiwalled carbon nanotubes," Chem. Commun., vol. 30 (2005), pp. 3799-3801.
Zekorn, et al., "Biocompatibility and immunology in the encapsulation of islets of Langerhans (bioartificial pancreas)," Int. J. Artif. Organs, vol. 19, No. 4 (1996), pp. 251-257.
Zeng, et al., "Synthesis and Characterization of DOPA-PEG Conjugates," Polymer Preprints, vol. 41, No. 1 (2000), pp. 989-990.
Zhan, et al., "Functionalization of Nano-Faujasite Zeolite with PEG-Grafted PMA Tethers Using Atom Transfer Radical Polymerization," Macromolecules, vol. 37 (2004), pp. 2748-2753.
Zhang et al., Reactive coupling of poly(ethylene glycol) on electroactive polyaniline films for reduction in protein adsorption and platelet adhesion. Biomaterials 2002,23, (3), 787-795.
Zhao, et al., "Polymer brushes: surface-immobilized macromolecules," Prog. Polym. Sci., vol. 25 (2000), pp. 677-710.
Zimmer Collagen Repair Patch. Tissue Science Laboratories, 2005.
Zuckermann, et al., "Efficient Method for the Preparation of Peptoids [Oligo(N-substituted glycines)) by Submonomer Solid-Phase Synthesis," J. Am. Chem. Soc., vol. 114 (1992), pp. 10646-10647.
Oxlund et al, Collagen deposition and mechanical strength of colon anastomoses and skin incisional wounds of rats, J Surg Res. Nov. 1996;66(1):25-30.
Jorgensen et al., Dose-response study of the effect of growth hormone on mechanical properties of skin graft wounds, J Surg Res. Mar. 1995;58(3):295-301.
da Silva, L.F.M., T.N.S.S. Rodrigues, M.A.V. Figueiredo, M.F.S.F. de Moura, and J.A.G. Chousal, Effect of Adhesive Type and Thickness on the Lap Shear Strength J. Adh., 2006. 82: p. 1091-1115.
Santillan-Doherty, P., R. Jasso-Victoria, A. Sotres-Vega, R. Olmos, J.L. Arreola, D. Garcia, B. Vanda, M. Gaxiola, A. Santibanez, S. Martin, and R. Cabello, Thoracoabdominal wall repair with glutaraldehyde-preserved bovine pericardium. Journal of investigative surgery : the official journal of the Academy of Surgical Research, 1996. 9(1): p. 45-55.
Burger, J.W.A., J.A. Halm, A.R. Wijsmuller, S. ten Raa, and J. Jeekel, Evaluation of new prosthetic meshes for ventral hernia repair. Surgical endoscopy, 2006. 20(8): p. 1320-5.
Lo Menzo, E., J.M. Martinez, S.A. Spector, A. Iglesias, V. Degennaro, and A. Cappellani, Use of biologic mesh for a complicated paracolostomy hernia. American journal of surgery, 2008. 196(5): p. 715-9.
Hajjaji, et al., Effect of N-Alkybetaines on the Corrosion of Iron in 1 M HCl Soluction, Corrosion, vol. 49, No. 4 (1993), p. 326-334.
Hanawa, et al., "XPS Characterization of the Surface Oxide Film of 316L Stainless Steel Samples that were Located in Quasi-Biological Environments," 2002 Mater. Trans., JIM vol. 43, No. 12 pp. 3088-3092.
Hansen, et al., "Enzymatic Tempering of a Mussel Adhesive Protein Film," Langmuir 14 (1998). p. 1139-1147.
Harkness, R.D., Biological functions of collagen. Biol. Rev. Camb. Philos. Soc., 1961. 36: p. 399-463.
Harrell, A.G., Novitsky, Yuri W., et al, Prospective histologic evaluation of intra-abdominal prosthetics four months after implantation in a rabbit model. Surg. Endosc., 2007. 21: p. 1170-1174.
Harris (ed.), "Introduction to Biotechnical and Biomedical Applications of Poly(Ethylene Glycol)" in Poly(Ethylene Glycol) Chemistry: Biotechnical and Biomedical Applications, Plenum Press: New York, 1992 pp. 1-14.

Harris, "Laboratory Synthesis of Polyethylene Glycol Derivatives," JMS—Rev. Macramol. Chern. Phys., vol. C25, No. 3 (1985), co. 325-373.
Harrison et al., Compendium of Synthetic Organic Methods, vols. 1 8, 1971 1996, John Wiley & Sons, NY.
Hay, J.-M., et al, Shouldice Inguinal Hernia Repair in the Male Adult: The Gold Standard? Annals of Surgery, 1995. 222(6): p. 719-727.
Hennick et al., "Novel crosslinking methods to design hydrogels," 2002 Adv. Drug Deliver. Rev., vol. 54 pp. 13-36.
Hern, et al., "Incorporation of adhesion peptides into nonadhesive hydrogels useful for tissue resurfacing," J. Biomed. Mater. Res., vol. 39, Issue 2 (1998), pp. 266-276.
Hillery, et al., The effect of adsorbed poloxamer 188 and 407 surfactants on the intestinal uptake of 60-nm polystyrene particles after oral administratin in the rat, Int. J. Pharm. 132 (1996). p. 123-130.
Hirooka, A., et al, Augmentation with a Gore-Tex patch for repair of large rotator cuff tears that cannot be sutured. J Orthopaedic Science, 2002. 7: p. 451-456.
Ho, et al., "Nanoseparated Polymeric Networks with Multiple Antimicrobial Properties," Adv. Mater. 16 (12),2004. p. 957-961.
Hoffman, "Hydrogels for biomedical applications," Adv. Drug Deliver. Rev., vol. 43 (2002), p. 3-12.
Hohenadl, et al., "Two Adjacent N-terminal Glutamines of BM-40 (Osteonectin, SPARC) Act as Amine Acceptor Sites in Transqlutamlnase.-catalyzed Modification," J. Biol. Chem. 270 (40),1995. p. 23415-23420.
Holl et al., Solid-State NMR Analysis of Cross-Linking in Mussel Protein Glue. Archives of Biochemistry and Biophysics 1993, 302, (1),255-258.
Hrkach, et al., "Synthesis of Poly(L-lactic acid-co-L-lysine) Graft Copolymers," Macromolecules, vol. 28 (1995), p. 4736-4739.
Hu, et al., "Protection of 3,4-dihydroxyphenylalanine (DOPA) for Fmoc solid-phase peptide synthesis," Tetra. Lett. 41 (2000). p. 5795-5798.
Hu, et al., Rational Design of Transglutaminase Substrate Peptides for Rapid Enzymatic Formation of Hydroqels, J. Am. Chem. Soc., vol. 125, (2003), p. 14298-14299.
Huang et al., "Poly(L-lysine)-g-poly(ethylene glycol) Layers on Metal Oxide Surfaces: Surface-Analytical Characterization and resistance to Serum and Fibrinogen Adsorption," 2001 Langmuir vol. 17 pp. 489-498.
Huang, "Molecular aspects of Muco- and bioadhesion: Tethered Structures and Site specific surfaces," 2000 J. Controlled Release vol. 65 pp. 63-71.
Huang, et al., "Covalent Attachment of Novel Poly(ethylene glycol)-Poly(DL-lactic acid) Copolymeric Micelles to Ti02 Surfaces," 2002 Langmuir 18 pp. 252-258.
Huang, et al., "Functionalization of Surfaces by Water-Accelerated Atom-Transfer Radical Polymerization of Hydroxyethyl Methacrylate and Subsequent Derivatization," 2002 Macromolecules 35 pp. 1175-1179.
Huang, et al., "Synthesis and Characterization of Self-Assembling Block Copolymers Containing Adhesive Moieties," Polym. Prepr. 42(2) 2001 pp. 147-148.
Huang, et al., "Synthesis and Characterization of Self-Assembling Block Copolymers Containing Bioadhesive End Groups," Biomacromolecules 3 (2002). p. 397-406.
Huber, et al., "Evidence for capillarity contributions to gecko adhesion from single spatula nanomechanical measurements," Proc. Nat. Acad. Sci. USA, 102 (45), 2005. pp. 16293-16296.
Huber, et al., "Resolving the nanoscale adhesion of individual gecko spatulae by atomic force microscopy," Biol. Lett. 1 (2005). p. 2-4.
Huin-Amargier, C., et al., New physically and chemically crosslinked hyaluronate (HA)-based hydrogels for cartilage repair. Journal of Biomedical Materials Research, Part A, 2006. 76A(2): p. 416-424.
Hunter, "Molecular hurdles in polyfectin design and mechanistic background to polycation inducted cytotoxicity," Adv. Drug Deliver. Rev., vol. 58 (2006). p. 1523-1531.
Hutter, et al., "Calibration of atomic-force microscope tips," Rev. Sci. Instrum. 64 (7), Jul. 1993. p. 1868-1873.

(56) References Cited

OTHER PUBLICATIONS

Hvidt, et al., "Micellization and Gelation of Aqueous Solutions of a Triblock Copolymer Studied by Rheological Techniques and Scanning Calorimetry," J. Phys. Chem. 98 (1994). p. 12320-12328.

Hwang et al., "Expression of Functional Recombinant Mussel Adhesive Protein Mgfp-5 in *Escherichia coli*," 2004 Appl. Environ. Microbiol. 70 (6) pp. 3352-3359.

Ikada, Tissue Adhesives,"in Wound Closure Biomaterials and Devices," Chu, et al.(eds.), CRC Press, Inc.: Boca Raton, FL, 1997. p. 317-346.

Ireland, M.L., Anterior Cruciate Ligament Injury in Female Athletes: Epidemiology. Journal of Athletic Training, 1999. 34(2): p. 150-154.

Ishihara et al. "Photocrosslinkable chitosan as a dressing wound occlusion and accelerator in healing process," Biomaterials, vol. 23, No. 3 (2002), pp. 833-840.

Jackson, "Fibrin sealants in surgical practice: An overview," Am. J. Surg., vol. 182 (2001), pp. 1S-7S.

Jackson, "Tissue sealants: Current status, future potential," Nat. Med., vol. 2, No. 5, (May 1996), pp. 637-638.

Janchen, et al., "Adhesion Energy of Thin Collagen Coatings and Titanium," Surf. Interface Anal., vol. 27 (1999), pp. 444-449.

Jaschke, A., Oligonucleotide-poly(ethylene glycol) conjugates: synthesis, properties, and applications, in Poly(ethylene glycol) : chemistry and biological applications, J.M. Harris and S. Zalipsky, Editors. 1997, American Chemical Society: Washington, DC. p. 265-283.

Jensen, et al., "Lipopeptides Incorporated into Supported Phospholipid Monolayers Have High Specific Activity at Low Incorporation Levels," J. Am. Chem. Soc., vol. 126, No. 46 (2004), 15223-15230.

Jeon, et al., "Protein-Surface Interactions in the Presence of Polyethylene Oxide," J. Colloid. Interface Sci., vol. 142, No. 1 (1991), p. 159-166.

Jewell, et al., "Pharmacokinetics of RheothRx Injection in Healthy Male Volunteers," J. Pharo Sci. vol. 86, No. 7 (1997), pp. 808-812.

Jo, et al., "Surface modification using silanated poly(ethylene glycol)s," Biomaterials, vol. 21 (2000), p. 605-61.

Johnson, et al., "Surface Energy and Contact of Elastic Solids," Proc. R. Soc. Lond., A, vol. 324, No. 1558 (1971), 301-313.

Beynnon et al., The Treatment of Injuries of the Anterior Cruciate Ligament. The Journal of Bone and Joint Surgery, 1992. 74-A(1): p. 140-151.

Jones, et al., "Controlled Surface-Initiated Polymerization in Aqueous Media," Adv. Mater., vol. 13, No. 16 (2001), pp. 1256-121259.

Jones, et al., "In Situ forming biomaterials," Oral Maxillofacial Surg. Clin. N. Am., vol. 14 (2002), pp. 29-38.

Jose et al., Vancomycin covalently bonded to titanium beads kills *Staphylococcus aureus*.Chemistry &Biology 2005,12, (9),1041-1048.

Jozsa, L., Kvist, M., Balint, B.J., et al, the role of recreational sport activity in Achilles tendon rupture: A clinical, pathoanatomical, and sociological study of 292 cases. The American Journal of Sports Medicine, 1989. 17: p. 338-343.

Lucast, "Adhesive considerations for developing stick-to-skin products," Adhesives Age 43 (2000). p. 36, 38-39.

Luijendijk, R.W., et al, A comparison of suture repair with mesh repair for incisional hernia. The New England Journal of Medicine, 2000. 343(6): p. 392-398.

Luo et al., "Surface-initiated Photopolymerization of Poly(ethylene glycol) Methyl Ether Methacrylate on a Diethyldithiocarbamate-Mediated Polymer Substrate," 2002 Macromolecules vol. 35 pp. 2487-2493.

Lyman, et al., "Characterization of the formation of interfacially photopolymerized thin hydrogels in contact with arterial tissue," Biomaterials 17 (1996). p. 359-364.

Lynn, T., Repair of the Torn Achilles Tendon, Using the Plantaris Tendon as a Reinforcing Membrane. The Journal of Bone and Joint Surgery, 1964. 48-A(2): p. 268-272.

Maffulli, N., Rupture of the Achilles Tendon. The Journal of Bone and Joint Surgery, 1999. 81-A(7): p. 1019-1036.

Mandelbaum, B.R., Myerson, M.S., Forster, R., Achilles tendon ruptures: a new method of repair, early range of motion, and functional rehabilitation. The American Journal of Sports Medicine, 1995. 23(4): p. 392-395.

Martin, et al., "Surface Structures of a 4-Chlorocatechol Adsorbed on Titanium Dioxide," Environ. Sci. Technol., vol. 30 (1996), p. 2535-2542.

Matyjaszewski, et al., "Atom Transfer Radical Polymerization," Chem. Rev. 101 (2001). p. 2921-2990.

Maugh, et al., "Recombinant bioadhesive proteins of marine animals anad their use in adhesive compositions," in Genex Corp. 1988: USA. p. 196 (1987).

McBride, "Adsorption and Oxidation of Phenolic Compounds by Iron and Manganese Oxides," Soil Sci. Soc. Am. J., vol. 51 (1987), pp. 1466-1472.

McWhitrter, et al., "Siderophore-Mediated Covalent Bonding to Metal (Oxide) Surfaces during Biofilm Initiation by Pseudomonas aeruginosa Bacteria," 2003 Langmuir vol. 19 pp. 3575-3577.

Meisel, et al., "Estimation of calcium-binding constants of casein phosphopeptides by capillary zone electrophoresis," Anal. Chim. Acta 372 (1998). pp. 291-297.

Mellott et al., "Release of protein from highly cross-linked hydrogels of poly(ethyleneglycol) diacrylate fabricated by UV polymerization," Biomaterials, vol. 22 (2001), pp. 929-941.

Merrifield, "Solid Phase Peptide Synthesis. I. The Synthesis of a Tetrapeptide," J. Am. Chem. Soc., vol. 85 (Jul. 20, 1963), pp. 2149-2154.

Merrill, "Distinctions and Correspondences among Surfaces Contacting Blood," Annals of the NY Acad. Sci. 516 (1987). pp. 196-203.

Metcalf, M.H., F.H.S. III, and B. Kellum, Surgical technique for xenograft (SIS) augmentation of rotator-cuff repairs. 2002. 12(3): p. 204-208.

Minghetti, P., F. Cilurzo, and A. Casiraghi, Measuring adhesive performance in transdermal delivery systems. American Journal of Drug Delivery, 2004. 2(3): p. 193-206.

Miron, et al., "A Simplified Method for the Preparation of Succinimidyl Carbonate Polyethylene Glycol for Coupling to Proteins," Bioconj. Chem. 4 (1993). pp. 568-569.

Morgan, et al., "Biochemical characterisation of polycation-induced cytotoxicity to human vascular endothelial cells," Journal of Cell Science 94 (3), 1989,. pp. 553-559.

Morikawa, "Tissue sealing," Am. J. Surg., vol. 182 (2001), p. 29S-35S.

Mougin, et al., "Construction of Cell-Resistant Surfaces by Immobilization of Poly(ethylene glycol) on Gold," Langmuir, vol. 20 (2004), p. 4302-4305.

Mowery, et al., "Adhesion of Thermally Reversible Gels to Solid Surfaces," Langmuir, vol. 13 (1997), pp. 6101-6107.

Mrksich, et al., "Using Self-Assembled Monolayers that Present Oligo(ethylene glycol) Groups to Control the Interactions of Proteins with Surfaces," American Chemical Society Symposium Series on Chemistry and Biological Applications of Polyethylene Glycol, vol. 680 (1997), pp. 361-373.

Mukkamala, et al., "Hydrogel Polymers from Alkylthio Acrylates for Biomedical Applications," Polymer Gels: Fundamentals and Applciations 833 (2003). p. 163-174.

Muller, et al., "Interaction of differentiated HL60 cells with poloxamer and poloxamine surface modified model drug carriers," Eur. J. Pharo Sci. 5 (1997). p. 147-153.

Musahl, V., et al., The use of porcine small intestinal submucosa to enhance the healing of the medial collateral ligament—a functional tissue engineering study in rabbits. J. Orthop. Res., 2004 22(1): p. 214-20.

Nagata, M. and I. Kitazima, Photocurable biodegradable poly(epsilon-caprolactone)/poly(ethylene glycol) multiblock copolymers showing shape-memory properties Colloid & Polymer Science, 2006. 284: p. 380-386.

Nakagawa, et al., "ENH, Containing PDZ and LIM Domains, Heart/Skeletal Muscle-Specific Protein, Associates with Cytoskeletal Proteins through the PDZ Domain," 2000 Biocehm. Biophys. Res. Commun. 272 pp. 505-512.

(56) References Cited

OTHER PUBLICATIONS

Nakayama, et al., "Development of high-performance stent: gelatinous photogel-coated stent that permits drug delivery and gene transfer," 2001 J Biomed. Mater. Res., vol. 57, Issue 4 pp. 559-566.

Nakayama, et al., "Newly Designed Hemostatic Technology Based on Photocurable Gelatin," ASAIO J., vol. 41, No. 3 (1995), p. M374-M378.

Nakayama, et al., "Photocurable Surgical Tissue Adhesive Glues Composed of Photoreactive Gelatin and Poly (ethylene glycol) Diacrylate," J Biomed. Mater. Res., vol. 48, Issue 4 (1999), pp. 511-521.

Nakonieczna, et al., "A New Convenient Route for the Synthesis of DOPA Peptides," Liebigs Annalen der Chemie, Issue 10 (1994). p. 1055-1058.

Neff, et al., "A novel method for surface modification to promote cell attachment to hydrophobic substrates," J. Biomed. Mater. Res. 40 (1998). p. 511-519.

Neumayer, L., et. al., Open mesh versus Laparoscopic mesh repair of inguinal hernia. The New England Journal of Medicine, 2004. 350(18): p. 1819-1827.

Neumayer, L., et. al., Tension-Free Inguinal Hernia Repair: The Design of a Trial to Compare Open and Laparoscopic Surgical Techniques. J Am Coll Surg, 2003. 196(5): p. 743-752.

Nho, K., et al., PEG-modified hemoglobin as an oxygen carrier, in Poly(ethylene glycol) chemistry : biotechnical and biomedical applications, J.M. Harris, Editor. 1992, Plenum Press: New York. p. 171-182.

Nicholson, G.P., et al., Evaluation of a cross-linked acellular porcine dermal patch for rotator cuff repair augmentation in an ovine model. J. Shoulder Elbow Surg., 2007. 16(5S): p. 184S-190S.

Ninan, et al., "Adhesive strength of marine mussel extracts on porcine skin," Biomaterials 24 (2003). pp. 4091-4099.

Nishiyama, et al., "Adhesion mechanisms of resin to etched dentin primed with Nmethacryloyl glycine studied by 13C-NMR," J. Biomed. Mater. Res., vol. 40 (1998). pp. 458-463.

Nishiyama, et al., "Adhesion of N-Methacryloyl-w-Amino Acid Primers to Collagen Analyzed by 13C NMR," J. Dent. Res., vol. 80, No. 3 (2001), p. 855-859.

Nishiyama, et al., "Effects of a structural change in collagen upon binding to conditioned dentin studied by 13C NMR," J. Biomed. Mater. Res., vol. 29 (1995), pp. 107-111.

Nistor, L., Surgical and Non-surgical Treatment of Achilles Tendon Rupture. The Journal of Bone and Joint Surgery, 1981. 63-A(3): p. 394-399.

Northen, et al., "A batch fabricated biomimetic dry adhesive," Nanotechnology 16 (8), 2005. p. 1159-1166.

Northen, et al., "Meso-scale adhesion testing of integrated micro- and nano-scale structures," Sensors and Actuators A 130-131 (2006). p. 583-587.

Novitsky, Y., Harrell A.G., Hope, W.W., Kercher, K.W., Heniford, B.T., Meshes in Hernia Repair. Surgical Technology International, 2007(16): p. 123-127.

Novitsky, Y.W., Cristiano, J.A., Harrell, Andrew G., et al, Immunohistochemical analysis of host reaction to heavyweight-, reduced-weight-, and expanded polytetrafluoroethylene (ePTFE)-based meshes after short- and long-term intraabdominal implantations. Surg. Endosc., 2008.

Novitsky, Y.W., Harrell, Andrew G., et al, Comparative evaluation of adhesion formation, strength of ingrowth, and textile properties of prosthetic meshes after long-term intra-abdominal implantation in a rabbit. Journal of Surgical Research, 2007. 140(1): p. 6-11.

Nunalee, F.N., et al., QCM Studies of Polymer Gels and Solutions in Liquid Environment. Analytical Chemistry, 2006. 78: p. 1158-1166.

Nystrom, et al., "Dynamic Light Scattering and Rheological Studies of Thermoreversible Gelation of a Poly(ethylene oxide)-Poly(propylene oxide)-Poly(ethylene oxide) Triblock Copolymer in Aqueous Solution," Faraday Discuss. 101 (1995). pp. 335-344.

Burzio, et al., "Cross-Linking in Adhesive Ouinoproteins: Studies with Model Decapeptides," Biochemistry, vol. 39 (2000), p. 11147-11153.

Cabana, et al., "Study of the Gelation Process of Polyethylene Oxide, -Polypropylene Oxide, -Polyethylene Oxide, Copolymer (Poloxamer 407) Aqueous Solutions," J. Colloid Interface Sci., vol. 190 (1997), p. 307-312.

Campbell, et al., "Evaluation of Absorbable Surgical Sealants: In vitro Testing," Confluent Surgical, Inc. (2005) White Paper. Available from: http://www.confluentsurgical.com/pdf/ds/6070 DuraSeal Invitro WP13-25.pdf.

Carmichael, et al., "Selective Electroless Metal Deposition Using Microcontact Printing of Phosphine—Phosophonic Acid Inks," Langmuir, vol. 20 (2004), pp. 5593-5598.

Catena, F., Ansaloni, L., Gazzotti, F., Gagliardi, S., Di Saverio, S., D'Alessandro, L., Pinna, A.D., Use of porcine dermal collagen graft (Permacol) for hernia repair in contaminated fields. Hernia, 2007. 11: p. 57-60.

Chalykh, et al., "Pressure-Sensitive Adhesion in the Blends of POly(N-vinyl pyrrolidone) and Poly(ethylene glycol) of Disparate Chain Lengths," J. of Adhes., vol. 78 (2002), p. 667-694.

Champault, G., Rizk, N., Catheline, J.-M., Barrat, C., Turner, R., Boutelier, P., Inguinal Hernia Repair: Totally preperitoneal laparoscopic approach versus Stoppa operation. Hernia, 1997. 1: p. 31-36.

Chehimi, et al., "XPS investigations of acid-base interactions in adhesion. Part 3. Evidence for orientation of carbonyl groups from poly(methylmethacrylate) (PMMA) at the D D PMMA-glass and PMMA-SiOz interfaces," J. Electron. Spectrosc. Relat. Phenom., vol. 63 (1993), pp. 393-407.

Chen, et al., "Enzymatic Methods for in Situ Cell Entrapment and Cell Release," Biomacromolecules, vol. 4 (2003), pp. 1558-1563.

Chen, et al., "Temperature-Induced Gelation Pluronic-g-Poly(acrylic acid) Graft Copolymers for Prolonged Drug Delivery to the Eye," in Harris, et al. (eds.) Poly(ethylene glycol): Chemistry and Biological Applications. New York, NY: Oxford University Press USA, 1997. p. 441-451.

Chirdon, W.M., W.J. O'Brien, and R.E. Robertson, Adsorption of catechol and comparative solutes on hydroxyapatite. J. Biomed. Mat. Res. B, 2003. 66B(2): p. 532-538.

Cobb, W.S., et al., Normal intraabdominal pressure in healthy adults. The Journal of Surgical Research, 2005. 129(2): p. 231-5.

Cohn, D., et al., Biodegradable poly(ethylene oxide)/poly(e-caprolactone) multiblock copolymers. Journal of Biomedical Materials Research, 2002. 59(2): p. 273-281.

Collier, et al., "Enzymatic Modification of Self-Assembled Peptide Structures with Tissue Transglutaminase," Bioconjugate Chem., vol. 14 (2003), op. 748-755.

Collier, et al., "Self-Assembling Polymer-Peptide Conjugates: Nanostructural Tailoring," Adv. Mater., vol. 16, No. 11 (2004), pp. 907-910.

Collins, et al., "Use of collagen film as a dural substitute: Preliminary animal studies," J. Biomed. Mater. Res., vol. 25 (1991), p. 267-276.

Connor, et al., "New Sol-Gel Attenuated Total Reflection Infrared Spectroscopic Method for Analysis of Adsorption at Metal Oxide Surfaces in Aqueous Solutions. Chelation of Ti02, Zr02, and Al203 Surfaces by Catechol, 8-Quinolinol, and Acetylacetone," Langmuir, vol. 11 (1995), pp. 4193-4195.

Cosgrove, "Safety and Efficacy of a Novel PEG Hydrogel Sealant (DuraSeal®) for Watertight Closure after Dural Repair," Presented at the Congress of Neurological Surgeons 55th Annual Meeting, Boston, MA, Oct. 2005. Available from: http://www.confluentsurQical.com/pdf/ds/CosQroveAbstractCNS2005.pdf.

Cosgrove, et al., "Safety and efficacy of a novel polyethylene glycol hydrogel sealant for watertight dural repair," J. Neurosurg., vol. 106 (2007), p. 52-58.

Crescenzi, et al., "New Gelatin-Based Hydrogels via Enzymatic Networking," Biomacromolecules, vol. 3 (2002), pp. 1384-1391.

Creton. "Pressure-Sensitive Adhesives: An Introductory Course" 2003 MRS Bulletin vol. 26 No. 6 pp. 434-439.

Crosby, et al., "Controlling Polymer Adhesion with "Pancakes"," Langmuir, vol. 21 (2005), pp. 11738-11743.

Crosby, et al., "Rheological properties and adhesive failure of thin viscoelastic layers," J. Rheol., vol. 46, No. 1 (2002), pp. 273-294.

(56) References Cited

OTHER PUBLICATIONS

Cruise, et al., "A Sensitivity Study of the Key Parameters in the Interfacial Photopolymerization of Poly(etheylene glycol) Dlacrylate upon Porcine Islets," Biotechnol. Bioeng., vol. 57, Issue 6 (1998), p. 655-665.
Dai, et al., "Novel pH-Responsive Amphiphilic Diblock Copolymers with Reversible Micellization Properties," Langmuir 19 (2003). p. 5175-5177.
Dalsin et al., Bioinspired Antifouling Polymers. Materials Today 2005,8,9 (38-46).
Dalsin, et al., "Antifouling Performance of Poly(ethylene glycol) Anchored onto Surfaces by Mussel Adhesive Protein Mimetic Peptides," Polymeric Materials Science and Engineering 90 (2004). pp. 247-248.
Dalsin, et al., "Mussel Adhesive Protein Mimetic Polymers for the Preparation of Nonfouling Surfaces," J. Am. Chem. Soc. 125(14) p. 4253-4258. 2003.
Dalsin, et al., "Protein Resistance of Titanium Oxide Surfaces Modified by Biologically Inspired mPEG-DOPA," Lenamuir 21 (2005). p. 640-646.
Dalsin, et al., "Surface Modification for Protein Resistance Using a Biomimetic Approach," Mat. Res. Soc. Symp. Proc., vol. 774 (2002), p. 75-80.
Daly W H et al: "Synthesis of poly(vinylcatechols)", Journal of Polymer Science, Interscience Publishers, XX, vol. 74, Jan. 1, 1986, pp. 227-242, XP008086907.
Davis, et al., "Polymeric microspheres as drug carriers," Biomaterials 9 (1), 1988. p. 111-115.
Deacon, M.P., et al., Structure and Mucoadhesion of Mussel Glue Protein in Dilute Solution. Biochem., 1998. 37(40): p. 14108-14112.
Deible, et al., "Creating molecular barriers to acute platelet deposition on damaged arteries with reactive polyethylene glycol," J. Biomed. Maters. Res. 41 (1998). p. 251-256.
Deming, "Mussel byssus and biomolecular materials," Current Opinion in Chemical Biology, 3(1), 1999. pp. 100-105.
Deming, et al., "Mechanistic Studies of Adhesion and Crosslinking in Marine Adhesive Protein Analogs," Polym. Mater. Sci. Eng., 80 (1999). pp. 471-472.
Deruelle, et al., "Adhesion at the Solid-Elastomer Interface: Influence of the Interfacial Chains," Macromolecules, vol. 28 (1995), p. 7419-7428.
Desai et al., Surface-Immobilized Polyethylene Oxide for Bacterial Repellence. Biomaterials 1992,13, (7), 417-420.
Desai, et al., "In Vitro Evaluation of Pluronic F127-Based Controlled-Release Ocular Delivery Systems for Polocarpine," J. Pharo Sci., 87 (2),1998. p. 226-230.
Dillow, et al., "Adhesion of a5b1 receptors to biomimetic substrates constructed from peptide amphiphiles," Biomaterials, vol. 22 (2001), pp. 1493-1505.
Djurasovic, M., Marra, G., Arroyo, J.S., et al, Revision Rotator Cuff Repair: Factors Influencing Results. The Journal of Bone and Joint Surgery, 2001. 83-A(12): p. 1849-1855.
Donkerwolcke, et al., "Tissue and bone adhesives—historical aspects," Biomaterials 19 (1998). p. 1461-1466.
Dossot, et al., "Role of Phenolic Derivatives in Photopolymerization of an Acrylate Coating," J. Appl. Polymer. Sci., 78 (2000). p. 2061-2074.
Drumheller, et al., "Polymer Networks with Grafted Cell Adhesion Peptides for Highly Biosoecific Cell Adhesive Substrates," Anal. Biochem., vol. 222 (1994), p. 380-388.
Elbert, et al., "Reduction of fibrous adhesion formation by a copolymer possessing an affinity for anionic surfaces," J. Biomed. Mater Res., vol. 42, Issue 1 (1998), p. 55-65.
Elisseeff et al., "Photoencapsulation of chondrocytes in poly(ethylene oxide)-based semi-interpenetrating networks," 2000 J. Biomed. Mater Res. vol. 51 Issue 2 pp. 164-171.
Engelsman, A.F., van der Mei, H.C., Ploeg, R.J., Busscher, H.J., The phenomenon of infection with abdominal wall reconstruction. Biomaterials, 2007. 28: p. 2314-2327.

Erli et al., "Surface pretreatments for medical application of adhesion," BioMed Eng. Online, 2(15)2003 Available from: http://www.biomedical-engineering-online.com/content/2/2/15.
Evans et al., Iron Chelator, Exopolysaccharide and Protease Production in *Staphylococcus-epidermidis*—a Comparative-Study of the Effects of Specific Growth-Rate in Biofilm and Planktonic Culture. Microbiology—Uk 1994,140,153-157.
Fan et al., "Surface-Initiated Polymerization from Ti02 Nanoparticle Surfaces Through a Biomimetic Initiator: A New Route toward Polymer-Matrix Composites," 2006 Comp. Sci. Tech. 66(9) pp. 1195-1201.
Rzepecki, et al., "Wresting the muscle from mussel beards: research and applications," Mol. Mar. Biol. Biotech. 4 (4) (1995). pp. 313-322.
Saby, et al., "Mytilus edulis Adhesive Protein (MAP) as an Enzyme Immobilization Matrix in the Fabrication of Enzyme-Based Electrodes," Electroanalysis 10 (17) (1998). pp. 1193-1199.
Sagert, J., C. Sun, and J.H. Waite, Chemical Subtleties of Mussel and Polychaete Holdfasts, in Biological Adheisves, A.M. Smith and J.A. Callow, Editors. 2006, Springer-Verlag. p. 125-143.
Saltz, R., et al., Experimental and clinical applications of fibrin glue. Plast Reconstr Surg, 1991. 88(6): p. 1005-15; discussion 1016-7.
Sanbom, et al., "In situ crosslinking of a biomimetic peptide-PEG hydrogel via thermally triggered activation of factor XIII," Biomaterials, vol. 23 (2002), pp. 2703-2710.
Sawada, et al., "Micropatterning of Copper on a Poly(ethylene terephthalate) Substrate Modified with a Self-Assembled Monolayer," Lenqmuir 22 (2006). pp. 332-337.
Sawhney, et al., Bioerodible Hydrogels Based on Photopolymerized Poly(ethylene glycol)-co-poly(a-hydroxy acid) Diacrylate Macrorners, Macromolecules, vol. 26 (1993), p. 581-587.
Sawhney, et al., "Interfacial photopolymerization of poly(ethylene glycol)-based hydrogels upon alginate-poly(I-lysine) microcapsules for enhanced biocompatibility," Biomaterials, vol. 14, No. 13 (1993), p. 1008-1016.
Schacht, E.H. and K. Hoste, Poly(ethylene glycol)-grafted polymers as drug carriers, in Poly(ethylene glycol) : chemistry and biological applications, J.M. Harris and S. Zalipsky, Editors. 1997, American Chemical Society: Washington, DC. p. 297-315.
Schmolka, "Articifial Skin. I. Preparation and Properties of Pluronic F-127 Gels for Treatment of Burns," J. Biomed. Mater. Res. 6 (6) (1972). pp. 571-582.
Schnurrer, et al., "Mucoadhesive properties of the mussel adhesive protein," Int. J. Pharm. 141 (1996). pp. 251-256.
Schwab, R., Eissele, S., Bruckner, U.B., Gebhard, F., Becker, H.P., Systemic inflammatory response after endoscopic (TEP) versus Shouldice groin hernia repair. Hernia, 2004. 8: p. 226-232.
Schwab, R. Willms A., Kroger, A., Becker, H.P., Less chronic pain following mesh fixation using fibrin sealant in TEP inguinal hernia repair. Hernia, 2006. 10: p. 272-277.
Sever, et al., "Metal-Mediated Cross-Linking in the Generation of a Marine-Mussel Adhesive," Angew. Chem. Int. Ed., vol. 43 (2004), pp. 448-450.
Sever, et al., "Synthesis of peptides containing DOPA (3.4-dihydroxyphenylalanine)," Tetrahedron 57(2001). pp. 6139-6146.
Shaieb, M.D., Singer, D.I., Tensile Strengths of various suture techniques. The Journal of Hand Surgery (British and European Volume), 1997. 22B(6): p. 764-767.
Shaikh, F.M., Giri, S.K., Durrani, S., Waldron, D., Grace, P.A., Experience with porcine acellular dermal collagen implant in one-stage tension-free reconstruction of acute and chronic abdominal wall defects. World J. Surg., 2007. 31: p. 1966-1972.
Shull, "Contact mechanics and the adhesion of soft solids," Mater. Sci. Eng., R 36 (2002). p. 1-45.
Shull, et al., "Fracture Mechanics Studies of Adhesion in Biological Systems," Interface Sci., vol. 8 (2000), pp. 95-110.
Sichel, et al., "Relationship Between Melanin Content and Superoxide Dismutase (SOD) Activity in the Liver of Various Species of Animals," Cell Biochem. Funct. 5 (1987). pp. 123-128.
Sierra, "Fibrin Sealant Adhesive Systems: A Review of Their Chemistry, Material Properties and Clinical Applications," J. Biomed. Appl., vol. 7 (1993), p. 309-352.

(56) References Cited

OTHER PUBLICATIONS

Sierra, D. and R. Saltz, Surgical Adhesives and Sealants: Current Technology and Applications. 1996, Lancaster, PA: Technomic Publishing Company, Inc.
Sikkink, C.J.J.M., et al, Adhesion formation and reherniation differ between meshes used for abdominal wall reconstruction. Hernia, 2006. 10: p. 218-222.
Sitti, et al., "Synthetic Gecko Foot-Hair Micro/Nano-Structures as Dry Adhesives," J. Adhes. Sci. Technol., vol. 17, No. 8 (2003), p. 1055-1073. Available from: http://nanolab.me.cmu.edu/publications/papers/Sitti-JAST2003.pdf.
Skelhorne, et al., "Hydrogel Adhesives for Wound-Care Applications," Medical Device Technology (Nov. 2002). p. 19-23.
Smart, N., Immanuel, A., Mercer-Jones, M., Laparoscopic repair of a Littre's hernia with porcine dermal collagen implant (Permacol). Hernia, 2007. 11: p. 373-376.
Soriaga, et al., "Determination of the Orientation of Adsorbed Molecules at Solid-Liquid Interfaces by Thin-Layer Electrochemistry: Aromatic Compounds at Platinum Electrodes," J. Am. Chem. Soc. 104 (1982). p. 2735-2742.
Sousa, et al., "Human Serum Albumin Adsorption on TiO2from Single Protein Solutions and from Plasma," Langmuir, vol. 20 (2004), p. 9745-9754.
Speck, M., Klaue, K., Early Full Weightbearing and Functional Treatment after Surgical Repair of Acute Achilles Tendon Rupture. The American Journal of Sports Medicine, 1998. 26(6): p. 789-793.
Sperinde, et al., "Control and Prediction of Gelation Kinetics in Enzymatically Cross-Linked Poly(ethylene glycol) Hydroqels," Macromolecules 33 (2000). p. 5476-5480.
Sperinde, et al., "Synthesis and Characterization of Enzymatically-Cross-Linked Poly(ethylene glycol) Hydrogels," Macromolecules 30 (18) (1997). p. 5255-5264.
Spolenak, et al., "Adhesion design maps for bio-inspired attachment systems," Acta. Biomater. 1 (2005). pp. 5-13.
Spotnitz, "Commercial fibrin sealants in surgical care," Am. J. Surg. 182 (2001). p. 8S-14S.
Spotnitz, "History of Tissue Adhesives." In: Sierra, et al. (eds.), Surgical Adhesives and Sealants: Current Technology and Applications. Technomic Publishing Company, Inc.: Lancaster, PA (1997). PD. 3-11.
Stark, E., et al., Nerve irritation after laparoscopic hernia repair. Surg. Endosc., 1999 13(9): p. 878-81.
Statz, et al., "New Peptidomimetic Polymers for Antifouling Surfaces," J. Am. Chem. Soc., vol. 127, No. 22 (2005), . 7972-7973.
Stevens, "Trace bio-organic constituents of gelatins—a review," Food Australia, vol. 44, No. 7 (1992), p. 320-324.
Stile, et al., "Sequential robust design methodology and X-ray photoelectron spectroscopy to analyze the grafting of hyaluronic acid to glass substrates," J. Biomed. Mater Res., vol. 61, Issue 3 (2002), pp. 391-398.
Stiles, et al., "Axisymmetric Adhesion Test to Examine the Interfacial Interactions between Biologically-Modified Networks and Models of the Extracellular Matrix," Langmuir, vol. 19 (2003) pp. 1853-1860.
Strausberg, et al., "Development of a microbial system for production of mussel adhesive protein." In: Adhesives from Renewable Resources. Hemingway, et al. (eds.), ACS Symposium Series 385, American Chemical Society, Washington, D.C. (1989). pp. 453-464.
Strausberg, et al., "Protein-based medical adhesives," Trends in Biotechnology 8 (2) (1990). p. 53-57.
Strauss, E.J., Ishak, C., Jazrawi, L., Sherman, O., Rosen, J., Operative Treatment of acute Achilles tendon ruptures: An institutional review of clinical outcomes. Injury, International Journal of the care of the Injured, 2007. 38: p. 832-838.
Sugumaran, "Unified Mechanism for Sclerotization of Insect Cuticle," Adv. Insect. Physiol., vol. 27 (1998), p. 229-334.
Sugumaran, et al., "Chemical- and Cuticular Phenoloxidase-Mediated Synthesis of Cysteinyl-Catechol Adducts," Arch. Insect Biochem. Physiol. 11 (2) (1989). pp. 127-137.
Sun, et al., "Improved antifouling property of zwitterionic ultrafiltration membrane composed of acrylonitrile and sulfobetaine copolymer," J. of Memr. Sci. 285 (2006). p. 299-305.
Sun, et al., "The Nature of the Gecko Lizard Adhesive Force," Biophys. J. 89 (2005). pp. L14-L16.
Swerdloff, et al., "Solid phase synthesis of bioadhesive analogue peptides with trifluoromethanesulfonic acid cleavage from PAM resin," Int. J. Peptide Protein Res., vol. 33 (1989), 318-327.
Tae, et al., "Sustained release of human growth hormone from in situ forming hydrogels using self-assembly of fluoroalkyl-ended poly-(ethylene glycol)," Biomaterials, vol. 26 (2005), pp. 5259-5266.
Taira, et al., "Analysis of Photo-iniators in Visible-light-cured Dental Composite Resins," J. Dent. Res., vol. 67, No. 1 (1988), pp. 24-28.
Tan, et al., "Surface modification of nanoparticles by PEO/PPO block copolymers to minimize interactions with blood components and prolong blood circulation in rats," Biomaterials, vol. 14, No. 11 (1993), p. 823-833.
Tatehata, et al., "Model Polypeptide of Mussel Adhesive Protein. I. Synthesis and Adhesive Studies of Sequential Polypeptides (x-Tyr-Lys)n and (Y-Lys)n," J. Appl. Polym. Sci., vol. 76, No. 6 (2000), 929-937.
Taylor, et al., "Ferric Ion Complexes of a DOPA-Containing Adhesive Protein from Mytilus edulis," Inorg. Chem., vol. 35 (1996), p. 7572-7577.
Taylor, et al., "Polargraphic and Spectrophotometric Investigation of Iron(III) Complexation to 3,4-Dihydroxyphenylalanine-Containing Peptides and Proteins from Mytilus edulis," Inorg. Chem., vol. 33 (1994); p. 5819-5824.
Taylor, et al., "trans-2,3-cis-3,4-Dihydroxyproline, a New Naturally Occurring Amino Acid, Is the Sixth Residue in the Tandemly Repeated Consensus Decapeptides of an Adhesive Protein from Mytilus edulis," J. Am. Chem. Soc., vol. 116 (1994), p. 10803-10804.
Tingart, M.J., et al, Pullout strength of suture anchors used in rotator cuff repair. The Journal of Bone and Joint Surgery, 2003. 85-A(11): p. 2190-2198.
Topart, P., Vandenbroucke, F., Lozac'h, P., Tisseel vs tack staples as mesh fixation in totally extraperitoneal laparoscopic repair of groin hernias. Surg. Endosc., 2005. 19: p. 724-727.
Tozer, S., Duprez, D., Tendon and Ligament: Development, Repair and Disease. Birth Defects Research (Part C), 2005. 75: p. 226-236.
Ueno, T., Pickett, L.C., de la Fuente, S.G., Lawson, D.C., Pappas, T.N., Clinical application of porcine small intestinal submucosa in the management of infected or potentially contaminated abdominal defects. Journal of Gastrointestinal Surgery, 2004. 8(1): p. 109-112.
Uyama, et al., "Surface Modification of Polymers by Grafting," Advances in Polymer Science, vol. 137 (1998), pp. 1-39.
Valentin, J.E., et al., Extracellular Matrix Bioscaffolds for Orthopaedic Applications. A Comparative Histologic Study. J. Bone Joint Surg. Am., 2006. 88: p. 2673-2686.
Venkatraman, et al., "Skin adhesives and skin adhesion. 1. Transdermal drug delivery systems," Biomaterials, vol. 19 (1998), 1119-1136.
Voros, et al., "Optical grating coupler biosensors," Biomaterials, vol. 23 (2002), pp. 3699-3710.
Waite, "Adhesion ala Moule," Integr. Compo Biol., vol. 42 (2002), pp. 1172-1180.
Waite, "Evidence for a Repeating 3,4-Dihydroxyphenylalanine- and Hydroxyprolinecontaining Decapeptide in the Adhesive Protein of the Mussel, *Mytilus edulis l*.," J. Biol. Chem., vol. 258, No. 5 (1983), pp. 2911-2915.
Waite, "Mussel Beards: A Coming of Age" Chem. Ind. (Sep. 2, 1991), pp. 607-611.
Waite, "Nature's underwater adhesive specialist," Chemtech, vol. 17 (1987), pp. 692-697.
Waite, "Nature's underwater adhesive specialist," Int. J. Adhes. Adhes., vol. 7, No. 1 (1987), . 9-14.
Waite, "Precursors of Quinone Tanning: Dopa-Containing Proteins," Methods Enzymol., vol. 258 (1995), op. 1-21.
Waite, et al., "3,4-Dihydroxyphenylalanine in an Insoluble Shell Protein of Mytilus edulis," Biochem. Bioohvs. Acta, vol. 541 (1978), pp. 107-114.

(56) References Cited

OTHER PUBLICATIONS

Waite, et al., "Assay of Dihdroxyphenylalanine (Dopa) in Invertebrate Structural Proteins," Methods Enzymol., vol. 107 (1984), pp. 397-413.

Waite, et al., "Polyphenolic Substance of Mytilus edulis: Novel Adhesive Containing L-Dopa and Hydroxyproline," Science, vol. 212, No. 4498 (1981), p. 1038-1040.

Waite, et al., "Polyphosphoprotein from the Adhesive Pads of Mytilus edulis," Biochemistry, vol. 40 (2001), pp. 2887-2893.

Waite, et al., "The Bioadhesive of Mytilus byssus: A Protein Containing L-DOPA," Biochem. & Biophv. Res. Comm., vol. 96, No. 4 (1980), p. 1554-1561.

Waite, etal., "Mussel Adhesion: Finding the Tricks Worth Mimicking," J. Adhes., vol. 81 (2005), 297-317.

Waite, J.H., in Redox-Active Amino Acides in Biology, 1995, vol. 258, p. 1-20.

Waite, J.H., The phylogeny and chemical diversity of quinone-tanned glues and varnishes. Comp. Biochem. Physiol. B., 1990. 97(1): p. 19-29.

Waite, Reverse engineering of bioadhesion in marine mussels. Bioartificial Organs ii: Technology, Medicine, and Materials 1999,875,301-309.

Wang, et al., "Facile Atom Transfer Radical Polymerization of Methoxy-Capped Oligo(ethylene glycol) Methacrylate in Aqueous Media at Ambient Temperature," Macromolecules, vol. 33 (2000), p. 6640-6647.

Wang, et al., "Facile synthesis of well-defined water-soluble polymers via atom transfer radical polymerization in aqueous media at ambient temperature," Chem. Commun. (1999), p. 1817-1818.

Wanka, et al., "The aggregation behavior of poly-(oxyethylene)-poly-(oxypropylene)-poly-(oxyethylene)-blockcopolymers in aqueous solution," Cooloid. Polym. Sci., vol. 268 (1990), pp. 101-117.

Warner, et al., "Expression of multiple forms of an adhesive plaque protein in an individual mussel, *Mvtilus edulis*," Mar. Biol., vol. 134 (1999), pp. 729-734.

Watanabe, et al., "Bonding durability of photocured phenyl-P in TEGDMA to smear layer-retained bovine dentin," Quint. Int., vol. 24, No. 5 (1993), co. 335-342.

Webber, et al., "Effects of geometric confinement on the adhesive debonding of soft elastic solids," Phys. Rev. E, vol. 68 (2003), pp. 021805-1-to-021805-11.

Whitesides, "The origins and the future of microfluidics," Nature, vol. 442 (2006), pp. 368-373.

Williams, G.R.J., et al, Rotator Cuff Tears: Why do we repair them? The Journal of Bone and Joint Surgery, 2004. 86-A(12): p. 2764-2776.

Winter, E., Weise, K., Weller, S., Ambacher, T., Surgical Repair of Achilles Tendon Rupture: Comparison of Surgical with Conservative Treatment. Arch. Orthop. Trauma Surg., 1998. 117: p. 364-367.

Wisniewski, et al., "Methods for reducing biosensor membrane biofouling," Colloids Surf., B, vol. 18 (2000), pp. 197-219.

Yamada, "Chitosan Based Water-Resistant Adhesive. Analogy to Mussel Glue," Biomacromolecules, vol. 1 (2000), pp. 252-258.

Yamamoto, "Adhesive studies of synthetic polypeptides: A model for marine adhesive proteins," J. Adhesion Sci. Tech., vol. 1, No. 2 (1987), pp. 177-183.

Yamamoto, "Insolubilizing and adhesive studies of water-soluble synthetic model proteins," Int. J. Bioi. Macramol., vol. 12 (1990), pp. 305-310.

Yamamoto, "Marine Adhesive Proteins and Some Biotechnological Applications," Biotechnol. Genet. Eng. Rev., vol. 13 (1996), pp. 133-165.

Yamamoto, "Synthesis and Adhesive Studies of Marine Polypeptides," J. Chem. Soc. Perkin Trans., vol. 1 (1987), pp. 613-618.

Yamamoto, et al., "Synthesis and Adhesives of Marine Adhesive Proteins of the Chilean Mussel Aula comve ater," . Biomimetics, vol. 1, No. 3 (1992), pp. 219-238.

Yamamoto, et al., "Wettability and Adhesion of Synthetic Marine Adhesive Proteins and Related Model Compounds," J. Colloid Interface Sci., vol. 176 (1995), pp. 111-116.

Yamamoto, et al., "Work of Adhesion of Synthetic Polypeptides Containing L-Lysine," J. Colloid Interface Sci., vol. 156 (1993), pp. 515-517.

Yamamoto, H. and K. Ohkawa, Synthesis of adhesive protein from the vitellaria of the liver fluke Fasciola hepatica. Amino Acids, 1993. 5(1): p. 71-5.

Yang Z et al: "The synthesis of poly(3,4-dihydroxystyrene) and pol (soium 4-styrenesulfonate)-co-(3,4-dihydroxystyre ne)", Macromolecular: Rapid Communications, Wiley VCH Verlag, Weinheim, DE, vol. 19, Jan. 1, 1998, pp. 241-246.

Yang, et al., "Physicochemical aspects of drug delivery and release from polymer-based colloids," Curro Opin. Colloid Interface Sci., vol. 5 (2000), pp. 132-143.

Yao et al., Association behavior of poly(methyl methacrylate-b-methacrylic acid-b-methyl methacrylate) in aqueous medium, 2004, Polymer, vol. 45, pp. 2781-2791.

Young, et al., "Marine Animals and Adhesion." In: Allen (ed.), Adhesion 6. Applied Science Publishers: London and New Jersey, 1982. pp. 19-39.

Abraham, G.A., Murray, J., Billiar, K., Sullivan, S.J., Evaluation of the porcine intestinal collagen layer as a biomaterial. J. Biomed. Mater. Res., 2000. 51: p. 442-452.

ACL Injury: Does it Require Surgery? 2007.

Advincula, "Surface Initiated Polymerization from Nanoparticle Surfaces," J. Dispersion Sci. Technol., vol. 24, Nos. 3 &4 (2003), p. 343-361.

Ahmed, et al., "Synthesis and Application of Fluorescein-Labeled Pluronic Block Copolymers to the Study of Polymer-Surface Interactions," Langmuir, vol. 17, No. 2 (2001), p. 537-546.

Alexandridis, P., "Poly(ethylene oxide)-Poly(propylene oxide) Block Copolymer Surfactants," Curro Opin. Col/aid Interface Sci., vol. 2, No. 5, (1997), pp. 478-489.

Alexandridis, P.; Nivaggioli, T.; Hatton T. A., "Temperature Effects on Structural Properties of Pluronic P104 and F108 PEO-PPO-PEO Block Copolymer Solutions," Langmuir, vol. 11, No. 5, (1995), p. 1468-1476.

Alivisatos, P., The use of nanocrystals in biological detection, Nature Biotechnology, vol. 22, No. 1 (2004), pp. 47-52.

Alleyne, Jr., et al., "Efficacy and biocompatibility of a photopolymerized, synthetic, absorbable hydrogel as a dural sealant in a canine craniotomy model," J. Neurosurg., vol. 88 (1998), pp. 308-313.

Amid, P.K., Classification of biomaterials and their related complications in abdominal wall hernia surgery. Hernia, 1997. 1: p. 15-21.

Amid, P.K., Groin Hernia Repair: Open Techniques. World J. Surg., 2005. 29: p. 1046-1051.

Andreopoulos, et al., "Light-induced tailoring of PEG-hydrogel properties," Biomaterials, vol. 19 (1998), pp. 1343-1352.

Andrzejewska, et al., "The role of oxygen in camphorquinone-initiated photopolvmerization," Macromol. Chern. Pnys., vol. 199 (1998), pp. 441-449.

Ansaloni, L. Catena, F., Gagliardi, S., Gazzotti, F., D'Alessandro, L., Pinna, A.D., Hernia repair with porcine small-intestinal submucosa. Hernia, 2007. 11(4): p. 321-326.

Ansaloni, L., et al., Immune response to small intestinal submucosa (surgisis) implant in humans: preliminary observations. J. Invest. Surg. , 2007. 20(4): p. 237-41.

Araujo, et al., "Interaction of Catechol and Gallic Acid with Titanium Dioxide in Aqueous Suspensions. 1. Equilibrium Studies," Langmuir, vol. 21 (2005), pp. 3470-3474.

Armstrong et al., "Scanning Microcalorimetric Investigations of Phase Transitions in Dilute Aqueous Solutions of Poly (oxypropylene)," J. Phys. Chem., vol. 99 (1995), pp. 4590-4598.

Arnow, "Colorimetric Determination of the Component of 3, 4-Dihydroxyphemylalanine-Tyrosine Mixtures," J. Biol. Chem., vol. 118 (1937), p. 531-538.

Arregui, M.E., Young, S.B., Groin Hernia Repair by Laparoscopic Techniques: Current Status and Controversies. World J. Surg., 2005. 29: p. 1052-1057.

(56) References Cited

OTHER PUBLICATIONS

Arzt et al., "From micro to nano contacts in biological attachment devices," Proc. Nat. Acad. Sci. USA, vol. 100 (2003), p. 10603-10606.
Arzt, "Biological and artificial attachment devices: Lessons for materials scientists from flies and geckos," Mater. Sci. Eng. C, vol. 26 (2006), p. 1245-1250.
Autumn et al., "Adhesive force of a single gecko foot-hair," Nature, vol. 405 (2000), p. 681-685.
Autumn et al., "Evidence for van der Waals adhesion in gecko setae," Proc. Nat. Acad. Sci. USA, vol. 99 (2002), p. 12252-12256.
Badylak, S., et al., Resorbable bioscaffold for esophageal repair in a dog model. J. Pediatr. Surg., 2000 35(7): p. 1097-103.
Badylak, S.F., et al, The Use of Xenogeneic small intestinal submucosa as a biomaterial for Achilles tendon repair in a dog model. Journal of Biomedical Materials Research, 1995. 29: p. 977-985.
Badylak, S.F., The extracellular matrix as a biologic scaffold material. Biomaterials, 2007. 28: p. 3587-3593.
Bae, Y.H., et al., Biodegradable amphiphilic multiblock copolymers and their implications for biomedical applications. Journal of Controlled Release, 2000. 64(1-3): p. 3-13.
Bain et al., Molecular-level Control over Surface Order in Self-Assembled Monolayer Films of Thiols on Gold. Science 1988, 240, (4848), 62-63.
Baird, et al. (2007), "Reduction of Incisional Cerebrospinal Fluid Leak Following Posterior Foss Surgery with the use of Duraseal," American Association of Neurosurgeons. Abstract retrieved Jul. 23, 2008, from AANS Abstract Center database. Available from: http://www.aans.orq/librarv/article.aspx?ArticleId=42392.
Balsa-Canto, et al., "Reduced-Order Models for Nonlinear Distributed Process Systems and Their Application in Dynamic Optimization," Ind. Eng. Chem. Res., vol. 43 (2004), p. 3353-3363.
Banerjee, et al., "Derivatives of 3, 4-Dihydroxyphenylalanine for Peptide Synthesis," J. Org. Chem., vol. 41, No. 18 (1976), p. 3056-3058.
Banninger, H., et al., Fibrin glue in surgery: frequent development of inhibitors of bovine thrombin and human factor V. British Journal of Haematology, 1993. 85(3): p. 528-32.
Barbakadze, V. et ai, "Poly[3-(3,4-Dihydroxyphenyl)glyceric Acid]: A New Biologically Active Polymer from Symphytum Asperum Lepech. And S. caucasicum Bieb.(Boraginaceae)", Molecules, 10, p. 1135-1144. Sep. 30, 2005.
Barichello et al., "Absorption of insulin from Pluronic F-127 gels following subcutaneous administration in rats" 1999 Int. J. Pharm. vol. 184 pp. 189-198.
Bax, T., Sheppard, B.C., Crass, R.A., Surgical Options in the Management of Groin Hernias. American Family Physician, 1999. 59(1).
Benedek, "End Uses of Pressure-Sensitive Products" in Developments in Pressure-Sensitive Products, Benedek (ed.), CRC Press Boca Raton FL 2006 pp. 539-596.
Berndsen, F.H., et al, Discomfort five years after laparoscopic and Shouldice inguinal hernia repair: a randomised trial with 867 patients. Hernia, 2007, pp. 307-313.
Bharathi et al., "Direct Synthesis of gold nanodispersions in sol-gel derived silicate sols, gels and films," Chem. Commun. 1997 pp. 2303-2304.
Billiar, K, Murray, J., Laude, D., Abraham, G., Bachrach, N., Effects of carbodiimide crosslinking conditions on the physical properties of laminated intestinal submucosa. J. Biomed. Mater. Res., 2001. 56: p. 101-108.
Bontempo, et al., "Atom Transfer Radical Polymerization as a Tool for Surface Functionalization," Adv. Mater., vol. 14, No. 17 (2002), p. 1239-1241.
Boogaarts, et al., "Use of a novel absorbable hydrogel for augmentation of dural repair: results of a preliminary clinical study," Neurosurg., vol. 57 (2005), p. 146-151.
Bromberg, "Novel Family of Thermogelling Materials via C—C Bonding between Poly(acrylic acid) and Poly(ethylene oxide)-b-poly(propylene oxide)-b-poly(ethyleneoxide)," J. Phys. Chem. B, vol. 102 (1998), pp. 1956-1963.
Bromberg, "Self-Assembly in Aqueous Solutions of Polyether-Modified Poly(acrylic acid)," Langmuir, vol. 14 (1998), p. 5806-5812.
Bromberg, "Temperature-responsive gels and thermogelling polymer matrices for protein and peptide delivery," Advanced Drug Reviews, vol. 31 (1998), pp. 197-221.
Brown, C.H., Carson, E.W, Revision Anterior Cruciate Ligament Surgery. Clin Sports Med, 1999. 18: p. 109-171.
Brown, et al., "Micelle and Gel Formation in a Poly(ethylene oxide)/Poly(propylene oxide)/Poly(ethylene oxide) Triblock Copolymer in Water Solution. Dynamic and Static Light Scattering and Oscillatory Shear Measurements," J. Phys. Chem., vol. 95 (1991), pp. 1850-1858.
Bruinsma et al., "Bacterial adhesion to surface hydrophilic and hydrophobic contact lenses" 2001 Biomaterials vol. 22 pp. 3217-3224.
Bryant, et al., "Cytocompatibility of UV and visible light photoinitiating systems on cultured NIH/3T3 fobroblasts in vitro," J. Biomater. Sci. Polymer Edn, vol. 11, No. 5 (2000), p. 439-457.
Burdick, et al., "Synthesis and Characterization of Tetrafunctional Lactic Acid Oligomers: A potential in Situ Forming Degradable Orthopaedic Biomaterial," J. Polym. Sci., Part A: Polvm. Chem., vol. 39 (2001), pp. 683-692.
Burdinski et al., Universal Ink for Microcontact Printing. Angwandte Chemie 2006, 45, 1-5.
Burke, S.A., et al., Thermal gelation and tissue adhesion of biomimetic hydrogels. Biomed. Mater., 2007. 2: p. 203-210.
Nystrom, et al., "Dynamic Viscoelasticity of an Aqueous System of a Poly(ethylene oxide)-Poly(propylene oxide)-Poly(ethylene oxide) Triblock Copolymer during Gelation," J. Phys. Chem. 100 (1996). pp. 5433-5439.
Oelschlager, B.K., Barreca, M., Chang, L., Pellegrini, C.A., The use of small intestine submucosa in the repair of paraesophageal hernias: Initial observations of a new technique. The American Journal of Surgery, 2003. 186: p. 4-8.
Oiwa, H., et al., Experimental study of small arterial anastomosis with gelatin-resorcin-formaldehyde glue and collagen sheet. Artif Organs, 2001 25(4): p. 281-91.
O'Keefe, et al., "Poloxamer-188 as an Adjunct to Primary Percutaneous Transluminal Coronary Angioplasty for Acute Myocardial Infarction," Am. J. Cardiol. 78 (1996). pp. 747-750.
Okino, et al., "In situ hydrogelation of photocurable gelatin and drug release," J. Biomed. Mater. Res., vol. 59, Issue 2 (2001), p. 233-245.
Olivier ten Hallers, E.J., Jansen, J.A., Marres, H.A.M., Rakhorst, G., Verkerke, G.J., Histological assessment of titanium and polypropylene fiber mesh implantation with and without fibrin tissue glue. Journal of Biomedical Materials Research Part A, 2006: p. 372-380.
Online Medical Dictionary. "Amino acid." Available from: httpl/cancerweb.ncl.ac.uk/cgi- bin/omd?query=amino+acid.
Ono, et al., "Photocrosslinkable chitosan as a biological adhesive," J. Biomed. Mater. Res., vol. 49, Issue 2 (1999), pp. 289-295.
Ooka, et al., "Surface-Enhanced Raman Spectroscopy of DOPA-Containing Peptides Related to Adhesive Protein of Marine Mussel, *Mytilus edulis*," Biopolymers (Biospectroscopy), vol. 57, Issue 2 (2000), pp. 92-102.
Orban, et al., "Cytomimetic Biomaterials. 4. In-Situ Photopolymerization of Phospholipids on an Alkylated Surface," Macromolecules 33 (2000). p. 4205-4212.
Ostuni, et al., "A Survey of Structure-Property Relationships of Surfaces that Resist the Adsorption of Protein," Langmuir 17 (2001). p. 5605-5620.
Pajala, A., Kangas, J., Ohtonen, P., Leppilahti, J., Rerupture and Deep Infection Following Treatment of Total Achilles Tendon Rupture. The Journal of Bone and Joint Surgery, 2002. 84-A(11): p. 2016-2021.
Palmer, et al., "Surfactant Administration Reduces Testicular Ischemia-Reperfusion Injury," J. Urol. 159 (1998). p. 2136-2139.
Papov, et al., "Hydroxyarginine-containing Polyphenolic Proteins in the Adhesive Plaques of the Marine Mussel Mvtilus edulis," J. Biol. Chem. 270 (34) (1995). p. 20183-20192.
Pardo, et al., "Purification of Adhesive Proteins from Mussels," Protein Expression and Purif.1 (2),1990. p. 147-150.

(56) References Cited

OTHER PUBLICATIONS

Parker, D.M., Armstrong, P.J., Frizzi, J.D., North, J.H. Jr, Porcine Dermal Collagen (Permacol) for Abdominal Wall Reconstruction. Current Surgery, 2006. 63(4): p. 255-258.
Parsons, "Characteristics of the amino acids as components of a peptide hormone sequence," in Peptide Hormones, University Park Press: 1976. p. 1-7.
Pasche et al., Poly(I-lysine)-graft-poly(ethyleneglycol) assembled monolayers on niobium oxide surfaces: A quantitative study of the influence of polymer interfacial architecture on resistance to protein adsorption by ToF-SIMS and in situ OWLS. Lanumulr 2003,19, (22), 9216-9225.
Pasche, et al., "Effects of Ionic Strength and Surface Charge on Protein Adsorption at PEGylated Surfaces," J. Phys. Chem. B 109 (2005). p. 17545-17552.
Patel, et al., "Synthesis of Benzyl Esters of a-Amino Acids," J. Org. Chern. 30 (1965). p. 3575-3576.
Peiper, C., Junge, K., Futing, A., Bassalay, P., Conze, J., Schumpelick, V., Inguinal Tensile Strength and Pain Level after Shouldice Repair. Hernia, 2001. 5: p. 129-134.
Peressadko, A. and S.N. Gorb, When less is more: Experimental evidence for tenacity enhancement by division of contact area. J. Adhesion, 2004. 80: p. 1-5.
Peressadko, et ai, "When Less is More: Experimental Evidence for Tenacity Enhancement by Division of Contact Area," J. Adhes. 80 (2004). p. 247-261.
Perruchot, et al., "Synthesis of Well-Defined, Polymer-Grafted Silica Particles by Aqueous ATRP," Langmuir, vol. 17 (2001), p. 4479-4481.
Pierpont, et al., "Transition Metal Complexes of a-Benzoquinone, a-Semiquinone, and Catecholate Ligands," Coord. Chern. Rev., vol. 38 (1981), pp. 45-87.
Preul, et al., A Unique Dual-Function Device: A Dural Sealant with Adhesion Prevention Properties.
Preul, et al., "Obtaining Watertight Closures of Duraplasty Onlay Grafts in a Craniotomy Preclinical Model," Confluent Surgical, Inc. (2005), 'White Paper.' Available from: http://www.confJuentsurgical.com/pdf/LT-6000-034RevADuraSealduraplastystudywhiteoaoer.odf.
Preul, et al., "Use of a Novel Hydrogel Sealant in a Canine Dural Repair Model," Presented at the American Association of Neurological Surgeons; Apr. 2002, Chicago, IL. Available from: http://www.confluentsurqical.com/pdf/ds/AbstractOBNI PreulAbstract.pdf.
Prime, et al., "Adsorption of Proteins onto Surfaces Containing End-Attached Oligo(ethylene oxide): A Model System Using Self-Assembled Monolayers," 1993 J. Am. Chem. Soc. 115 pp. 10714-10721.
Probst, A., et al, A New Clamping Technique for Biomechanical Testing of Tendons in Small Animals. Journal of Investigative Surgery, 2000. 13: p. 313-318.
Prucker, et al., "Polymer Layers through Self-Assembled Monolayers of Initiators," Langmuir, vol. 14 (1998), pp. 6893-6898.
Pyun, et al., "Synthesis of Polymer Brushes Using Atom Transfer Radical Polymerization," Macromol. Rapid. Commun. 24 (2003). pp. 1043-1059.
R. Cristescua, R. et al. "Processing of mussel adhesive protien analog thin films by matrix assited plused laser evaporation", Applied surface Science, 247(1-4) pp. 217-224. Jul. 15, 2005. See whole document.
Rajh, et al., "Surface Restructuring of Nanoparticles: An Efficient Route for Ligand-Metal Oxide Crosstalk," J. Phys. Chem. B, vol. 106 (2002), pp. 10543-10552.
Ramakrishna, et al., "Effect of Particle Size on the Reactivity of Quantum Size ZnO Nanoparticles and Charge-Transfer Dynamics with Adsorbed Catechols," Langmuir, vol. 19 (2003), pp. 3006-3012.
Ranger, et al., "Pneumostasis of Experimental Air Leaks with a New Photopolymerized Synthetic Tissue Sealant," Am. Surg., vol. 63, Issue 9 (1997), pp. 788-795.

Ratner, B.D. Titanium in Medicine: Material Science, Surface Science, Engineering, Biological Responses and Medical Applications, ed. D.M. Brunette, et al., 2000, Heidelberg: Springer-Verlag.
Rauth, T.P., Poulose, B.K., Nanney, L.B., Holzman, M.D., A Comparative Analysis of Expanded Polytetrafluoroethylene and Small Intestinal Submucosa—Implications for Patch Repair in Ventral Herniorrhaphy. Journal of Surgical Research, 2007. 143(1): p. 43-49.
Reed, et al., "A One-Step Synthesis of Monoprotected Polyethylene Glycol Ethers," J. Org. Chem., vol. 65 (2000), pp. 5843-5845.
Refojo, M.E, C.H. Dohlman, and J. Koliopoulos, Adhesives in ophthalmology: a review. Surv. Ophthamol., 1971. 15 (4): p. 217-36.
Restore Orthobiologic Implants for Use in Rotator Cuff Shoulder Surgery. Mercer-Buck Orthopaedics, 2005.
Rodriguez, et al., "Surface Complexation at the Ti02 (anatase)/Aqueous Solution Interface: Chemisorption of Catechol," J. Colloid Interface Sci., vol. 177 (1996), pp. 122-131.
Rodriguez-Hernandez, et al., "High Branched Poly(L-lysine)," Biomacromolecules, vol. 4 (2003), . 249-258.
Ross-Murphy, "Rheological Characterization of Polymer Gels and Networks," Polym. Gels Networks, vol. 2 (1994), pp. 229-237.
Rozier, et al., Gelrite®: A novel, ion-activated, in situ gelling polymer for ophthalmic vehicles. Effect on bioavailability of timolol, Int. J. Pharm. 57 (2),1989. pp. 163-168.
Ruel-Gariepy, et al., "In situ-forming hydrogels—review of temperature-sensitive systems," Eur. J. Pharm. Biopharm. 58 (2004). p. 409-426.
Ruibal, et al., "The Structure of the Digital Setae of Lizards," J. Morph. 117 (1965). p. 271-294.
Ryu, et al., "A Generalized Approach to the Modification of Solid Surfaces," Science 308 (2005). 236-239.
Rzepecki, et al., "a,β-Dehydro-3,4-dihydroxyphenylalanine Derivatives: Potential Schlerozation Intermediates in Natural Composite Materials," Arch. Biochem. Biophys. 285 (1)(1991). pp. 17-26.
Rzepecki, et al., "Bioadhesives: DOPA and Phenolic proteins as components of organic composite materials", Principles of Cell Adhesion, P.D. Richardson and M. Steiner (eds.), CRC Press, Boca Raton, FL. (1995). pp. 107-142.
Junge, K., Peiper, C., Rosch, R., Lynen, P., Schumpelick, V., Effect of tension induced by shoulder repair on postoperative course and long-term outcome. Eur. J. Surg., 2002. 168: p. 329-333.
Juul, P., Christensen, K., Randomized clinical trial of laparoscopic versus open inguinal hernia repair. British Journal of Surgery, 1999. 86: p. 316-319.
Kacher, et al., "DuraSeal MR and CT Imaging: Evaluation in a Canine Craniotomy Model,".
Kahlem, et al., "Peptides containing glutamine repeats as substrates for transglutaminasecatalyzed cross-linking: Relevance to diseases of the nervous system," Proc. Natl. Acad. Sci. USA, vol. 93 (Dec. 1996), p. 14580-14585.
Kellaway, et al., "Oral Mucosal Drug Delivery," in Oral Mucosal Drug Delivery, Rathbone (ed.). 1996, Marcel Dekkers, Inc.: New York, NY. pp. 221-239.
Kenausis, et al., "Poly(L-lysine)-g-Poly(ethylene glycol) Layers on Metal Oxide Surfaces: Attachment Mechanism and Effects on Polymer Architecture on Resistance to Protein Adsoprtion," J. Phys. Chem. B, vol. 104 (2000), pp. 3298-3309.
Khor, E., Methods for the treatment of collagenous tissues for bioprostheses. Biomaterials, 1997 18(2): p. 95-105.
Khudyakov, et al., "Kinetics of Photopolymerization of Acrylates with Functionality of 1-6," Ind. Eng. Chem. Res. 38 (1999). pp. 3353-3359.
Kingshott, et al., "Effects of cloud-point grafting, chain length, and density of PEG layers on competitive adsorption of ocular proteins," Biomaterials 23 (2002). pp. 2043-2056.
Kirschenbaum, et al., "Sequence-specific polypeptoids: A diverse family of heteropolymers with stable secondary structure," Proc. Natl. Acad. Sci. USA 95 (1998). pp. 4303-4308.
Kitano, et al., "Resistance of zwitterionic telomers accumulated on metal surfaces against nonspecific adsorption of proteins," J. Colloid Interface Sci. 282 (2005). pp. 340-348.
Kiudelis, M., et al, Effects of different kinds of meshes on postoperative adhesion formation in New Zealand White rabbit. Hernia, 2007. 11: p. 19-23.

(56) References Cited

OTHER PUBLICATIONS

Klug, et ai, "In Situ Analysis of Peptidyl DOPA in Mussel Byssus Using Rotational-Echo Double-Resonance NMR," Arch. Biochem. Biophys., vol. 333, No. 1 (Sep. 1, 1996), pp. 221-224.
Ko, R., et al, Tensile strength comparison of small intestinal submucosa body wall repair. Journal of Surgical Research, 2006. 135(1): p. 9-17.
Kolb, et al., "Click Chemistry: Diverse Chemical Function from a Few Good Reactions," Agnew. Chem. Int. Ed., vol. 40 (2001), pp. 2005-2021.
Koniger, J., Redecke, J., Butters, M., Chronic pain after hernia repair: a randomized trial comparing Shouldice, Lichtenstein and TAPP. Langenbecks Arch. Surg., 2004. 389: p. 361-365.
Konstantinovic, M.L., Lagae, P., Zheng, F., Verbeken, E.K., De Ridder, D., Deprest, J.A., Comparison of host response to polypropylene and non-cross-linked porcine small intestine serosal-derived collagen implants in a rat model. BJOG: an International Journal of Obstetrics and Gynecology, 2005. 112: p. 1554-1560.
Koob, et al., "Mechanical and thermal properties of novel polymerized NDGA-gelatin hydrogels," Biomaterials, vol. 24 (2003), pp. 1285-1292.
Korenkov, M., Sauerland, S., Arndt, M., Bograd, L., Neugebauer, E.A.M., Troidl, H., Randomized clinical trial of suture repair, polypropylene mesh or autodermal hernioplasty for incisional hernia. British Journal of Surgery, 2002. 89: p. 50-56.
Korobkova, et al., "From molecular noise to behavioural variability in a single bacterium," Nature 428 (2004). p. 574-578.
Kramer, K.J., et al., Insect cuticle tanning: Enzymes and cross-link structure, in Natural Occurring Pest Bioregulators. 1991. p. 87-105.
Kummer, F.J., Iesaka, K., The Role of Graft Materials in Suture Augmentation for Tendon Repairs and Reattachment. J. Biomed. Mater. Res. Part B: Appl. Biomater, 2005. 74B: p. 789-791.
Kummert, et al., "The Surface Complexation of Organic Acids of Hydrous y-Al2O3," J. Colloid Interface Sci., vol. 75, No. 2 (Jun. 1980), pp. 373-385.
Kurtz, C.A., et al, Insulin-Like Growth Factor I Accelerates Functional Recovery from Achilles Tendon Injury in a Rat Model. The American Journal of Sports Medicine, 1999. 27(3): p. 363-369.
Lantis, J.C.J., Gallivan, E.K., Hekier, R., Connolly, R., Schwaitzberg, S.D., A comparison of collagen and PTFE patch repair in a rabbit model of congenital diaphragmatic hernia. Journal of Investigative Surgery, 2000. 13: p. 319-325.
Laucournet, et al., "Catechol derivatives and anion adsorption onto alumina surfaces in aqueous media: influence on the electrokinetic properties," 2001 J. Eur. Ceram. Soc. 21 pp. 869-878.
LaVoie, et al., "Dopamine covalently modifies and functionally inactivates parkin," Nature Med. 11 (11),2005. pp. 1214-1221.
Ledet, E.H., et al., A pilot study to evaluate the effectiveness of small intestinal submucosa used to repair spinal ligaments in the goat. Spine J., 2002 2(3): p. 188-96.
Lee, B.P., et al., Synthesis of 3,4-Dihydroxyphenylalanine (DOPA) Containing Monomers and Their Copolymerization with PEG-Diacrylate to from Hydrogels. Journal of Biomaterials Science, Polymer Edition, 2004. 15: p. 449-464.
Lee, et al., "Bioadhesive-Based Dosage Forms: The Next Generation," J. Pharm. Sci. 89 (7) (2000). p. 850-866.
Lee, et al., "Enzymatic and Non-Enzymatic Pathways to Formation of DOPA-Modified PEG Hydrogels," Polymer Preprints 42 (2), 2001. pp. 151-152.
Lee, et al., "Rapid Gel Formation and Adhesion in Photocurable and Biodegradable Block Copolymers with High DOPA Content," Macromolecules 39 (2006). pp. 1740-1748.
Lee, et al., "Single-Molecule Mechanics of Mussel Adhesion," Proc. Natl. Acad. Sci. USA, vol. 103, No. 35 (2006), pp. 12999-13003.
Lee, et al., "Synthesis and Gelation of DOPA-Modified Poly(ethylene glycol) Hydrogels," Biomacromolecules 3 (2002). p. 1038-1047.
Lee, et al., "Biomimetic Adhesive Polymers based on Mussel Adhesive proteins," in Biological Adhesives, Smith, et al., (eds.), Springer-Verlag: Berlin Heidelberg 2006 pp. 257-278.
Lee, et al., "Hydrogels for Tissue Engineering," 2001 Chem. Rev. vol. 101 No. 7 pp. 1869-1879.
Lee, H., B.P. Lee, and P.B. Messersmith, A Reversible Wet/Dry Adhesive Inspired by Mussels and Geckos. Nature, 2007. 448(Jul. 19): p. 338-341.
Lemieux, et al., "Block and Graft Copolymers and Nanogel Copolymer Networks for DNA Delivery into Cell," J. of Drug Targeting 8 (2), 2000. p. 91-105.
Leonard, E.F., V.T. Turitto, and L. Vroman, "Blood in contact with natural and artificial surfaces" NewYork Academy of Sciences, 1987 516: p. 688.
Leppilahti, J., Orava, S., Total Achilles Tendon Rupture: A Review. Sports Med., 1998. 25(2): p. 79-100.
Li et al., "Protein Adsortion on Oligo(ethylene glycol)-Terminated Alkanethiolate Self-Assembled Monolayers: The Molecular Basis for Nonfouling Behavior," 2005 J. Phys. Chem. B 109 pp. 2934-2941.
Li, et al., "Chemical Modifications of Surface Active Poly(ethylene oxide)-Poly(propylene oxide) Triblock Copolymers," Bioconj. Chem. 7 (1996). p. 592-599.
Li, et al., "Copper-Based Metallization for ULSI Applications," MRS Bulletin 18 (6), Jun. 1993. pp. 18-21.
Li, et al., "Two-Level Antibacterial Coating with Both Release-Killing and Contact-Killing Capabilities," Langmuir 22 (24), 2006. p. 9820-9823.
Liem, M.S.L., et al, Comparison of conventional anterior surgery and laparoscopic surgery for inguinal hernia repair. The New England Journal of Medicine, 1997. 336(22): p. 1541-1547.
Long, et al., "A peptide that inhibits hydroxyapatite growth is in an extended conformation on the crystal surface," Proc. Natl. Acad. Sci. USA 95 (1998). p. 12083-12087.
Lorand, et al., "Transglutaminases," Mol. Cell. Bioc..hem., vol. 58 (1984), p. 9-35.
Love, et al., "Self-Assembled Monolayers of Thiolates on Metals as a Form of Nanotechnology," Chem. Rev. 105 (2005). p. 1103-1169.
Lovich, et al., "Arterial heparin deposition: role of diffusion, convection, and extravascular space," Am. J. Phsviol.—Heart C., vol. 275 (1998), p. 2236-2242.
Lu et al. "Studies on the synthesis and antibacterial activities of polymeric quaternary ammonium salts from dimethylaminoethyl methacrylate," 2007 Reactive & Functional Polymers 67 pp. 355-366.
Fang, et al., "Effect of Molecular Structure on the Adsorption of Protein on Surfaces with Grafted Polymers," Langmuir, vol. 18 (2002), p. 5497-5510.
Faulkner, et al., "A New Stable Pluronic F68 Gel Carrier for Antibiotics in Contaminated Wound Treatment," Am. J. Emerg. Med., 15 (1),1997. p. 20-24.
Feldstein, et al., "Molecular Design of Hydrophilic Pressure-Sensitive Adhesives for Medical Applications," in Developments in Pressure-Sensitive Products, I. Benedek (ed.) 2006, CRC Press Boca Raton FL pp. 473-503.
Filpula, et al., "Structural and Functional Repetition in a Marine Mussel Adhesive Protein," Biotechnol. Prog. 6 (1990). p. 171-177.
Fischer, et al., "In vitro cytotoxicity testing of polycations: influence of polymer structure on cell viability and hemolysis," Biomaterials 24 (2003). p. 1121-1131.
Flanigan, et al., "Structural Development and Adhesion of Acrylic ABA Triblock Copolymer Gels," Macromolecules, vol. 32 (1999), p. 7251-7262.
Flanigan, et al., "Adhesive and Elastic Properties of Thin Gel Layers," 1999 Langmuir vol. 15 pp. 4966-4974.
Flood, et al., "Efficient Asymmetric Epoxidation of a δ-Unstarudated Ketones Using a Soluble Triblock Polyethylene Glycol-Polyamino Acid Catalyst," Org. Lett., vol. 3, No. 5 (2001), p. 683-686.
Floriolli et al., Marine surfaces and the expression of specific byssal adhesive protein variants in Mytilus. Mar Biotechnol 2000, 2, 352-363.
Flory, et al., "Effect of Volume Exclusion on the Dimensions of Polymer Chains," J. Chem. Phvs., vol. 44, No. 6 (1966), p. 2243-2248.

(56) References Cited

OTHER PUBLICATIONS

Floudas, et al., "Hierarchical Self-Assembly of Poly(y-benzyl-L-glutamate)-Poly(ethylene glycol)-Poly(y-benzyl-L-glutamate) Rod-Coil-Rod Triblock Copolymers," Macromolecules, vol. 36 (2003), p. 3673-3683.

Floyd-Smith, et al., "Interferon Action: RNA Cleavage Pattern of a (2'-5')0ligoadenylate-Dependent Endonuclease," Science, vol. 212, No. 4498 (May 29, 1981), p. 1030-1032.

Forslund, C., Rueger, D., Aspenberg, P., A Comparative Dose-Response Study of Cartilage-Derived Morphogenetic Protein (CDMP)-1, -2 and -3 for Tendon Healing in Rats. Journal of Orthopaedic Research, 2003. 21: p. 617-621.

Forte, A., D'Urso, A., Palumbo, P., Lo Storto, G., Gallinaro, M.S., Bezzi, M., Beltrami, V., Inguinal hernioplasty: the gold standard of hernia repair. Hernia, 2003. 7: p. 35-38.

Fortelny, R.H., et al., Cyanoacrylate tissue sealant impairs tissue integration of macroporous mesh in experimental hernia repair Surgical Endoscopy, 2007. 21(10): p. 1781-1785.

France, P.E., Paulos, L.E., Harner, C.D., Straight, C.B., Biomechanical evaluation of rotator cuff fixation methods. The American Journal of Sports Medicine, 1989. 17(2): p. 176-181.

Frank, C.B., Jackson, D.W., Current Concepts Review—The Science of Reconstruction of the Anterior Cruciate Ligament. The Journal of Bone and Joint Surgery, 1997. 79-A(10): p. 1556-1576.

Frank, et al., "Adhesion of Mytilus edulisFoot Protein 1 on Silica: Ionic Effects on Biofouling," Biotechnol. Prog. 18 (2002). p. 580-586.

Franklin, M.E.J., Gonzalez, J.J. Jr., Glass, J.L., Use of porcine small intestinal submucosa as a prosthetic device for laparoscopic repair of hernias in contaminated fields: 2 year follow-up. Hernia, 2004. 8: p. 186-189.

Fuchsbauer, et al., "Influence of Gelatin matrices cross-linked with transglutaminase on the properties of an enclosed bioactive material using β-galactosidase as model system," 1996 Biomaterials 17 pp. 1481-1488.

Fujisawa, et al., "Kinetic Evaluations of the Reactivity of Flavonoids as Radical Scavengers," 2002 SAR QSAR Environ. Res. Vo. 13 No. 6 pp. 617-627.

Fuller, et al., "A Procedure for the Facile Synthesis of Amino-Acid N-Carboxyanhydrides," Biopolymers 15 (1976). p. 1869-1871.

Fuller, et al., "DOPA-Containing Polypeptides. I. Improved Synthesis of High-Molecular-Weight Poly (L-DOPA) and Water-Soluble Copolypeptides," 1978 Bioploymers 17 pp. 2939-2943.

Garabito, A., Martinez-Miranda, J., Sanchez-Sotelo, J., Augmented Repair of Acute Achilles Tendon Ruptures Using Gastrocnemius-soleus Fascia. International Orthopaedics, 2005. 29: p. 42-46.

Garrett, W.E., Safran, M.R., Seaber, A.V., Glisson, R.R., Ribbeck, B.M., Biomechanical comparison of stimulated and nonstimulated skeletal muscle pulled to failure. The American Journal of Sports Medicine, 1987. 15(5): p. 448-454.

Geim, et al., "Microfabricated adhesive mimicking gecko foot-hair," Nat. Materials 2 (2003). pp. 461-463.

Ghosh, et al., N,N'-Disuccinimidyl Carbonate: A Useful Reagent for Alkoxycarbonylation of Amines. Tetra. Lett. 33 (20), 1992. p. 2781-2784.

Gidanian, et al., Redox behavior of melanins: direct electrochemistry of dihydroxyindole-melanin and its Cu and Zn adducts, J. Inorg. Biochem. 89 (2002). p. 54-60.

Gilbert, A.I., Graham, M.F., Voigt, W.J., A bilayer patch device for inguinal hernia repair. Hernia, 1999. 3: p. 161-166.

Gilbert, A.I., Graham, M.F., Voigt, W.J., Inguinal Hernia: Anatomy and Management. www.medscape.com, 2000.

Gilbert, T.W., et al., Degradation and Remodeling of Small Intestinal Submucosa in Canine Achilles Tendon Repair. The Journal of Bone and Joint Surgery (American), 2007. 89: p. 621-630.

Gloeckner, D.C., Sacks, M.S., Billiar, K.L., Bachrach, N., Mechanical evaluation and design of a multilayered collagenous repair biomaterial. J. Biomed. Mater. Res., 2000. 52: p. 365-373.

Gorna, K. and S. Gogolewski, Biodegradable polyurethanes for implants. II. In vitro degradation and calcification of materials from poly(e-caprolactone)-poly(ethylene oxide) diols and various chain extenders. J. Biomed. Mat. Res., 2002. 60(4): p. 592-606.

Gratzer, P.F., Santerre, J.P., Lee, J.M., The effect of chemical modification of amino acid side-chains on collagen degradation by enzymes. j. Biomed. Mater. Res. Part B: Appl. Biomater, 2006. 81B: p. 1-11.

Green, et al., "A surface plasmon resonance study of albumin adssoption to PEO-PPO-PEa triblock copolymers," J. . Biomed. Res. 42 (1998). p. 165-171.

Greene and Wuts, Protective Groups in Organic Chemistry, 3rd Ed., 1999, John Wiley & Sons, NY [book, no copy provided at this time].

Gristina, Biomaterial-Centered Infection—Microbial Adhesion Versus Tissue Integration. Science 1987, 237, (4822), 1588-1595.

Gross, et al., "Amine Binding Sites in Acyl Intermediates of Transglutaminases," 1977 J. Biol. Chem. 242 (11) pp. 3752-3759.

Grotenhuis, "Costs of postoperative cerebrospinal fluid leakage: 1-year, retrospective analysis of 412 consecutive nontrauma cases," Surg. Neurol., vol. 64, No. 6 (2005), pp. 493-494.

Grotenhuis, et al., "A Novel Absorbable Hydrogel for Dural Repair: Results of a Pilot Clinical Study," Confluent Surgical, Inc. (2005) White Paper. Available from: htto://www.confluentsurgical.com/pdf/ds/DuraSeal_Pilot_Study_WP4-7-05.pdf.

Grotenhuis, et al,. "Synthetic Dural Sealant for Prevention of Postoperative CSF Leakage," Presented at the American Association of Neurological Surgeons; Apr. 2003, San Diego, CA. Available from: htto://www.confluentsurgical.com/pdflds/AbstractGrotenhuisAbstract.pdf.

Gu, et al., "Synthesis of Aluminum Oxide/Gradient Copolymer Composites by Atom Transfer Radical Polymerization," Macromolecules 35 (2002). p. 8913-8916.

Gu, et al., "The role of microbial biofilms in deterioration of space station candidate materials," Int. Biodeterioration Biodegradation 41 (1998). p. 25-33.

Gunawan, R et al., Surface Presentation of Bioactive Ligands in a Non-Adhesive Background using DOPA-Tethered Biotinylated Poly(Ethylene Glycol). Langmuir, 2007. 23(21): p. 10635-10643.

Guvendiren, et al., "Adhesion in Self-Assembled Hydrogels with High DOPA Content," Proceedings of the 30th Annual Meeting of the Adhesion Society (2007).

Guvendiren, et al., Synthesis and Adhesion Properties of DOPA Incorporated Acrylic Triblock Hydroqels, Proceedings of the 29th Annual Meeting of the Adhesion Society (2006). p. 277-279.

Guvendiren, M., P.B. Messersmith, and K.R. Shull, Self-Assembly and Adhesion of DOPA-Modified Methacrylic Triblock Hydrogels. Biomacromol., 2008. 9(1): p. 122-128.

Guvendiren, M., P.B. Messersmith, and K.R. Shull. Adhesion of DOPA-Functional Methacrylic Membranes in 31st Annual Meeting of the Adhesion Society. 2008. Austin, Texas.

Hadjichristidis et al., Block copolymers. Synthetic Strategies, Physical Properties, and Applications, A John Wiley & Sons, Inc. 2003, pp. 14-17 and 116-117.

Haemers, et al., "Effect of Oxidation Rate on Cross-Linking of Mussel Adhesive Proteins," Biomacromolecules, vol. 4 (2003), pp. 632-640.

Anon., "Amino acid," Medical-dictionary.com, Free service of Google, Inc., (Nov. 1997), 1-1.

Lucast, Donald H., "Skin Tight," Adhesives Age, (Oct. 1, 2000).

* cited by examiner x = 16
y = 2
z = 1 y = 16
z = 1 x = 16
y = 2
z = 1

Histology: 4-Hour

QuadraSeal-OH 15%

QuadraSeal-OH 30%

Dermabond

Suture

Histology: 3-Day

QuadraSeal-DH 15%         QuadraSeal-DH 30%

Dermabond                 Suture

Histology: 7-Day

QuadraSeal-DH 15%

QuadraSeal-DH 30%

Dermabond

Suture

Thin Film Adhesive

Thin Film Adhesive coated onto Synthetic Mesh
(Pre-Coated Mesh Adhesive)

ADHESIVE COMPOUNDS AND METHODS USE FOR HERNIA REPAIR

CROSS REFERENCE TO RELATED APPLICATIONS

The present application claims priority to U.S. Provisional Application Ser. No. 61/411,747 filed Nov. 9, 2010, and U.S. Provisional Application Ser. No. 61/415,743 filed Nov. 19, 2010, the entirety of each of which is herein incorporated by reference.

REFERENCE TO FEDERAL FUNDING

This invention was made with government support under NIH (1R43DE017827-01, 2R44DE017827-02, 1R43GM080774-01, 1R43DK080547-01, 1R43DK083199-01, 2R44DK083199-02, 1R43AR056519-01A1) and NSF (IIP-0912221, IIP-1013156) grants. The government has certain rights in the invention.

FIELD OF THE INVENTION

The invention relates generally to new synthetic medical adhesives which exploit the key components of natural marine mussel adhesive proteins. The method exploits a biological strategy to modify surfaces that exhibit adhesive properties useful in a diverse array of medical applications. Specifically, the invention describes the use of peptides that mimic natural adhesive proteins in their composition and adhesive properties. These adhesive moieties are coupled to a polymer chain, and provide adhesive and cross-linking (cohesive properties) to the synthetic polymer.

BACKGROUND OF THE INVENTION

Mussel adhesive proteins (MAPs) are remarkable underwater adhesive materials secreted by certain marine organisms which form tenacious bonds to the substrates upon which they reside. During the process of attachment to a substrate, MAPs are secreted as adhesive fluid precursors that undergo a cross-linking or hardening reaction which leads to the formation of a solid adhesive plaque. One of the unique features of MAPs is the presence of L-3-4-dihydroxyphenylalanine (DOPA), an unusual amino acid which is believed to be responsible for adhesion to substrates through several mechanisms that are not yet fully understood. The observation that mussels adhere to a variety of surfaces in nature (metal, metal oxide, polymer) led to a hypothesis that DOPA-containing peptides can be employed as the key components of synthetic medical adhesives or coatings.

In the medical arena, few adhesives exist which provide both robust adhesion in a wet environment and suitable mechanical properties to be used as a tissue adhesive or sealant. For example, fibrin-based tissue sealants (e.g. Tisseel V H, Baxter Healthcare) provide a good mechanical match for natural tissue, but possess poor tissue-adhesion characteristics. Conversely, cyanoacrylate adhesives (e.g. Dermabond, ETHICON, Inc.) produce strong adhesive bonds with surfaces, but tend to be stiff and brittle in regard to mechanical properties and tend to release formaldehyde as they degrade.

Therefore, a need exists for materials that overcome one or more of the current disadvantages.

BRIEF SUMMARY OF THE INVENTION

The present invention provides phenyl derivative polymers. In one embodiment, blends of the compounds of the invention described herein can be prepared with various polymers. Polymers suitable for blending with the compounds of the invention are selected to impart non-covalent interactions with the compound(s), such as hydrophobic-hydrophobic interactions or hydrogen bonding with an oxygen atom on PEG and a substrate surface. These interactions can increase the cohesive properties of the film to a substrate. If a biopolymer is used, it can introduce specific bioactivity to the film, (i.e. biocompatibility, cell binding, immunogenicity, etc.).

Generally, there are four classes of polymers useful as blending agents with the compounds of the invention. Class 1 includes: Hydrophobic polymers (polyesters, PPG) with terminal functional groups (—OH, COOH, etc.), linear PCL-diols (MW 600-2000), branched PCL-triols (MW 900), wherein PCL can be replaced with PLA, PGA, PLAGA, and other polyesters.

Class 2 includes amphiphilic block (di, tri, or multiblock) copolymers of PEG and polyester or PPG, tri-block copolymers of PCL-PEG-PCL (PCL MW=500-3000, PEG MW=500-3000), tri-block copolymers of PLA-PEG-PLA (PCL MW=500-3000, PEG MW=500-3000). In other embodiments, PCL and PLA can be replaced with PGA, PLGA, and other polyesters. Pluronic polymers (triblock, diblock of various MW) and other PEG, PPG block copolymers are also suitable.

Class 3 includes hydrophilic polymers with multiple functional groups (—OH, —NH2, —COOH) along the polymeric backbone. These include, for example, PVA (MW 10,000-100,000), poly acrylates and poly methacrylates, and polyethylene imines.

Class 4 includes biopolymers such as polysaccharides, hyaluronic acid, chitosan, cellulose, or proteins, etc. which contain functional groups.

Abbreviations: PCL=polycaprolactone, PLA=polylactic acid, PGA=Polyglycolic acid, PLGA=a random copolymer of lactic and glycolic acid, PPG=polypropyl glycol, and PVA=polyvinyl alcohol.

It should be understood that the compounds of the invention can be coated multiple times to form bi, tri, etc. layers. The layers can be of the compounds of the invention per se, or of blends of a compound(s) and polymer, or combinations of a compound layer and a blend layer, etc.

Consequently, constructs can also include such layering of the compounds per se, blends thereof, and/or combinations of layers of a compound(s) per se and a blend or blends.

These adhesives of the invention described throughout the specification can be utilized for wound closure and materials of this type are often referred to as tissue sealants or surgical adhesives.

The compounds of the invention can be applied to a suitable substrate surface as a film or coating. Application of the compound(s) to the surface inhibits or reduces the growth of biofilm (bacteria) on the surface relative to an untreated substrate surface. In other embodiments, the compounds of the invention can be employed as an adhesive.

Exemplary applications include, but are not limited to fixation of synthetic (resorbable and non-resorbable) and biological membranes and meshes for hernia repair, void-eliminating adhesive for reduction of post-surgical seroma formation in general and cosmetic surgeries, fixation of synthetic (resorbable and non-resorbable) and biological membranes and meshes for tendon and ligament repair, sealing incisions after ophthalmic surgery, sealing of venous catheter access sites, bacterial barrier for percutaneous devices, as a contraceptive device, a bacterial barrier and/or drug depot for oral surgeries (e.g. tooth extraction, tonsillectomy, cleft palate, etc.), for articular cartilage repair, for antifouling or anti-bacterial adhesion.

In some embodiments, bioadhesives of the present invention are described, for example, in U.S. Provisional Patent Application No. 61/365,049, filed Jul. 16, 2010, entitled "BIOADHESIVE COMPOUNDS AND METHODS OF SYNTHESIS AND USE", and employed in constructs with polymer blends as described, for example in International Patent Application No. PCT/US2010/023382, International Filing Date: 5 Feb. 2010 entitled: "BIOADHESIVE CONSTRUCTS WITH POLYMER BLENDS", both of which are incorporated by reference herein in its entirety.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

DETAILED DESCRIPTION

Table 1. provides the Medhesive number, name, description and figure number of compounds of the present invention.

TABLE 1

Figure 1:
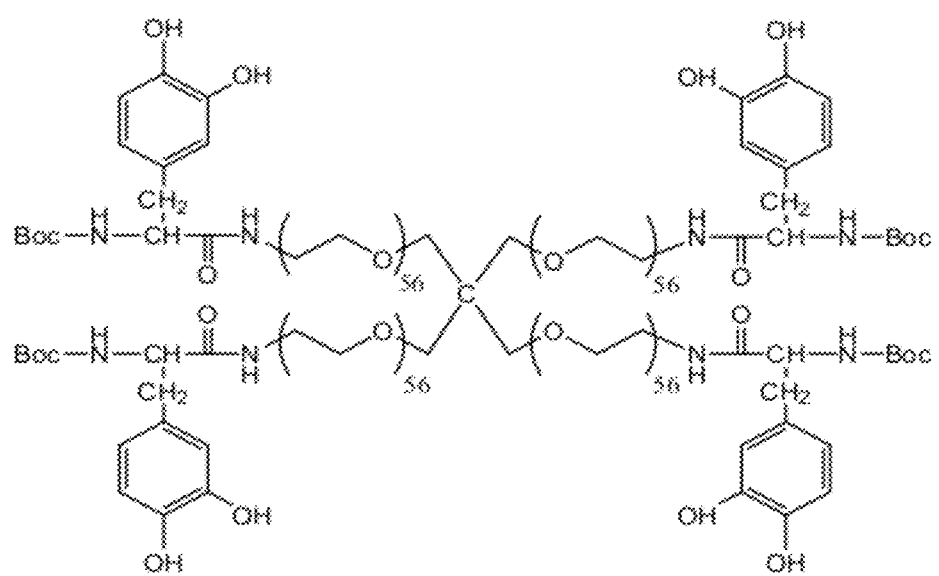
FIGS. 1-221 show compounds as embodiments of the present invention.
Figure 2:
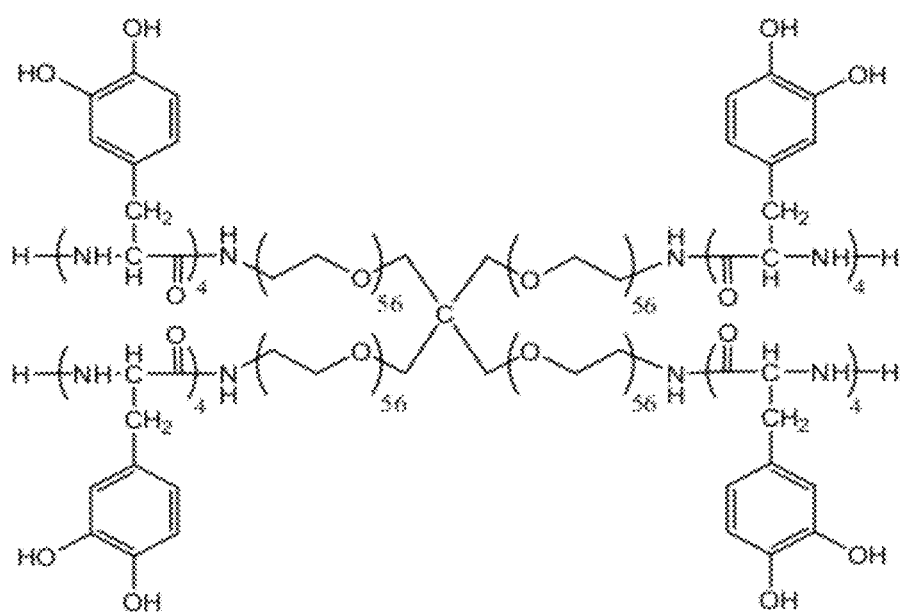
Figure 3:
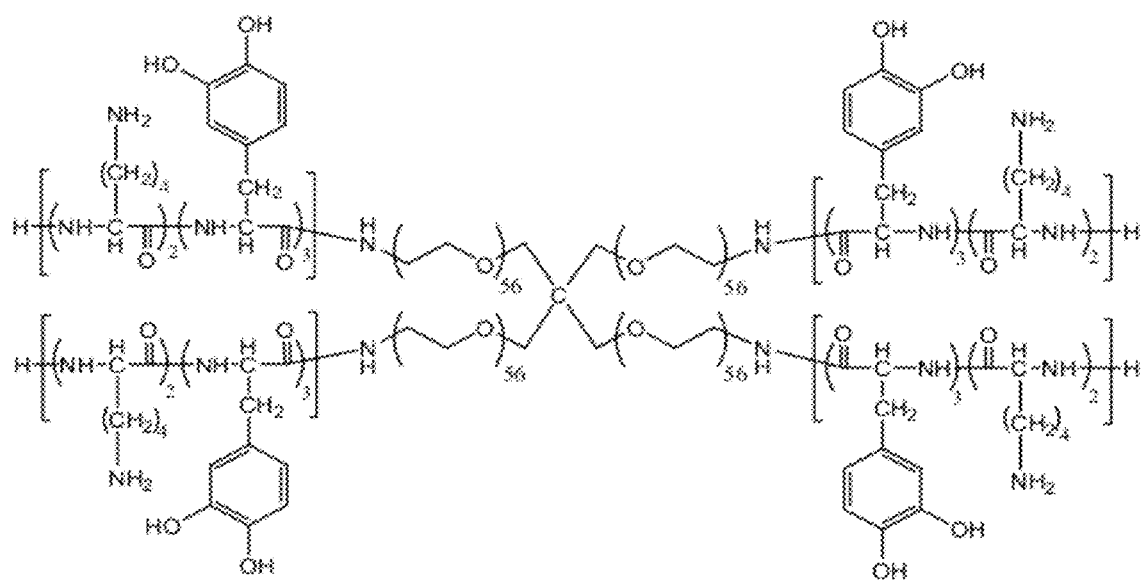
Figure 4:
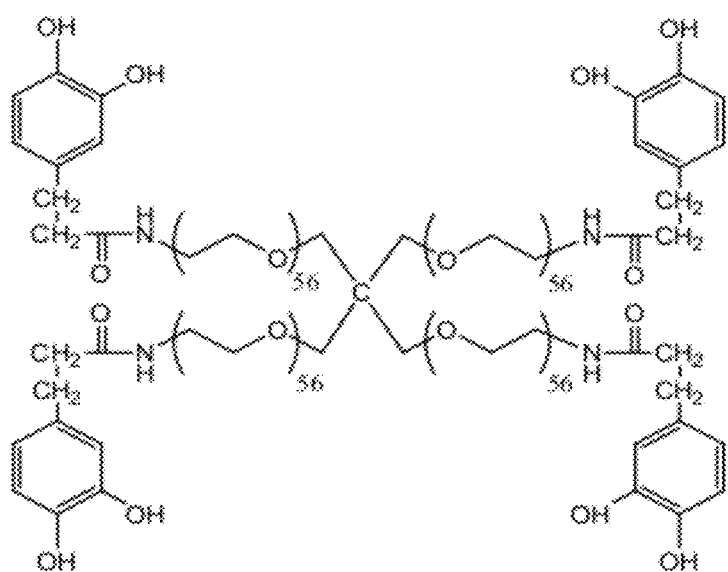
Figure 5:
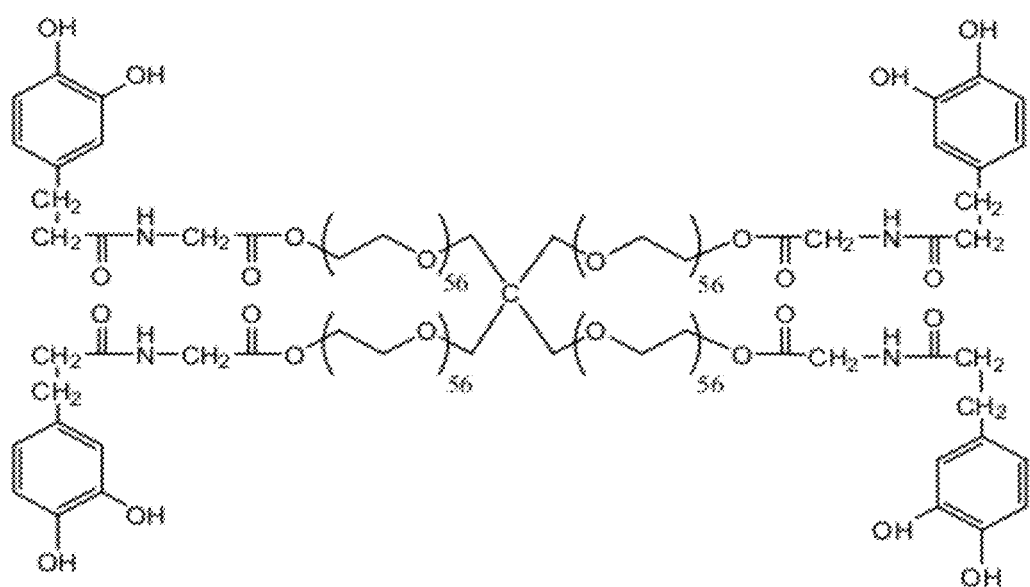
Figure 6:
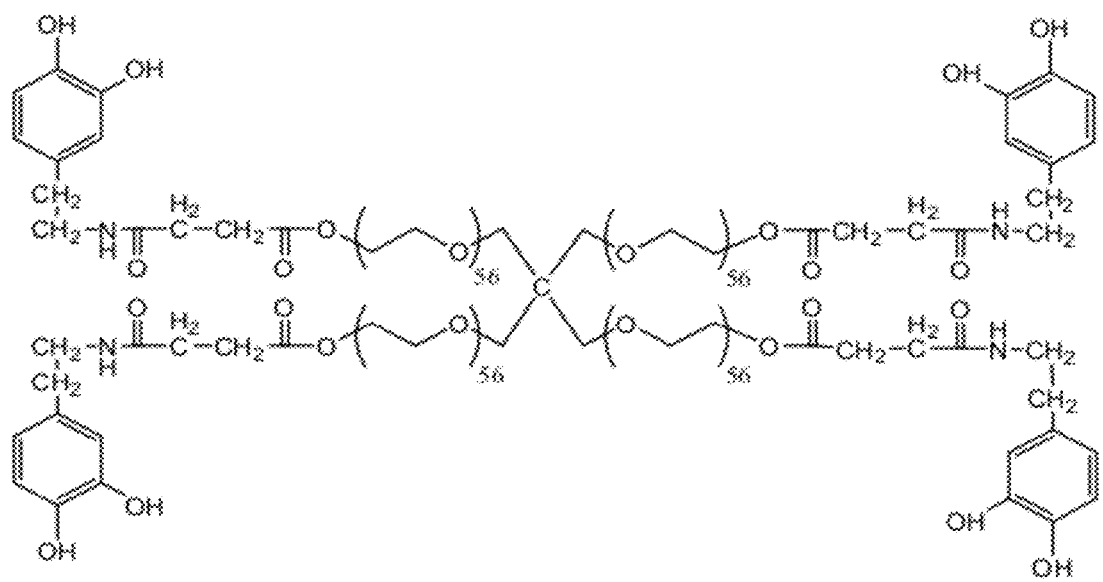
Figure 7:
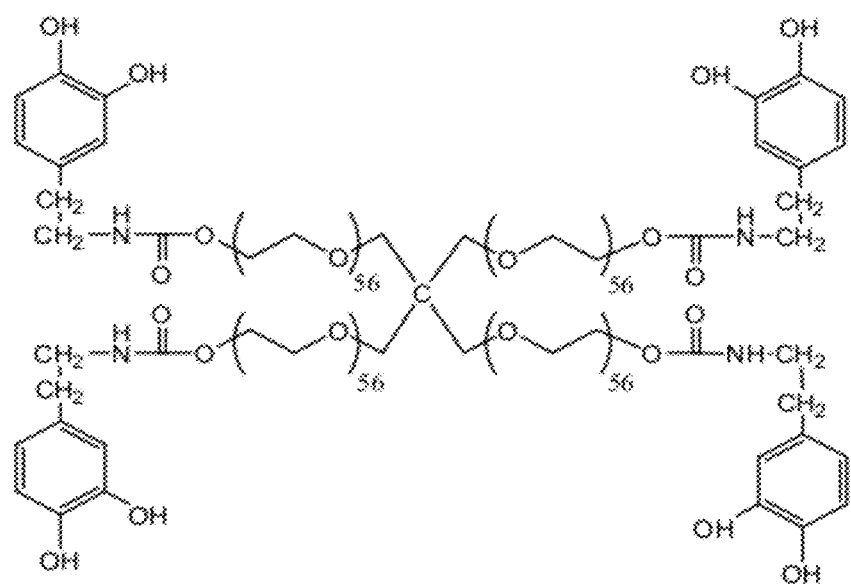
Figure 8:
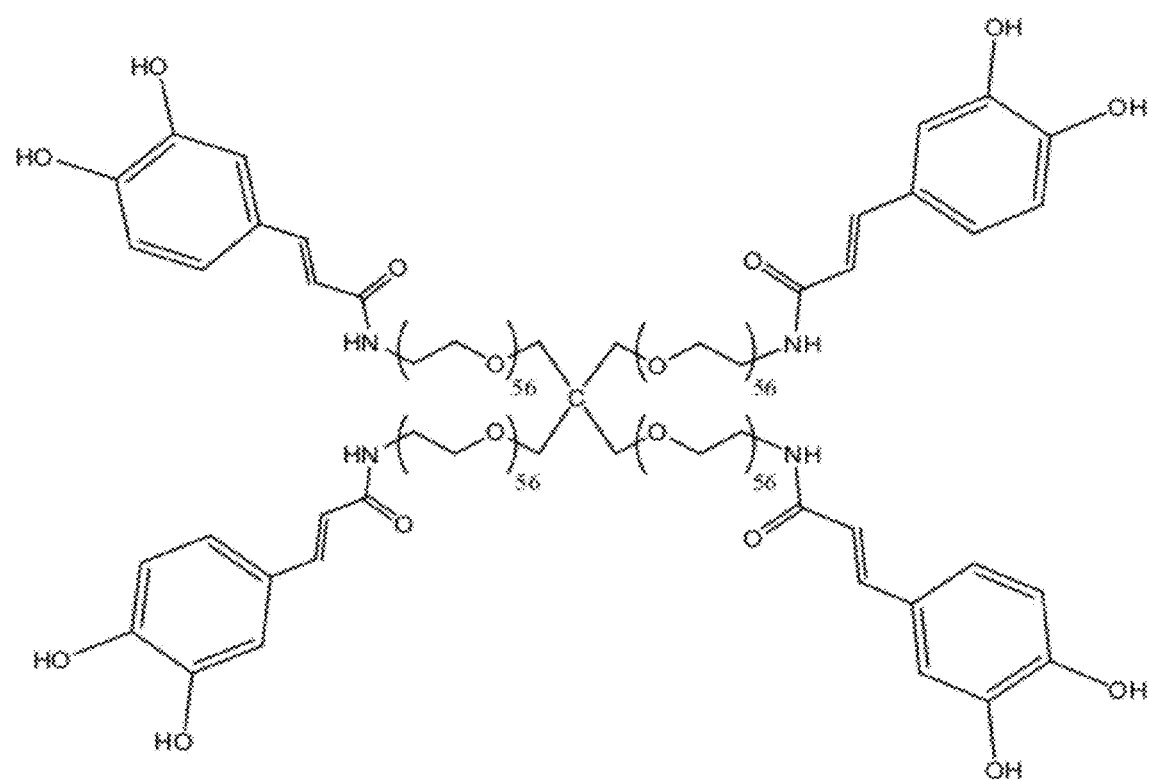
Figure 9:
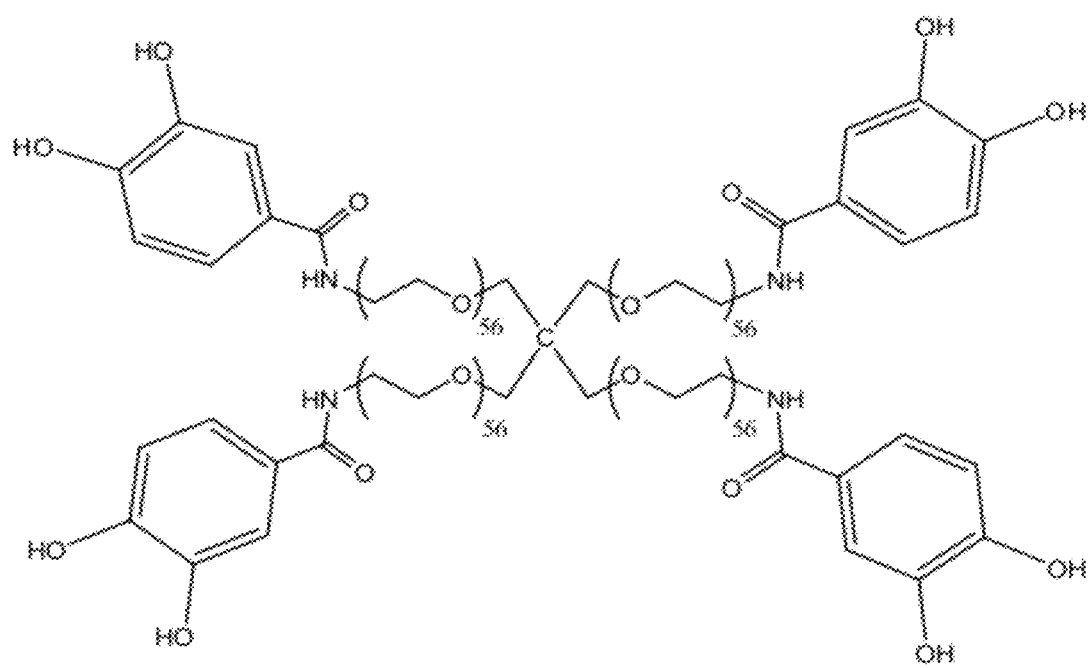
Figure 10:
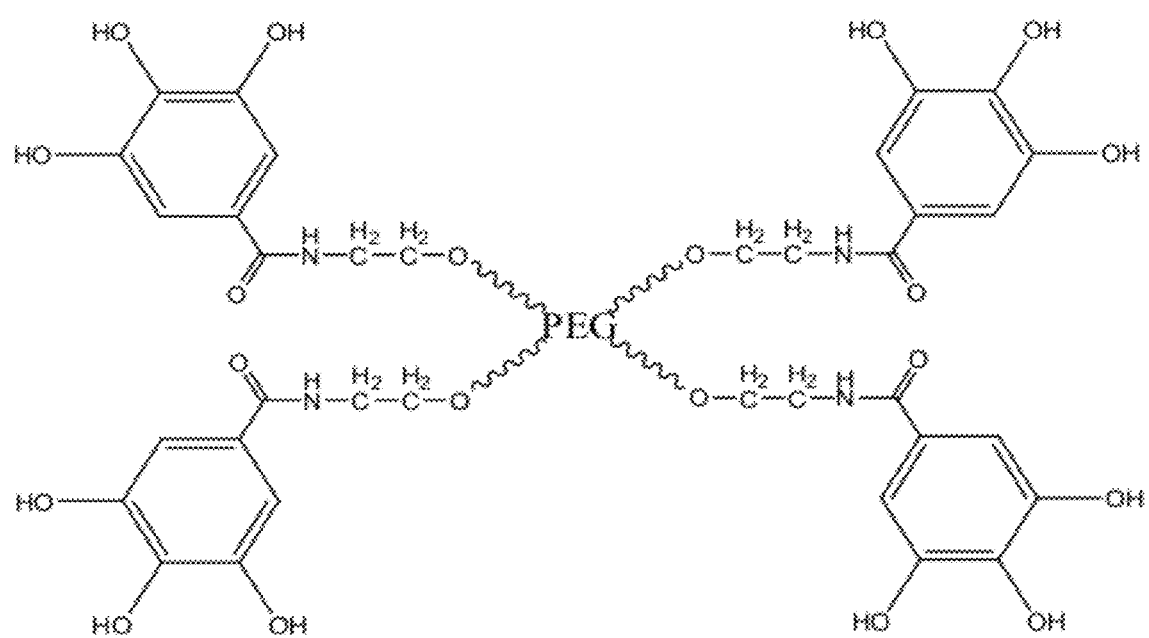
Figure 11:
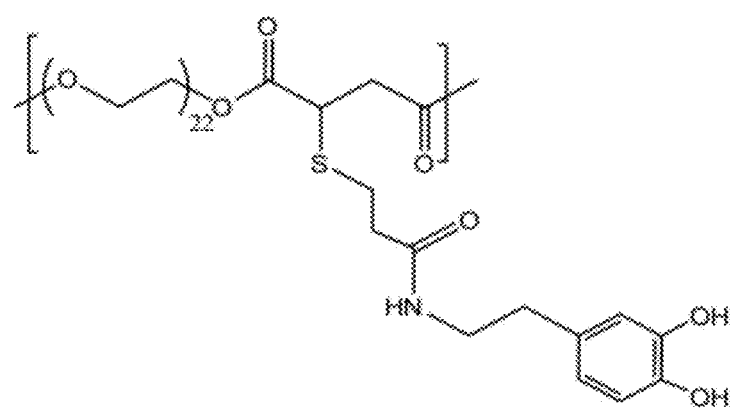
Figure 12:
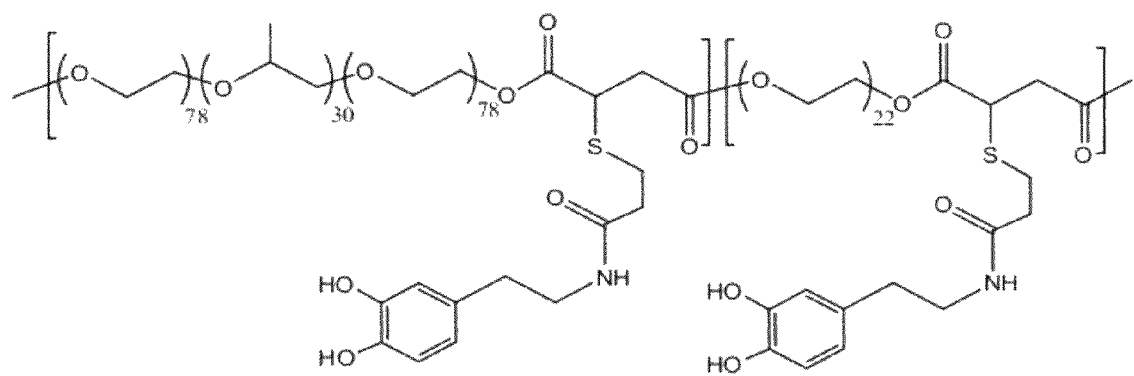

| Name | R&D Name | Description | FIG. No. |
|---|---|---|---|
| QuadraSeal-D | PEG10k-(Boc-DOPA)$_4$ | Branched, 4-armed PEG-NH2 (10k MW) coupled with terminal N-Boc-DOPA. | FIG. 1 |
| QuadraSeal-D4 | PEG10k-(DOPA$_4$)$_4$ | Branched, 4-armed PEG-NH2 (10k MW) coupled with terminal short peptide consisting of 4 DOPA residue. | FIG. 2 |
| QuadraSeal-DL | PEG10k-(DOPA$_3$-Lys$_2$)$_4$ | Branched, 4-armed PEG-NH2 (10k MW) coupled with terminal short peptide consisting of 3 DOPA and 2 Lys residue. | FIG. 3 |
| QuadraSeal-DH | PEG10k-(DOHA)$_4$ | Branched, 4-armed PEG-NH2 (10k MW) coupled with terminal 3,4-dihydroxyhydrocinnamic acid (DOHA). | FIG. 4 |
| QuadraSeal-DHe | PEG10k-(GDHe)$_4$ | Branched, 4-armed PEG-OH (10k MW) coupled with terminal Gly-DOHA dipeptide. | FIG. 5 |
| QuadraSeal-DMe | PEG10k-(SADMe)$_4$ | Branched, 4-armed PEG-OH (10k MW) coupled with terminal dopamine linked with succinic acid. | FIG. 6 |
| QuadraSeal-Dmu | PEG10k-(DMu)$_4$ | Branched, 4-armed PEG-OH (10k MW) coupled with terminal dopamine linked with urethane linkage. | FIG. 7 |
| QuadraSeal-CA | PEG10k-(CA)$_4$ | Branched, 4-armed PEG-NH$_2$ (10k MW) coupled with terminal caffeic acid through an amide linkage. | FIG. 8 |
| QuadraSeal-BA | PEG10k-(BA)$_4$ | Branched, 4-armed PEG-NH$_2$ (10k MW) coupled with terminal 3,4-dihydroxybenzoic acid through an amide linkage. | FIG. 9 |
| QuadraSeal-GA | PEG10k-(GA)$_4$ | Branched, 4-armed PEG-NH$_2$ (10k MW) coupled with terminal Gallic Acid through an amide linkage. | FIG. 10 |
| Medhesive-001 | p(EG1kf-g-DM) | Linear, repeating PEG (1k MW) grafted with dopamine. Chain extension achieved with fumaryl chloride and grafted with 3-mercaptopropionic acid (MPA). | FIG. 11 |
| Medhesive-002 | p(F68EG1kf-g-DM) | Linear, repeating polymer consisted of 80 wt % PEG (1k MW) and 20 wt % F-68 (8600 MW) grafted with dopamine. Chain extension achieved with fumaryl chloride and grafted with MPA. | FIG. 12 |

TABLE 1-continued

Figure 13:
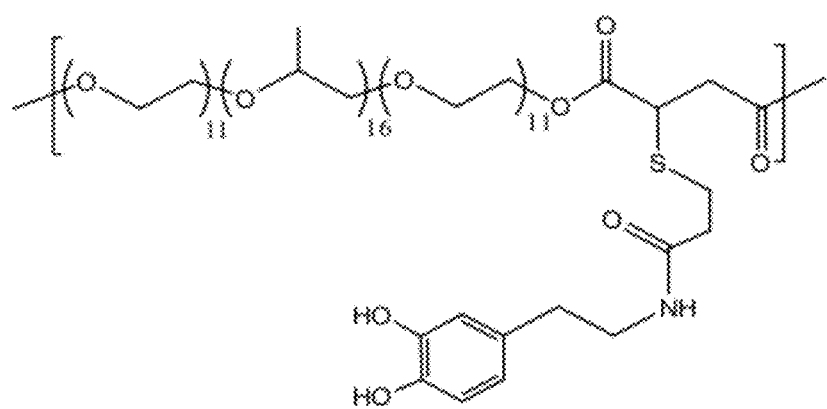
Figure 14:
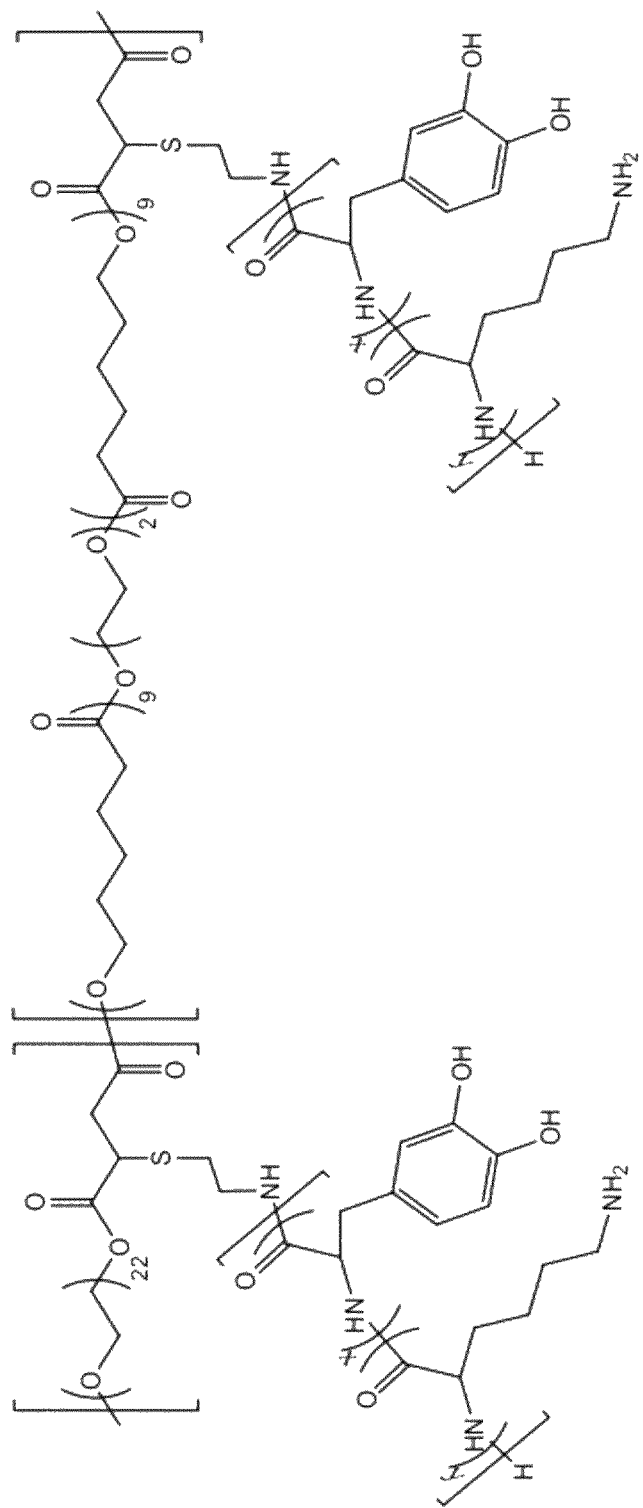
Figure 15:
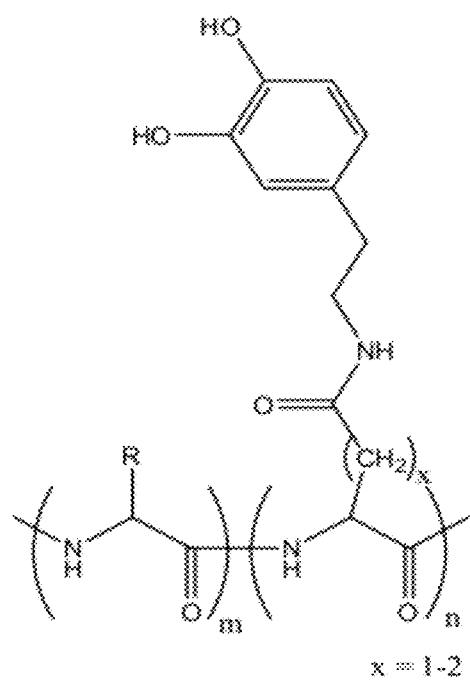
Figure 16:
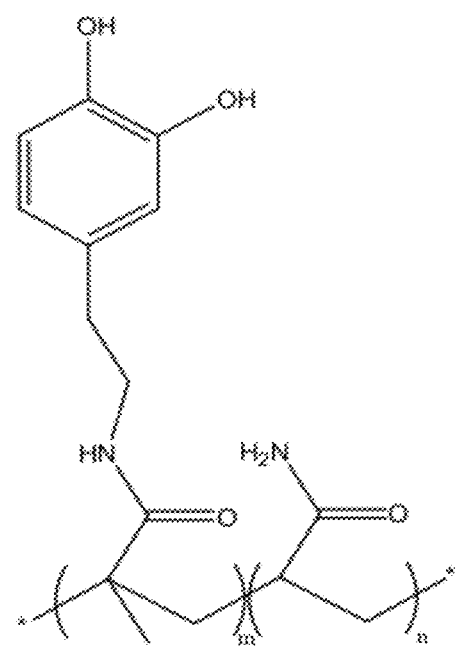
Figure 17:
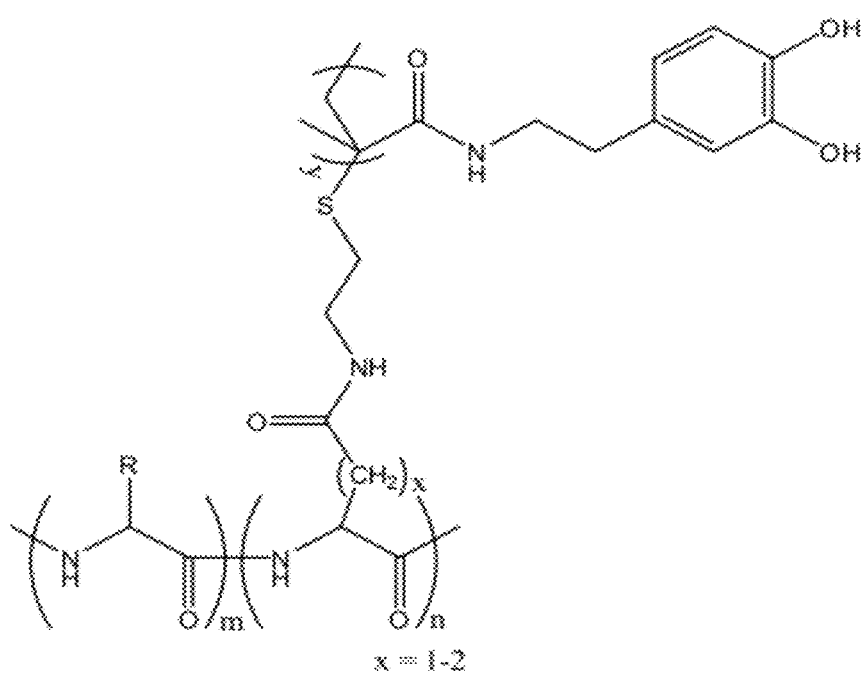
Figure 18:
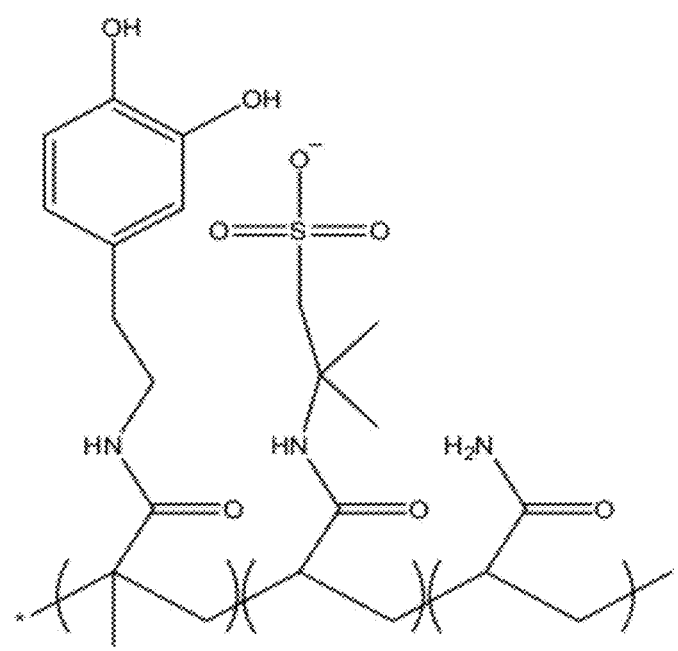
Figure 19:
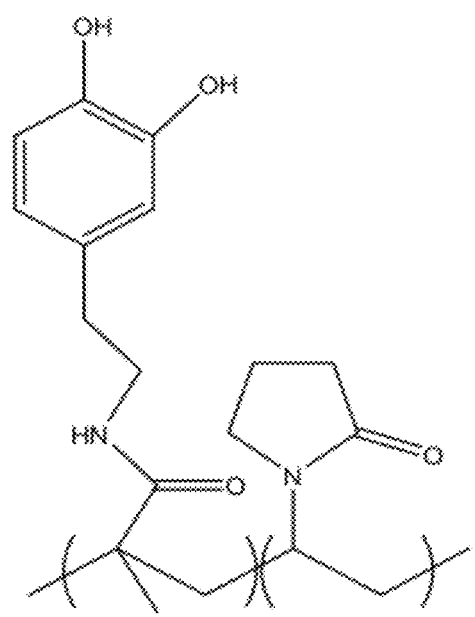
Figure 20:
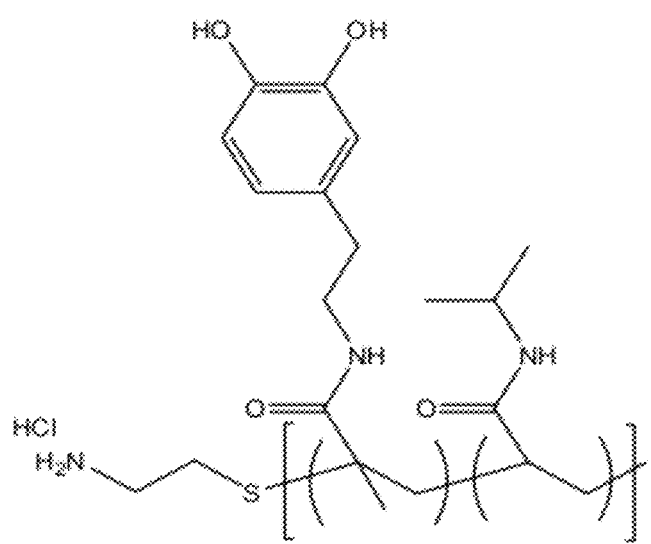
Figure 21:
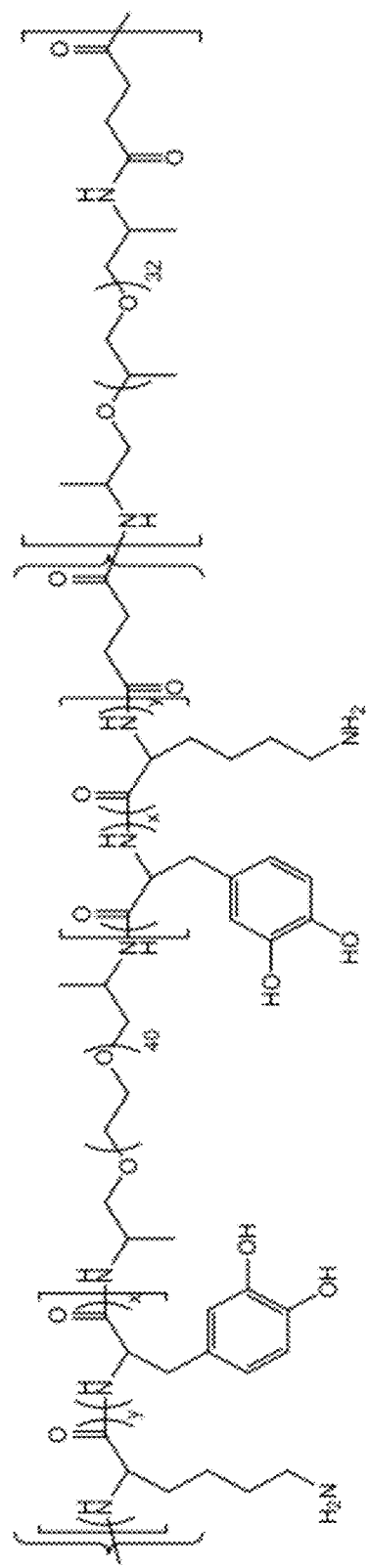
Figure 22:
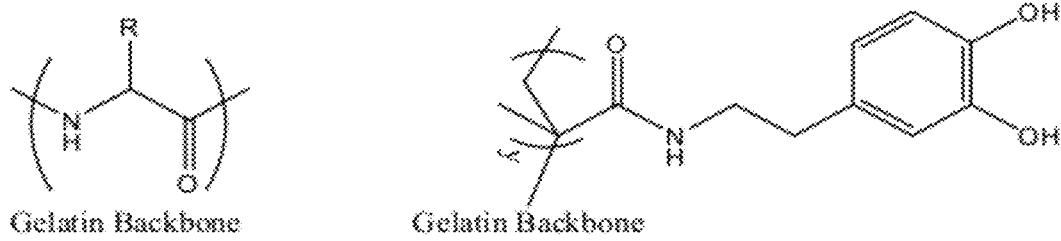
Figure 23:
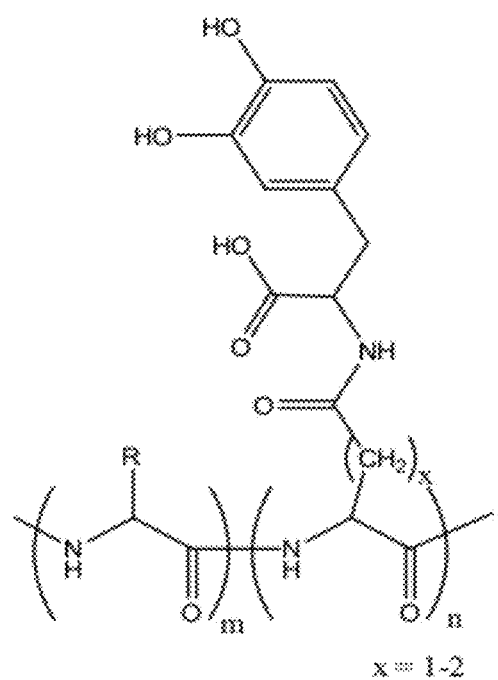
Figure 24:
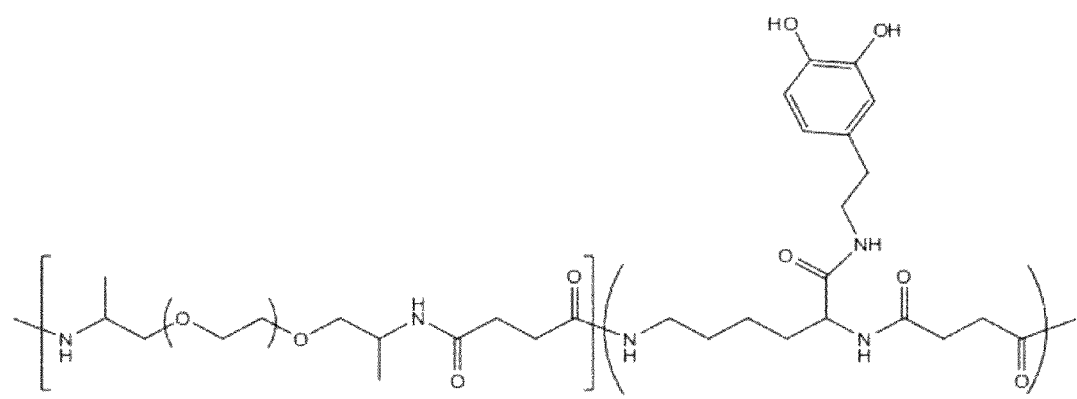
Figure 25:
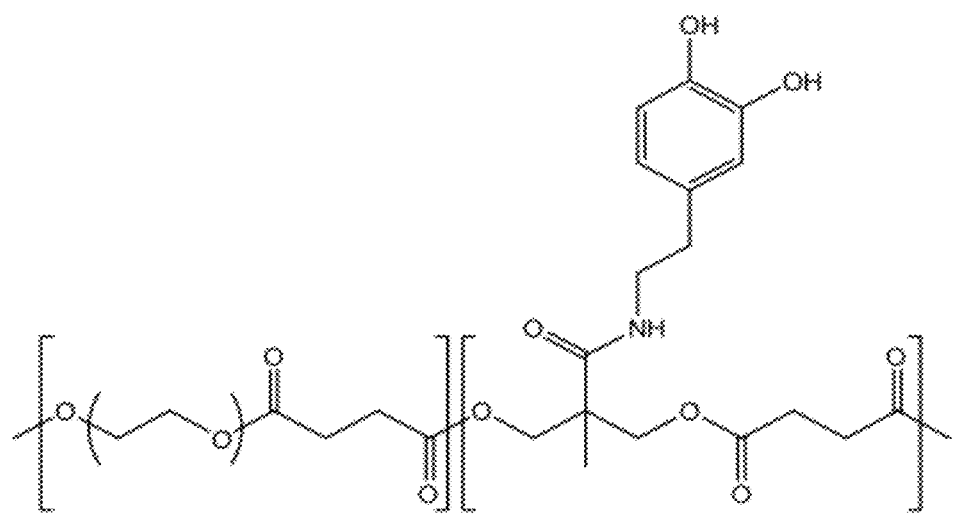
Figure 26:
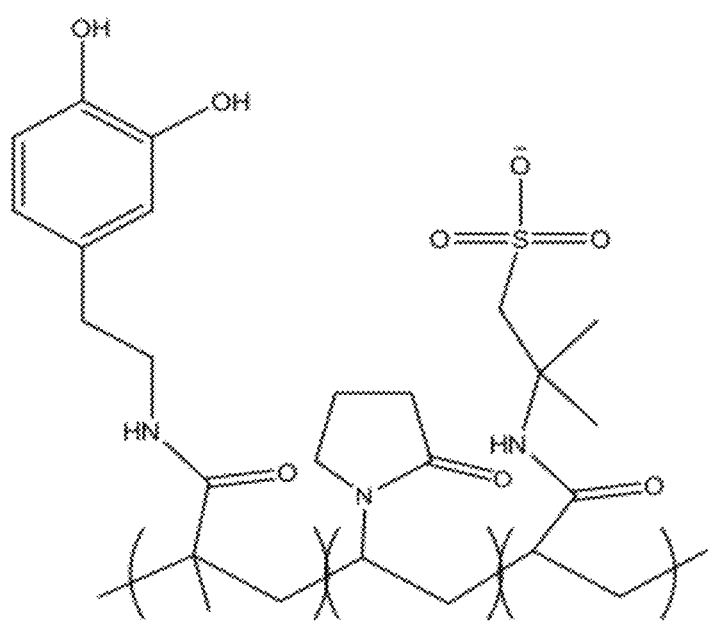
Figure 27:
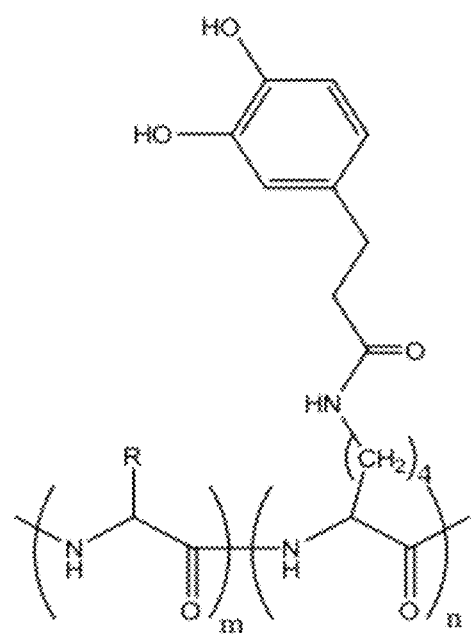
Figure 28:
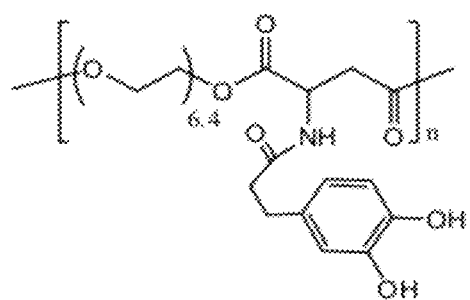
Figure 29:
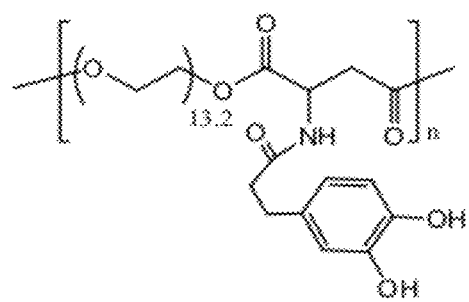
Figure 30:
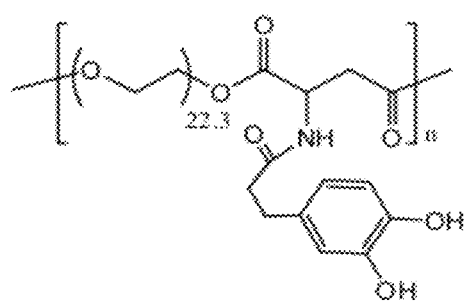
Figure 31:
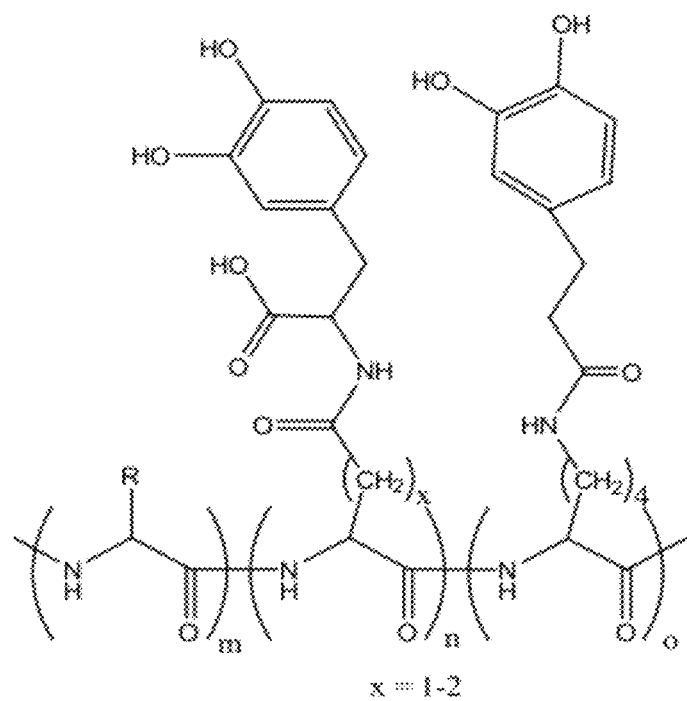
Figure 32:
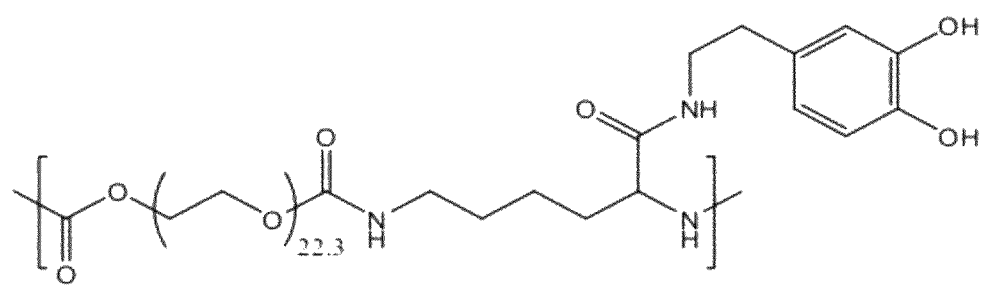
Figure 33:
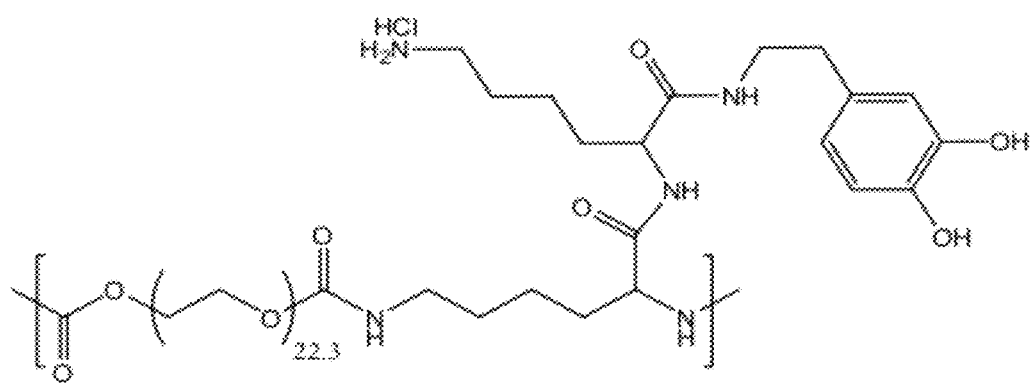

| Name | R&D Name | Description | FIG. No. |
|---|---|---|---|
| Medhesive-003 | p(F2k-g-DM) | Linear, repeating pluronic (1.9k MW, 50 wt % PEO 50 wt % PPO, $PEO_{11}$-$PPO_{16}$-$PEO_{11}$) grafted with dopamine. Chain extension achieved with fumaryl chloride and grafted with MPA. | FIG. 13 |
| Medhesive-004 | p(EG1kCL2kf-g-DxLy) | Linear, repeating polymer consisted of 50 wt % PEG (1k MW) and 50 wt % polycaprolactone (2k MW) grafted with dopamine. Chain extension achieved with fumaryl chloride and grafted with MPA. | FIG. 14 |
| Medhesive-005 | Gelatin75-g-DM | Gelatin (75 bloom, Type B, Bovine) grafted with dopamine. | FIG. 15 |
| Medhesive-006 | p(DMA3-AAm) | Polymerized from equal DMA3 and acrylamide. DMA3 accounts for 20-25 wt % | FIG. 16 |
| Medhesive-007 | Gelatin75CA-g-p(DMA3) | Gelatin (75 bloom, Type B, Bovine) grafted with polyDMA3. Polymerization achieved using cysteamine as the chain transfer agent (CTA). | FIG. 17 |
| Medhesive-008 | p(DMA3-AAm-AMPS) | Polymerized from equal DMA3, acrylamide, and AMPS. DMA3 accounts for 20-25 wt % and AMPS accounts for 10 wt %. | FIG. 18 |
| Medhesive-009 | p(DMA3-VP) | Polymerized from equal DMA3 and vinyl pyrrolidone DMA3 accounts for 25 wt % | FIG. 19 |
| Medhesive-010 | CA-p(DMA3-NIPAM) | DMA3-NIPAM copolymer formed usine cysteamine as the CTA. | FIG. 20 |
| Medhesive-011 | p(ED2kDL-SA) | Linear, repeating Jeffamine ED-2001 (1.9k MW) end coupled with short, random peptide consisting of DOPA and Lys. Chain extension achieved through succinyl chloride. | FIG. 21 |
| Medhesive-012 | Gelatin75-g-p(DMA3) | Gelatin (75 bloom, Type B, Bovine) grafted with polyDMA3. Polymerization directly on gelatin. | FIG. 22 |
| Medhesive-013 | Gelatin75-g-DOPA | Gelatin (75 bloom, Type B, Bovine) grafted with DOPA. | FIG. 23 |
| Medhesive-014 | p(ED2kLys-g-DM) | Linear, repeating Jeffamine ED-2001 (1.9k MW) and lysine grafted with dopamine. Chain extension achieved through succinyl chloride. | FIG. 24 |
| Medhesive-015 | p(EG600HMPA-g-DM) | Linear, repeating PEG (600 MW) and bis-hydroxymethyl propionic acid (DMPA) grafted with dopamine. Chain extension achieved through succinyl chloride. | FIG. 25 |
| Medhesive-016 | p(DMA3-AMPS-VP) | Polymerized from equal DMA3, VP, and AMPS. DMA3 accounts for 5-10 wt %. | FIG. 26 |
| Medhesive-017 | Gelatin75-g-DOHA | Gelatin (75 bloom, Type B, Bovine) grafted with DOHA. | FIG. 27 |
| Medhesive-018 | p(EG300Asp-g-DH) | Linear, repeating PEG (300 MW) and Asp grafted with DOHA. Chain extension achieved through melt polycondensation. | FIG. 28 |
| Medhesive-019 | p(EG600Asp-g-DH) | Linear, repeating PEG (600 MW) and Asp grafted with DOHA. Chain extension achieved through melt polycondensation. | FIG. 29 |
| Medhesive-020 | p(EG1kAsp-g-DH) | Linear, repeating PEG 1k MW) and Asp grafted with DOHA. Chain extension achieved through melt polycondensation. | FIG. 30 |
| Medhesive-021 | Gelatin75-g-DHDP | Gelatin (75 bloom, Type B, Bovine) grafted with DOHA and DOPA. | FIG. 31 |
| Medhesive-022 | p(EG1kLys-g-DM) | Linear, repeating PEG (1k MW) and Lys grafted with dopamine. Chain extension achieved through activation of PEG-OH with phosgene and 4-nitrophenol to form 4-nitrophenyl carbonate. | FIG. 32 |
| Medhesive-023 | p(EG1kLys-g-DL) | Linear, repeating PEG (1k MW) and Lys grafted with dopamine-lysine. Chain extension achieved | FIG. 33 |

TABLE 1-continued

Figure 34:
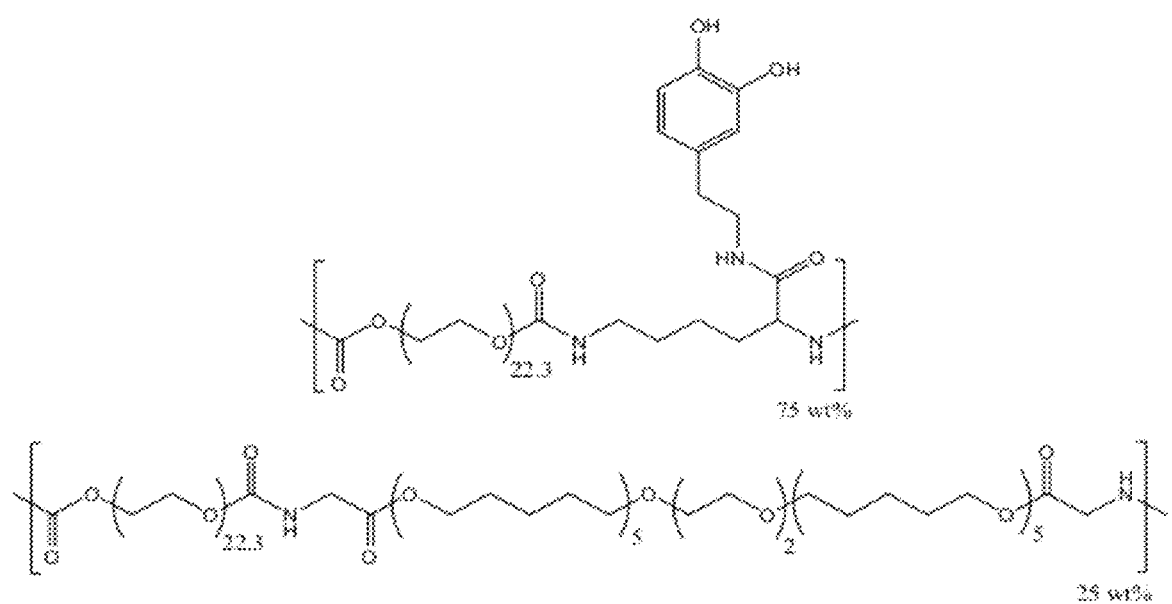
Figure 35:
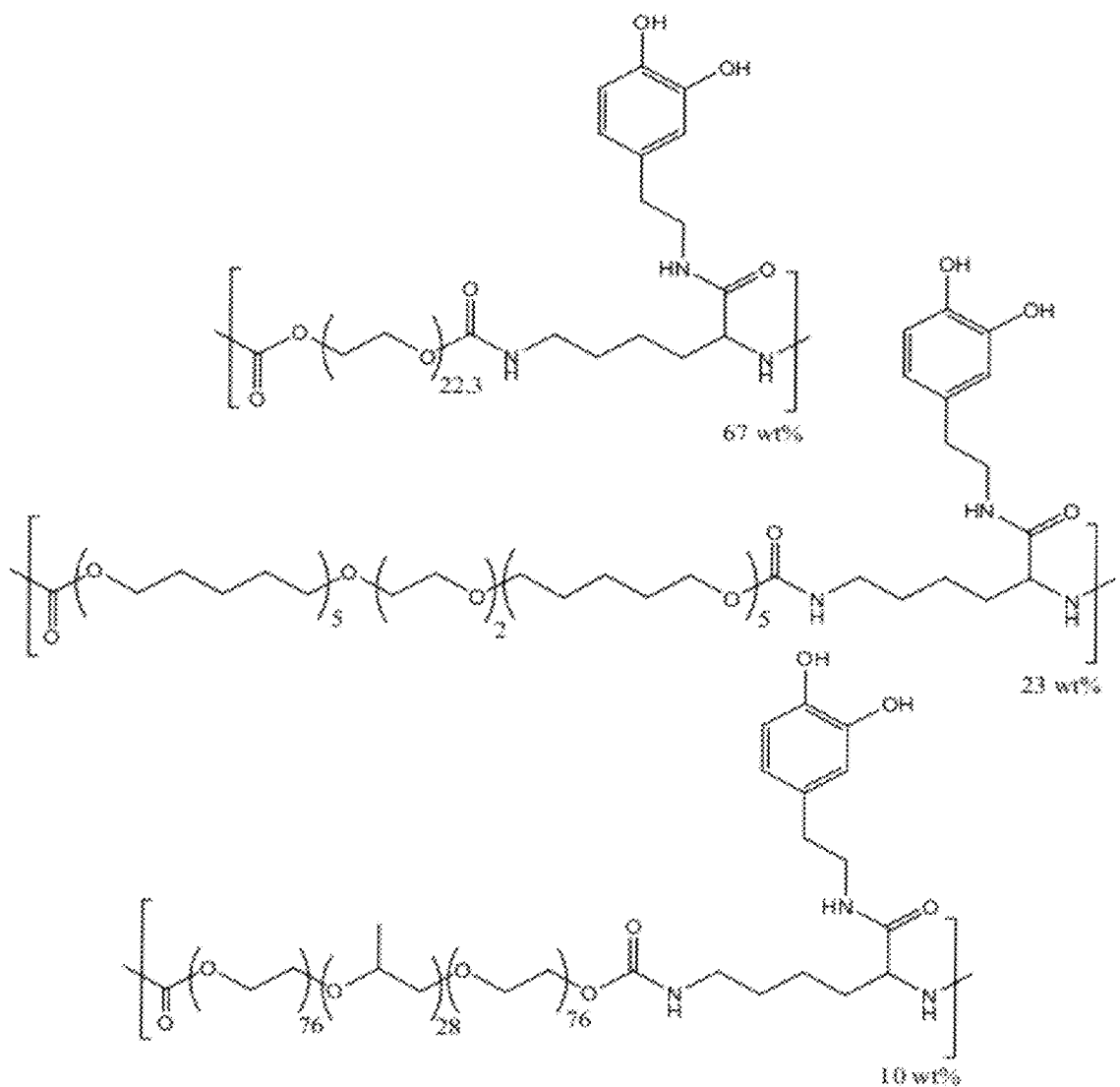
Figure 36:
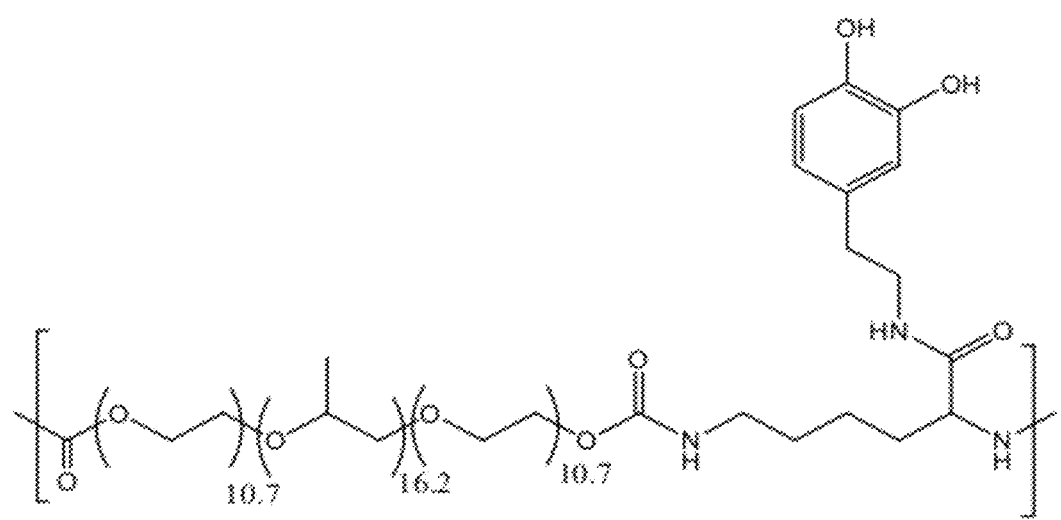
Figure 37:
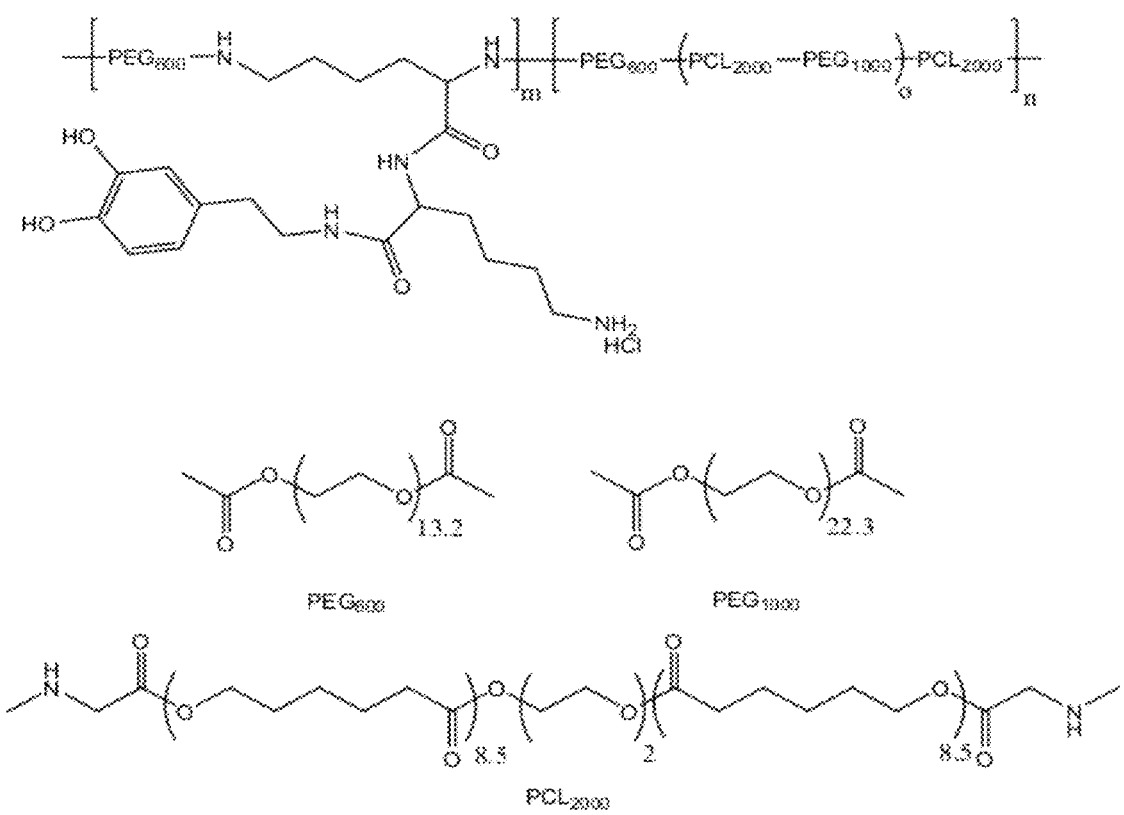
Figure 38:
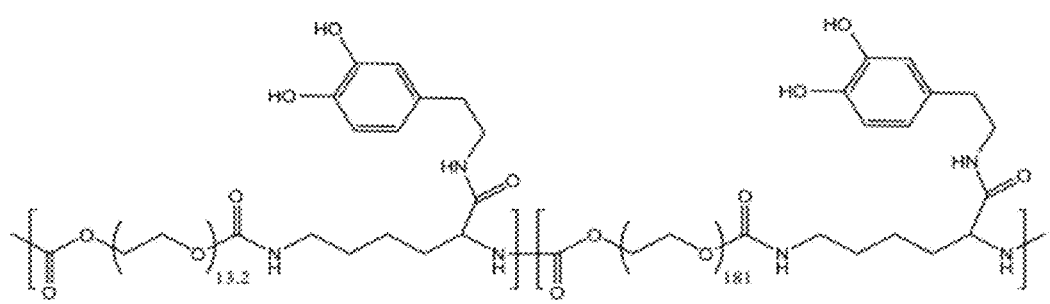
Figure 39:
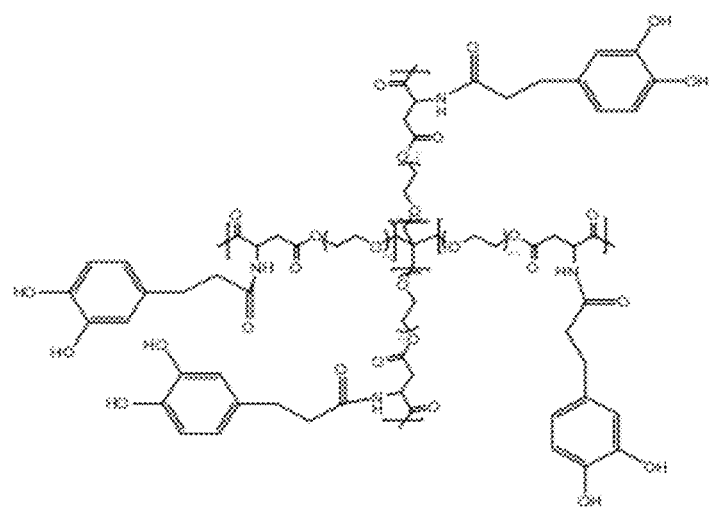
Figure 40:
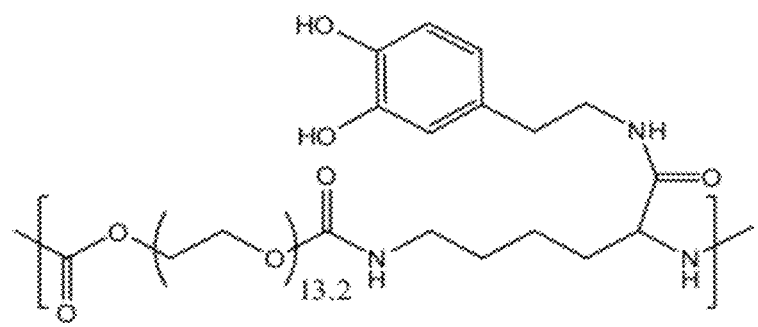
Figure 41:
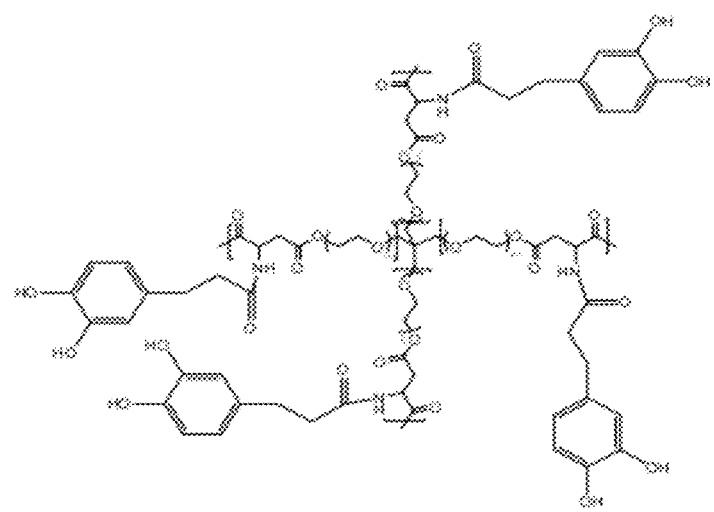
Figure 42:
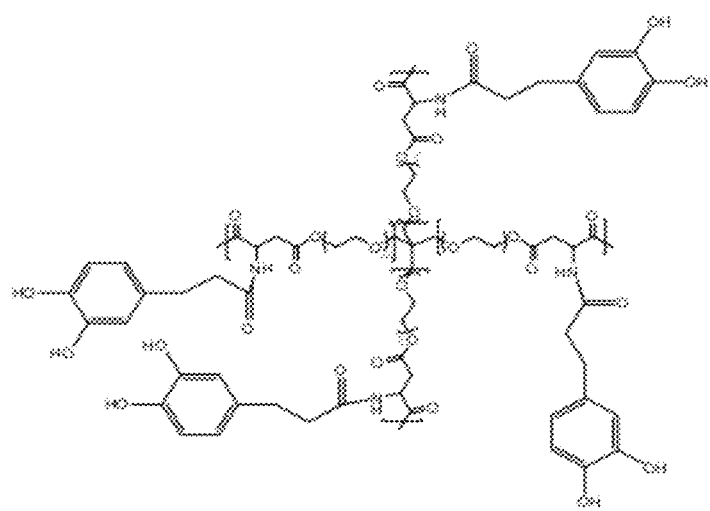
Figure 43:
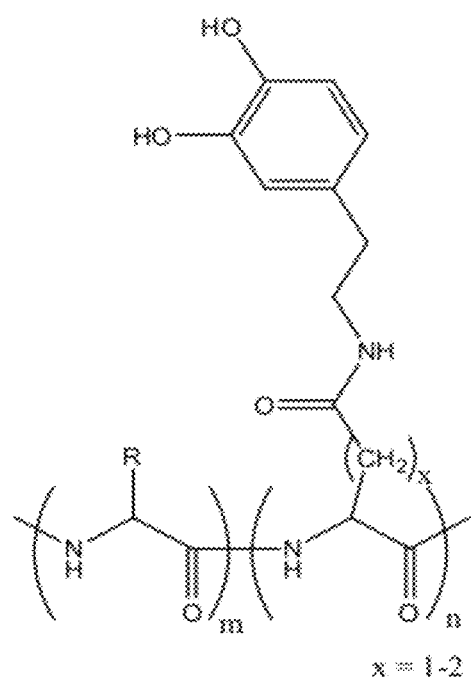
Figure 44:
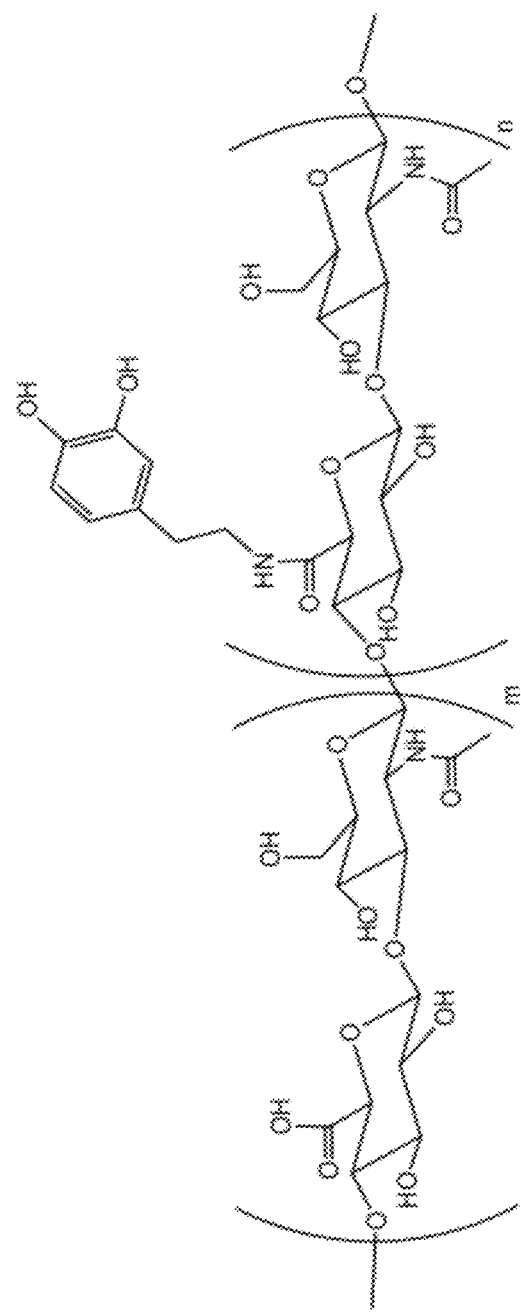
Figure 45:
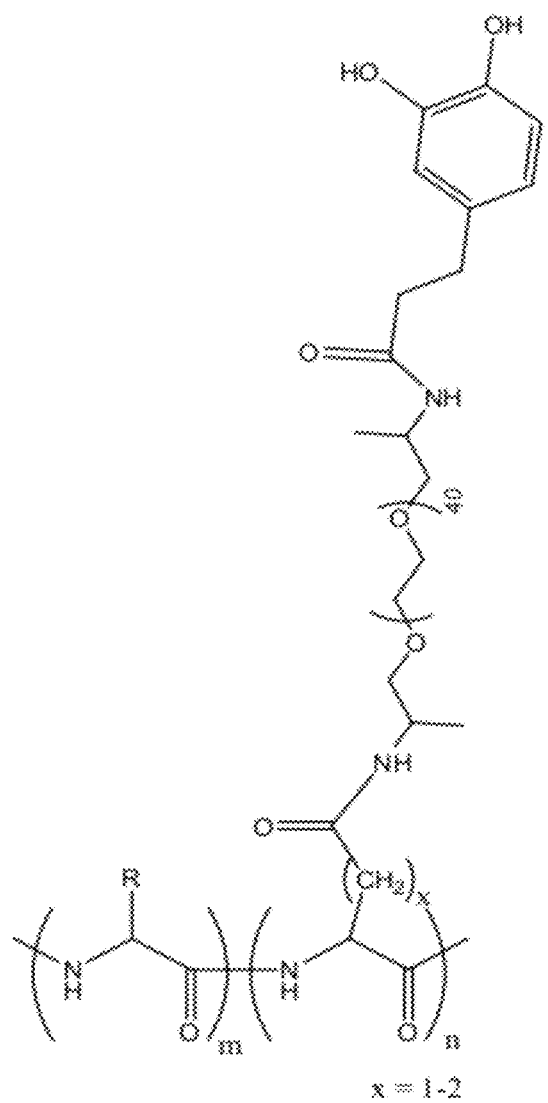
Figure 46:
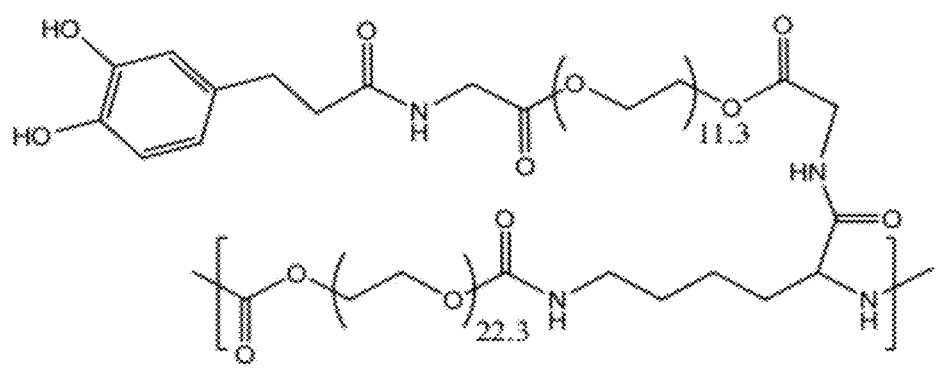
Figure 47:
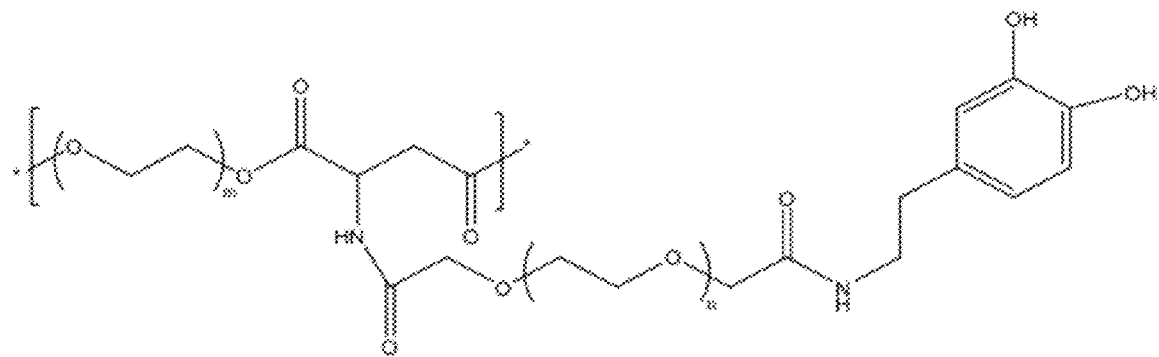
Figure 48:
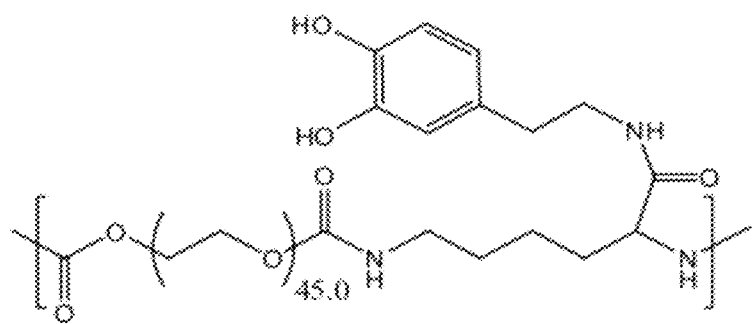
Figure 49:
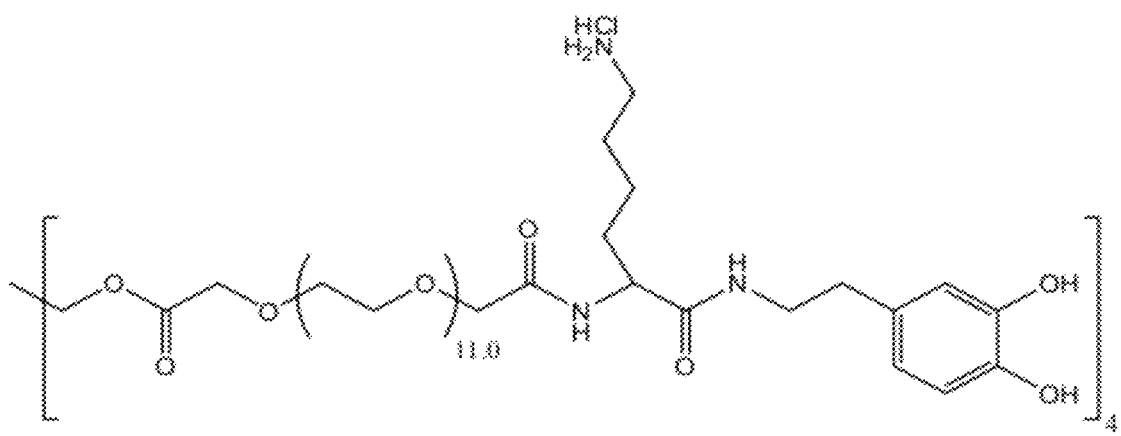
Figure 50:
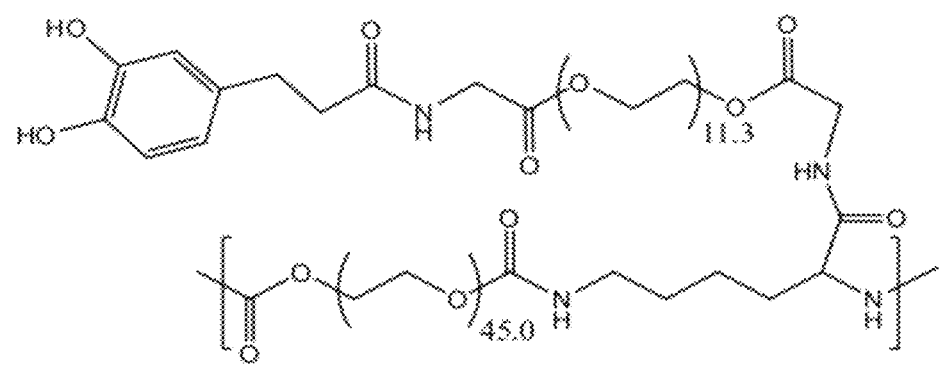

| Name | R&D Name | Description | FIG. No. |
|---|---|---|---|
| | | through activation of PEG-OH with phosgene and NHS. | |
| Medhesive-024 | p(EG1kCL1kGLys-g-DM) | Linear, repeating PEG (1k MW), PCL-(Gly-TSA) (25 wt %, 1250 MW) and Lys grafted with dopamine. Chain extension achieved through activation with triphosgene and NHS. | FIG. 34 |
| Medhesive-025 | p(EG1kCL1kf68Lys-g-DM) | Linear, repeating PEG (1k MW), PCL-diol (23 wt %, 1250 MW), F68 (10 wt % 8350 MW), and Lys grafted with dopamine. Chain extension achieved through activation with phosgene and NHS. | FIG. 35 |
| Medhesive-026 | p(F2kLys-g-DM) | Linear, repeating PEG-PPG-PEG (1.9k MW 50 wt % EG, EG11-PG16-EG11), and Lys grafted with dopamine. Chain extension achieved through activation with phosgene and NHS. | FIG. 36 |
| Medhesive-027 | p(EG600[EG1kCL2kG]Lys-g-DL) | Linear, repeating PEG (600 MW), copolymer (PCL-diol (25 wt %, 2000 MW), PEG (10 wt % 1000 MW), and Lys grafted with dopamine-Lys. Chain extension achieved through activation with phosgene and NHS. | FIG. 37 |
| Medhesive-028 | p(EG600EG8kLys-g-DM) | Linear, repeating PEG (600 MW), PEG (10 wt %, 8000 MW), and Lys grafted with dopamine. Chain extension achieved through activation with phosgene and NHS. | FIG. 38 |
| Medhesive-029 | Branched p(EG1kAsp-g-DH) | Branched, repeating PEG (1k Mw) and Asp grafted with DOHA. Chain extension achieved through melt polycondensation. Branching achieved with Pentaerythritol | FIG. 39 |
| Medhesive-030 | p(EG600Lys-g-DM) | Linear, repeating PEG (600 MW) and Lys grafted with dopamine. Chain extension achieved through activation with phosgene and NHS. | FIG. 40 |
| Medhesive-031 | Branched p(EG1kAsp-g-DH) | Branched, repeating PEG (1k Mw) and Asp grafted with DOHA. Chain extension achieved through melt polycondensation. Branching achieved with 4-arm PEG(10k). | FIG. 41 |
| Medhesive-032 | Branched p(EG600Asp-g-DH) | Branched, repeating PEG (600 Mw) and Asp grafted with DOHA. Chain extension achieved through melt polycondensation. Branching achieved with 4-arm PEG(10k) | FIG. 42 |
| Medhesive-033 | Gel225-g-DM | Gelatin 225 Bloom Type B (50,000 MW) grafted with dopamine. | FIG. 43 |
| Medhesive-034 | HA-g-DM | Hyluronic acid (low MW) grafted with dopamine. | FIG. 44 |
| Medhesive-035 | Gel225-g-ED2kDH | Gelatin 225 Bloom Type B (50,000 MW) grafted with ED2k-DH. | FIG. 45 |
| Medhesive-036 | p(EG1kLys-g-EG600GDH) | Linear, repeating PEG (1000 MW) and Lys grafted with Gly-EG600-Gly-DOHA with ester linkage. Chain extension achieved through activation with phosgene and NHS. | FIG. 46 |
| Medhesive-037 | p(EG1kAsp-g-EGDM) | Linear, repeating PEG (1000 MW) and Asp grafted with PEG (600 mw)-DM 'brushes'. Chain extension achieved through melt polycondensation. | FIG. 47 |
| Medhesive-038 | p(EG2kLys-g-DM) | Linear, repeating PEG (2000 MW) and Lys grafted with dopamine. Chain extension achieved through activation with phosgene and NHS. | FIG. 48 |
| Medhesive-039 | Branched-EG600-DL | Branched polymer constructed with a pentaerythrtol core and PEG600-diacid (1:4 feed ratio) end-capped with a Lys-dopamine dipeptide. | FIG. 49 |
| Medhesive-040 | p(EG2kLys-g-EG600GDH) | Linear, repeating PEG (2000 MW) and Lys grafted with Gly-EG600-Gly-DOHA with ester linkage. | FIG. 50 |

TABLE 1-continued

Figure 51:
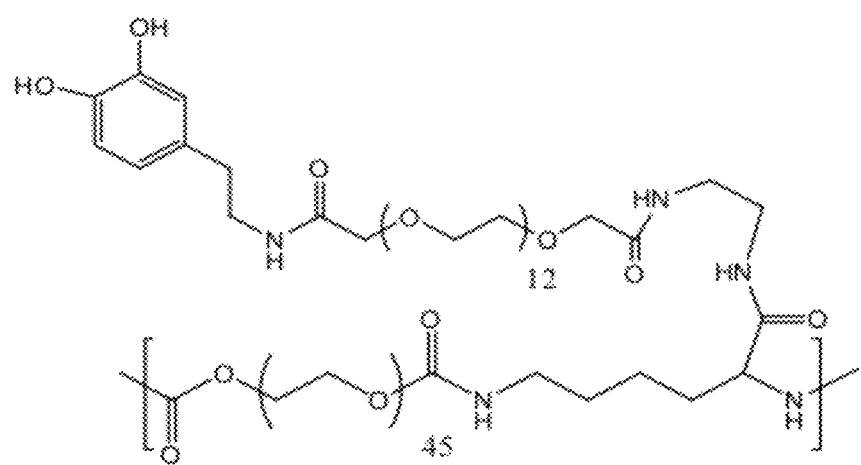
Figure 52:
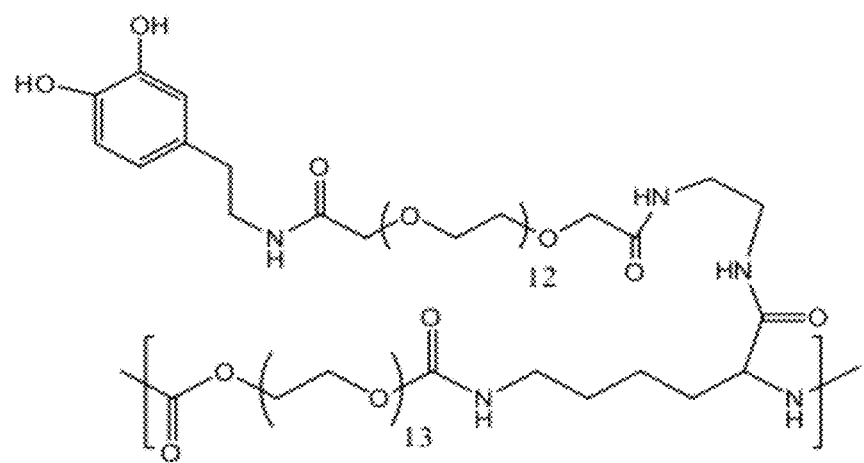
Figure 53:
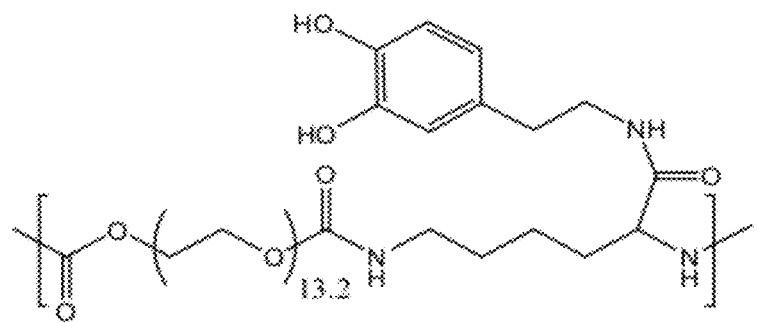
Figure 54:
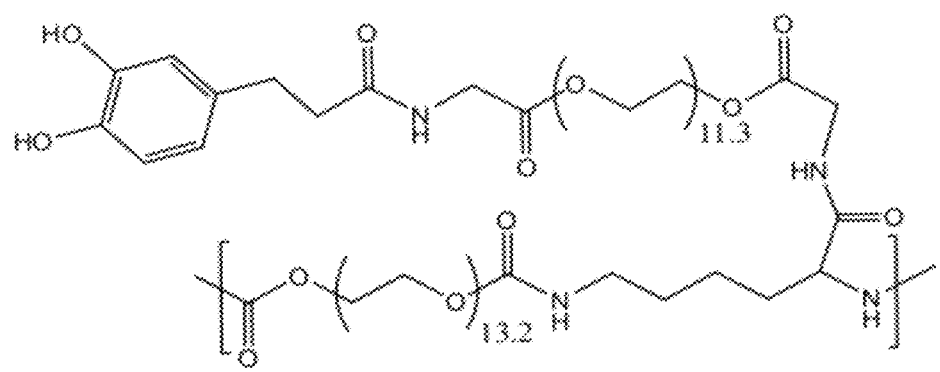
Figure 55:
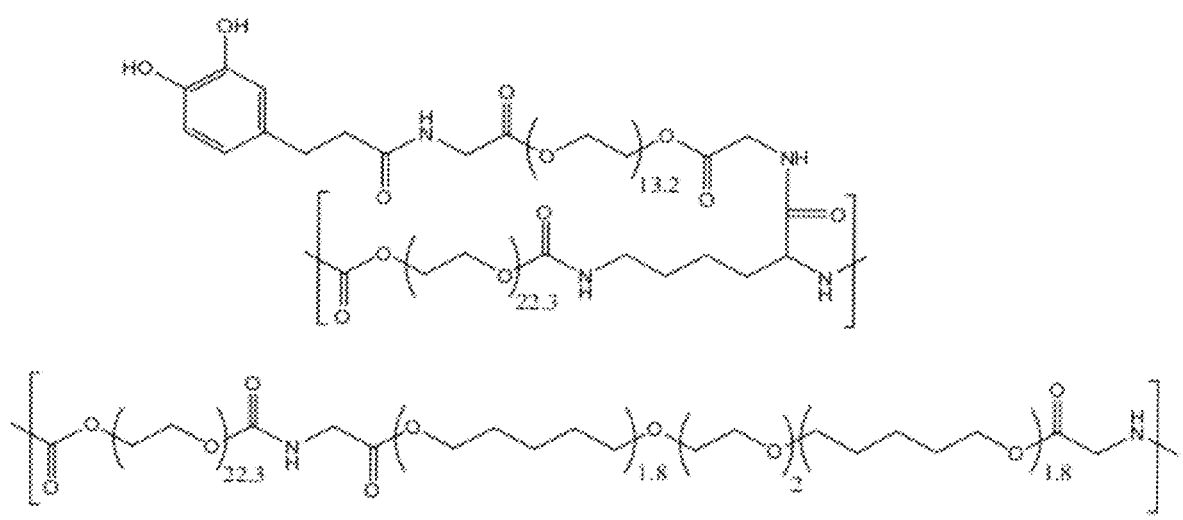
Figure 56:
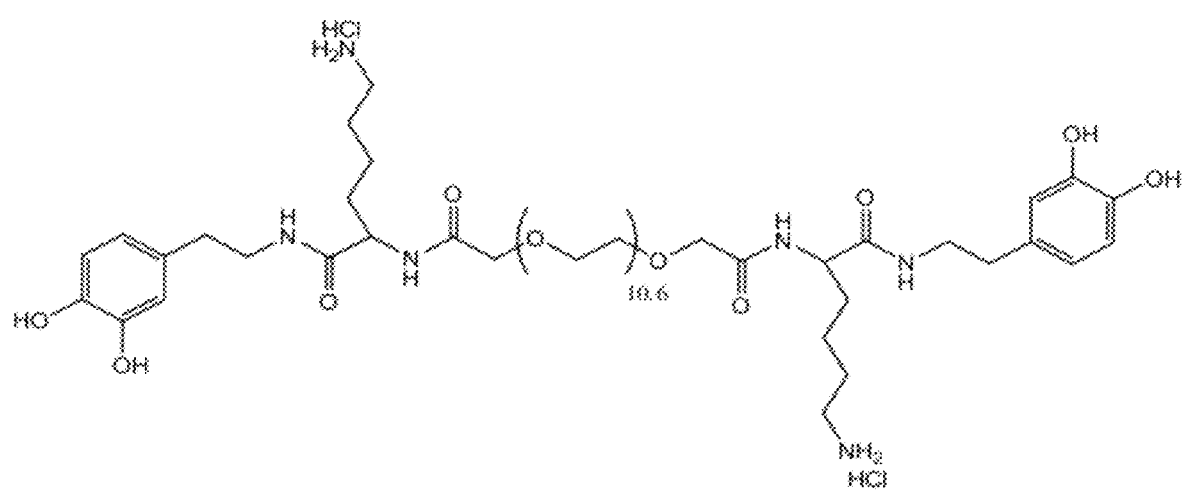
Figure 57:
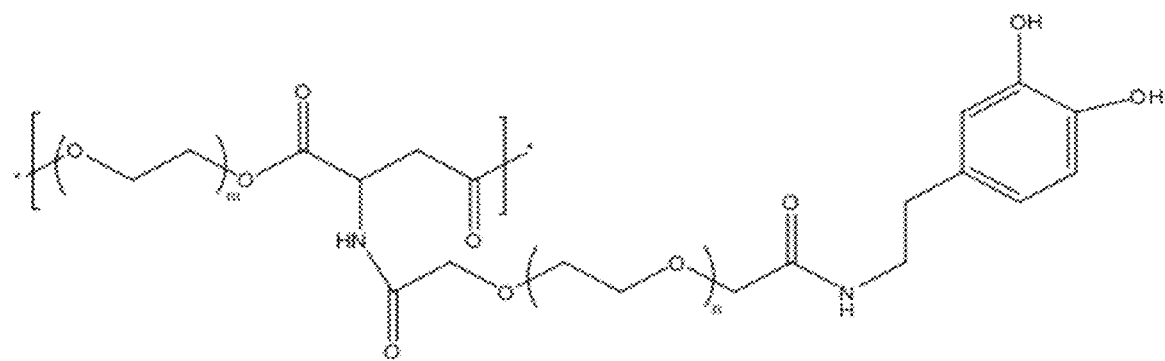
Figure 58:
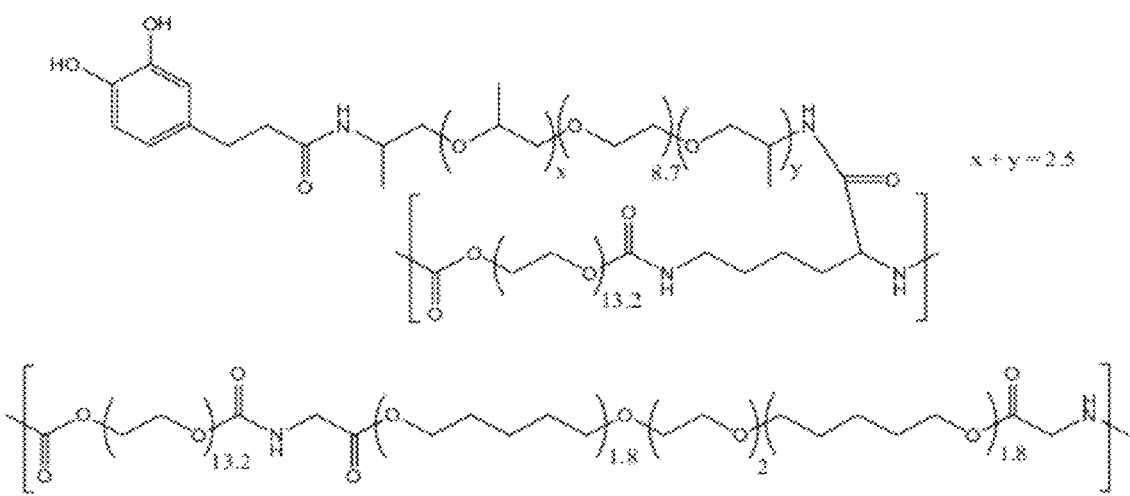
Figure 59:
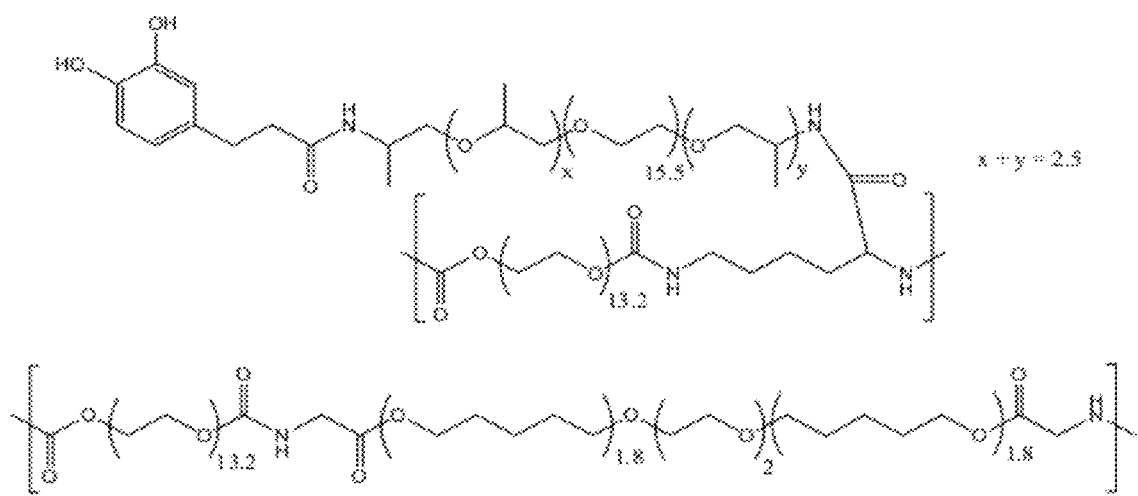
Figure 60:
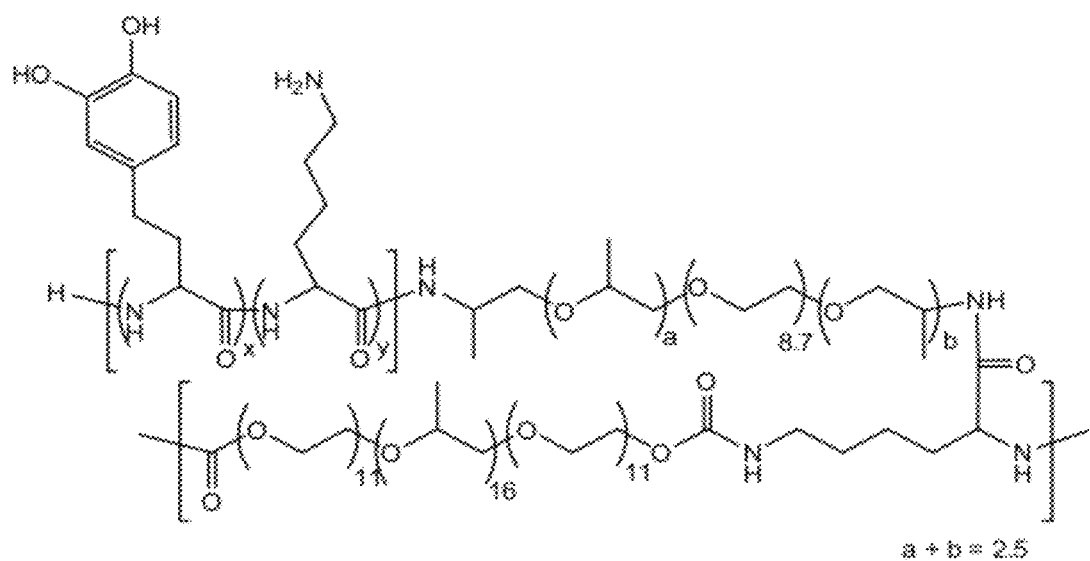
Figure 61:
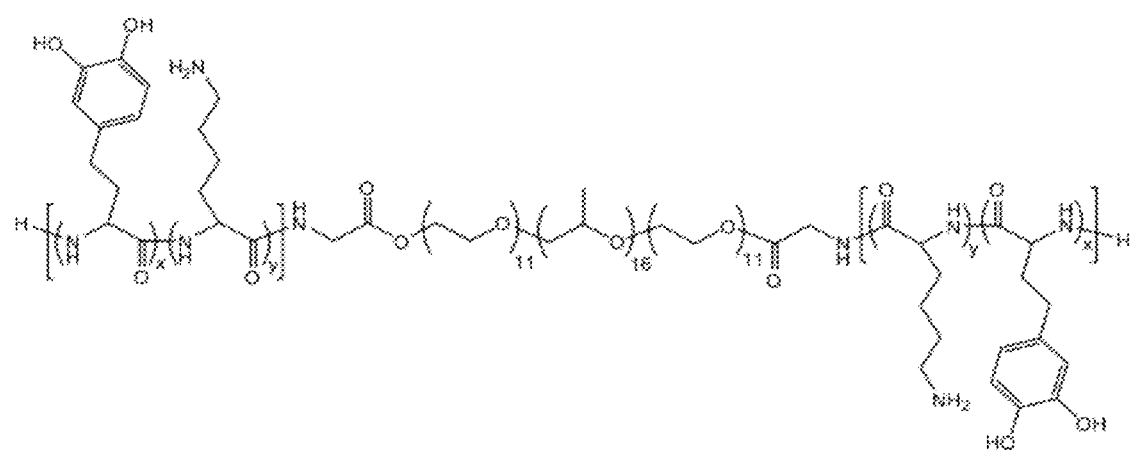
Figure 62:
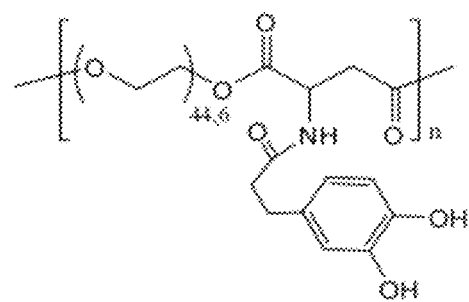
Figure 63:
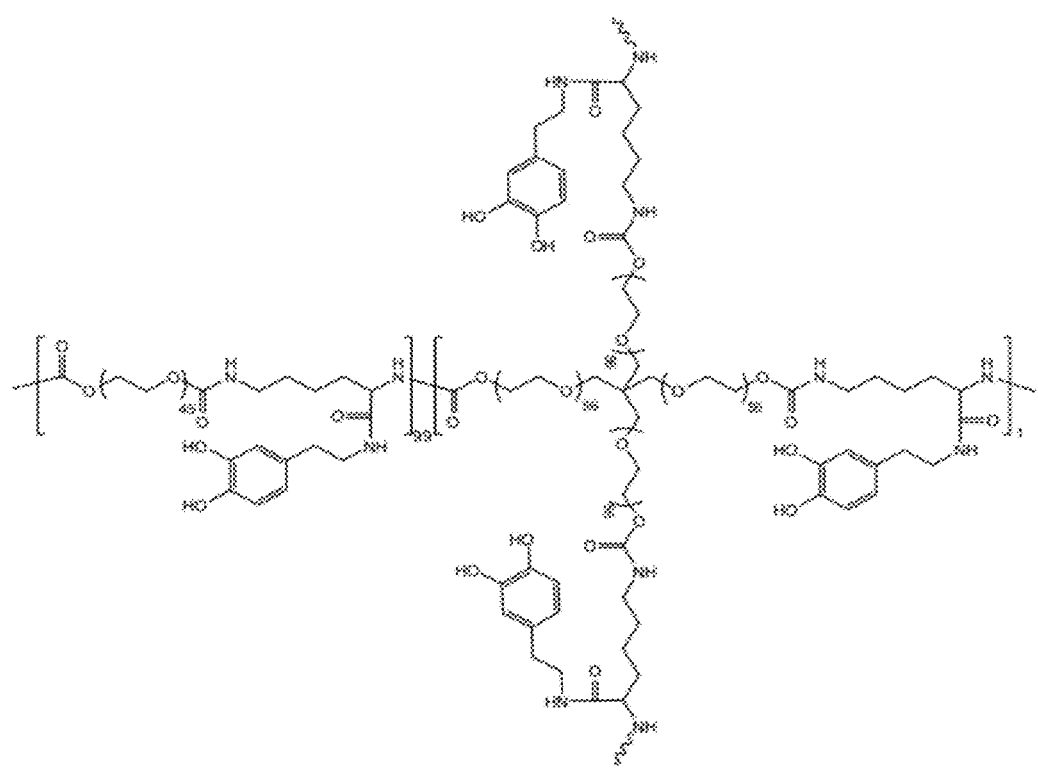
Figure 64:
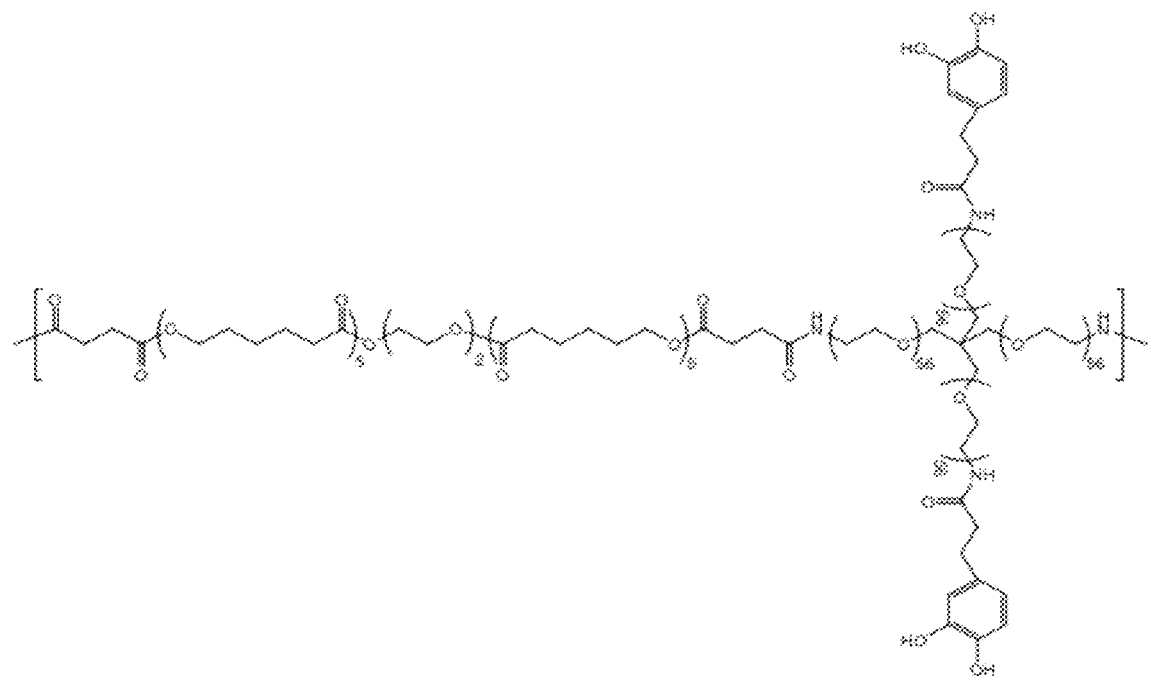

| Name | R&D Name | Description | FIG. No. |
|---|---|---|---|
| Medhesive-041 | p(EG2kLys-g-EDAEG600DM) | Chain extension achieved through activation with phosgene and NHS. Linear, repeating PEG (2000 MW) and Lys grafted with EDA-EG600-Dopamine with amide linkages. | FIG. 51 |
| Medhesive-042 | p(EG600Lys-g-EDAEG600DM) | Chain extension achieved through activation with phosgene and NHS. Linear, repeating PEG (600 MW) and Lys grafted with EDA-EG600-Dopamine with amide linkages. | FIG. 52 |
| Medhesive-043 | p(EG600Lys-g-DL) | Chain extension achieved through activation with phosgene and NHS. Linear, repeating PEG (1k MW) and Lys grafted with dopamine-lysine. Chain extension achieved through activation of PEG-OH with phosgene and NHS. | FIG. 53 |
| Medhesive-044 | p(EG600Lys-g-EG600GDH) | Linear, repeating PEG (600 MW) and Lys grafted with Gly-EG600-Gly-DOHA with ester linkage. Chain extension achieved through activation with phosgene and NHS. | FIG. 54 |
| Medhesive-045 | p(EG1kCL530Lys-g-EG600GDH) | Linear, repeating PEG (1k MW), PCL-(Gly)$_2$ (530 MW)and Lys grafted with Gly-EG600-Gly-DOHA with ester linkage. Chain extension achieved through activation with phosgene and NHS. Feed mole ratio PEG:PCL:Lys = 2:1:1 | FIG. 55 |
| Medhesive-046 | PEG600-(DL)$_2$ | PEG-diacid (600 MW) modified with dopamine-Lys. | FIG. 56 |
| Medhesive-047 | p(EG2kAsp-g-EGDM) | Linear, repeating PEG (2000 MW) and Asp grafted with PEG (600 mw)-DM 'brushes'. Chain extension achieved through melt polycondensation. | FIG. 57 |
| Medhesive-048 | p(EG600CL530GLys-g-ED600DH) | Linear, repeating PEG (600 MW), PCL-(Gly)$_2$ (530 MW)and Lys grafted with ED600-DOHA with amide linkage. Chain extension achieved through activation with phosgene and NHS. Feed mole ratio PEG:PCL:Lys = 2:1:1 | FIG. 58 |
| Medhesive-049 | p(EG600CL530GLys-g-ED900DH) | Linear, repeating PEG (600 MW), PCL-(Gly)$_2$ (530 MW)and Lys grafted with ED600-DOHA with amide linkage. Chain extension achieved through activation with phosgene and NHS. Feed mole ratio PEG:PCL:Lys = 2:1:1 | FIG. 59 |
| Medhesive-050 | p(F2kLys-g-ED600DL) | Linear, repeating PEG-PPG-PEG (1.9k MW 50 wt % EG, EG11-PG16-EG11), and Lys grafted with ED600-(DOPA$_x$-Lys$_y$). Chain extension achieved through activation with phosgene and NHS. | FIG. 60 |
| Medhesive-051 | F2k-(GDL)2 | PEG-PPG-PEG (1.9k MW 50 wt % EG, EG11-PG16-EG11) end-functionalized with glycine-(DOPA$_x$-Lys$_y$) peptide. | FIG. 61 |
| Medhesive-052 | p(EG2kAsp-g-DH) | Linear, repeating PEG (2k MW) and Asp grafted with DOHA. Chain extension achieved through melt polycondensation. | FIG. 62 |
| Medhesive-053 | p(EG2kEG10kb1Lys-g-DM) | Random repeating linear PEG (2000 MW, 99 mol %) and 4-armed PEG (10k MW, 1 mol %) linked together with Lys and grafted with dopamine. Chain extension achieved through activation with phosgene and NHS. | FIG. 63 |
| Medhesive-054 | p(CL1.25kEG10kb-g-DH2) | Branched polymer constructed from PCL-diSA 1.25k and 4-arm PEG-NH2 10k (1:1 feed ratio) modified with DOHA. | FIG. 64 |

TABLE 1-continued

Figure 65:
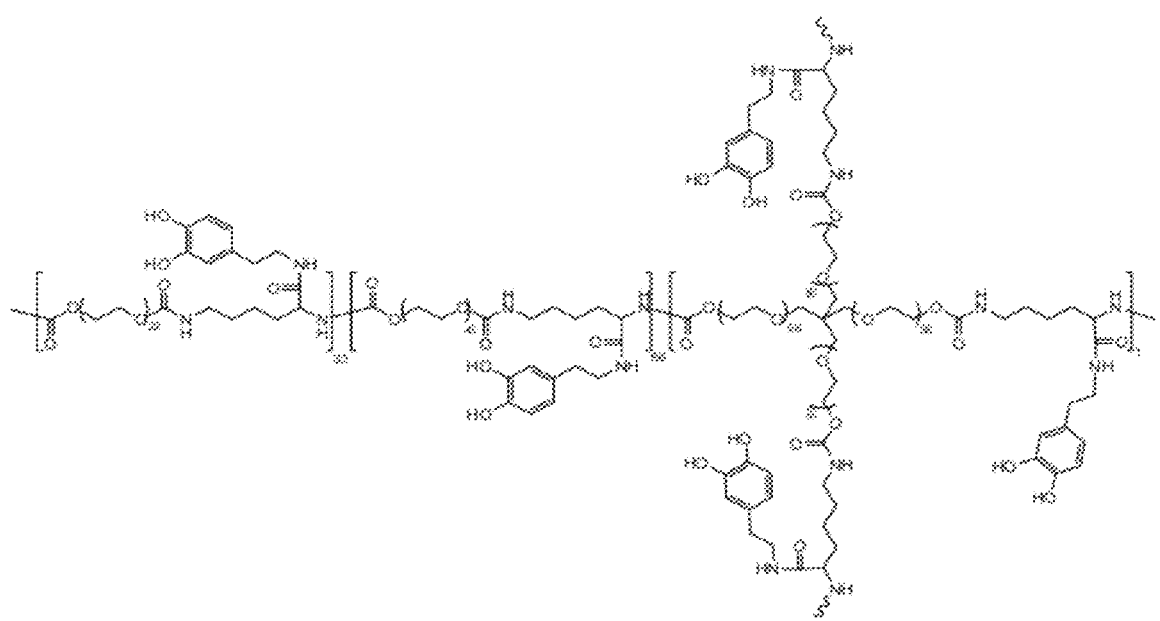
Figure 66:
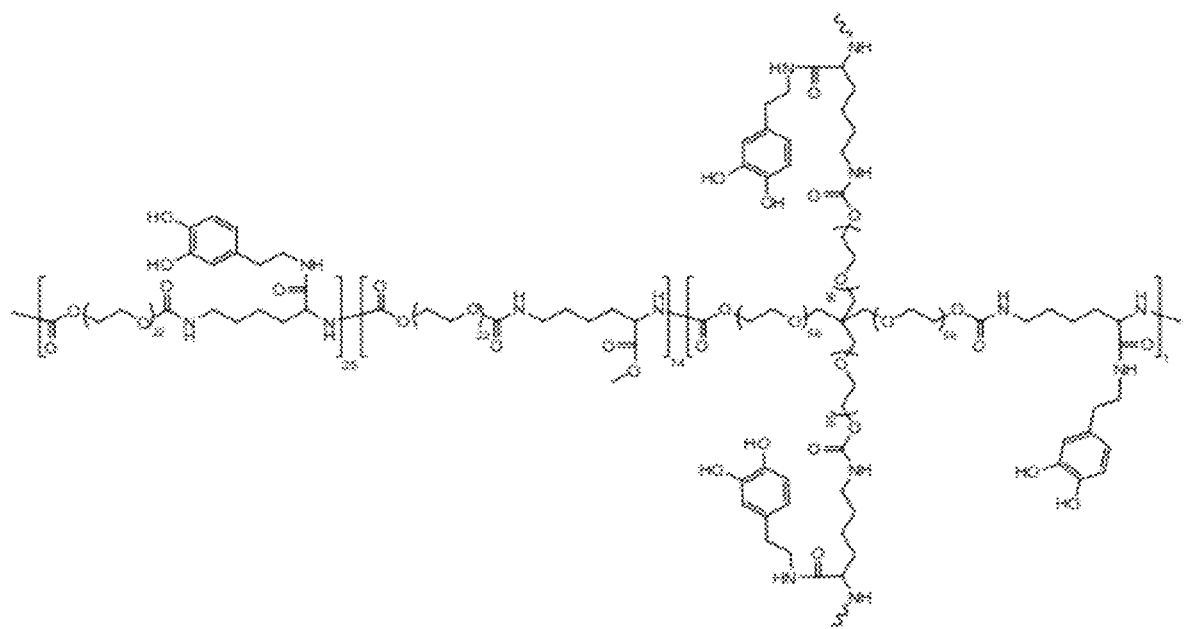
Figure 67:
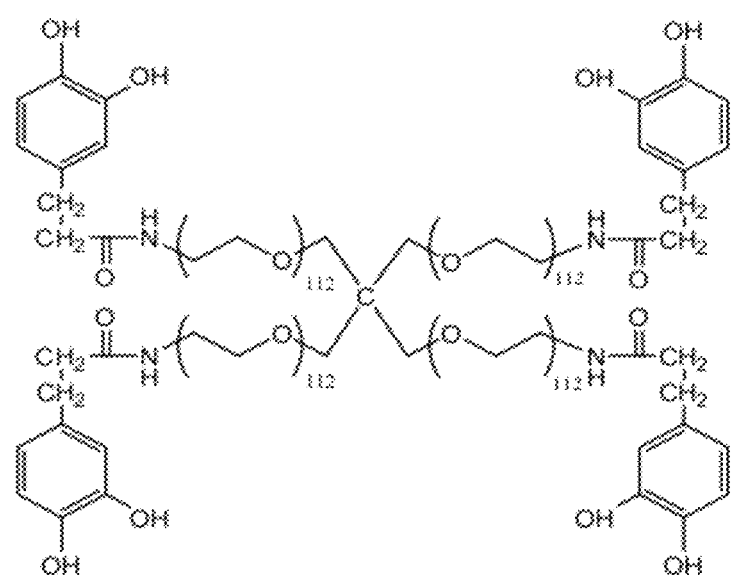
Figure 68:
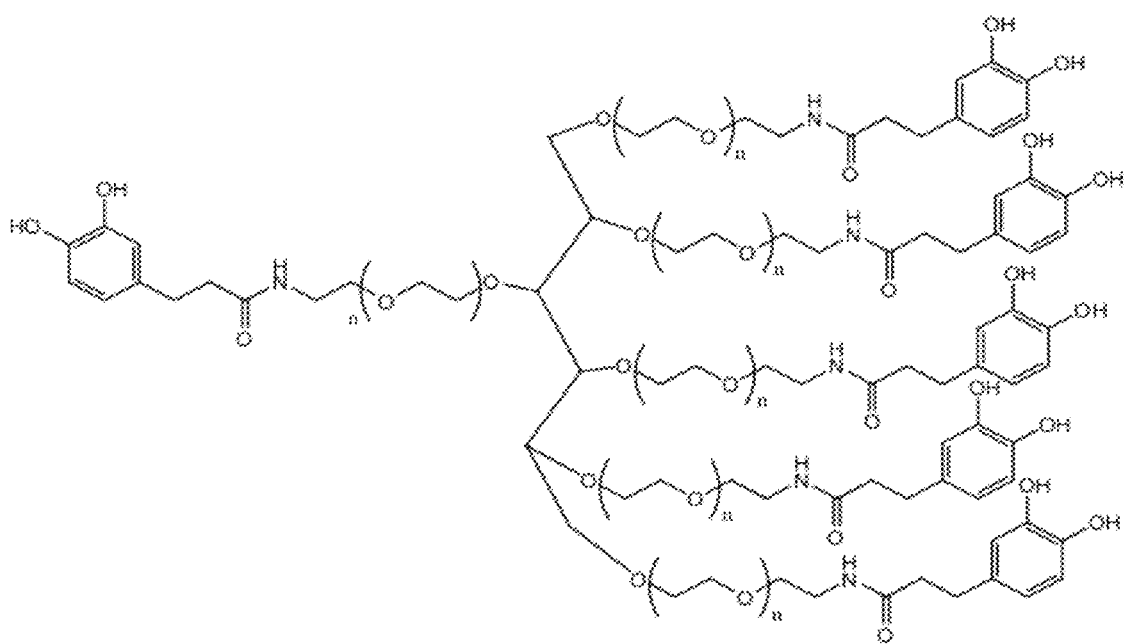
Figure 69:
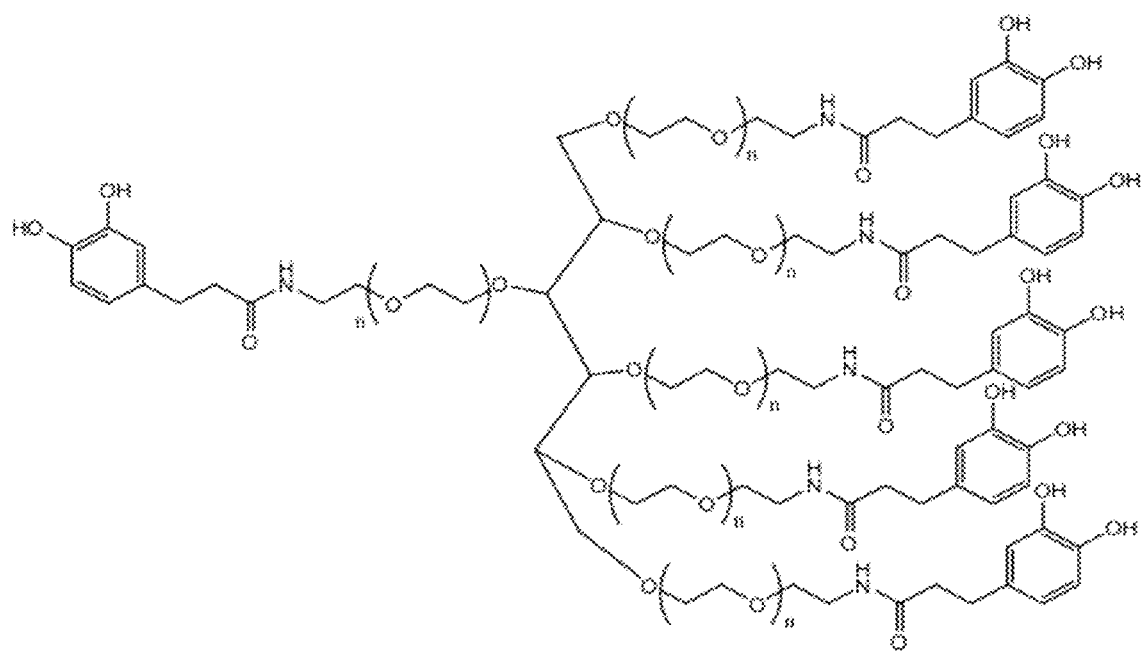
Figure 70:
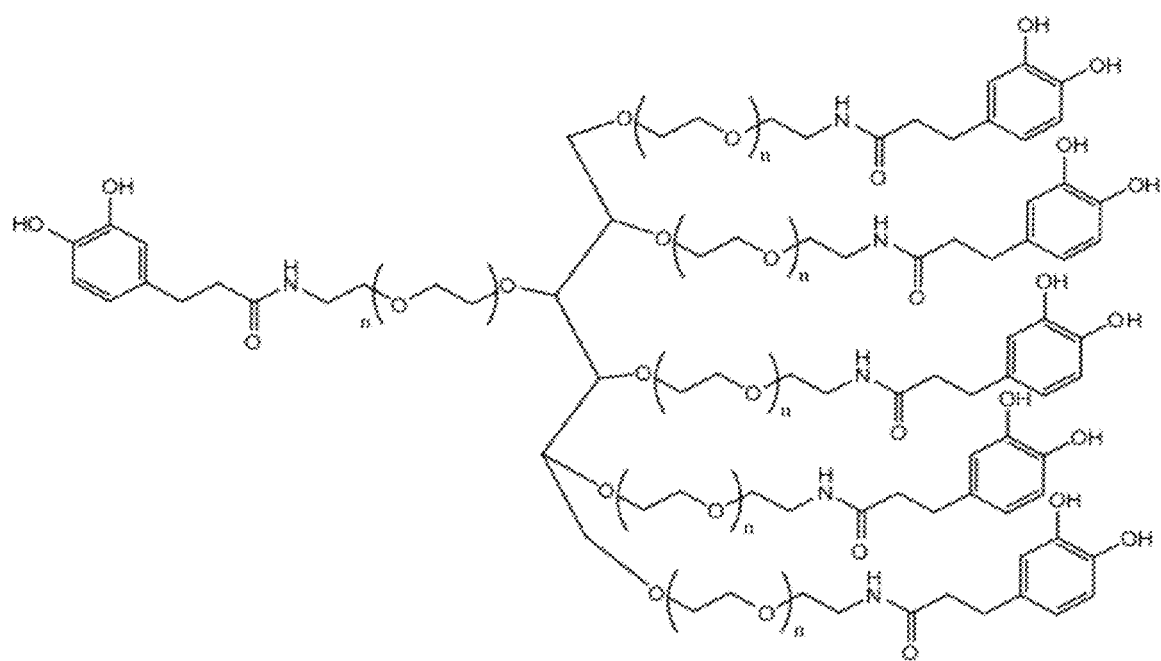
Figure 71:
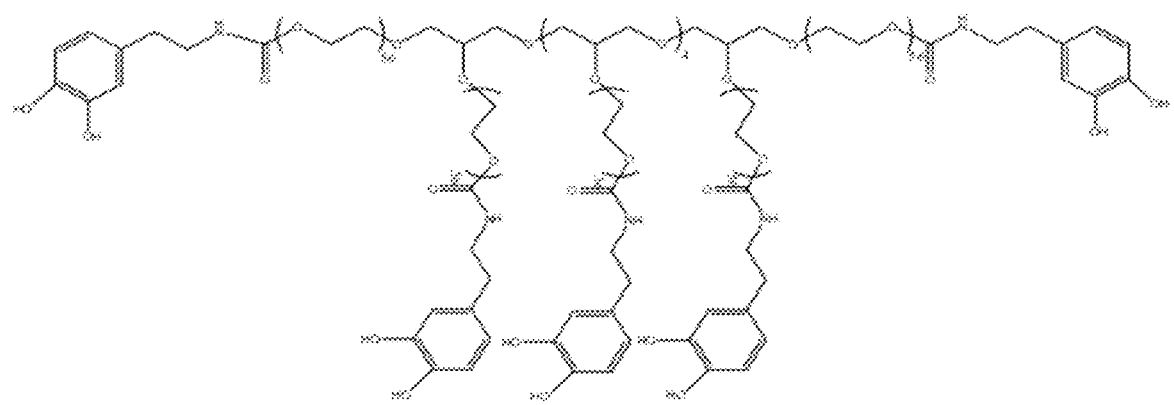
Figure 72:
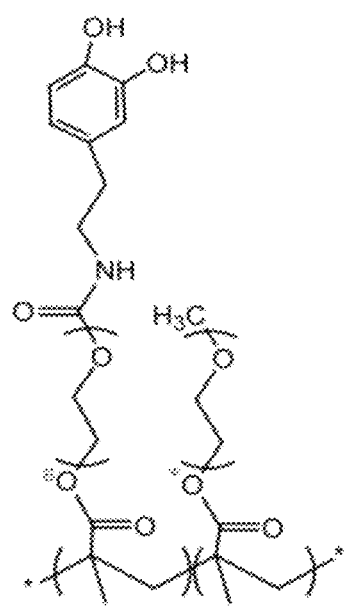
Figure 73:
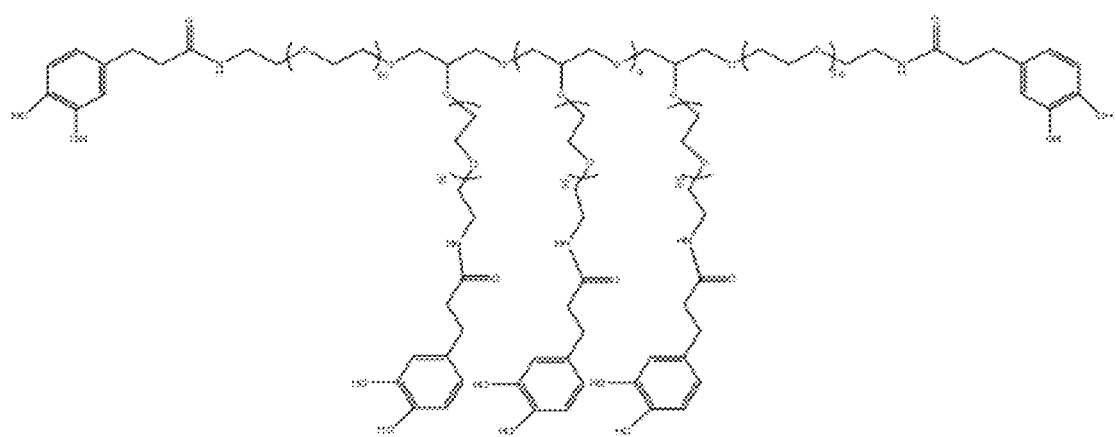
Figure 74:
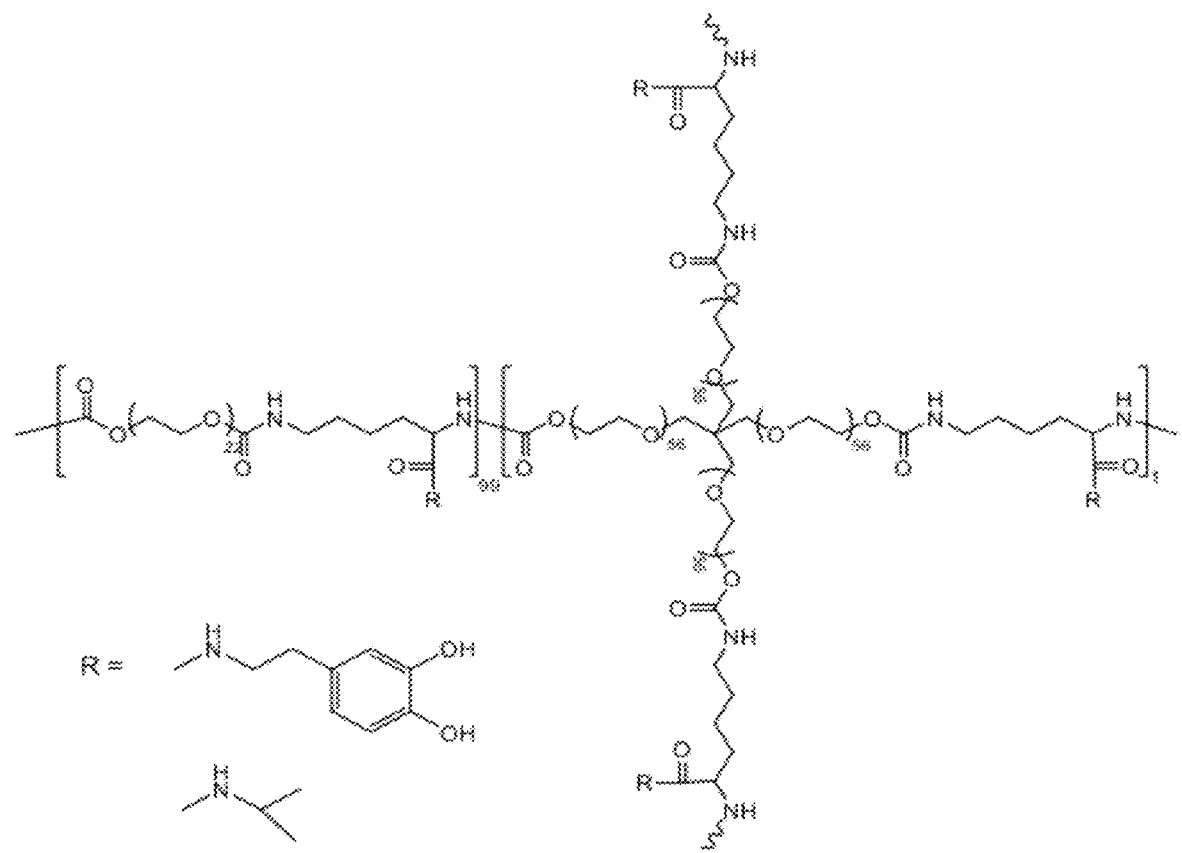
Figure 75:
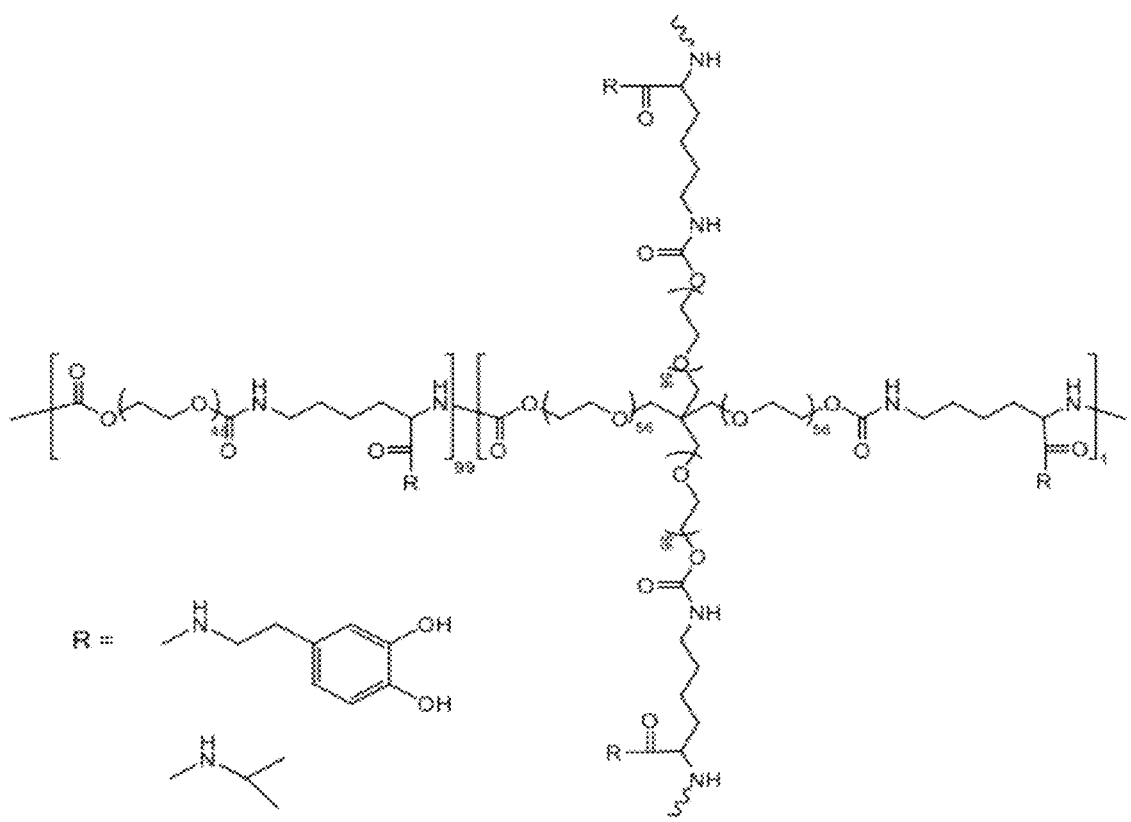
Figure 76:
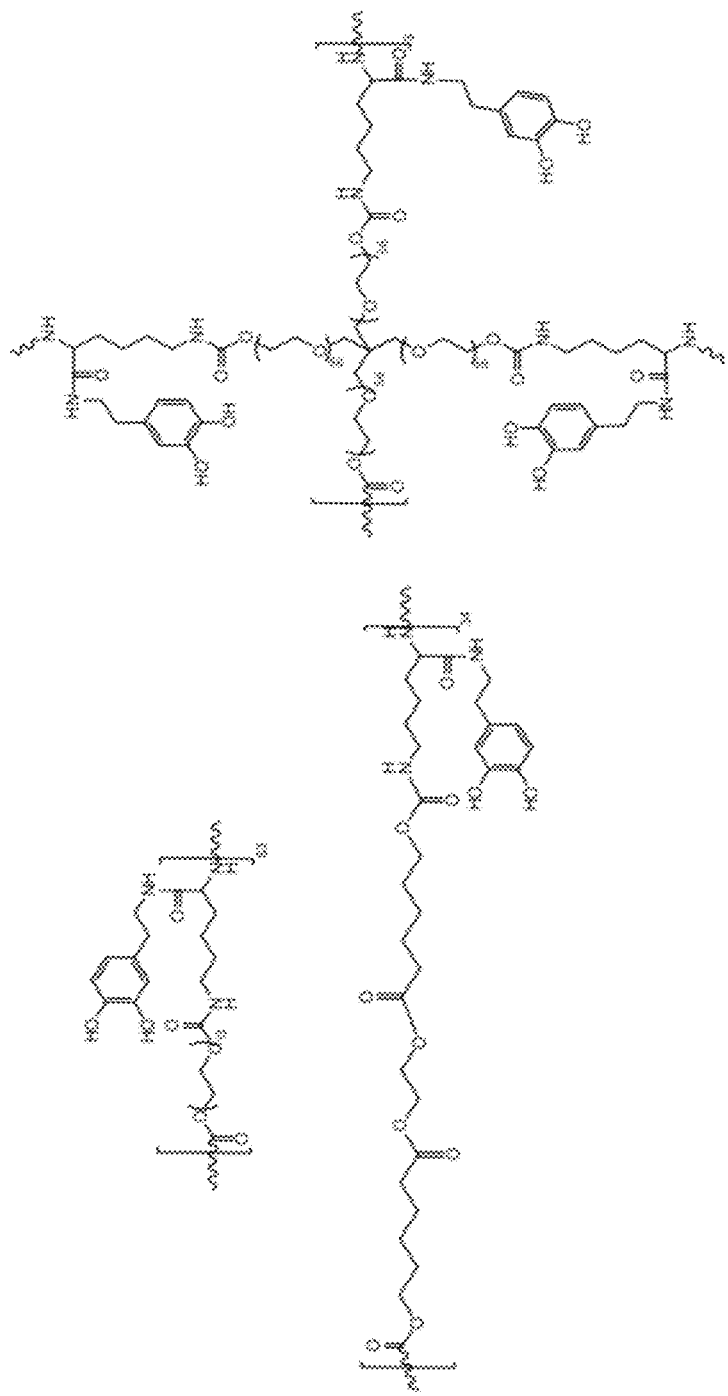
Figure 77:
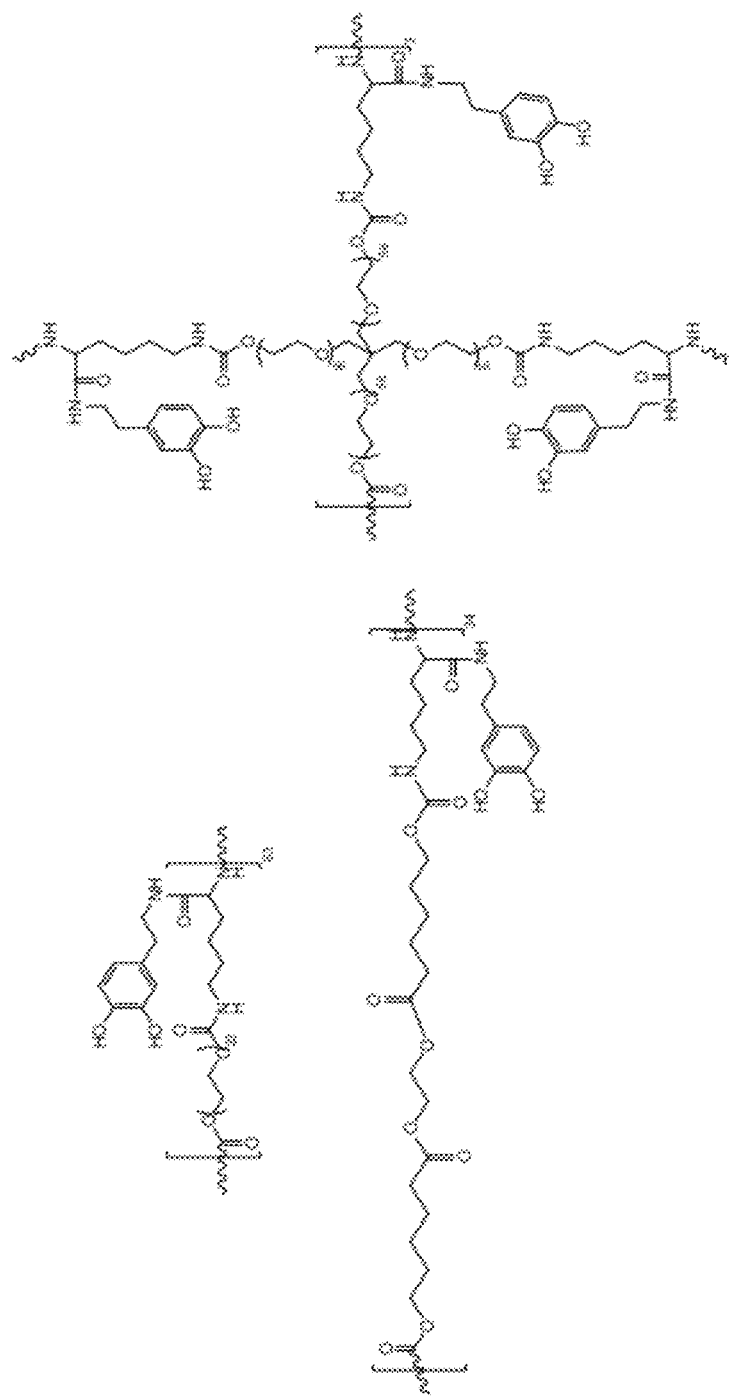

| Name | R&D Name | Description | FIG. NO. |
|---|---|---|---|
| Medhesive-055 | p(EG1k33EG2k66EG10kb1Lys-g-DM) | Random repeating linear PEG (1000 MW, 33 mol %), PEG (2000 MW, 66 mol %) and 4-armed PEG (10k MW, 1 mol %) linked together with Lys and grafted with dopamine. Chain extension achieved through activation with phosgene and NHS. | FIG. 65 |
| Medhesive-056 | p[EG1kEG10kb1(Lys-g-DM)33(LysOMe)66] | Random repeating linear PEG (1000 MW, 99 mol %) and 4-armed PEG (10k MW, 1 mol %) linked together with Lys and grafted with dopamine and Lys-Methylester (feed ratio = 1:2). Chain extension achieved through activation with phosgene and NHS. | FIG. 66 |
| Medhesive-057 | PEG20k-(DOHA)$_4$ | Branched, 4-armed PEG-NH2 (20k MW) coupled with terminal 3,4-dihydroxyhydrocinnamic acid (DOHA). | FIG. 67 |
| Medhesive-058 | PEG10k-(DOHA)$_6$ | Branched, 6-armed PEG-NH2 (10k MW) coupled with terminal 3,4-dihydroxyhydrocinnamic acid (DOHA). | FIG. 68 |
| Medhesive-059 | PEG15k-(DOHA)$_6$ | Branched, 6-armed PEG-NH2 (15k MW) coupled with terminal 3,4-dihydroxyhydrocinnamic acid (DOHA). | FIG. 69 |
| Medhesive-060 | PEG20k-(DOHA)$_6$ | Branched, 6-armed PEG-NH2 (20k MW) coupled with terminal 3,4-dihydroxyhydrocinnamic acid (DOHA). | FIG. 70 |
| Medhesive-061 | PEG20k-(Dmu)$_8$ | Branched, 8-armed PEG-OH (20k MW) coupled with terminal dopamine linked with urethane linkage. | FIG. 71 |
| Medhesive-062 | p[(EG10MA-Dmu)-EG9ME] | Random, repeating copolymer of 475 MW PEG Methyl ether methacrylate and 526 MW PEG Methacrylate with dopamine linked via urethane linkage. | FIG. 72 |
| Medhesive-063 | PEG20k-(DOHA)$_8$ | Branched, 8-armed PEG-NH2 (20k MW) coupled with terminal 3,4-dihydroxyhydrocinnamic acid (DOHA). | FIG. 73 |
| Medhesive-064 | p[EG1kEG10kb1Lys-g-(DM)(IPA)] | Random repeating linear PEG (1000 MW, 99 mol %) and 4-armed PEG (10k MW, 1 mol %) linked together with Lys and grafted with dopamine and isopropyl amine. Chain extension achieved through activation with phosgene and NHS. | FIG. 74 |
| Medhesive-065 | p[EG2kEG10kb1Lys-g-(DM)(IPA)] | Random repeating linear PEG (2000 MW, 99 mol %) and 4-armed PEG (10k MW, 1 mol %) linked together with Lys and grafted with dopamine and isopropyl amine. Chain extension achieved through activation with phosgene and NHS. | FIG. 75 |
| Medhesive-066 | p(EG600CL2kEG10kb3Lys-g-DM) | Random repeating linear PEG (600 MW, 63 mol %), PCL (2k MW, 34 mol %) and 4-armed PEG (10k MW, 3 mol %) linked together with Lys and grafted with dopamine. 50 wt % PEG and PCL each in feed. Chain extension achieved through activation with phosgene and NHS. | FIG. 76 |
| Medhesive-067 | p(EG1kCL2kGCLb3Lys-g-DM) | Random repeating linear PEG (1k MW, 63 mol %), PCL (2k MW, 34 mol %) and 4-armed PEG (10k MW, 3 mol %) linked together with Lys and grafted with dopamine. 50 wt % PEG and PCL each in feed. Chain extension achieved through activation with phosgene and NHS. | FIG. 77 |

TABLE 1-continued

Figure 78:
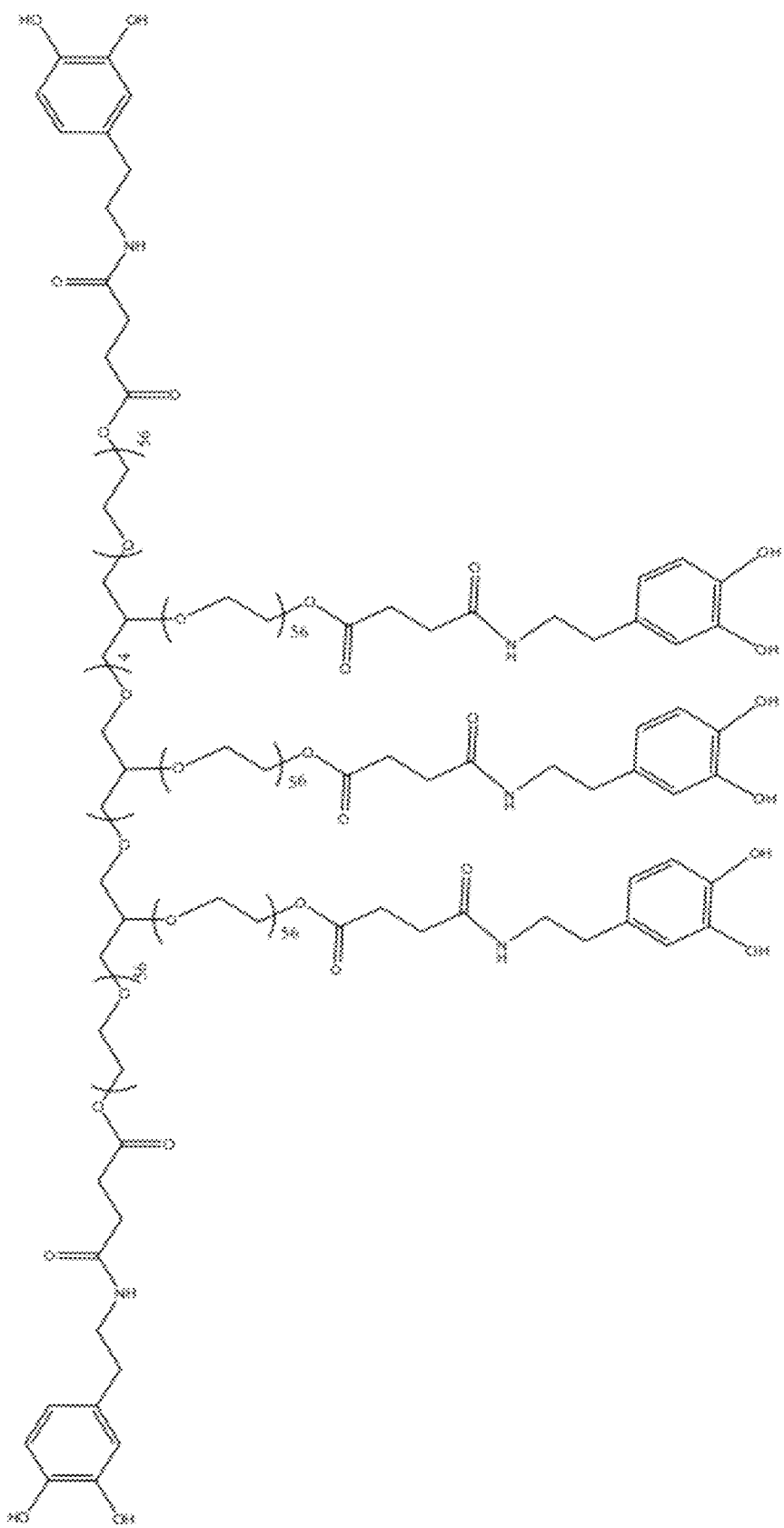
Figure 79:
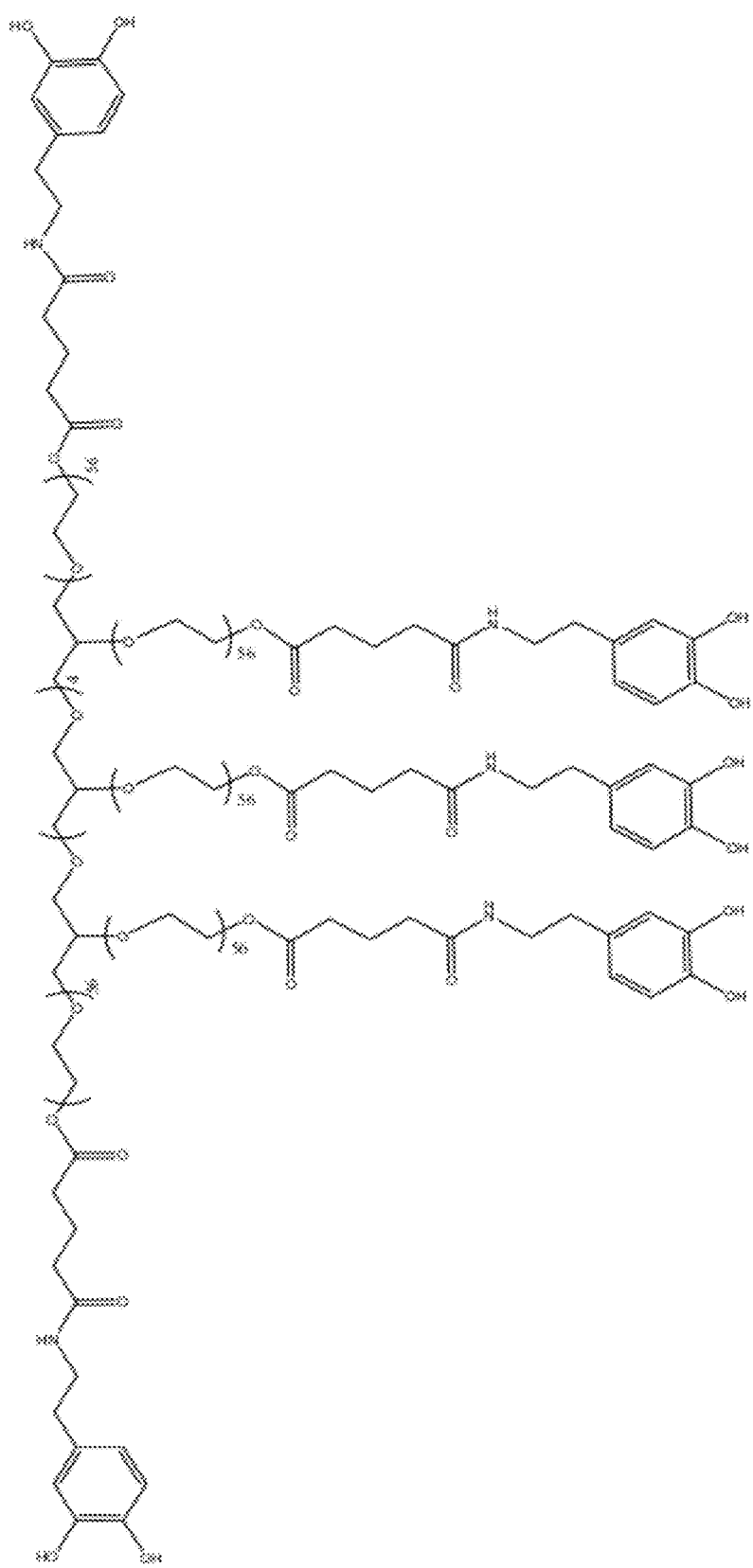
Figure 80:
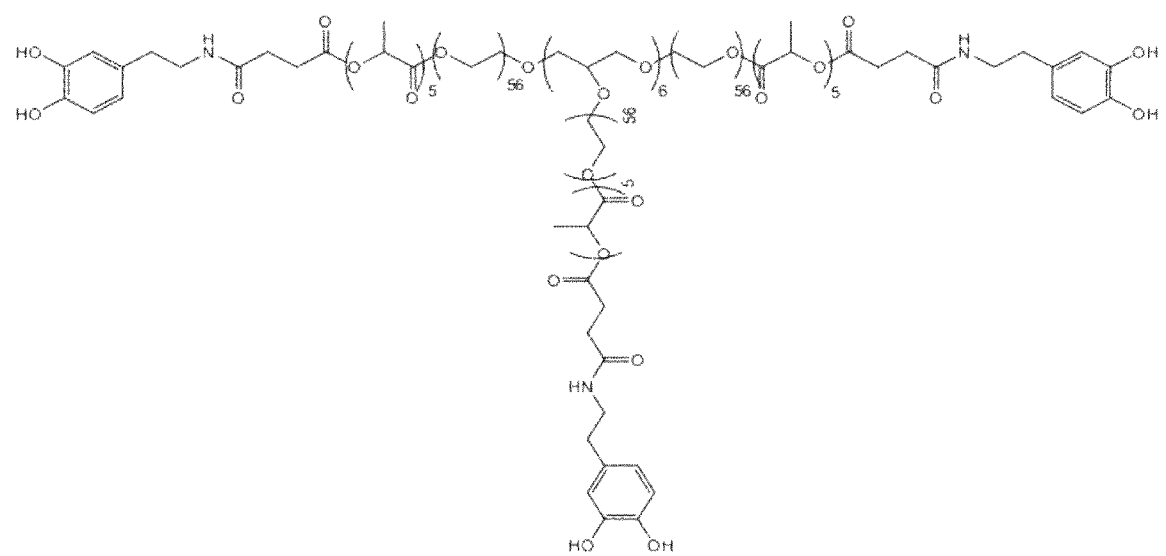
Figure 81:
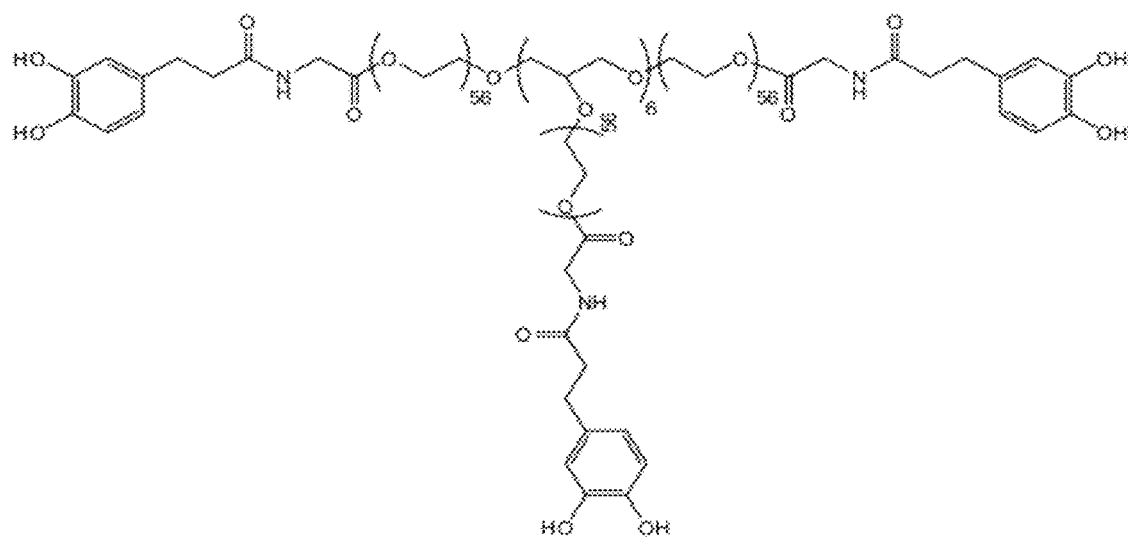
Figure 82:
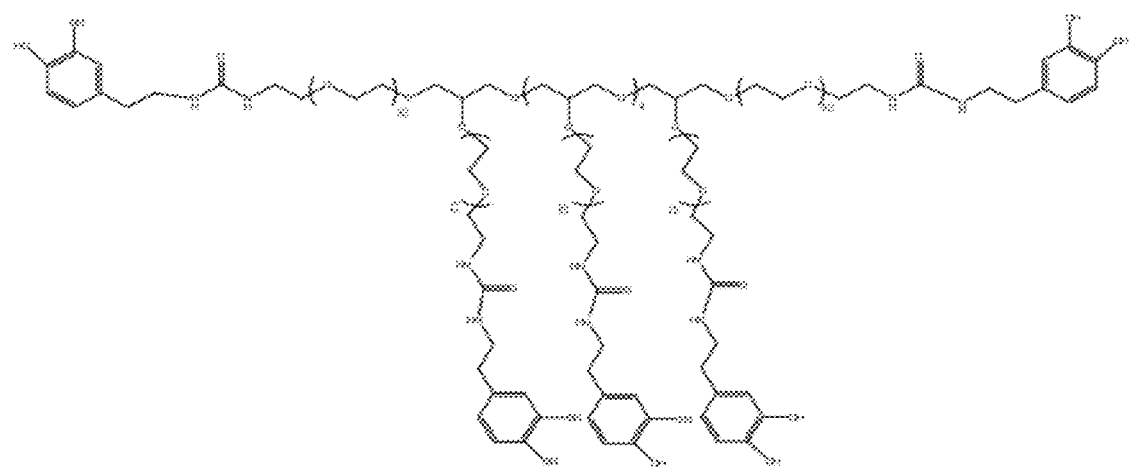
Figure 83:
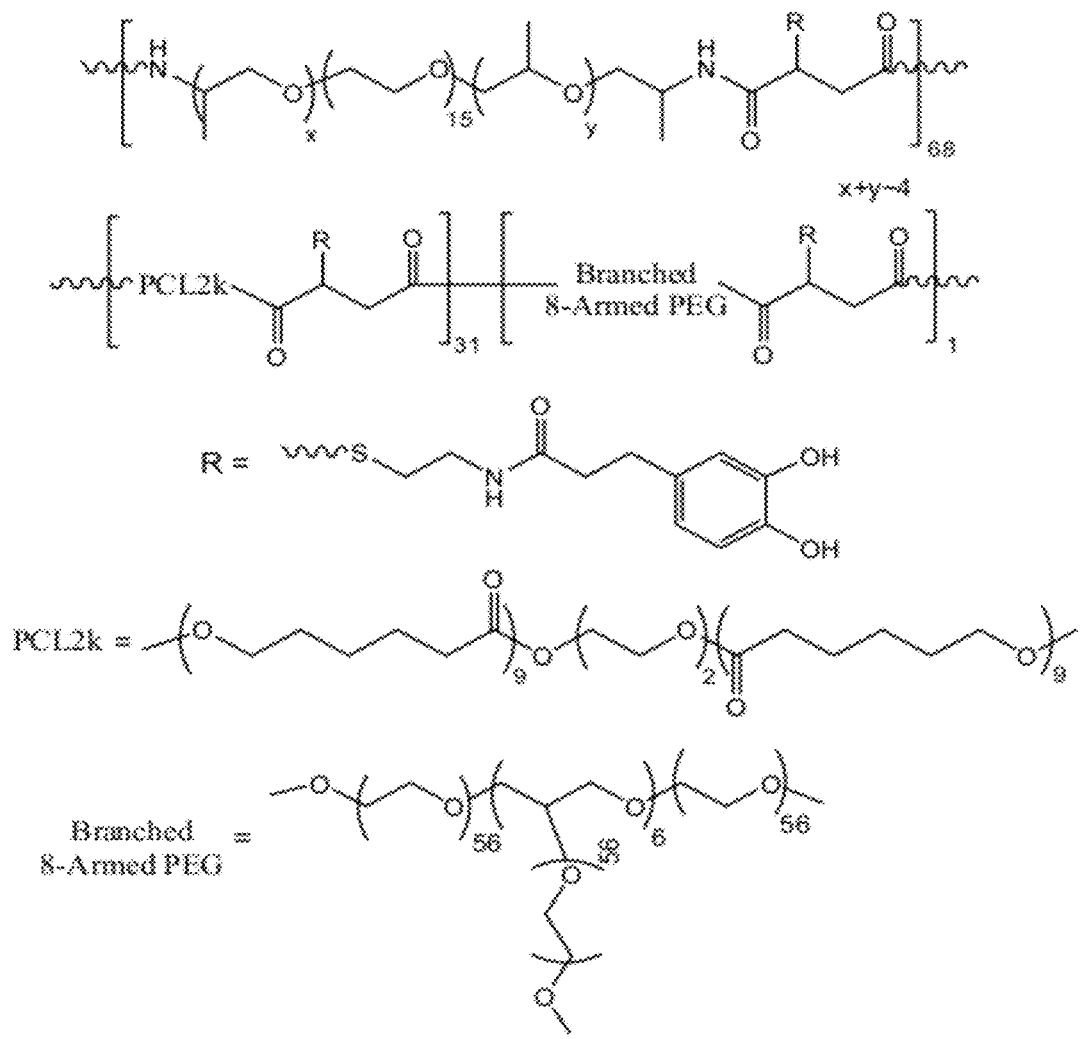
Figure 84:
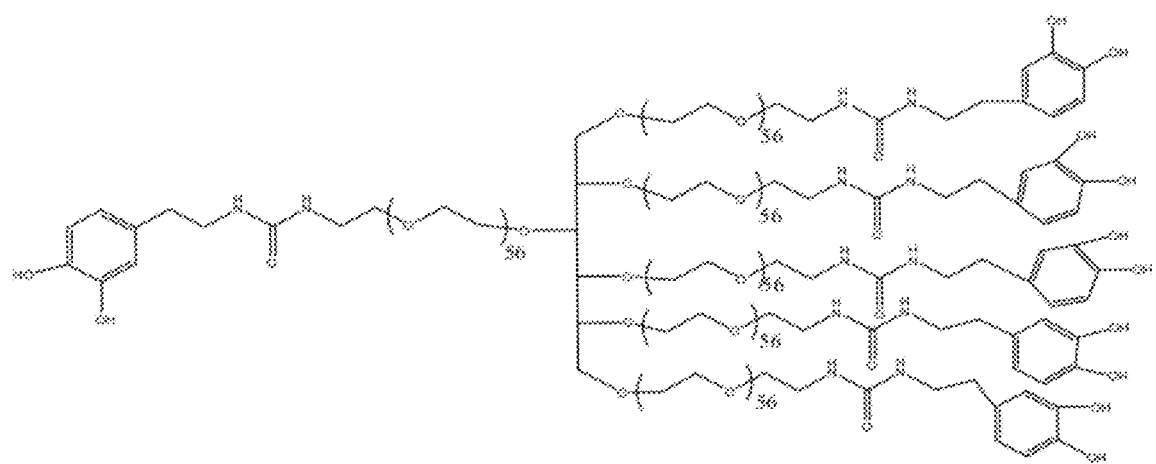
Figure 85:
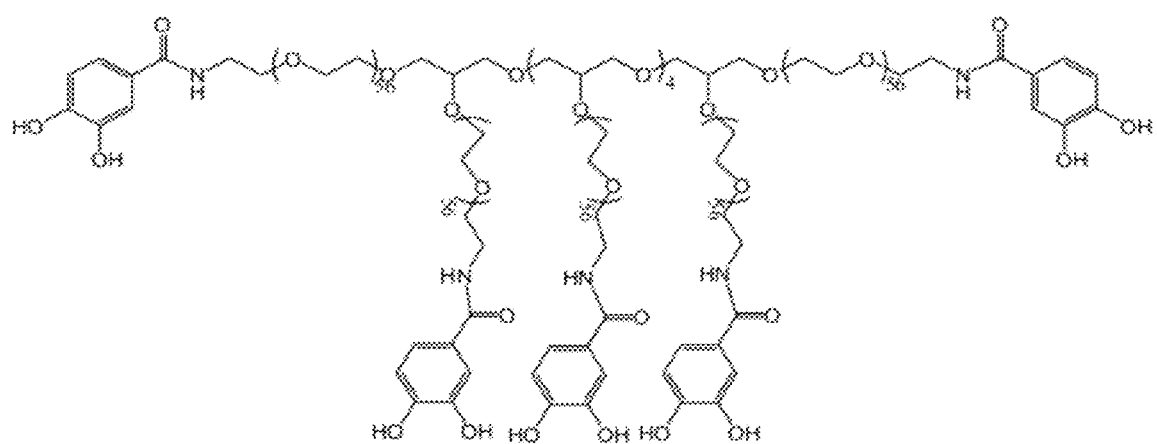
Figure 86:
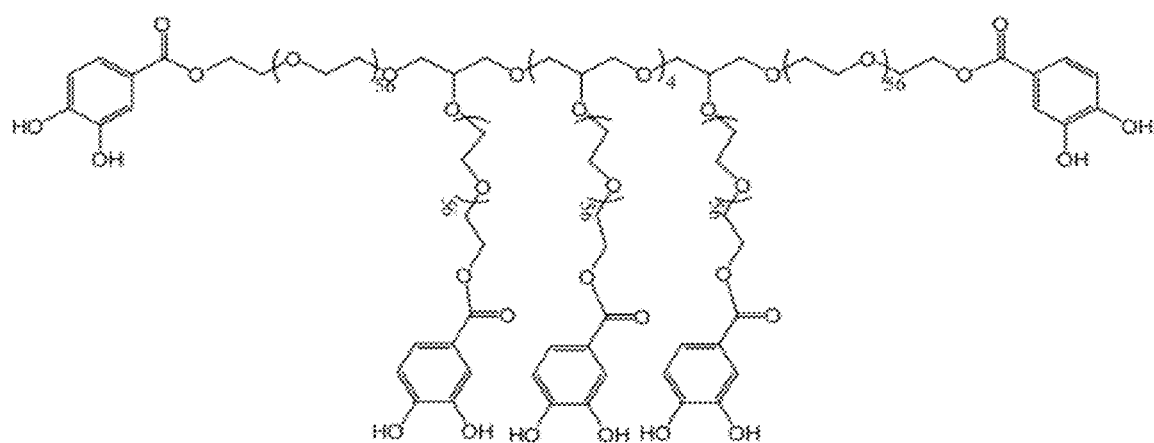
Figure 87:
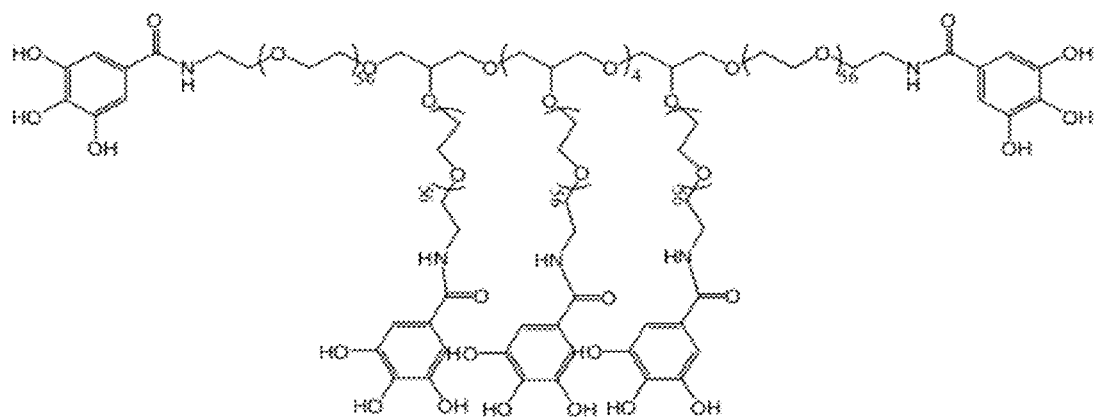
Figure 88:
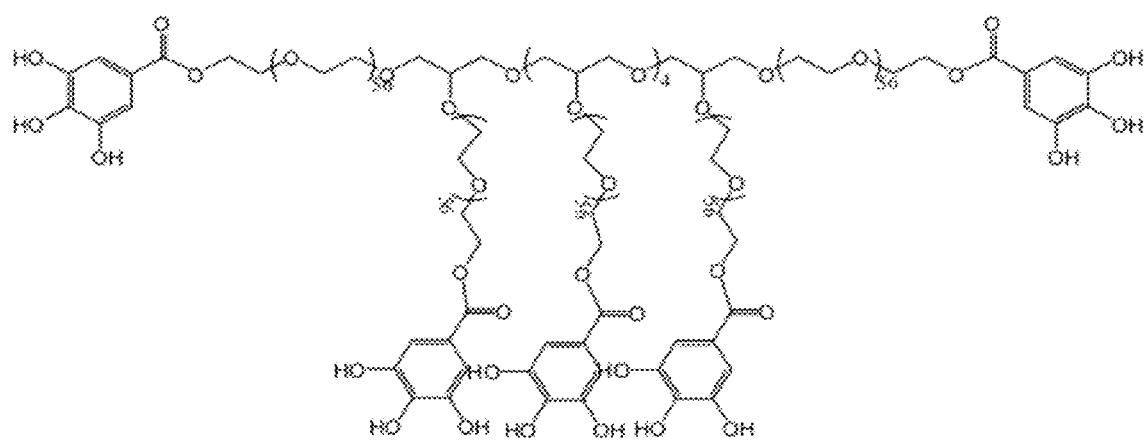
Figure 89:
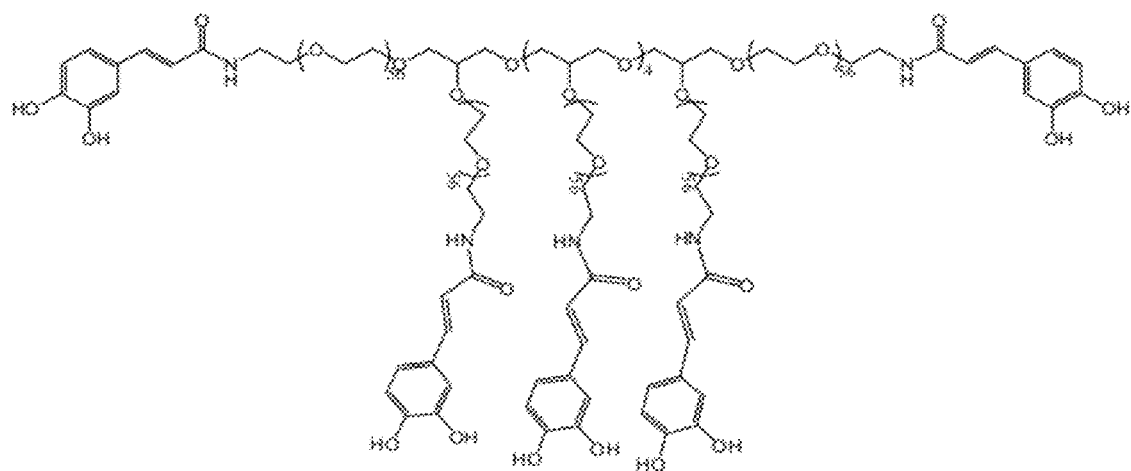
Figure 90:
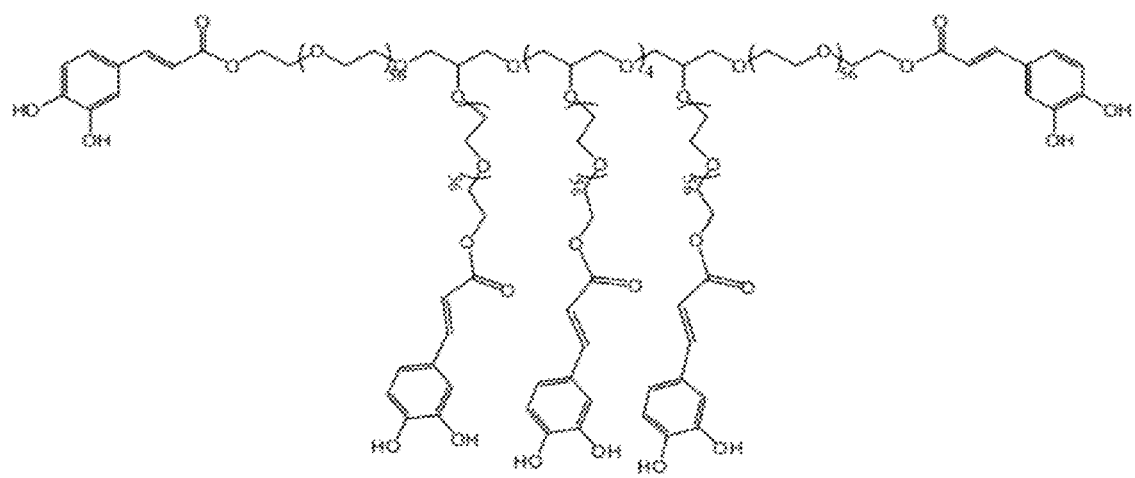
Figure 91:
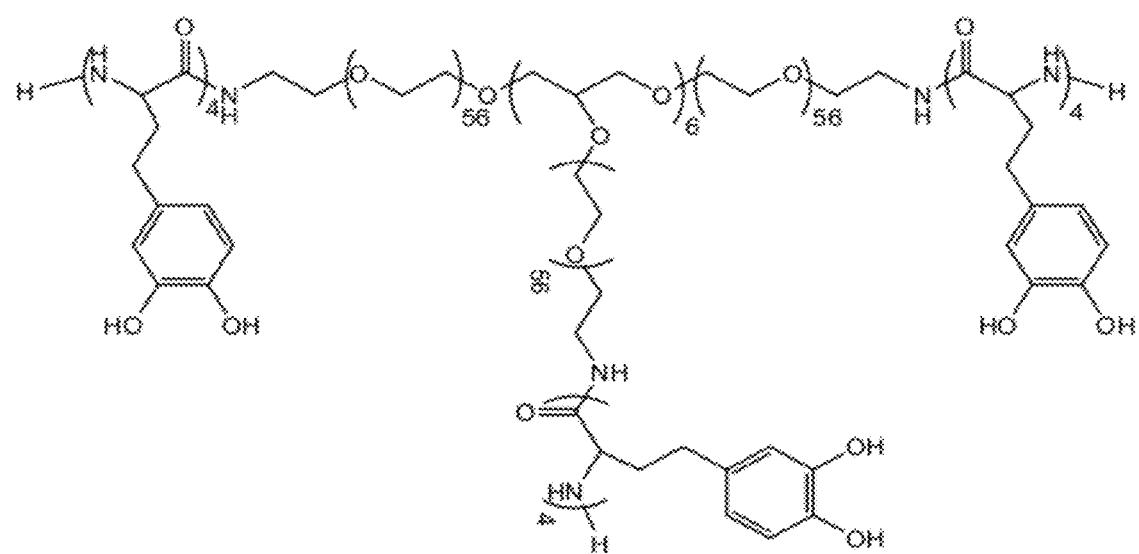
Figure 92:
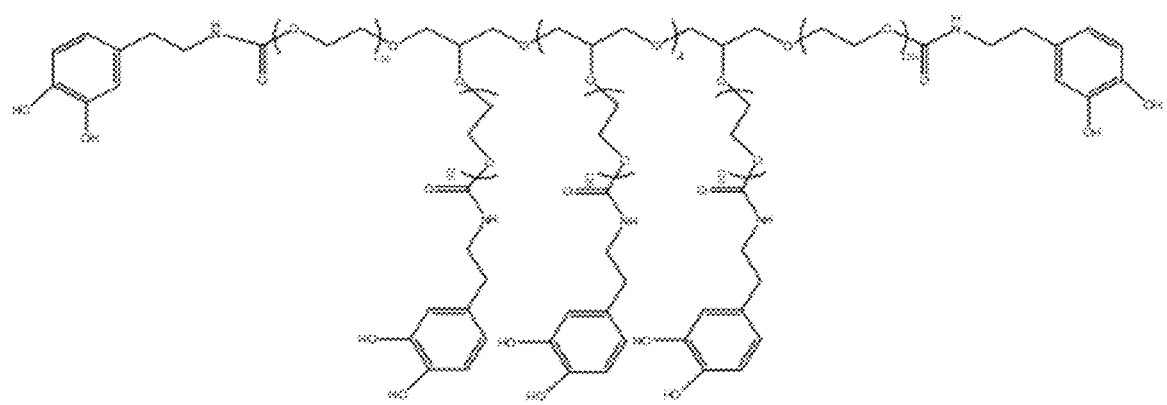
Figure 93:
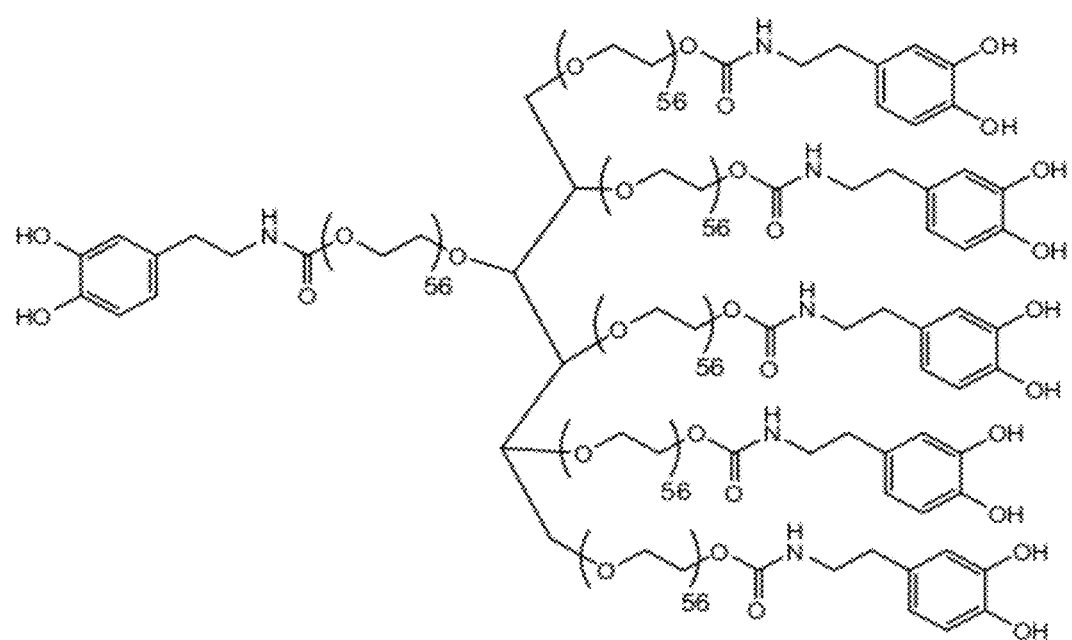
Figure 94:
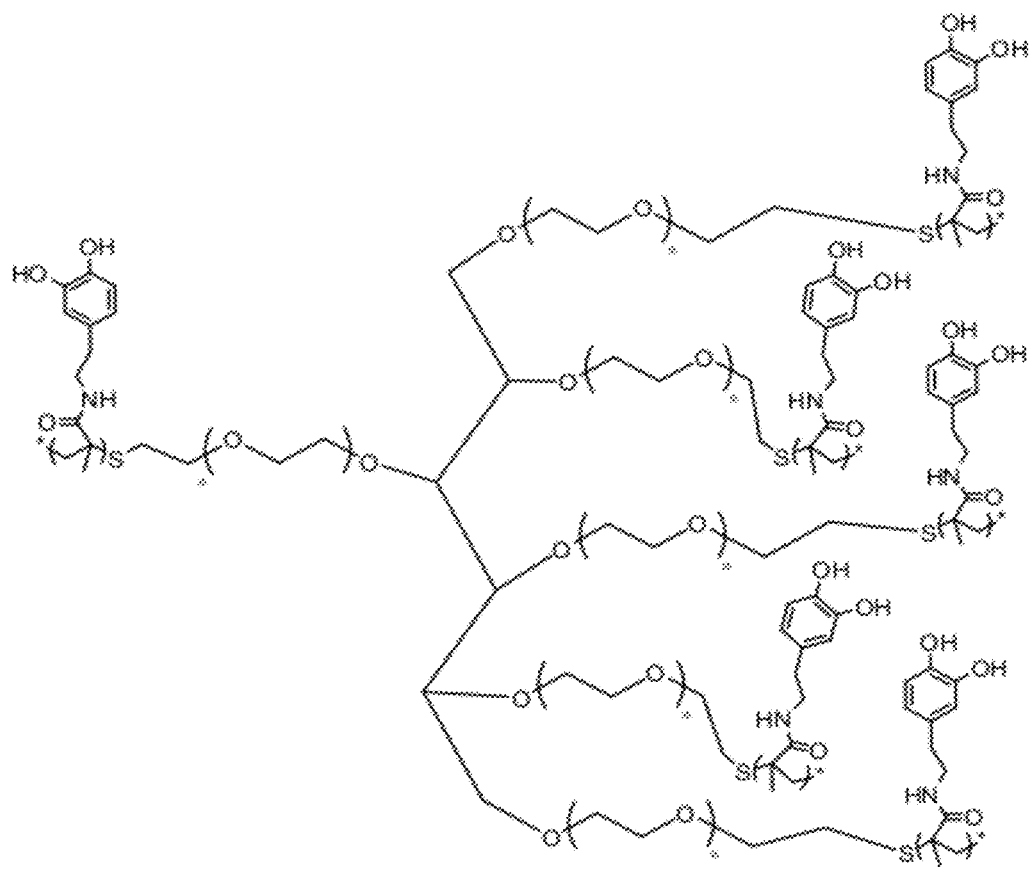
Figure 95:
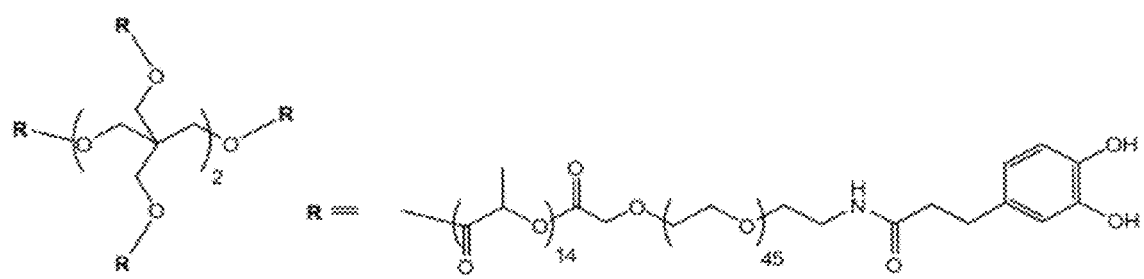
Figure 96:
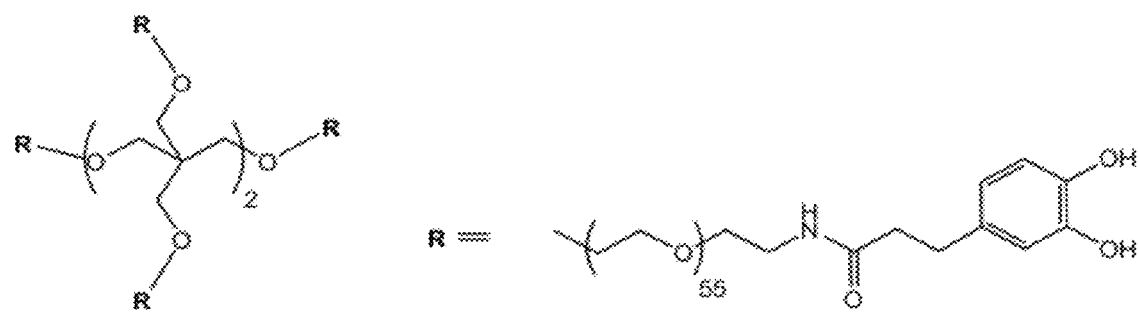
Figure 97:
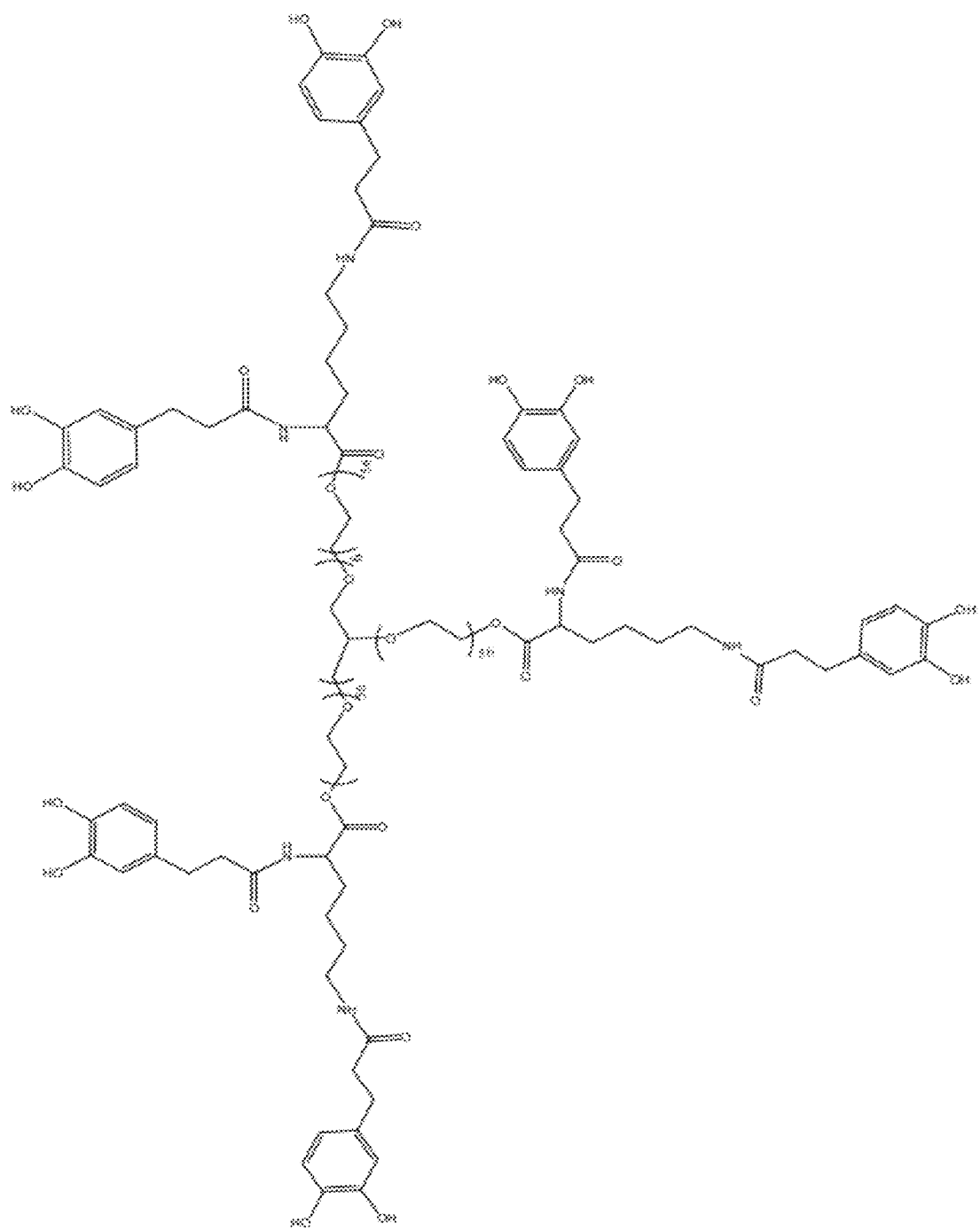

| Name | R&D Name | Description | FIG. No. |
|---|---|---|---|
| Medhesive-068 | PEG20K-(SADMe)8 | Branched, 8-armed PEG-OH (20k MW) coupled with terminal dopamine linked with succinic acid. (ester linkage) | FIG. 78 |
| Medhesive-069 | PEG20K-(GADMe)8 | Branched, 8-armed PEG-OH (20k MW) coupled with terminal dopamine linked with Glutaric acid. (ester linkage) | FIG. 79 |
| Medhesive-070 | PEG20K-(PLASADMe)8 | Branched, 8-armed PEG-OH (20k MW) coupled with terminal dopamine linked with succinic acid and short polylactide. (ester linkage) | FIG. 80 |
| Medhesive-071 | PEG20K-(GlyDHe)8 | Branched, 8-armed PEG-OH (20k MW) coupled with terminal DOHA linked with glycine (ester linkage) | FIG. 81 |
| Medhesive-072 | PEG20K-(DMurea)$_8$ | Branched, 8-armed PEG-NH2 (20k MW) coupled with terminal dopamine linked with urea linkage. | FIG. 82 |
| Medhesive-073 | p(ED1kCL2kEG8b20k1f-g-CADH) | Linear, repeating polymer consisted of PPG-PEG-PPG (900 MW, ~73 wt % PEG), polycaprolactone (2k MW), 8-armed PEG-NH2 (20k) (feed mole ratio = 68:31:1) grafted with DOHA. Chain extension achieved with fumaryl chlorideand grafted with cysteinamine. | FIG. 83 |
| Medhesive-074 | PEG15K-(DMUrea)$_6$ | Branched, 6-arm PEG-NH2 (15k) coupled with terminal dopamine linked with urea linkage. | FIG. 84 |
| Medhesive-075 | PEG20K-(BA)8 | Branched, 8-arm PEG-NH2 (20k MW) coupled with terminal 3,4-dihydroxybenzoic acid linked with amide linkage. | FIG. 85 |
| Medhesive-076 | PEG20K-(BAe)8 | Branched, 8-arm PEG-OH (20k MW) coupled with terminal 3,4-dihydroxybenzoic acid linked with ester linkage. | FIG. 86 |
| Medhesive-077 | PEG20K-(GA)8 | Branched, 8-arm PEG-NH2 (20k MW) coupled with terminal 3,4,5-trihydroxybenzoic acid (gallic acid) linked with amide linkage. | FIG. 87 |
| Medhesive-078 | PEG20K-(GAe)8 | Branched, 8-arm PEG-NH2 (20k MW) coupled with terminal 3,4,5-trihydroxybenzoic acid (gallic acid) linked with ester linkage. | FIG. 88 |
| Medhesive-079 | PEG20K-(CA)8 | Branched, 8-arm PEG-NH2 (20k MW) coupled with terminal caffeic acid linked with amide linkage. | FIG. 89 |
| Medhesive-080 | PEG20K-(CAe)8 | Branched, 8-arm PEG-NH2 (20k MW) coupled with terminal caffeic acid linked with ester linkage. | FIG. 90 |
| Medhesive-081 | PEG20k-(DOPA4)8 | Branched, 8-arm PEG-NH2 (20k MW) coupled with short oligo-peptide of poly(DOPA). | FIG. 91 |
| Medhesive-082 | PEG40k-(Dmu)$_8$ | Branched, 8-armed PEG-OH (40k MW) coupled with terminal dopamine linked via urethane linkage. | FIG. 92 |
| Medhesive-083 | PEG15k-(Dmu)$_6$ | Branched, 6-armed PEG-OH (15k MW) coupled with terminal dopamine linked via urethane linkage. | FIG. 93 |
| Medhesive-084 | PEG15k-(SH-p(DMA3))$_6$ | Branched, 6-arm PEG-0H (15k MW) modified with p(DMA3) via a thiol linkage. | FIG. 94 |
| Medhesive-085 | dpe-PLA6k-(EG2kDHe)6 | Branched 6-arm PLA (6k MW, based on dipentaerythritol) modified with a HOOC-PEG-NH2 (2k MW) and DOHA at each terminal group. | FIG. 95 |
| Medhesive-086 | dpe-PEG15k-(DH)6 | Branched 6-arm PEG (15k MW, based on dipentaerythritol) modified with DOHA. | FIG. 96 |
| Medhesive-087 | PEG20K-(LyseDH2)8 | Branched, 8-armed PEG-OH (20k MW) coupled with terminal DOHA linked with Lysine (ester linkage) | FIG. 97 |

TABLE 1-continued

Figure 98:
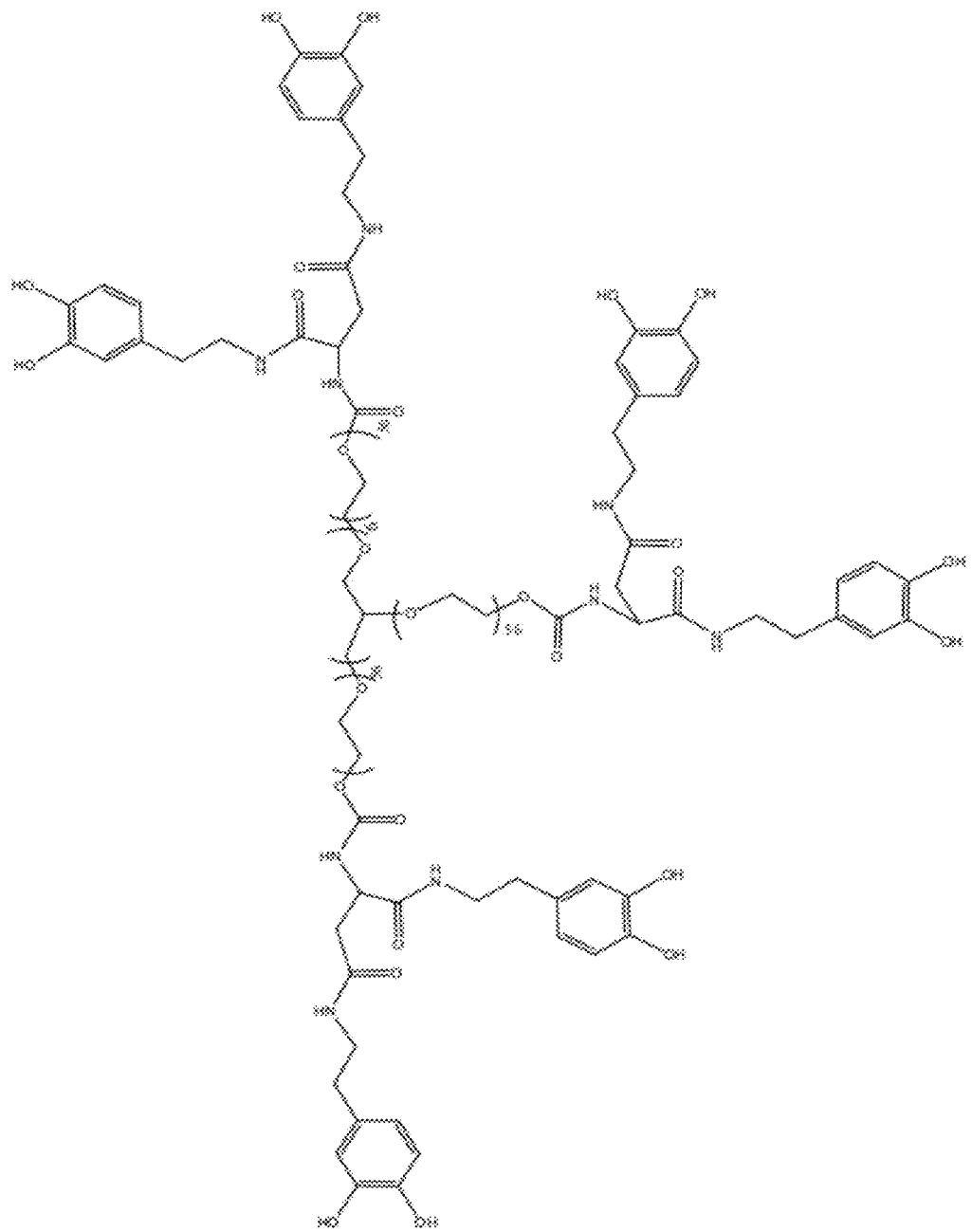
Figure 99:
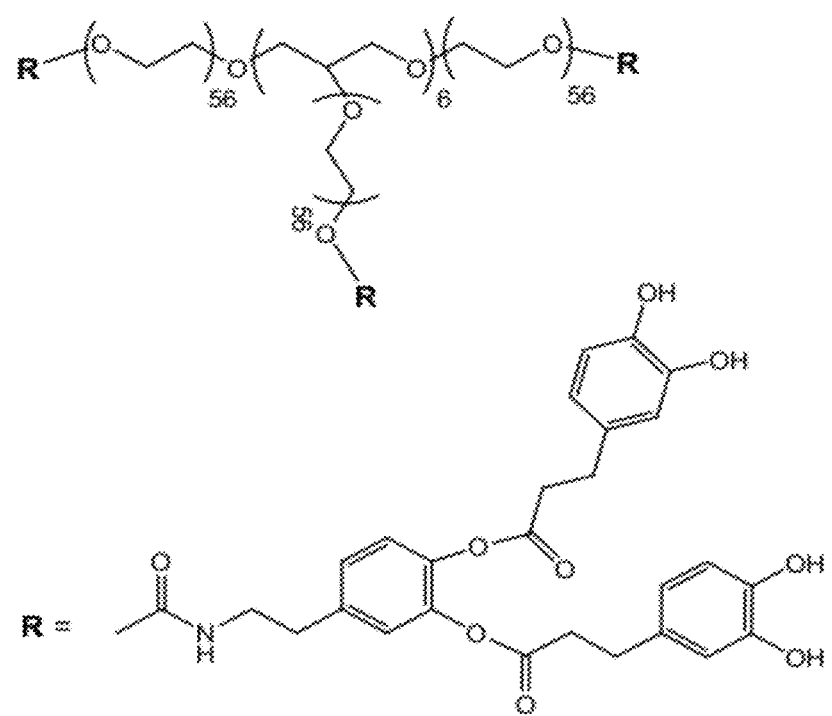
Figure 100:
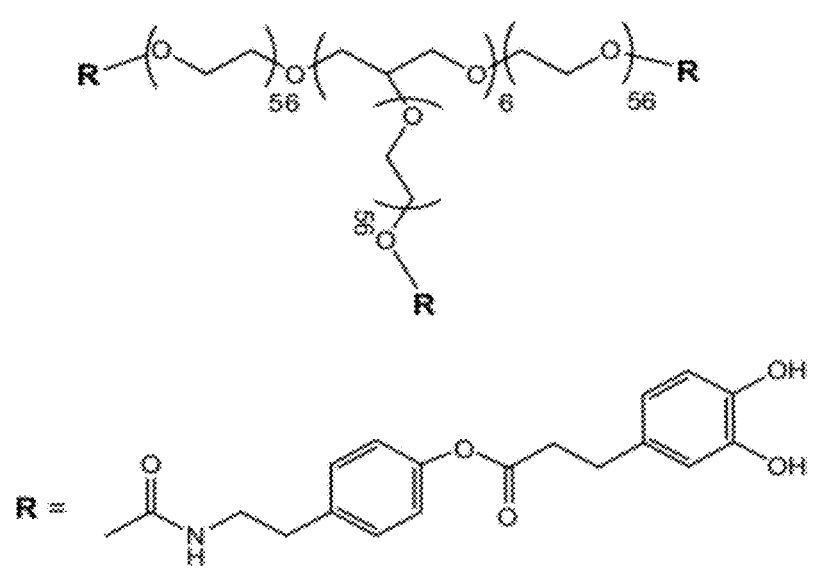
Figure 101:
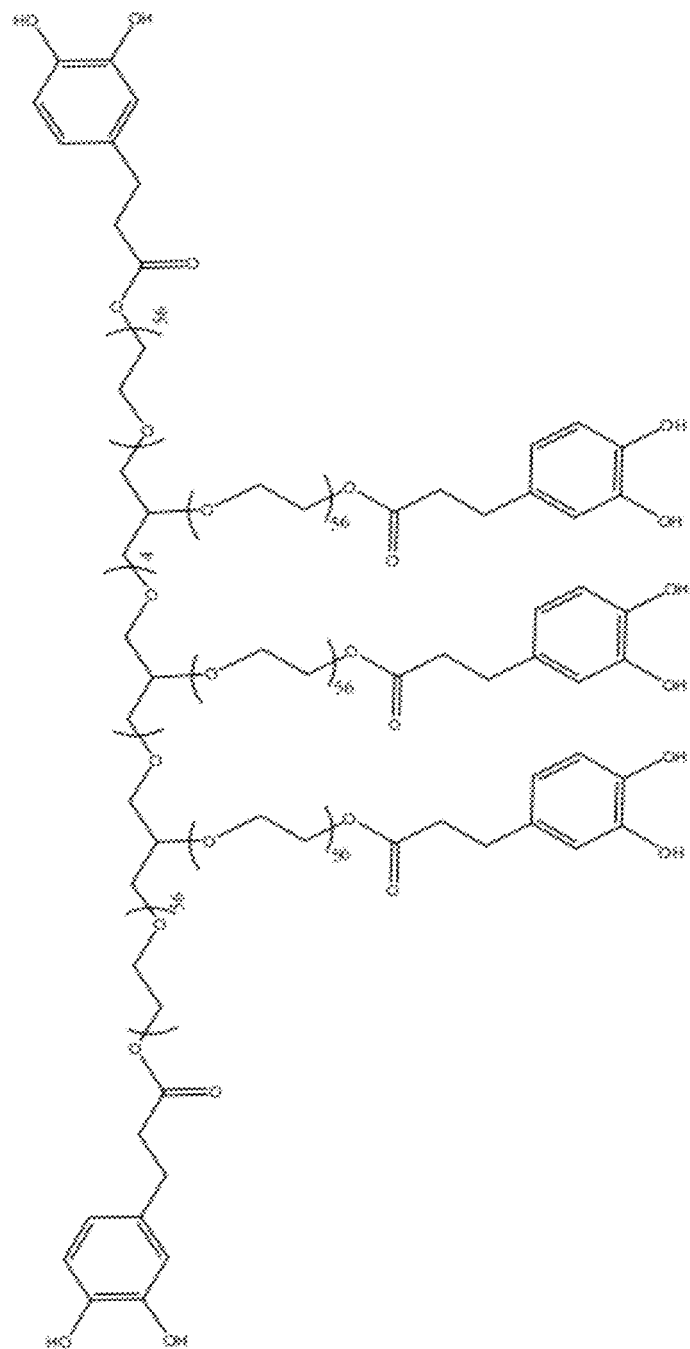
Figure 102:
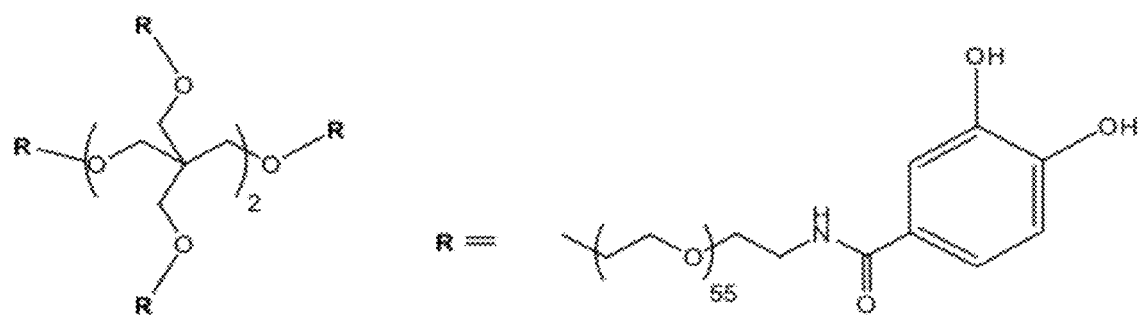
Figure 103:
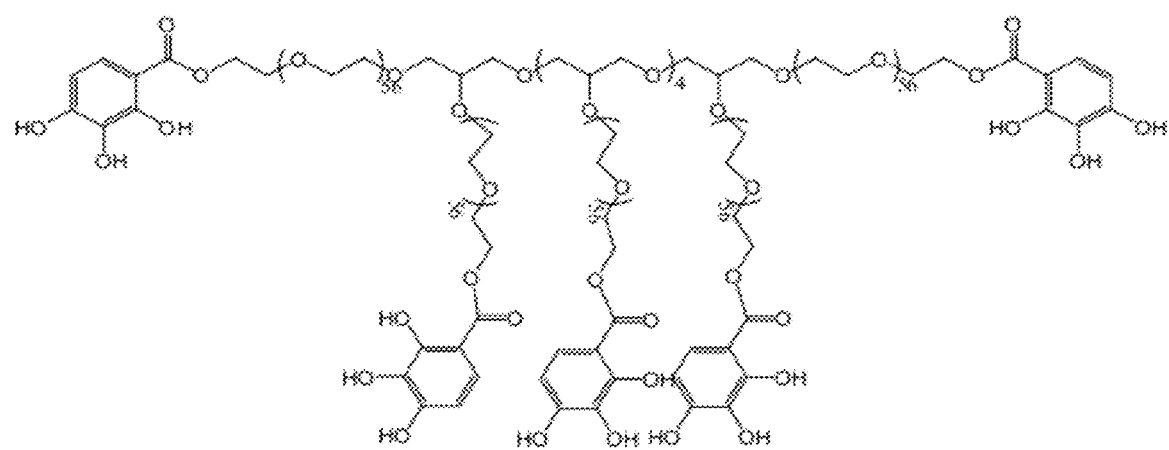
Figure 104:
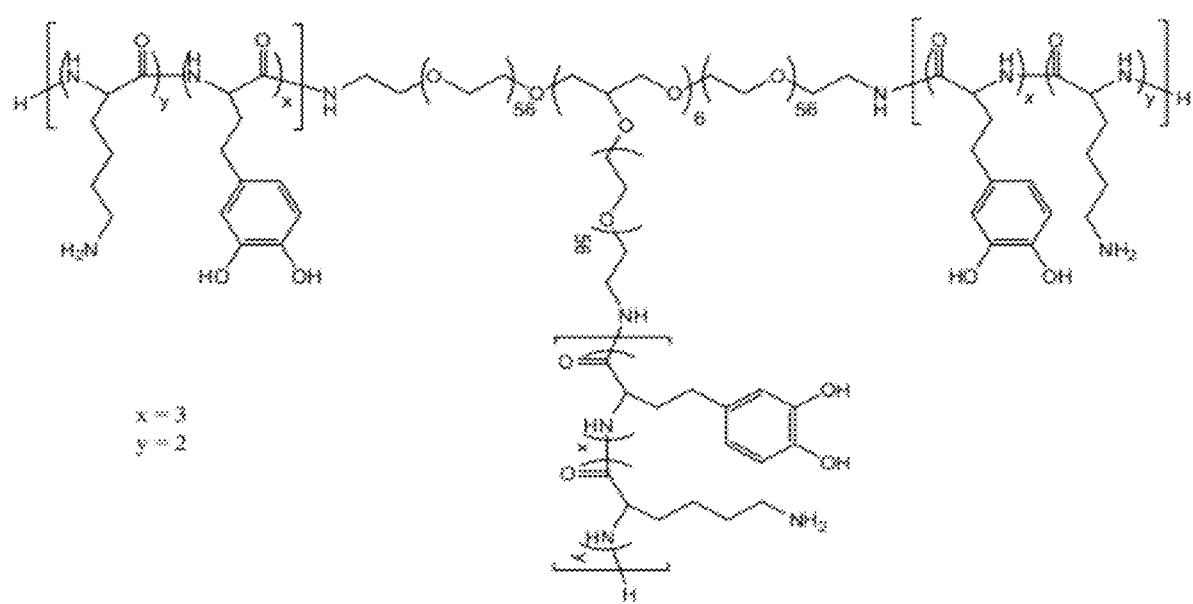
Figure 105:
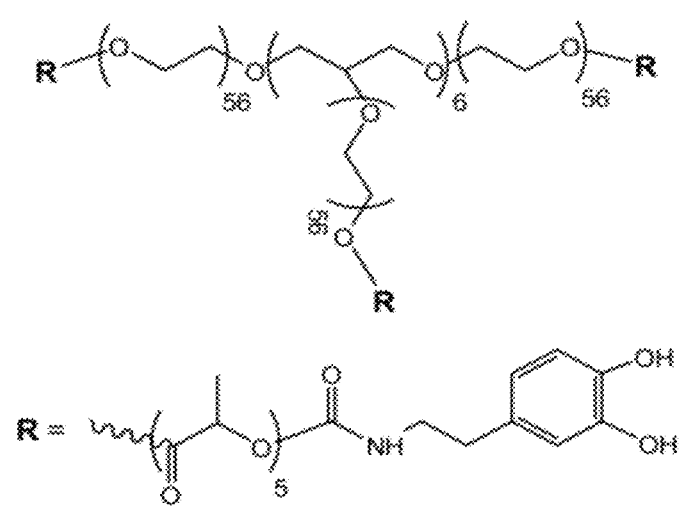
Figure 106:
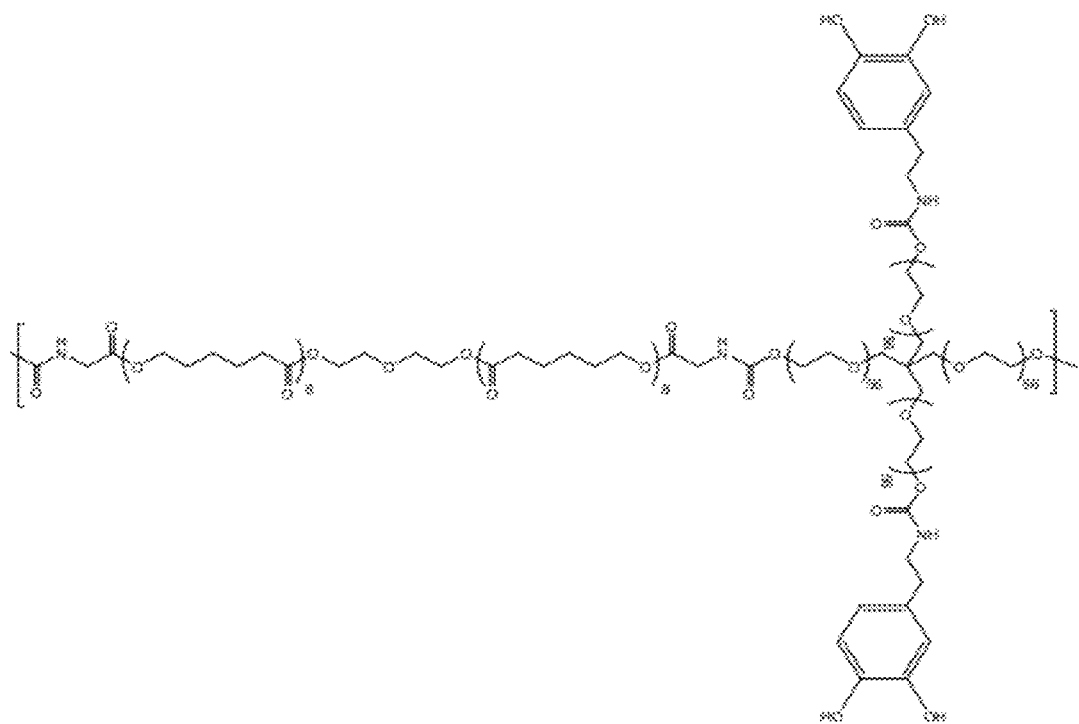
Figure 107:
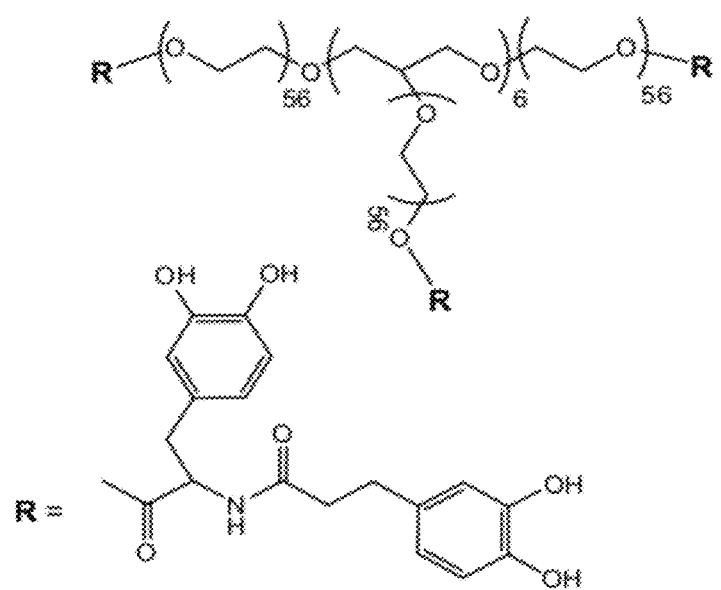
Figure 108:
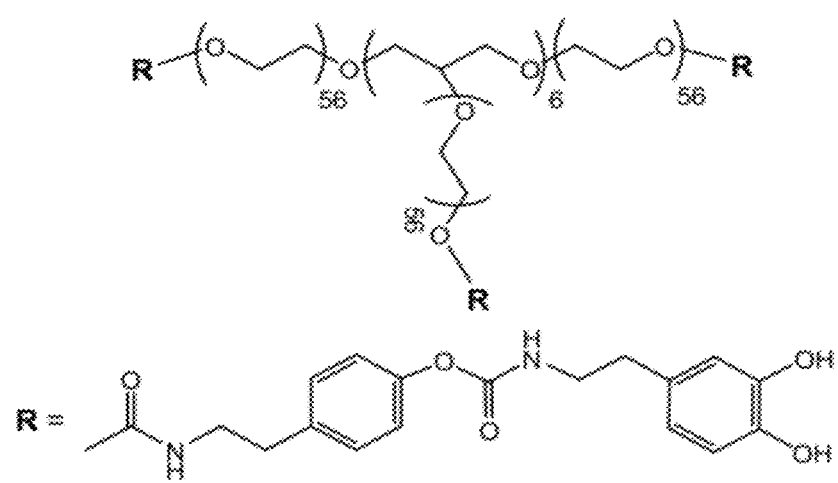
Figure 109:
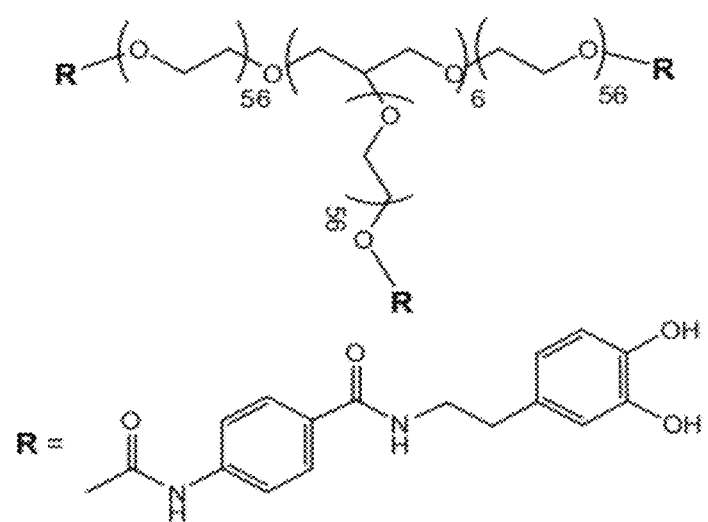
Figure 110:
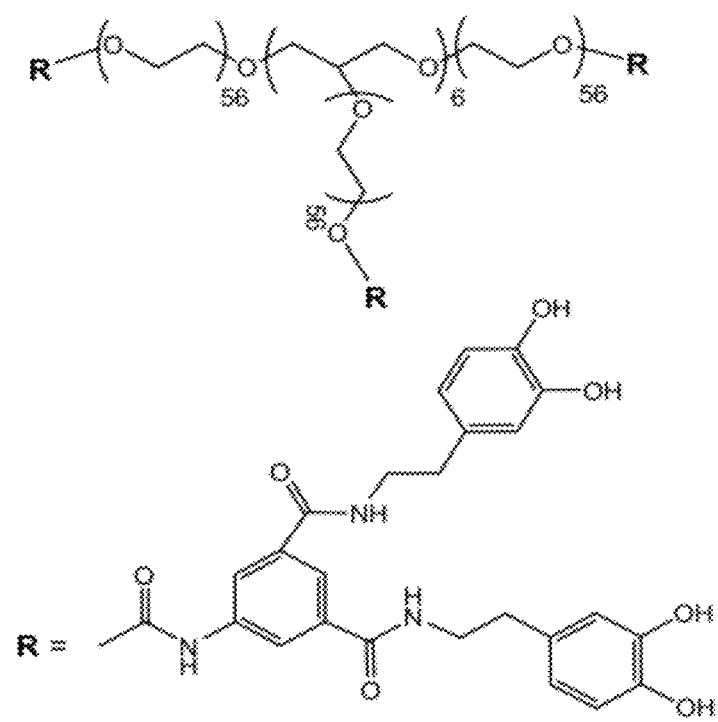
Figure 111:
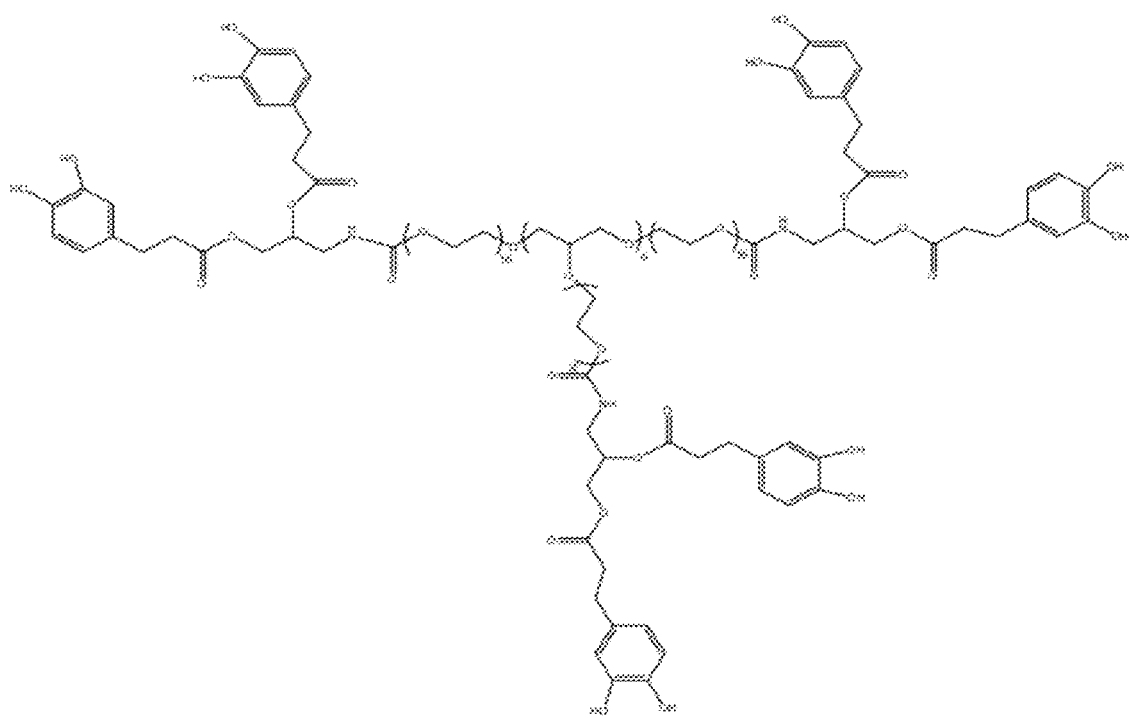
Figure 112:
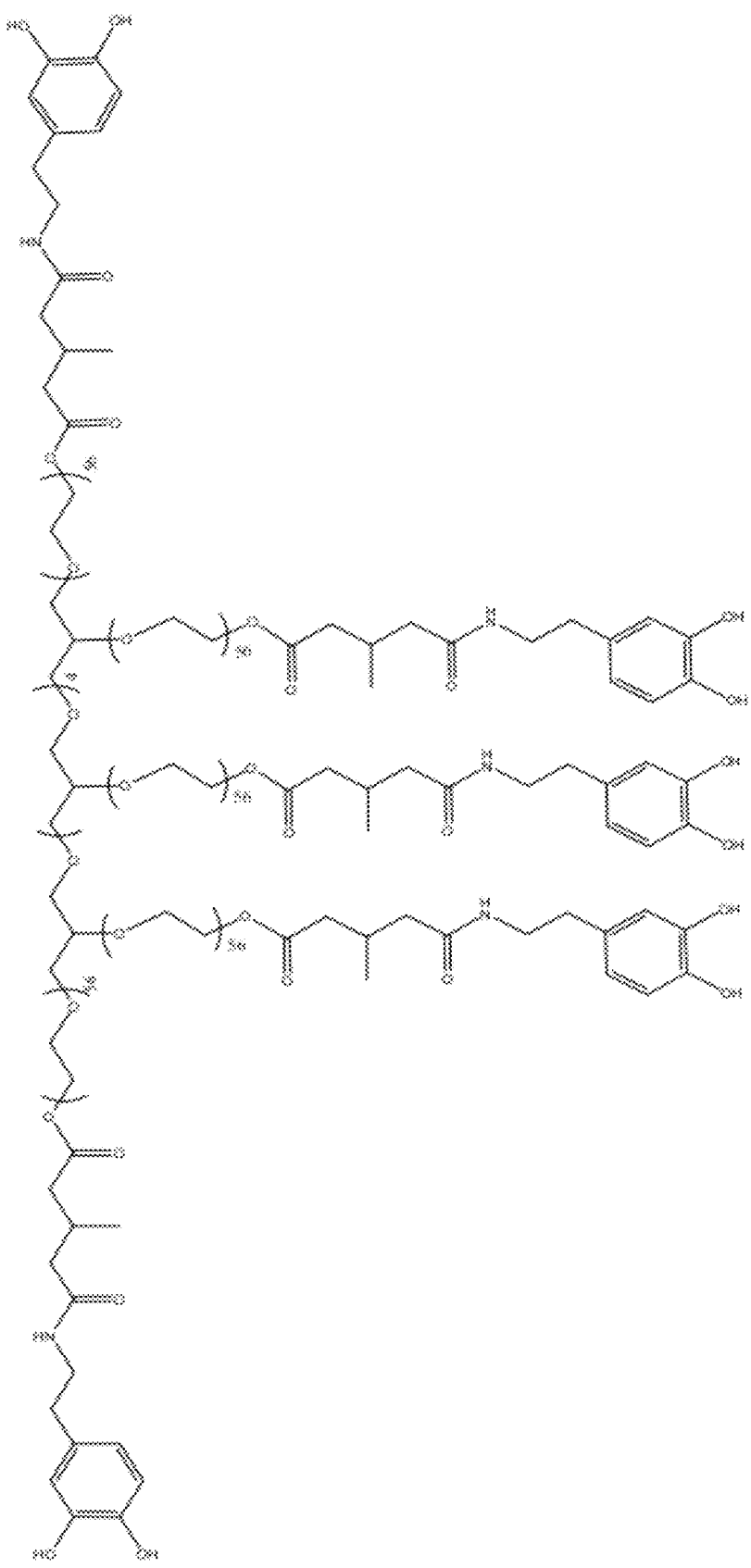
Figure 113:
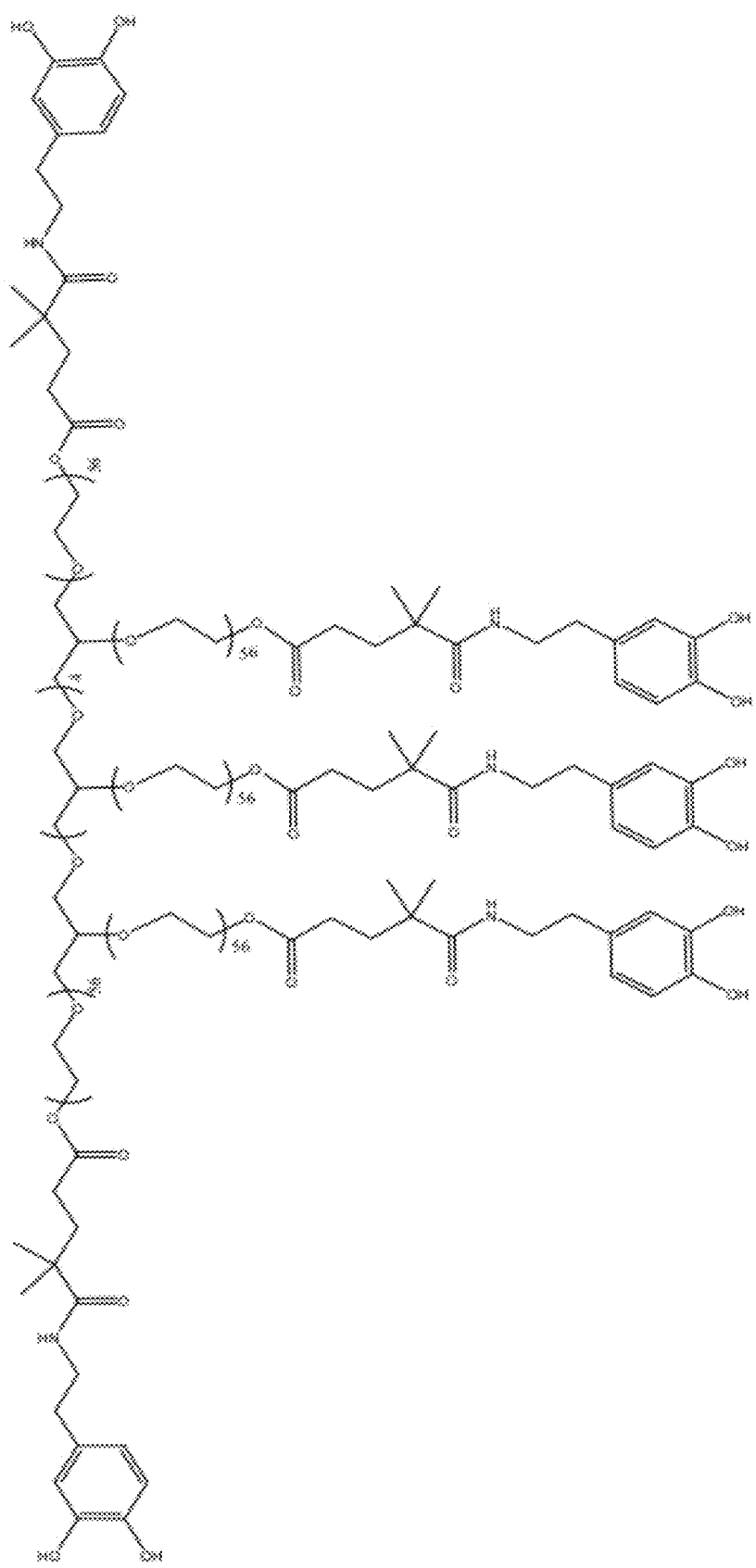
Figure 114:
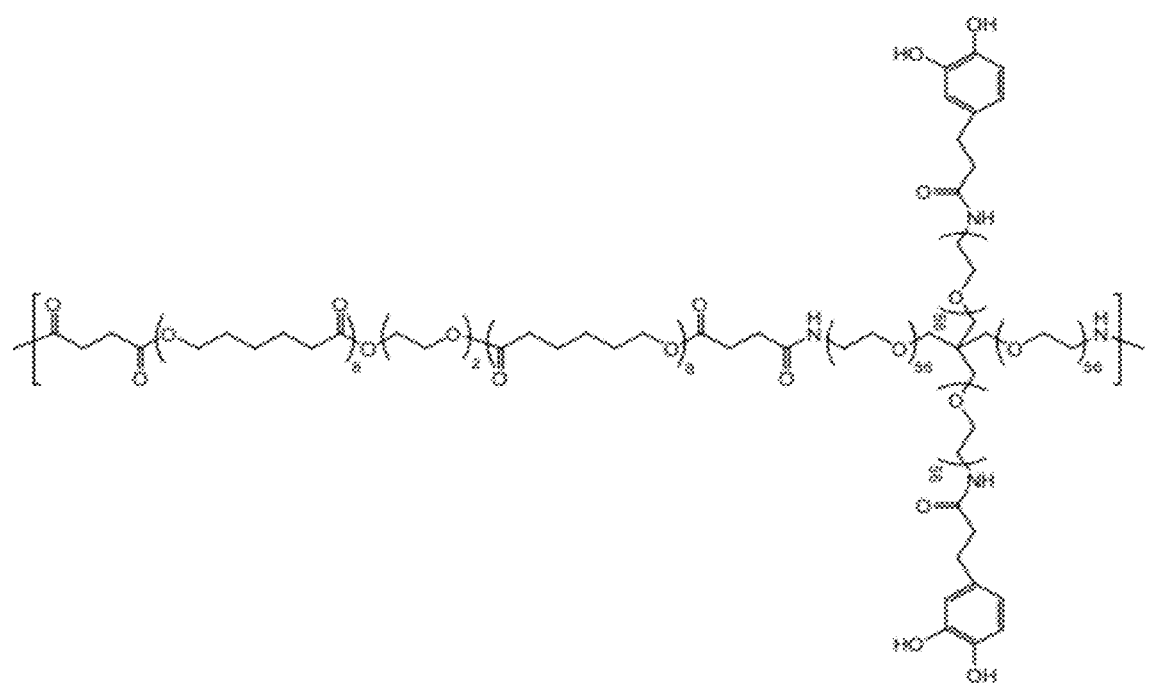

| Name | R&D Name | Description | FIG. No. |
|---|---|---|---|
| Medhesive-088 | PEG20K-(AspDH2)8 | Branched, 8-armed PEG-OH (20k MW) coupled with terminal DOHA linked with Aspartic acid (urethane linkage) | FIG. 98 |
| Medhesive-089 | PEG20K-(DMuDH2e)8 | Branched, 8-armed PEG-OH (20k MW) coupled with dopamine (urethane linkage), with its 2 sidechain phenols coupled with DOHA through ester linkages. | FIG. 99 |
| Medhesive-090 | PEG20K-(TMuDHe)8 | Branched, 8-armed PEG-OH (20k MW) coupled with tyramine (urethane linkage), with its sidechain phenol coupled with DOHA through ester linkage. | FIG. 100 |
| Medhesive-091 | PEG20K-(DH)8 | Branched, 8-armed PEG-OH (20k MW) coupled with terminal DOHA | FIG. 101 |
| Medhesive-092 | PEG15k-dpe-(BA)6 | Branched, 6-arm dipentaerythritol PEG-NH2 (15K MW) coupled to 3,4-dihydroxybenzoic acid through an amide linkage. | FIG. 102 |
| Medhesive-093 | PEG20k-(THBA)8 | Branched, 8-arm PEG-OH (20K MW) coupled to 2,3,4-trihydroxybenzoic acid through an ester linkage. | FIG. 103 |
| Medhesive-094 | PEG20k-(DOPA3-Lys2)8 | Branched, 8-arm PEG-NH2 (20k MW) coupled with short oligo-peptide of poly(DOPA-Lys). | FIG. 104 |
| Medhesive-095 | PEG20k-(PLADMu)8 | Branched, 8-armed PEG-OH (20k MW) with a short polylactide block terminated with dopamine coupled through urethane linkage | FIG. 105 |
| Medhesive-096 | p(CL2kGEG10kb-g-DMu2) | Multi-branched polymer constructed from PCL-(Gly)2 2k and 4-arm PEG-OH 10k (1:1 feed ratio) modified with Dopamine. Urethane linkages. | FIG. 106 |
| Medhesive-097 | PEG20k-(DeDH)8 | Branched, 8-armed PEG-OH (20k MW) terminated with a short DOPA-DOHA peptide, where the DOPA is couple to the PEG-OH with ester linkage | FIG. 107 |
| Medhesive-098 | PEG20k-(TMuDMu)8 | Branched, 8-armed PEG-OH (20k MW) coupled with tyramine (urethane linkage), with its sidechain phenol coupled with dopamine through urethane linkage. | FIG. 108 |
| Medhesive-099 | PEG20k-(ABAuDM)8 | Branched, 8-armed PEG-OH (20k MW) coupled with 4-aminobenzoic acid (urethane linkage), with its sidechain carboxyl group coupled with dopamine through amide linkage. | FIG. 109 |
| Medhesive-100 | PEG20k-(AIPuDM2)8 | Branched, 8-armed PEG-OH (20k MW) coupled with 5-Aminoisophthalic acid (urethane linkage), with its sidechain carboxyl group coupled with 2 dopamine through amide linkage. | FIG. 110 |
| Medhesive-101 | PEG20k-(APDuDH2)8 | Branched, 8-armed PEG-OH (20k MW) coupled with 3-Amino-1,2-propandiol (urethane linkage), with the sidechain hydroxyl groups coupled with DOHA through ester linkages. | FIG. 111 |
| Medhesive-102 | PEG20K-(MGADMe)8 | Branched, 8-armed PEG-OH (20k MW) coupled with terminal dopamine linked with 3-Methyl Glutaric acid. (ester linkage) | FIG. 112 |
| Medhesive-103 | PEG20K-(DMGADMe)8 | Branched, 8-armed PEG-OH (20k MW) coupled with terminal dopamine linked with 2,2-Dimethyl Glutaric acid. (ester linkage) | FIG. 113 |
| Medhesive-104 | p(CL2kEG10kb-g-DH2) | Branched polymer constructed from PCL-diSA 2k and 4-arm PEG-NH2 10k (1:1 feed ratio) modified with DOHA. (Amide linkage) | FIG. 114 |

TABLE 1-continued

Figure 115:
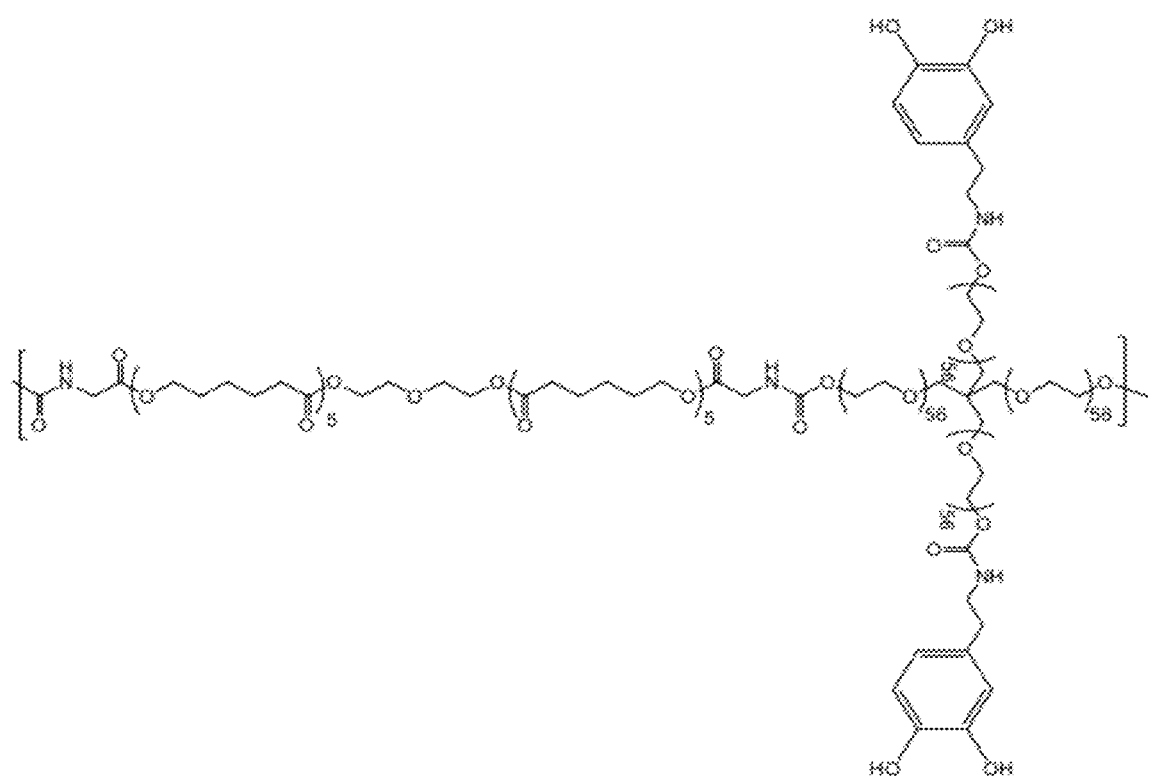
Figure 116:
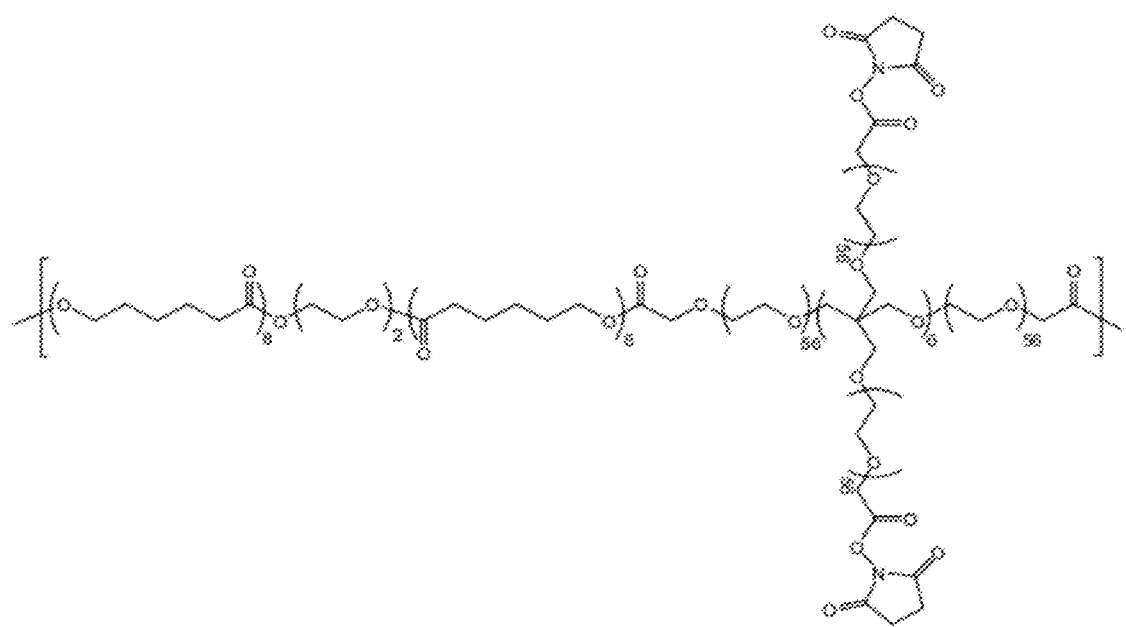
Figure 117:
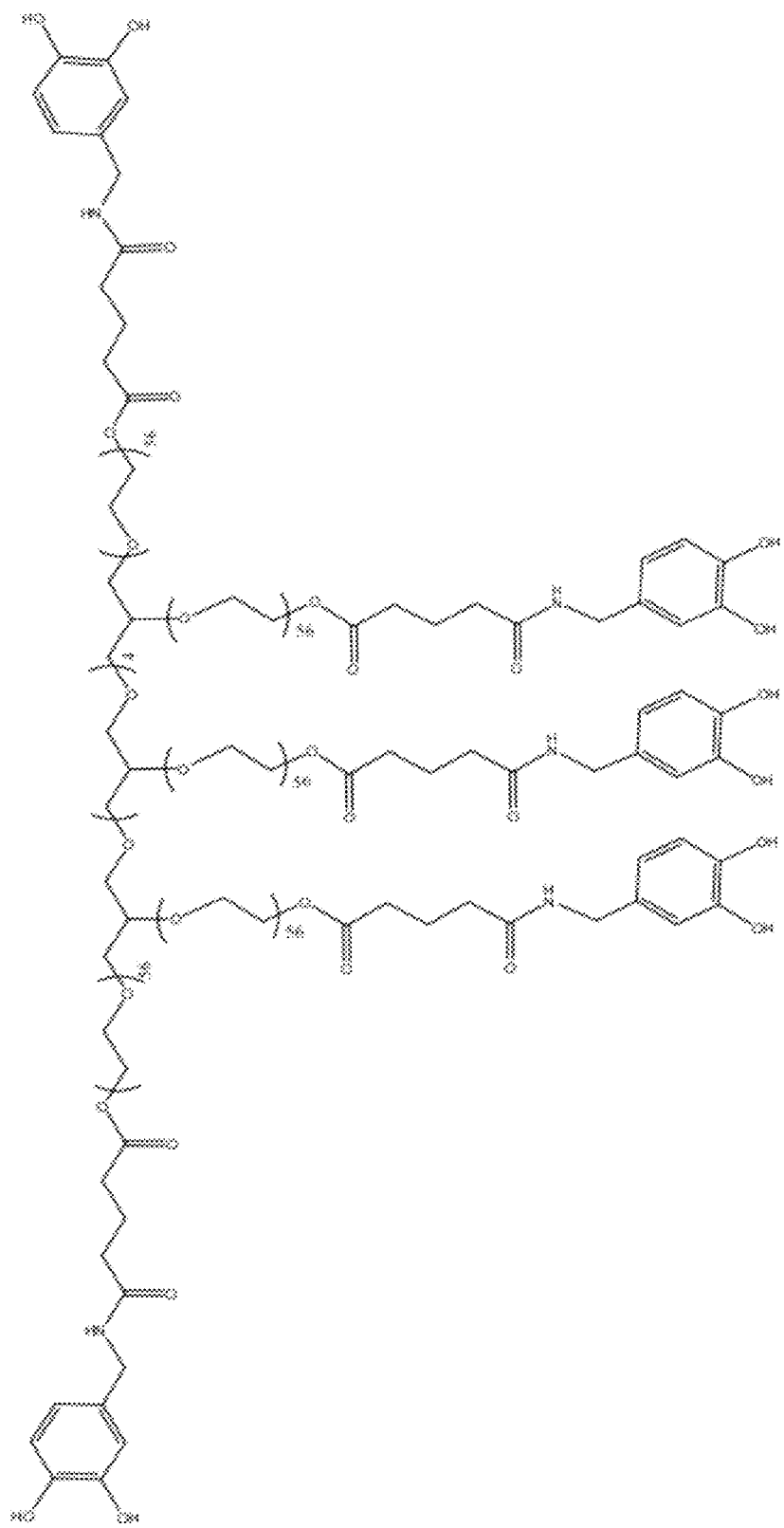
Figure 118:
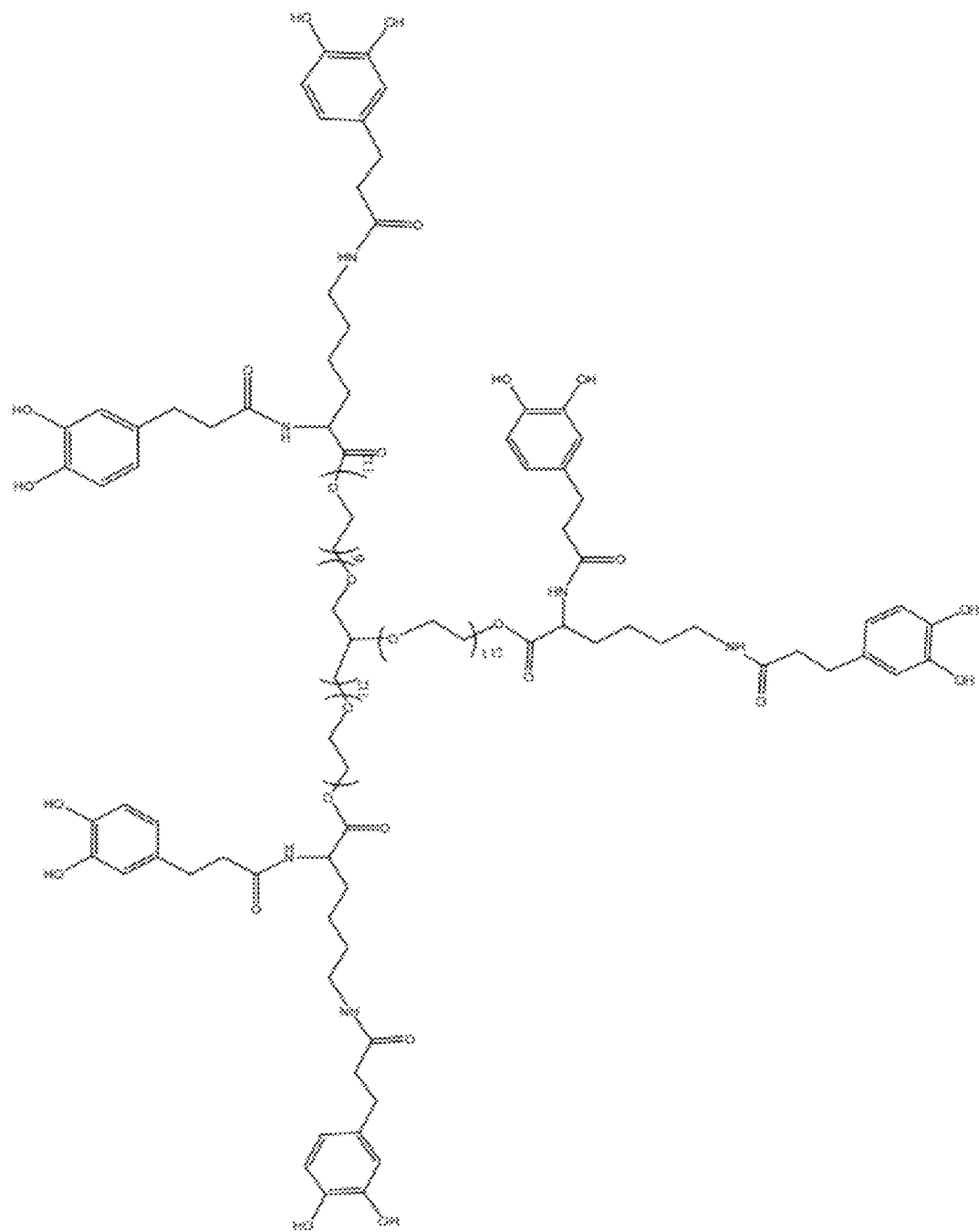
Figure 119:
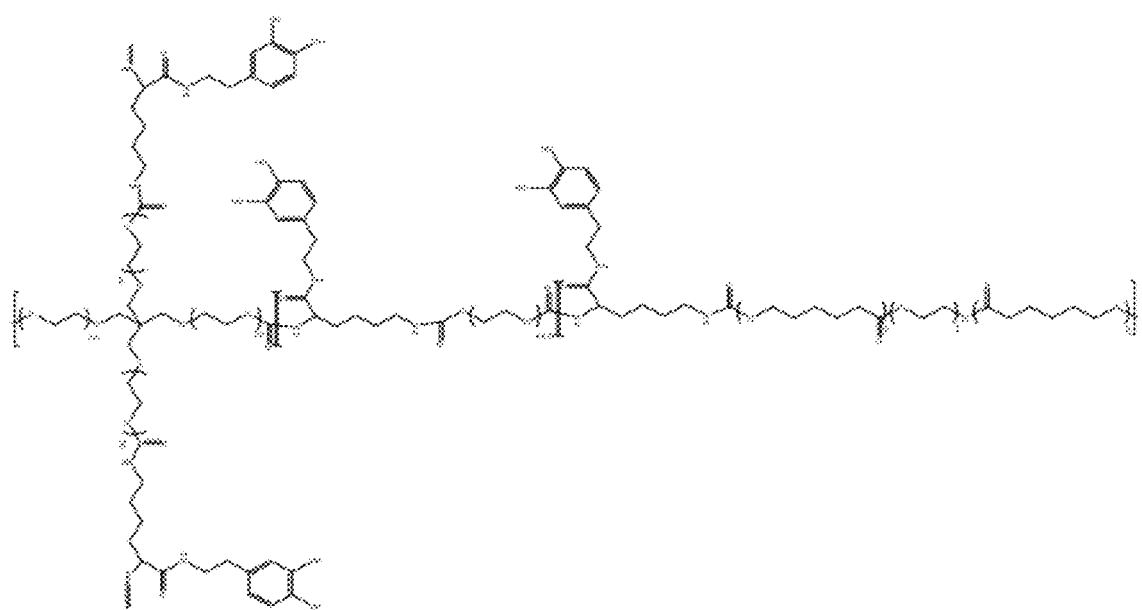
Figure 120:
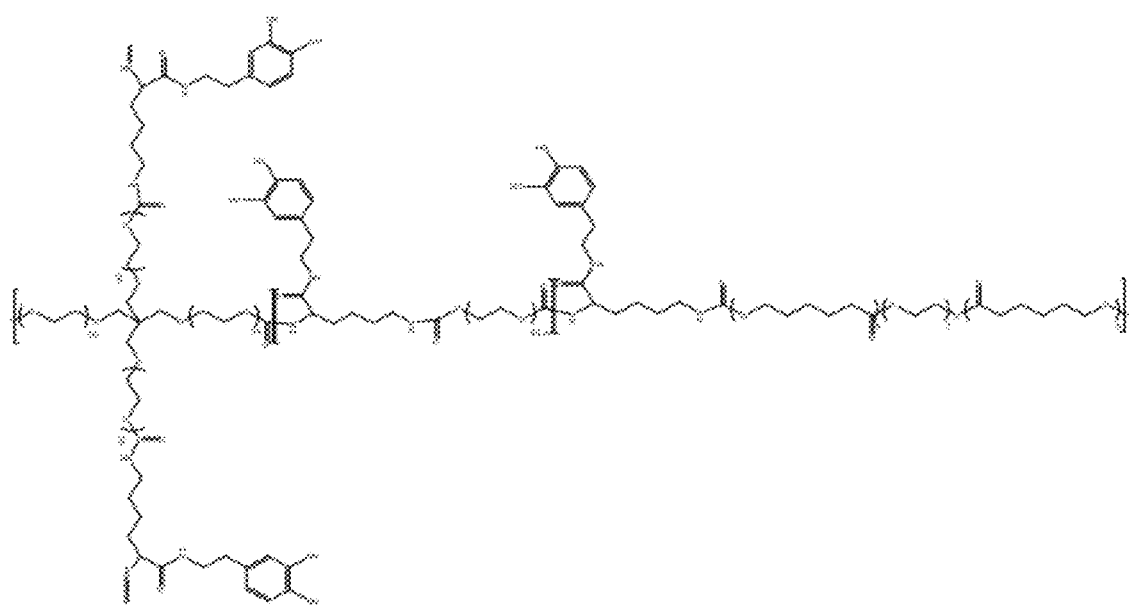
Figure 121:
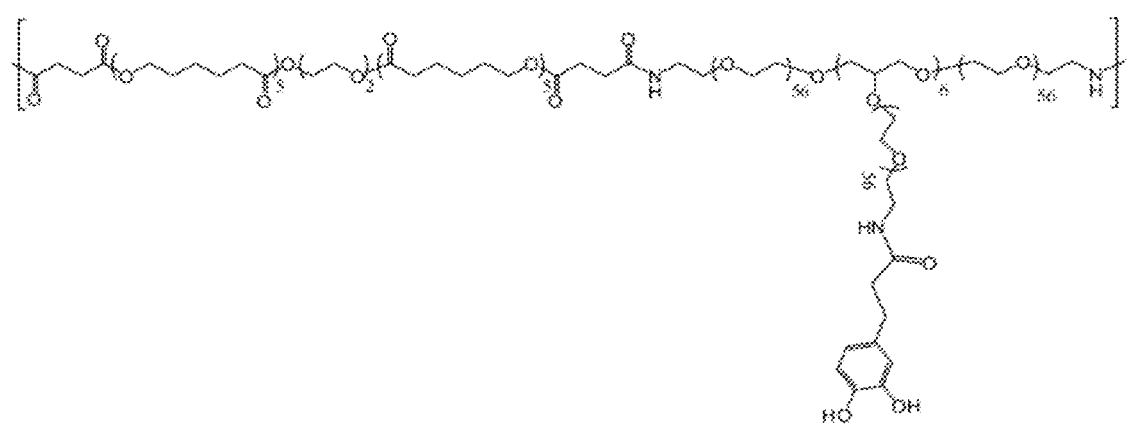
Figure 122:
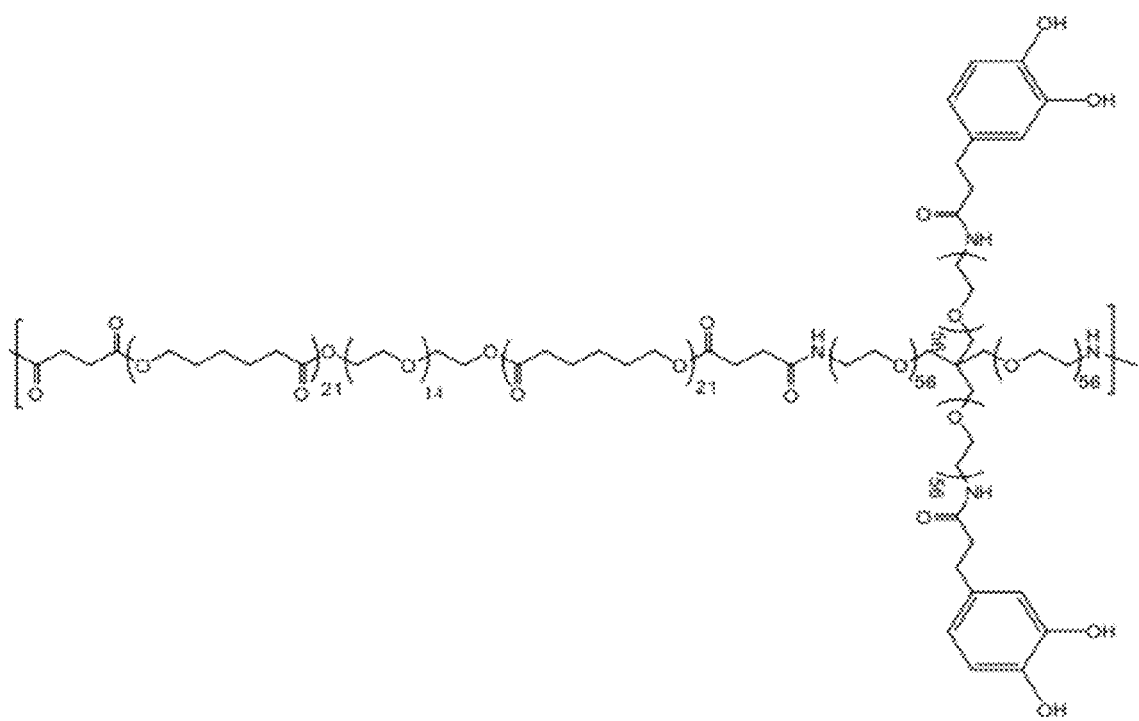
Figure 123:
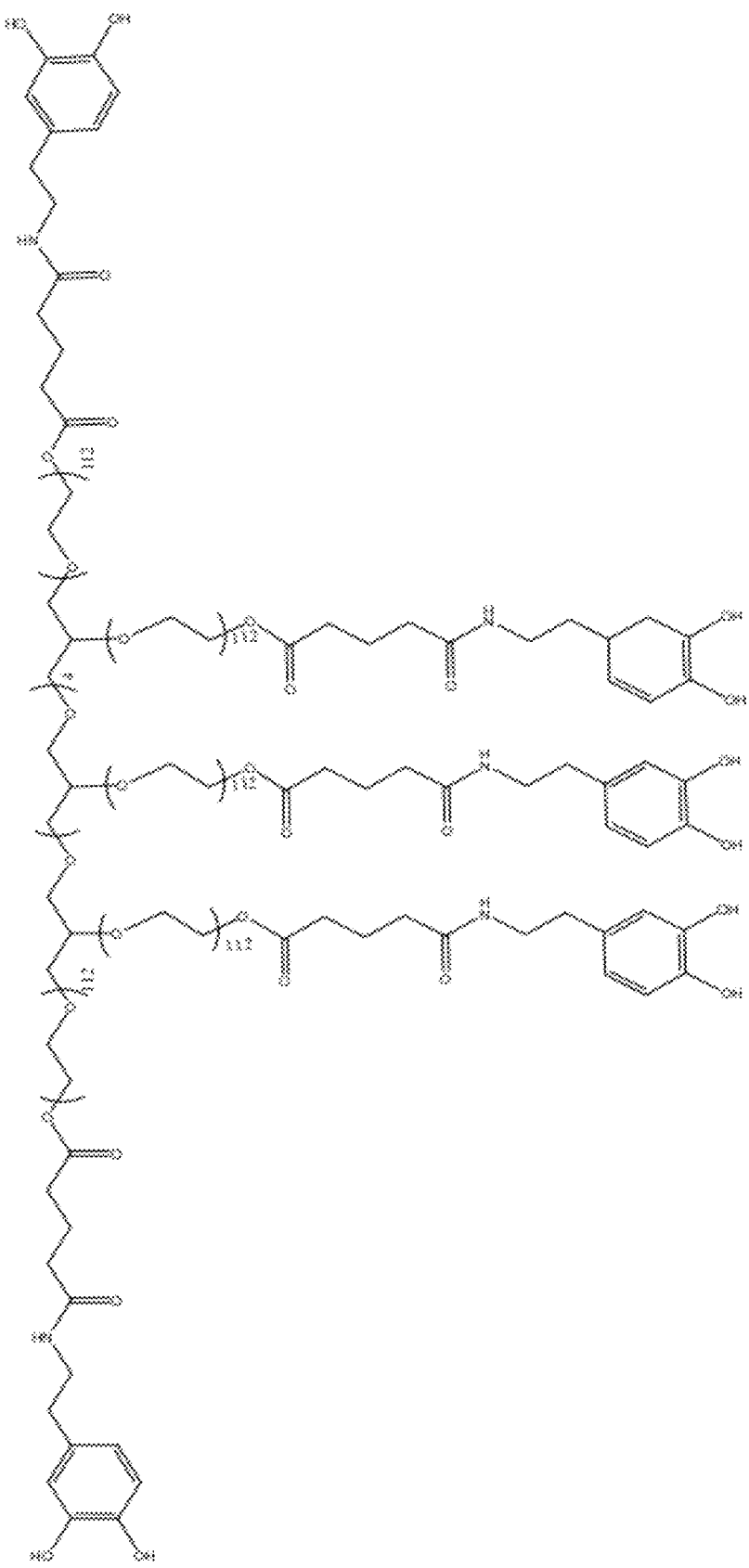
Figure 124:
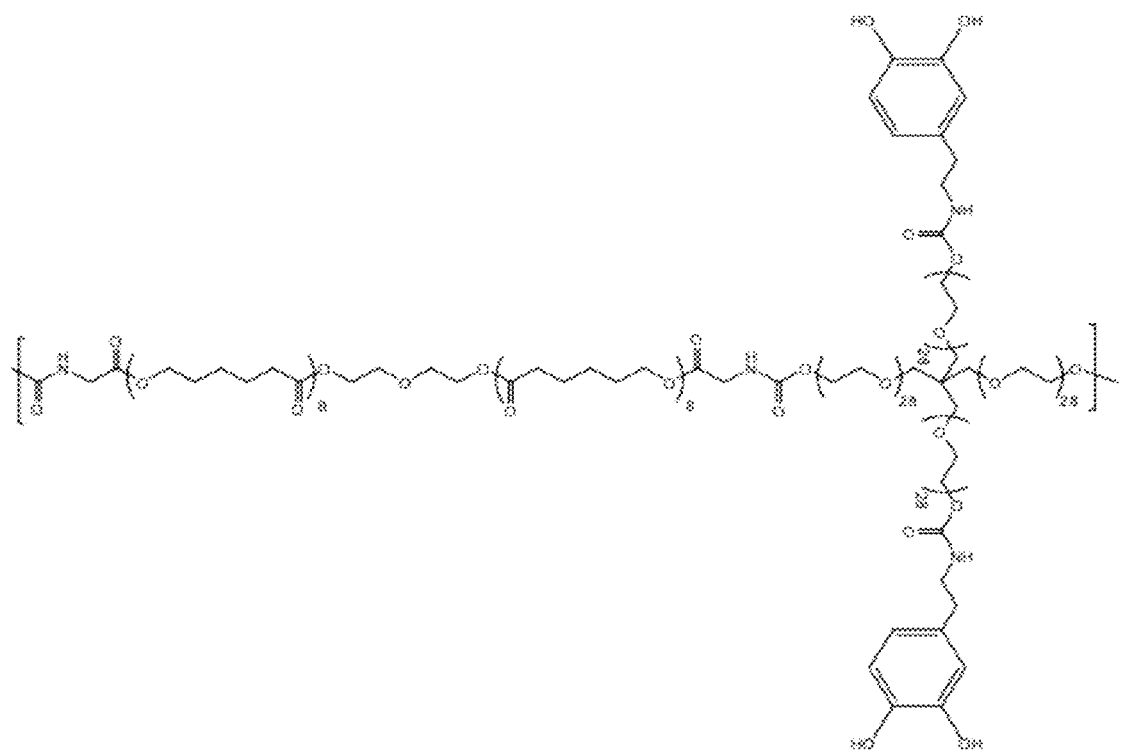
Figure 125:
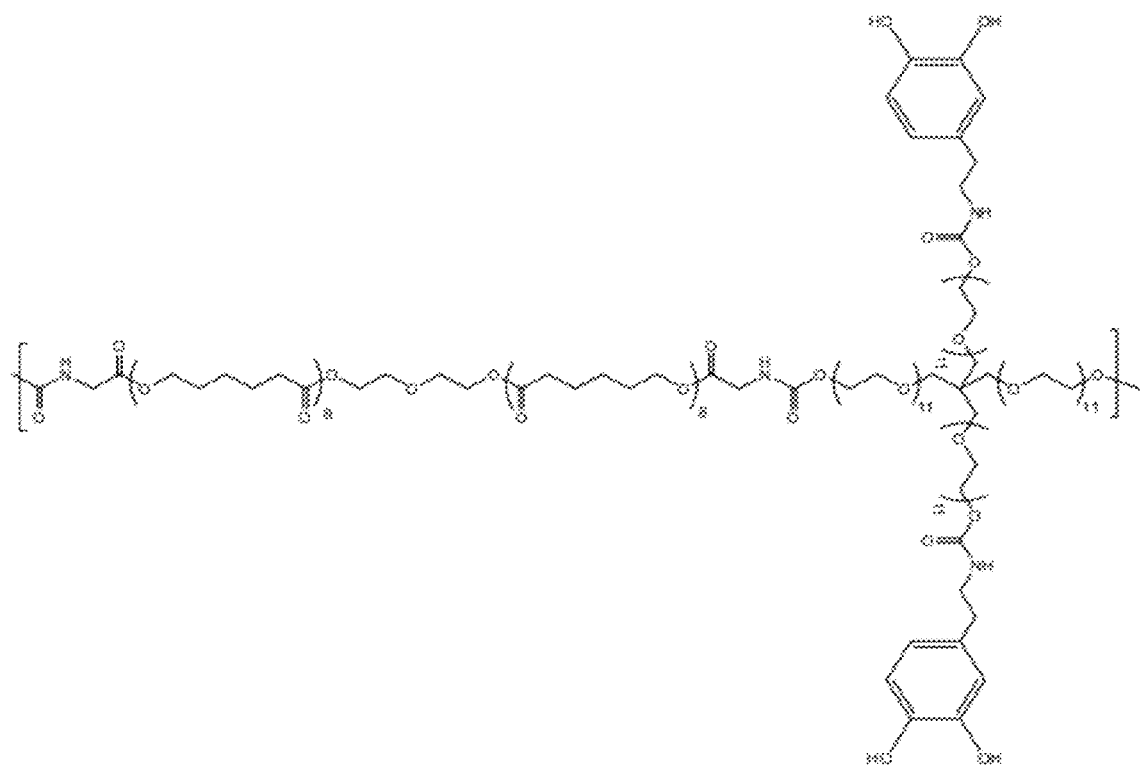
Figure 126:
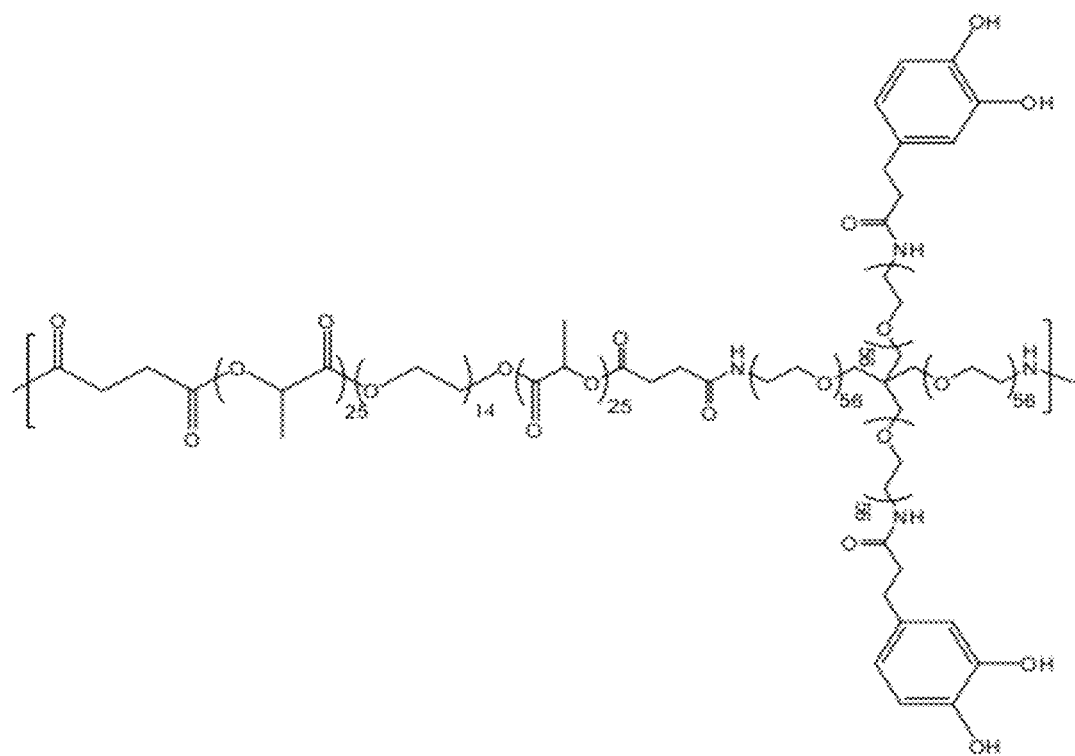
Figure 127:
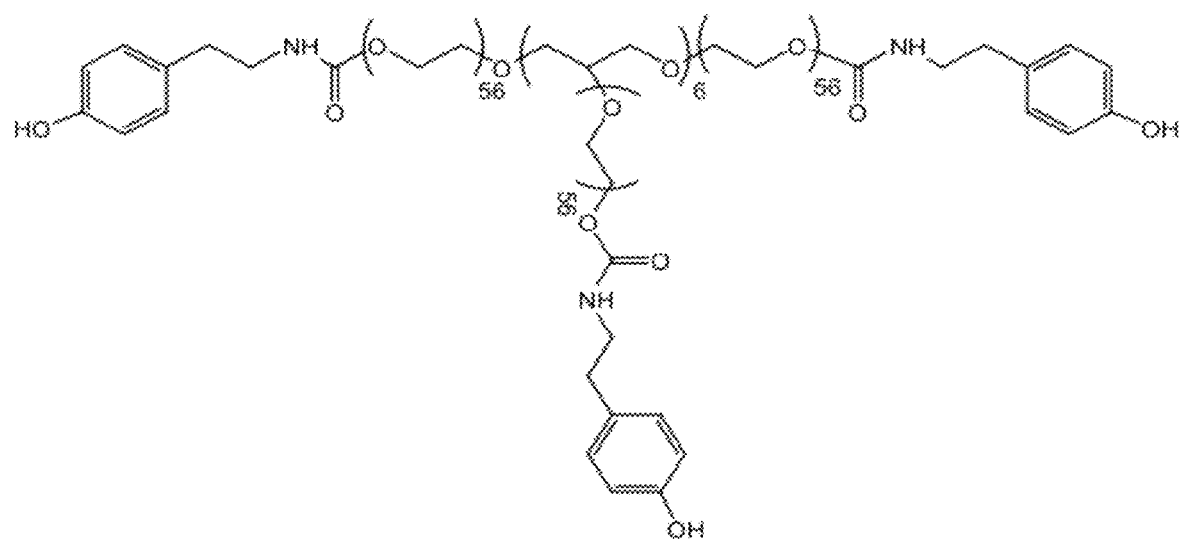
Figure 128:
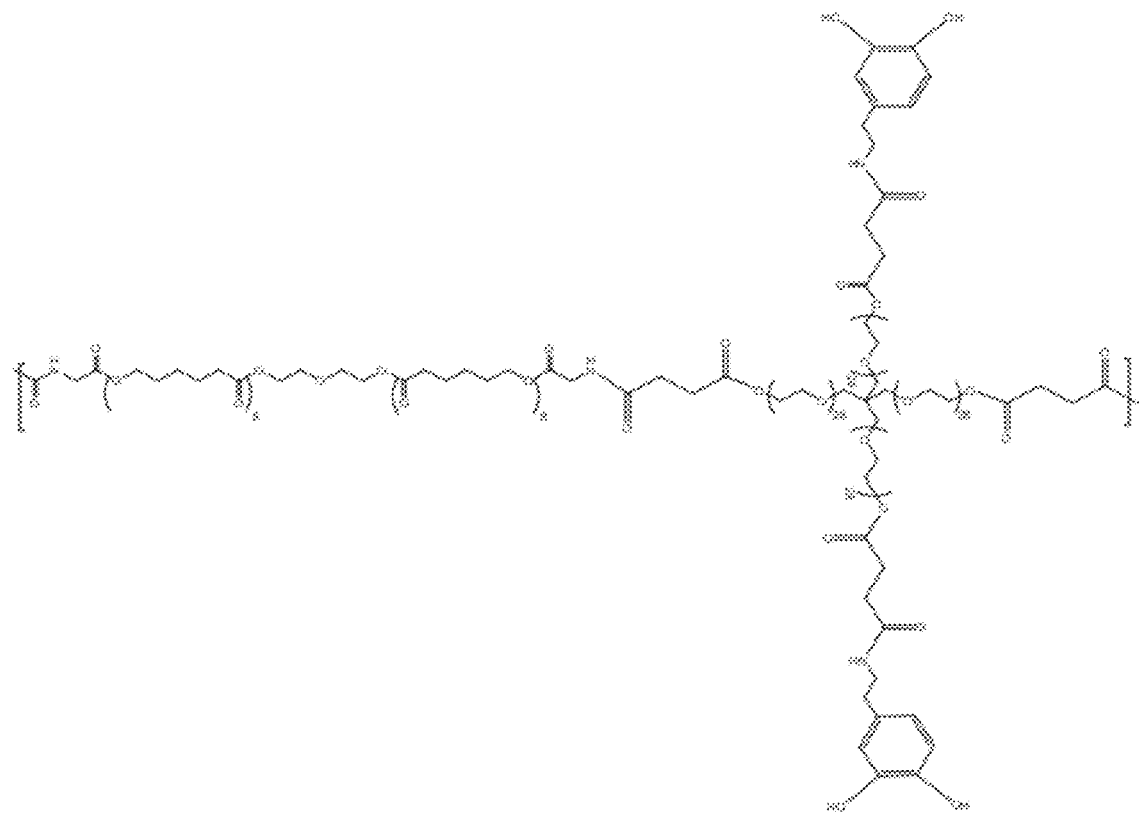
Figure 129:
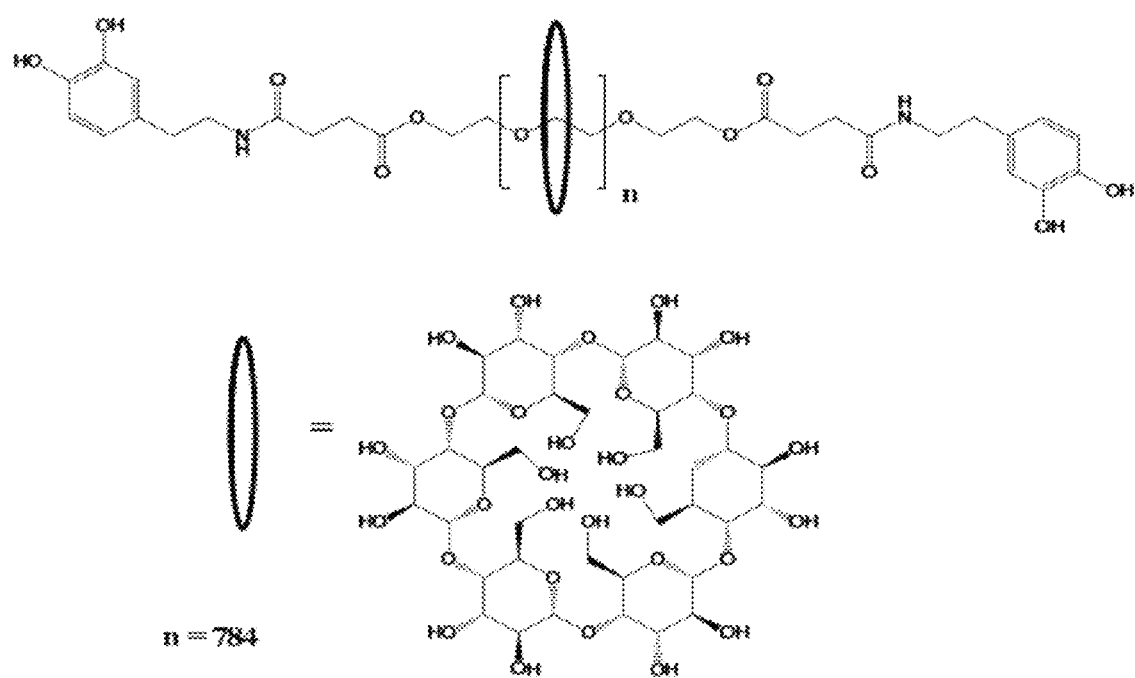
Figure 130:
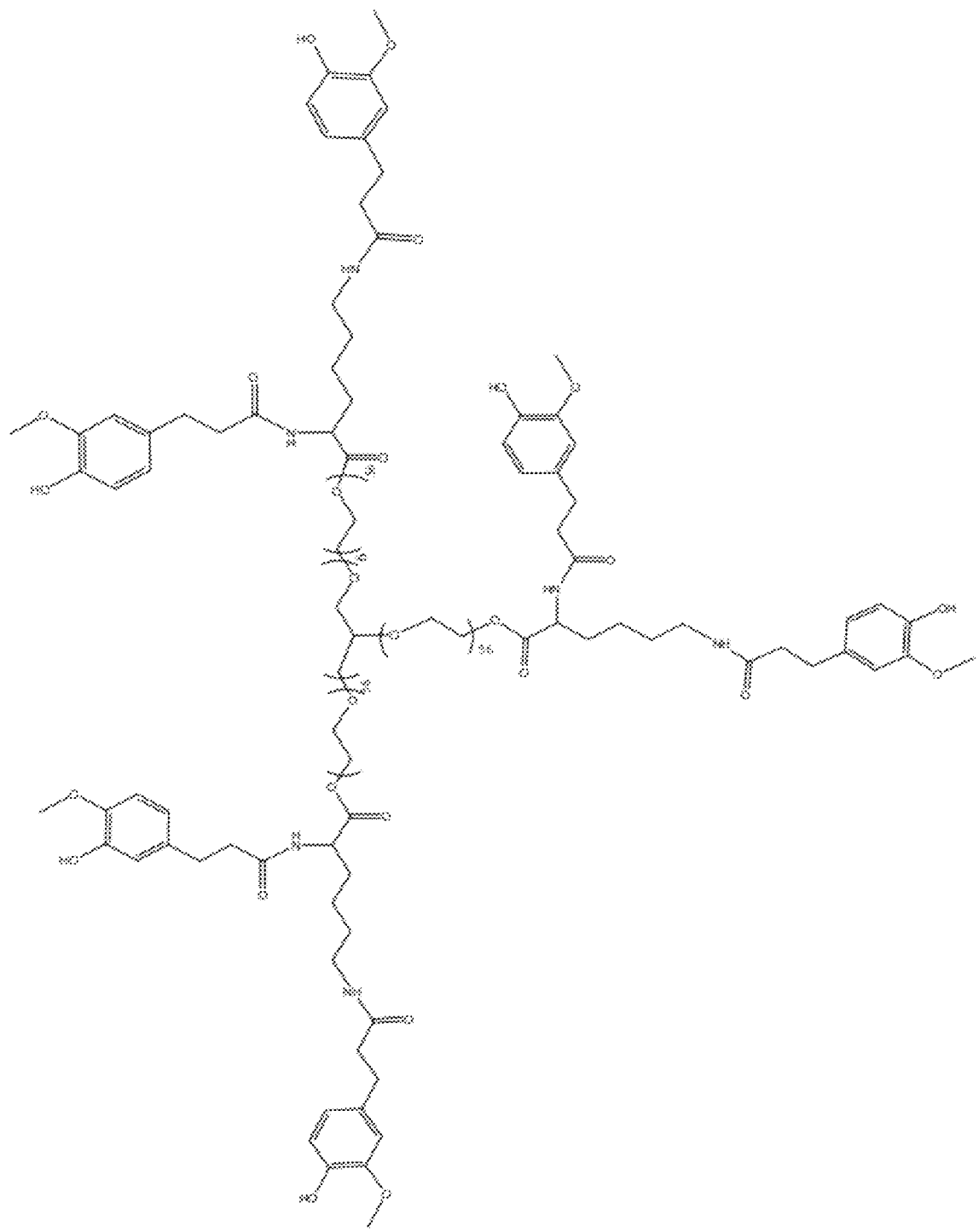

| Name | R&D Name | Description | FIG. No. |
|---|---|---|---|
| Medhesive-105 | p(CL1.25kEG10kb-g-DMu2) | Multi-branched polymer constructed from PCL-(Gly)2 1.25k and 4-arm PEG-OH 10k (1:1 feed ratio) modified with Dopamine. (Urethane linkage) | FIG. 115 |
| Medhesive-106 | p(EG2k8aCL2k-NHS6) | Multi-branched polymer constructed from PCL-(OH)2 2k and 8-arm PEG-OH 20k (1:1 molar feed ratio) modified with NHS. | FIG. 116 |
| Medhesive-107 | PEG20K-(GABMe)8 | Branched, 8-armed PEG-OH (20k MW) coupled with terminal dihydroxybenzylamine linked with Glutaric acid. (ester linkage) | FIG. 117 |
| Medhesive-108 | PEG40K-(LyseDH2)8 | Branched, 8-armed PEG-OH (40k MW) coupled with terminal DOHA linked with Lysine (ester linkage) | FIG. 118 |
| Medhesive-109 | p(EG2kCL2k75EG10kb1Lys-g-DM) | Random repeating linear PEG (2k, 3 mol %), PCL (2k MW, 37 mol %) and 4-armed PEG (10k MW, 1 mol %) linked together with Lys and grafted with dopamine. 75 wt % PCL and 6 wt % linear PEG. Chain extension achieved through activation with phosgene and NHS. | FIG. 119 |
| Medhesive-110 | p(EG2kCL2k50EG10kb1Lys-g-DM) | Random repeating linear PEG (2k, 15 mol %), PCL (2k MW, 25 mol %) and 4-armed PEG (10k MW, 1 mol %) linked together with Lys and grafted with dopamine. 50 wt % PCL and 30 wt % linear PEG. Chain extension achieved through activation with phosgene and NHS. | FIG. 120 |
| Medhesive-111 | p(CL1.252kEG20kb-g-DH6) | Branched polymer constructed from PCL-diSA 1.25k and 8-arm PEG-NH2 10k. | FIG. 121 |
| Medhesive-112 | p(CL5.6kEG10kb-g-DH2) | Branched polymer constructed from triblock copolymer PCL-PEG-PCL diSA 5.4k and 4-arm PEG-NH2 10k (1:1 feed ratio) modified with DOHA. | FIG. 122 |
| Medhesive-113 | PEG40K-(GADMe)8 | Branched, 8-armed PEG-OH (40k MW) coupled with terminal dopamine linked with Glutaric acid. (ester linkage) | FIG. 123 |
| Medhesive-114 | p(CL2kGEG5kb-g-DMu2) | Multi-branched polymer constructed from PCL-(Gly)2 2k and 4-arm PEG-OH 5k (1:1 feed ratio) modified with Dopamine. Urethane linkages. | FIG. 124 |
| Medhesive-115 | p(CL2kGEG2kb-g-DMu2) | Multi-branched polymer constructed from PCL-(Gly)2 2k and 4-arm PEG-OH 2k (1:1 feed ratio) modified with Dopamine. Urethane linkages. | FIG. 125 |
| Medhesive-116 | p(LA4.2kEG10kb g-DH2) | Branched polymer constructed from PLA-PEG(600)-PLA-diSA 4.2k and 4-arm PEG-NH2 10k (1:1 feed ratio) modified with DOHA. | FIG. 126 |
| Medhesive-117 | PEG20k-(TMu)8 | Branched, 8-armed PEG-OH (20k MW) coupled with tyramine (urethane linkage) | FIG. 127 |
| Medhesive-118 | p(PCL2KEG5k-g-DMe2) | Branched polymer constructed from PCL(2K)-Gly and 4-arm PEG-(SA)4 5k (1:2 feed ratio) modified with Dopamine HCl. | FIG. 128 |
| Medhesive-119 | | Polyrotaxane composed of linear PEG35k terminated with succinic acid and dopamine as well as alpha-cyclodextrin modified with succinic acid and dopamine. | FIG. 129 |
| Medhesive-120 | PEG20k-(LysHF2)8 | Branched, 8-armed PEG-OH (20k MW) coupled with terminal Hydroferulic acid linked with Lysine (ester linkage) | FIG. 130 |

TABLE 1-continued

Figure 131:
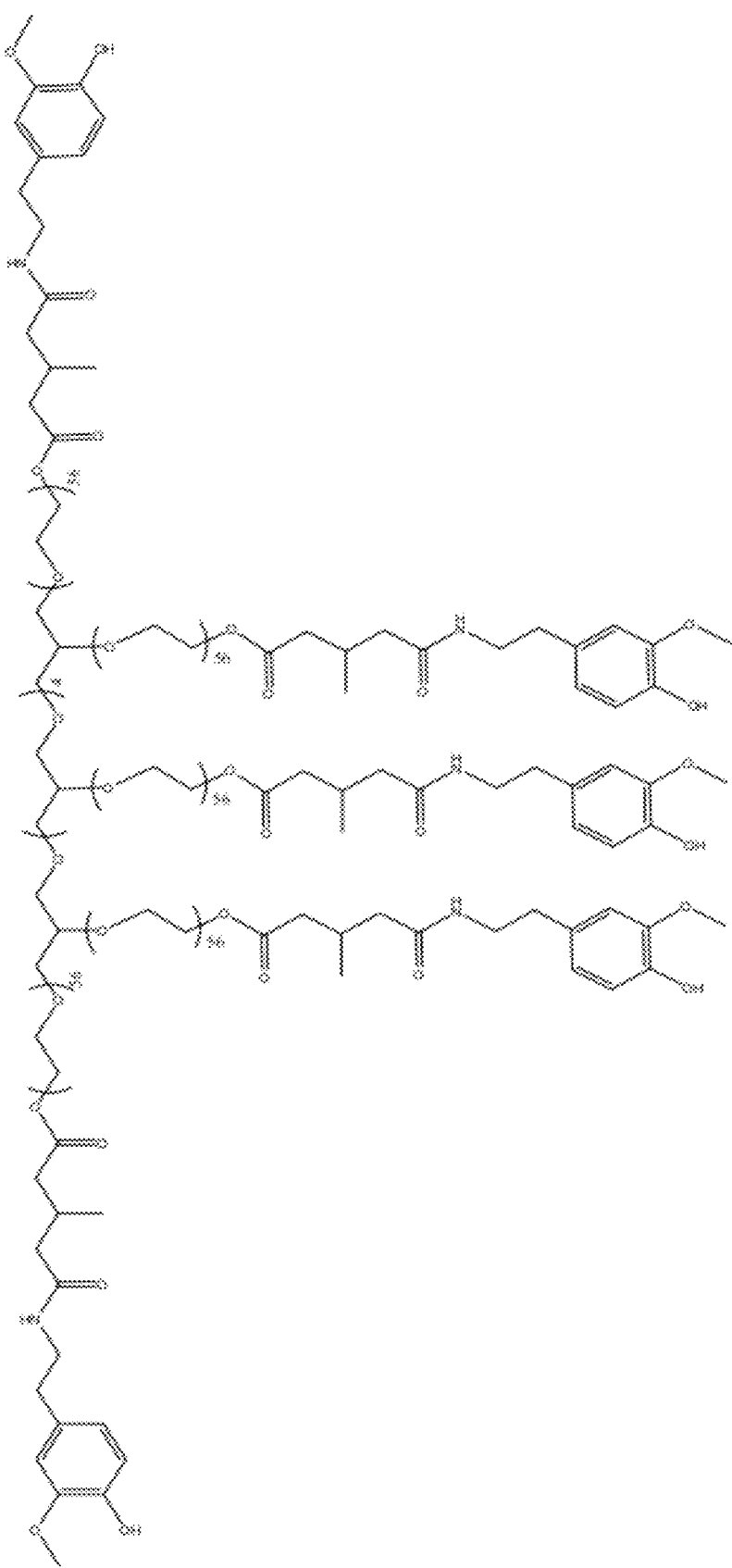
Figure 132:
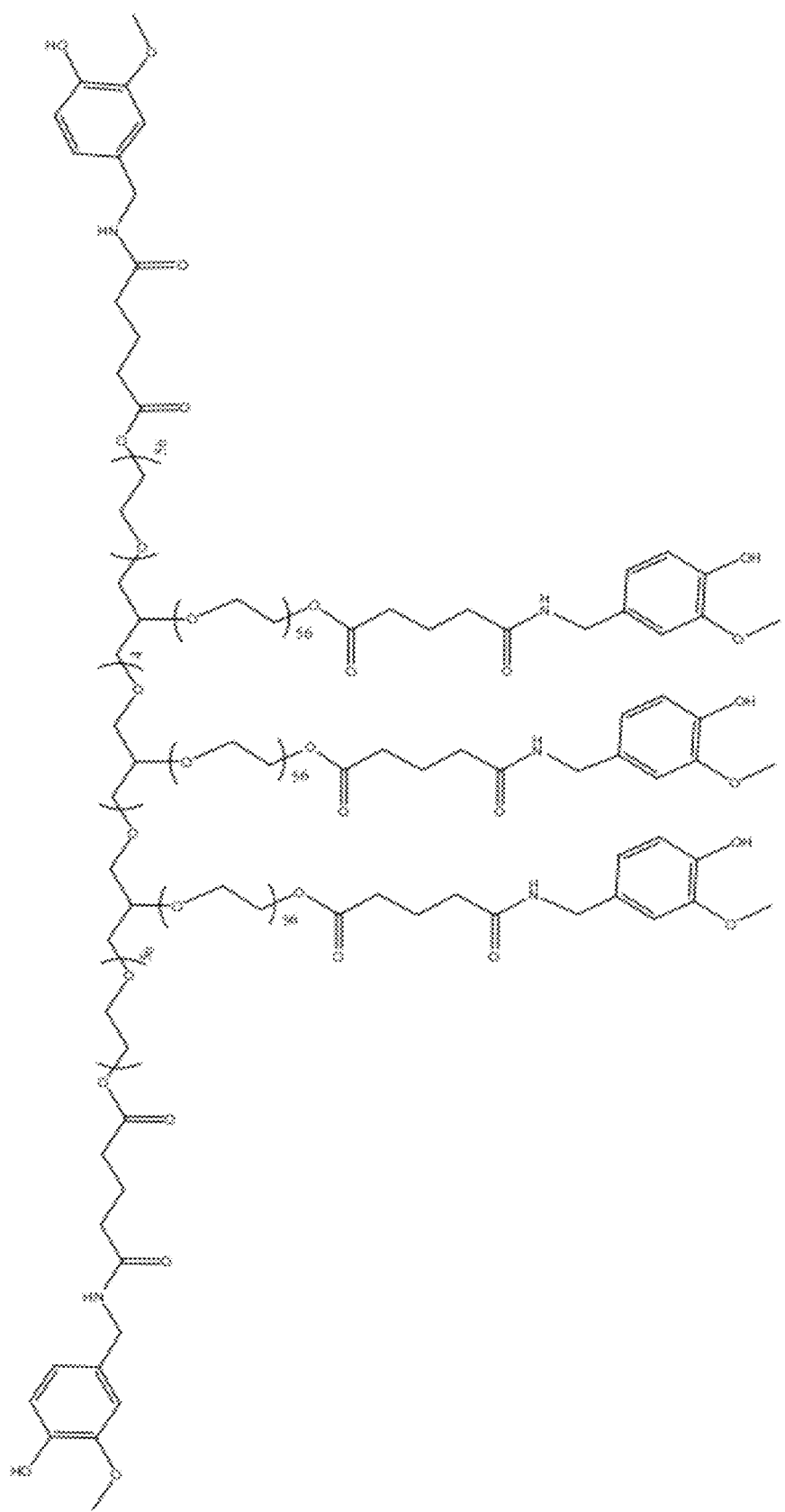
Figure 133:
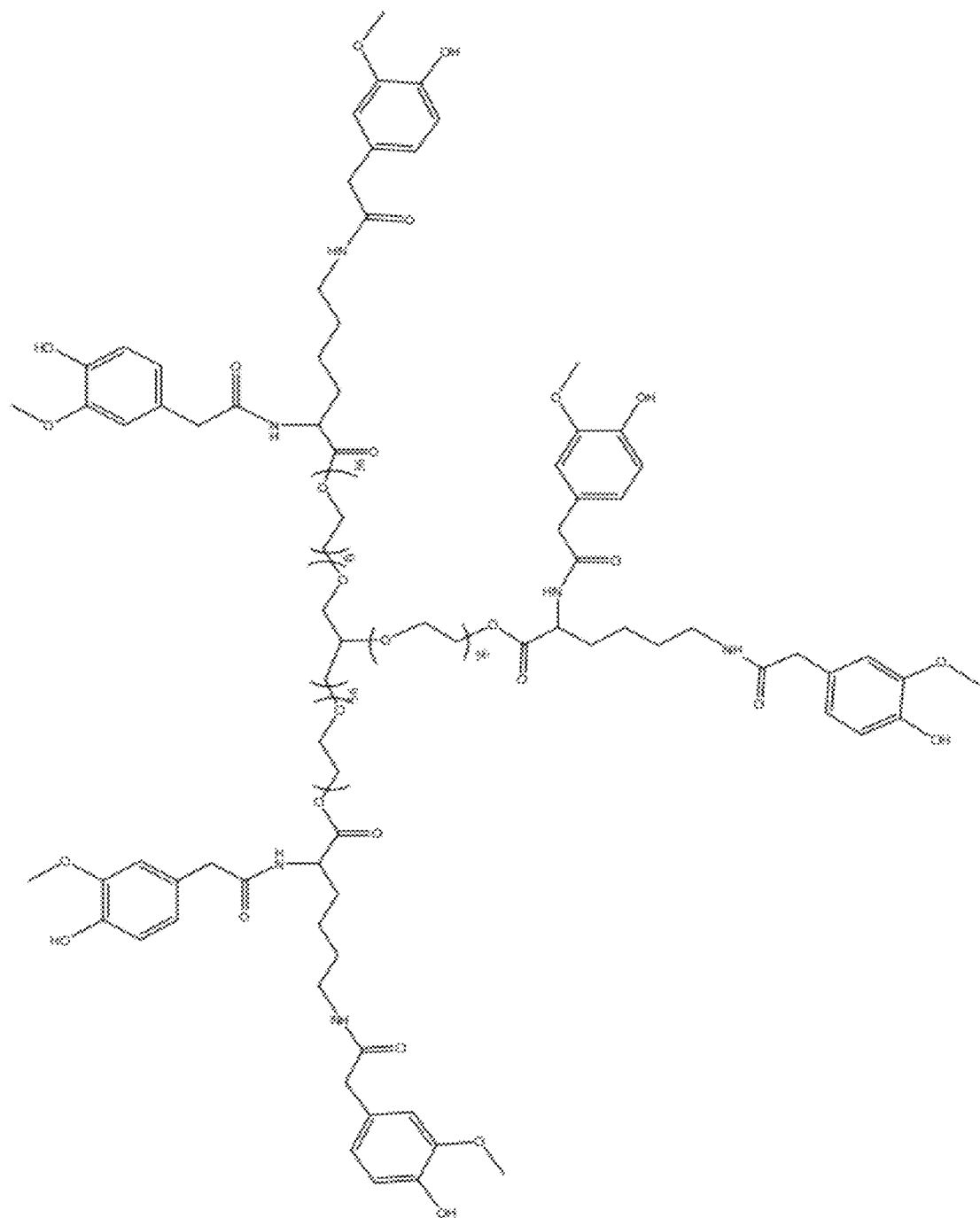
Figure 134:
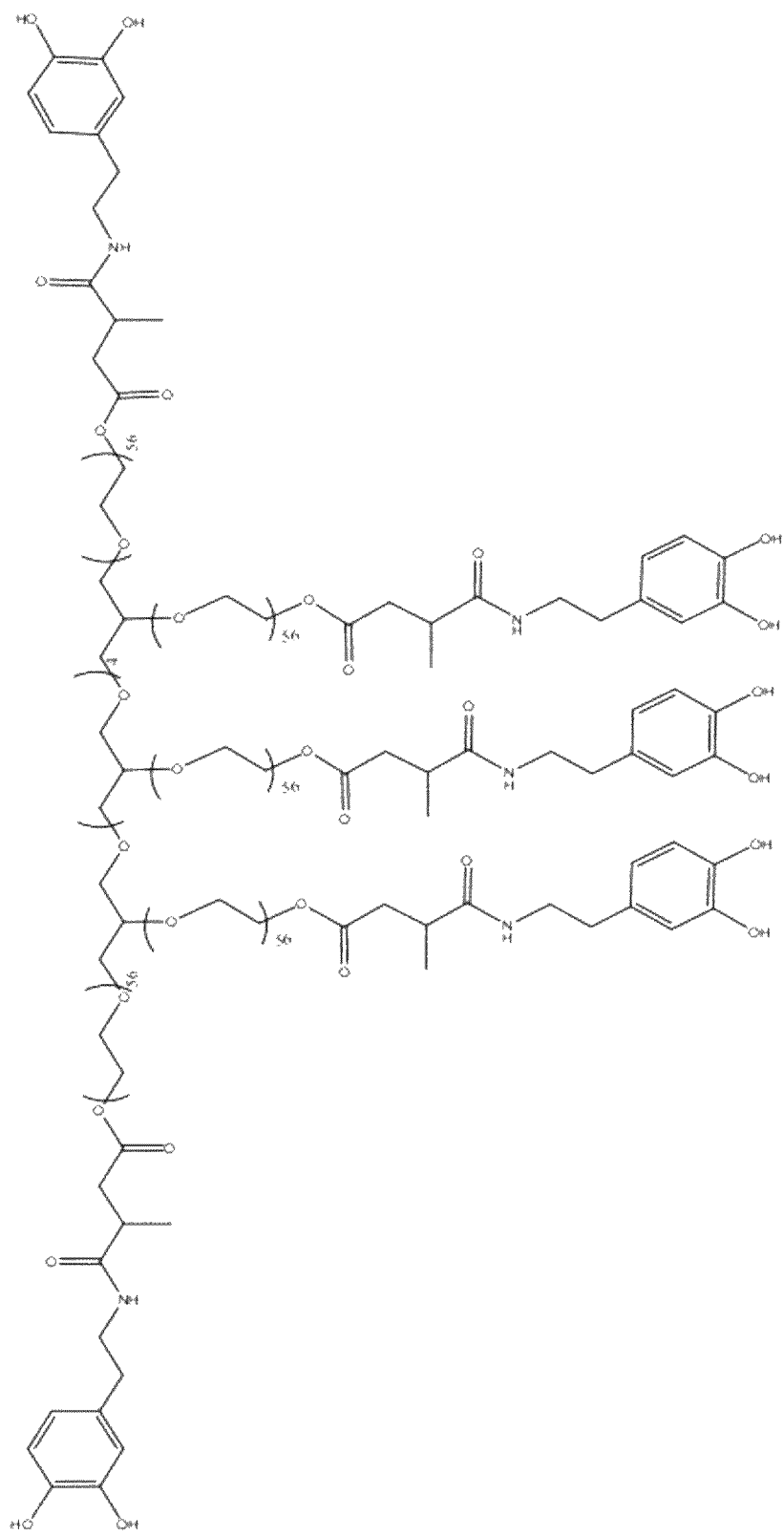
Figure 135:
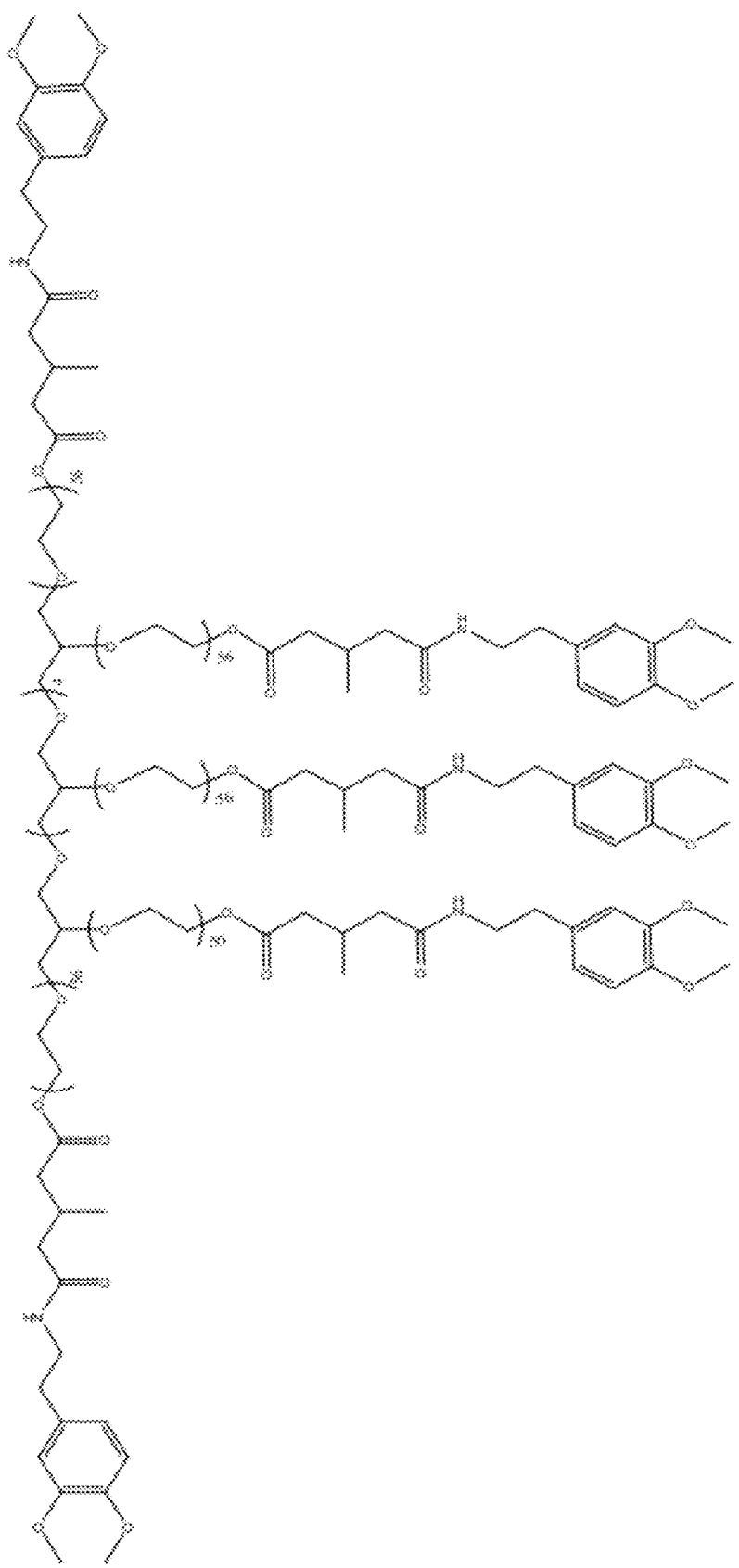
Figure 136:
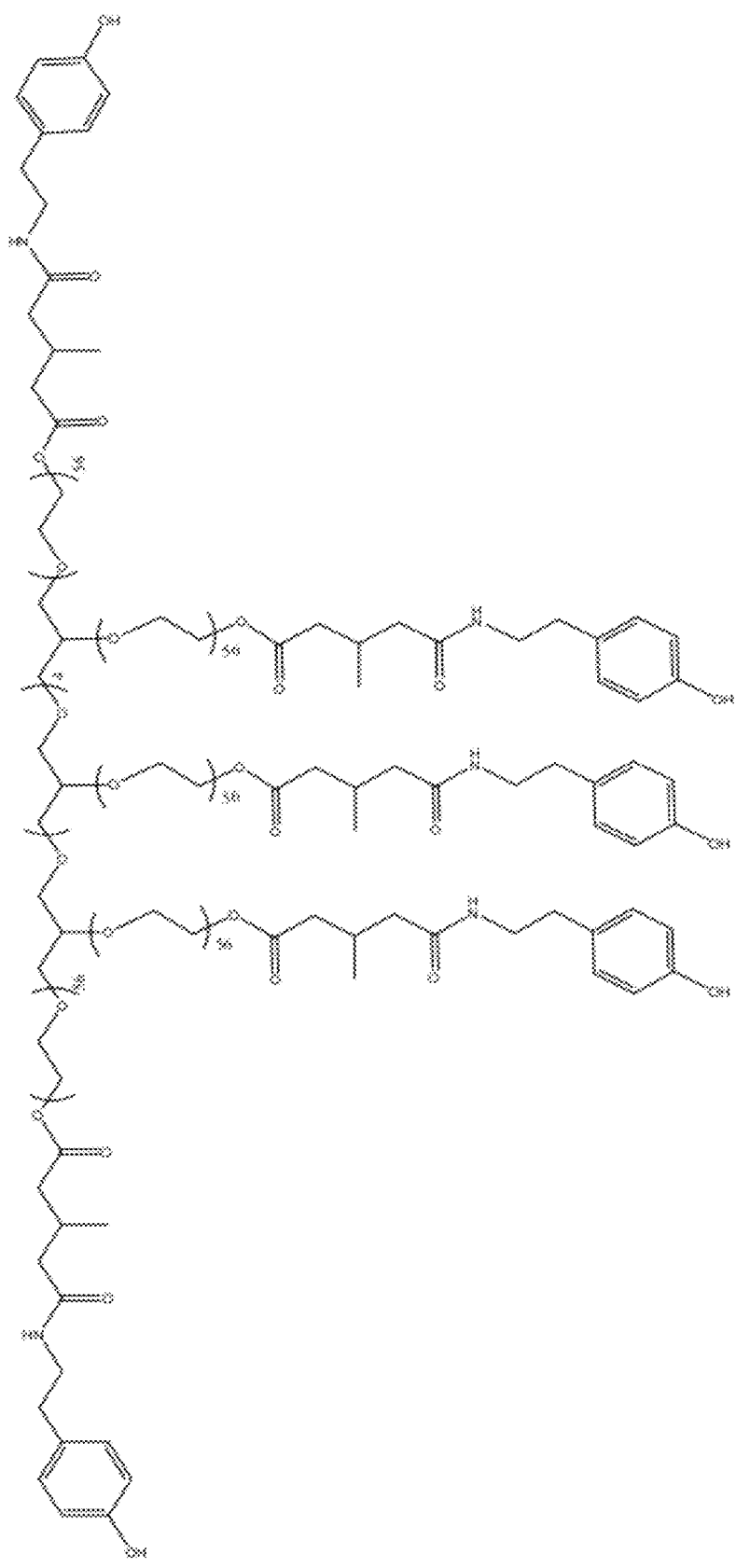
Figure 137:
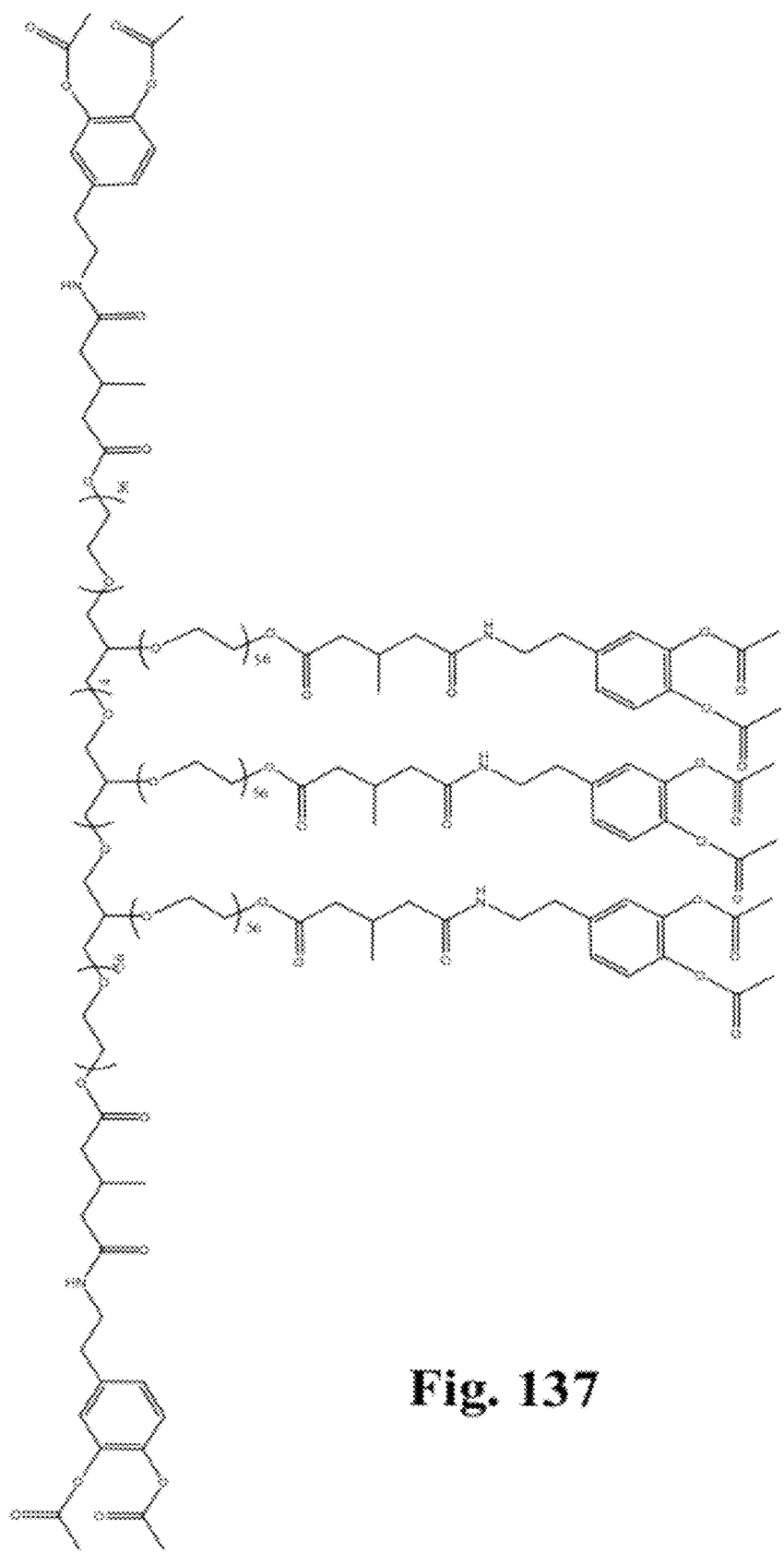
Figure 138:
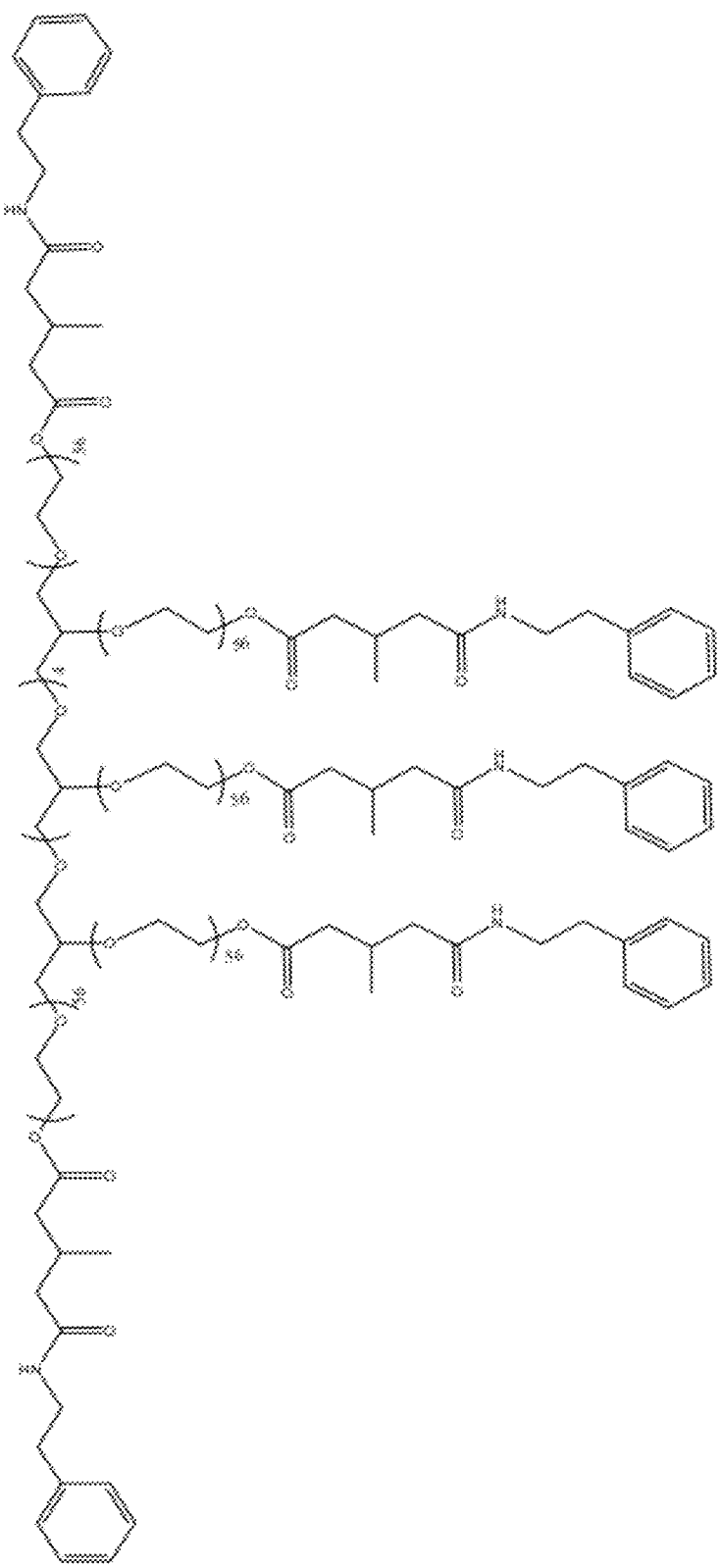
Figure 139:
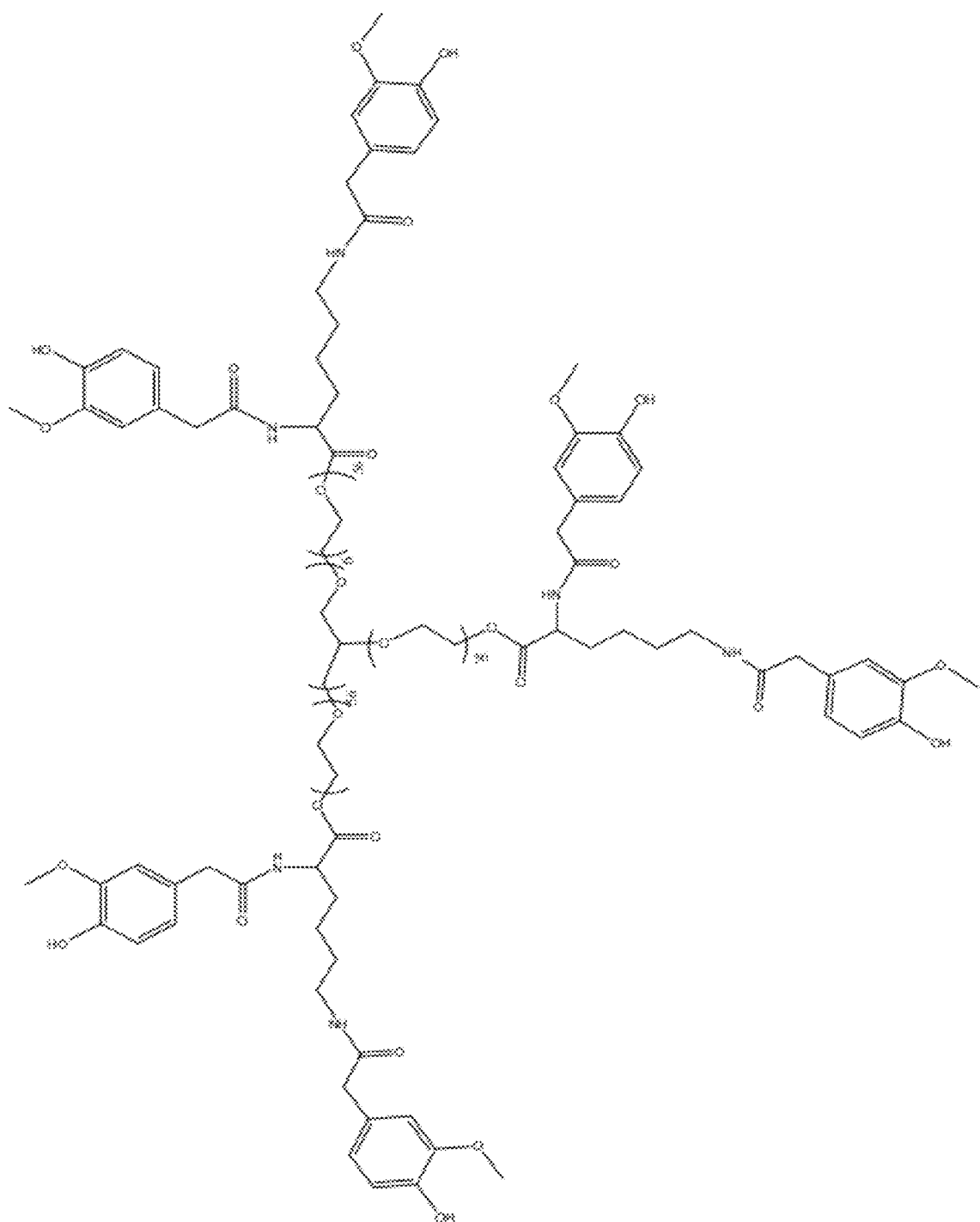
Figure 140:
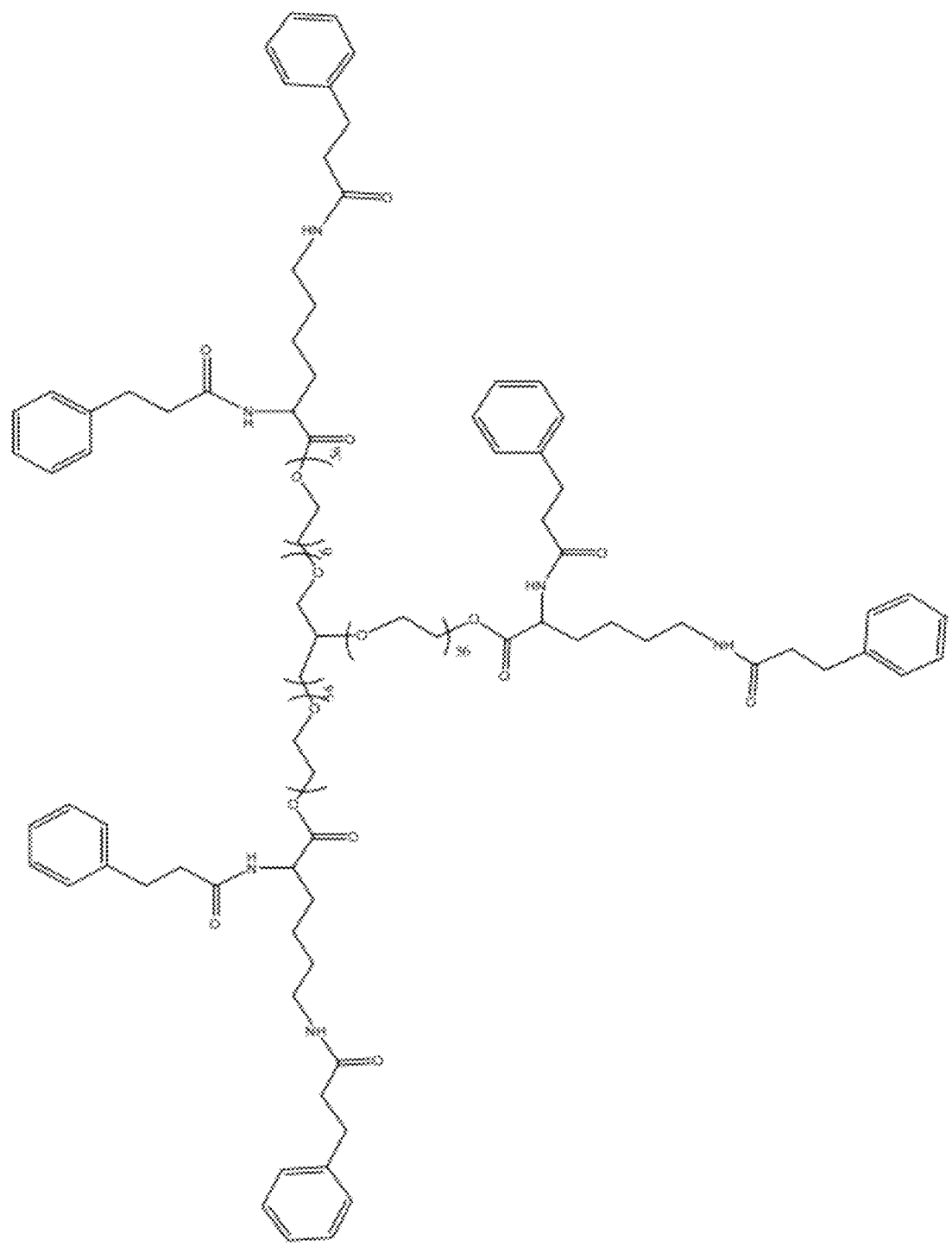
Figure 141:
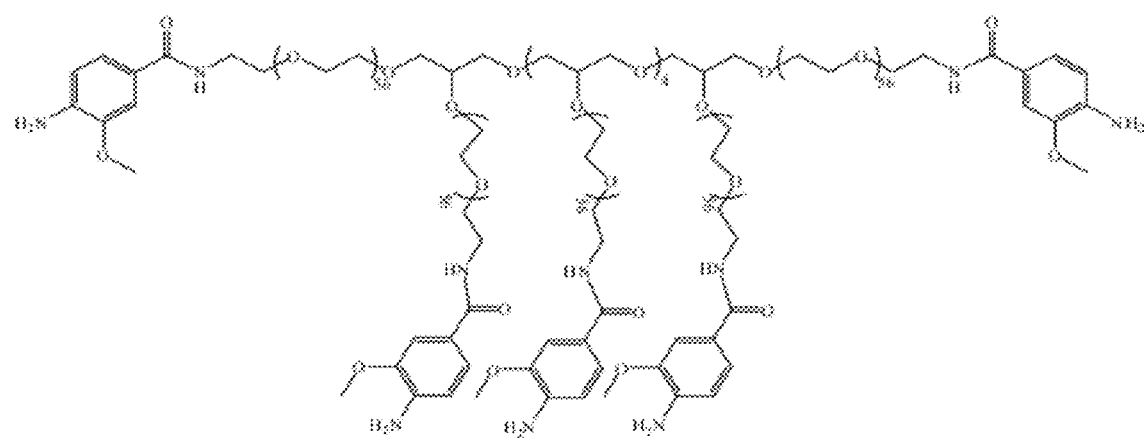
Figure 142:
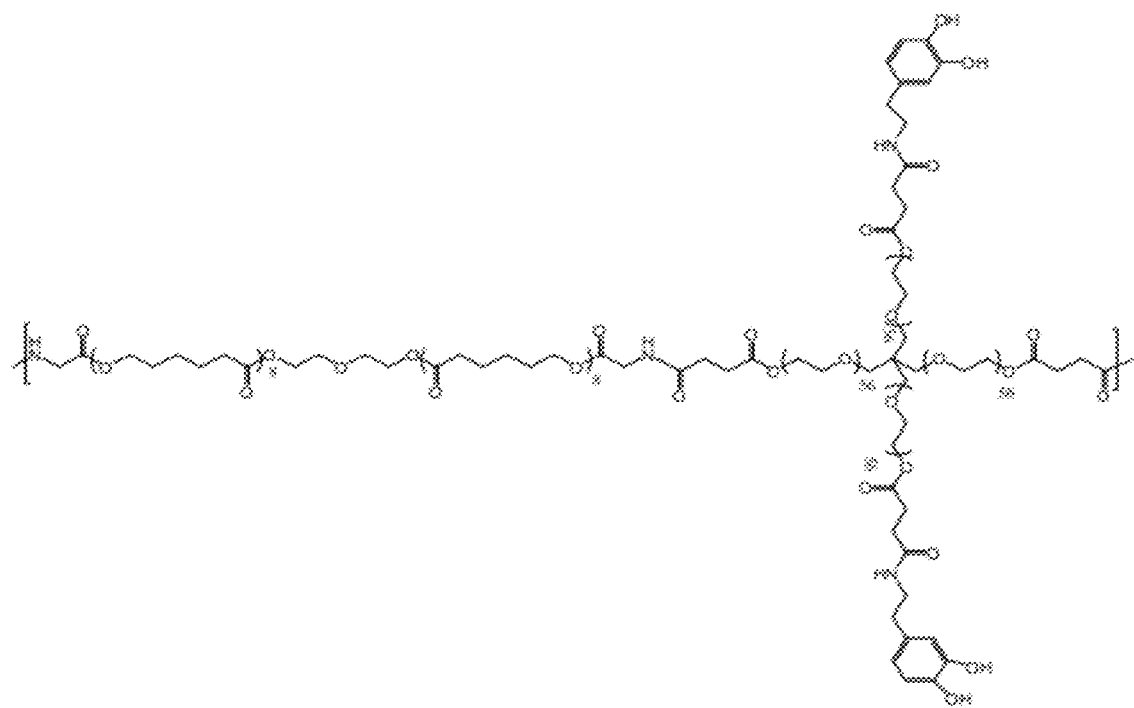
Figure 143:
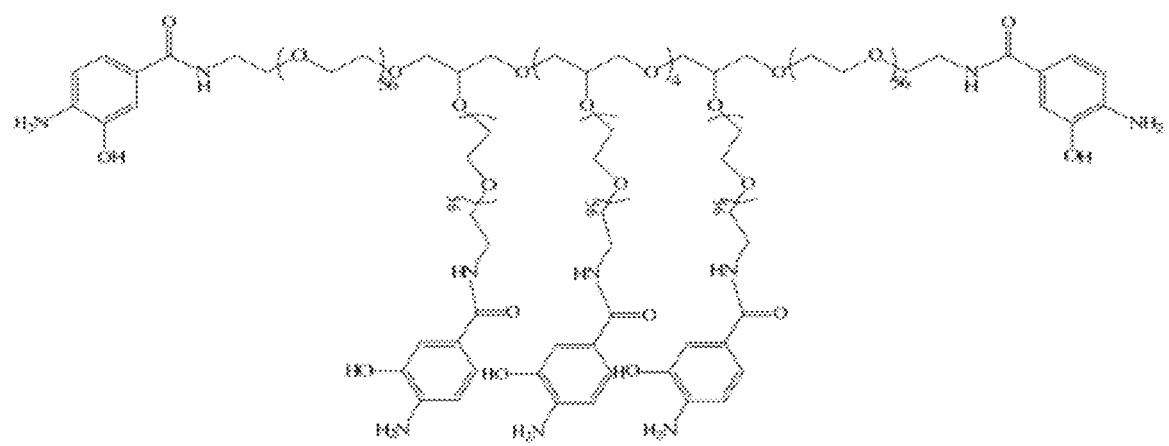
Figure 144:
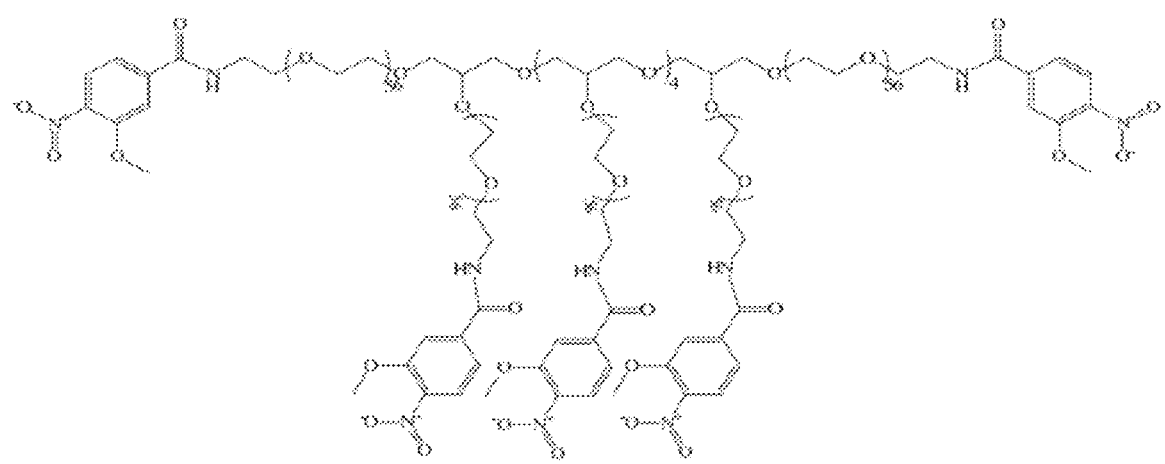
Figure 145:
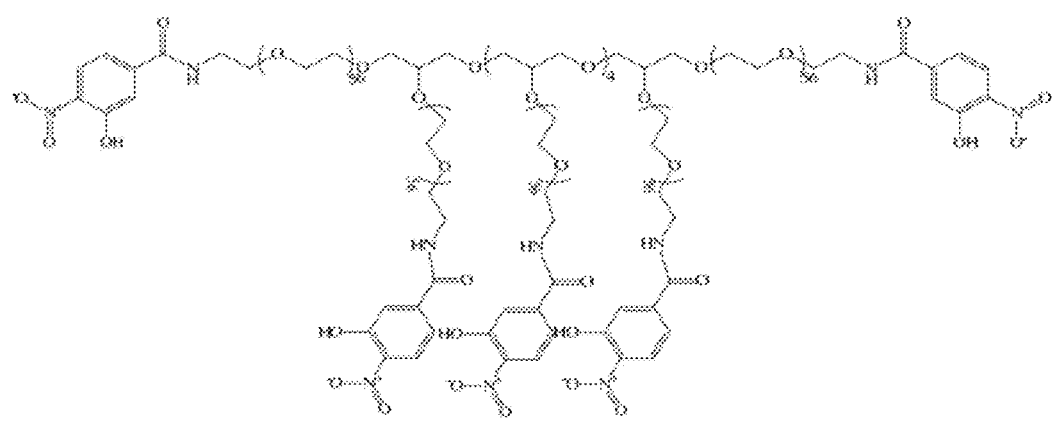
Figure 146:
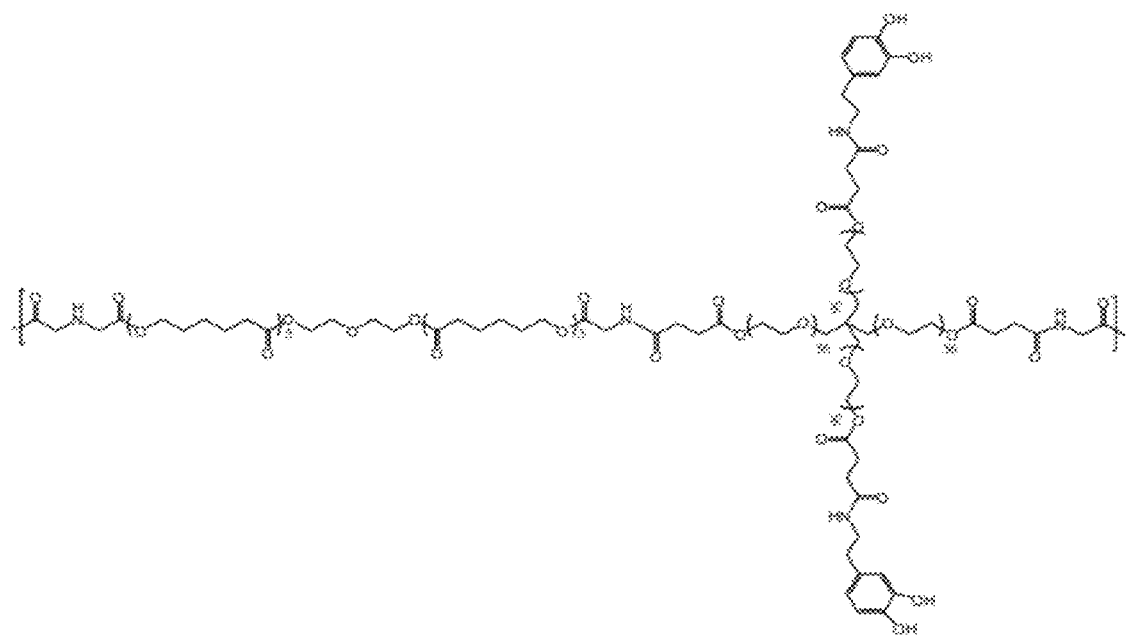
Figure 147:
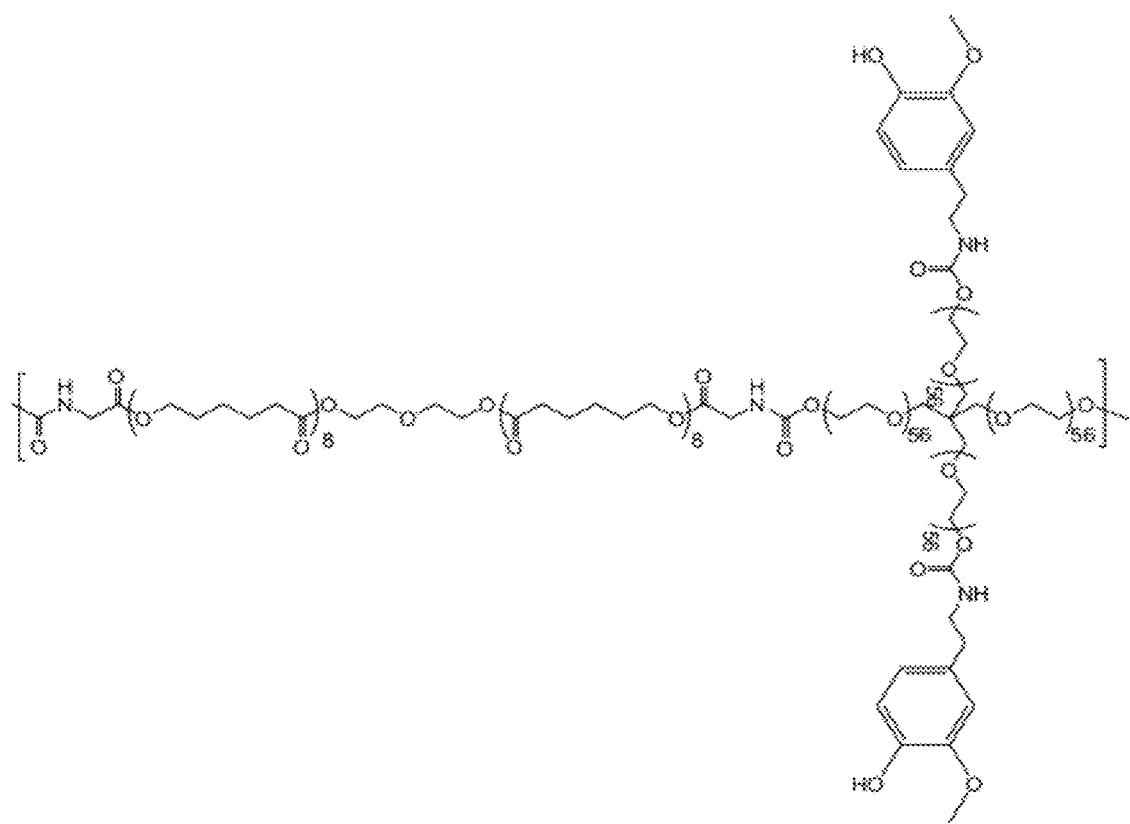

| Name | R&D Name | Description | FIG. NO. |
|---|---|---|---|
| Medhesive-121 | PEG20k-(MGAMTe)8 | Branched, 8-armed PEG-OH (20k MW) coupled with terminal 3-Methoxytyramine (3-MT) linked with 3-Methyl Glutaric acid. (ester linkage) | FIG. 131 |
| Medhesive-122 | PEG20k-(MGAVAe)8 | Branched, 8-armed PEG-OH (20k MW) coupled with terminal Vanillylamine (VA) linked with 3-Methyl Glutaric acid. (ester linkage) | FIG. 132 |
| Medhesive-123 | PEG20k-(LysHVA2)8 | Branched, 8-armed PEG-OH (20k MW) coupled with terminal Homovanillic acid linked with Lysine (ester linkage) | FIG. 133 |
| Medhesive-124 | PEG20k-(MSADMe)8 | Branched, 8-armed PEG-OH (20k MW) coupled with terminal dopamine linked with methylsuccinic acid (ester linkage) | FIG. 134 |
| Medhesive-125 | PEG20k-(MGAHVTAe)8 | Branched, 8-armed PEG-OH (20k MW) coupled with terminal Homoveratrylamine (HVTA) linked with 3-Methyl Glutaric acid. (ester linkage) | FIG. 135 |
| Medhesive-126 | PEG20k-(MGATMe)8 | Branched, 8-armed PEG-OH (20k MW) coupled with terminal Tyramine (TA) linked with 3-Methyl Glutaric acid. (ester linkage) | FIG. 136 |
| Medhesive-127 | PEG20k-(MGA(Ac)2DMe)8 | Branched, 8-armed PEG-OH (20k MW) coupled with terminal Ac2-dopamine linked with 3-Methyl Glutaric acid. (ester linkage) | FIG. 137 |
| Medhesive-128 | PEG20k-(MGAPEAe)8 | Branched, 8-armed PEG-OH (20k MW) coupled with terminal Phenylethylamine HCl linked with 3-Methyl Glutaric acid. (ester linkage) | FIG. 138 |
| Medhesive-129 | PEG20k-(LysDMHA2)8 | Branched, 8-armed PEG-OH (20k MW) coupled with terminal 3,4-Dimethoxyhydrocinnamic acid (DMHA) linked with Lysine (ester linkage) | FIG. 139 |
| Medhesive-130 | PEG20k-(LysHCA2)8 | Branched, 8-armed PEG-OH (20k MW) coupled with terminal Hydrocinnamic acid (HCA) linked with Lysine (ester linkage) | FIG. 140 |
| Medhesive-131 | PEG20k-(3M4ABA)8 | Branched, 8-armed PEG-NH2 (20k MW) coupled with terminal 3-Methoxy-4-AminoBenzoic Acid linked with amide linkage | FIG. 141 |
| Medhesive-132 | p(CL2kEG10k(SA)b-g-DMe2) | Multi-branched polymer constructed from PCL-(Gly)2 2k and 4-arm PEG-SA 10k (1:1 feed ratio) modified with Dopamine. | FIG. 142 |
| Medhesive-133 | | Branched, 8-armed PEG-NH2 (20k MW) coupled with terminal 3-Hydroxy-4-AminoBenzoic Acid linked with amide linkage | FIG. 143 |
| Medhesive-134 | | Branched, 8-armed PEG-NH2 (20k MW) coupled with terminal 3-Methoxy-4-NitroBenzoic Acid linked with amide linkage - Medhesive-131 Intermediate | FIG. 144 |
| Medhesive-135 | | Branched, 8-armed PEG-NH2 (20k MW) coupled with terminal 3-Hydroxy-4-NitroBenzoic Acid linked with amide linkage - Medhesive-133 | FIG. 145 |
| Medhesive-136 | p(CL1.25kEG10k(SA)b-g-DMe2) | Multi-branched polymer constructed from PCL-(Gly)2 1.25k and 4-arm PEG-SA 10k (1:1 feed ratio) modified with Dopamine. | FIG. 146 |
| Medhesive-137 | p(CL2kEG10kb-g-MTu2) | Multi-branched polymer constructed from PCL-(Gly)2 2k and 4-arm PEG-OH 10k (1:1 feed ratio) modified with 3-Methoxytyramine (3-MT). Urethane linkages. | FIG. 147 |

TABLE 1-continued

Figure 148:
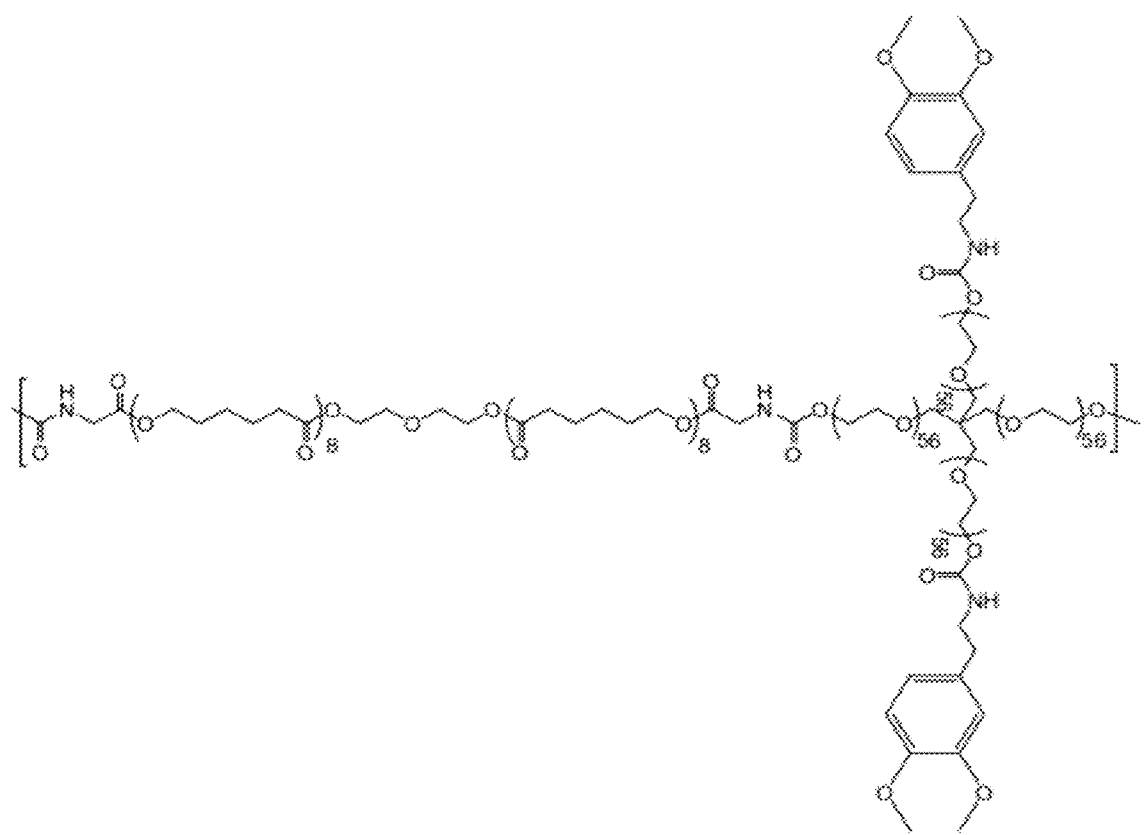
Figure 149:
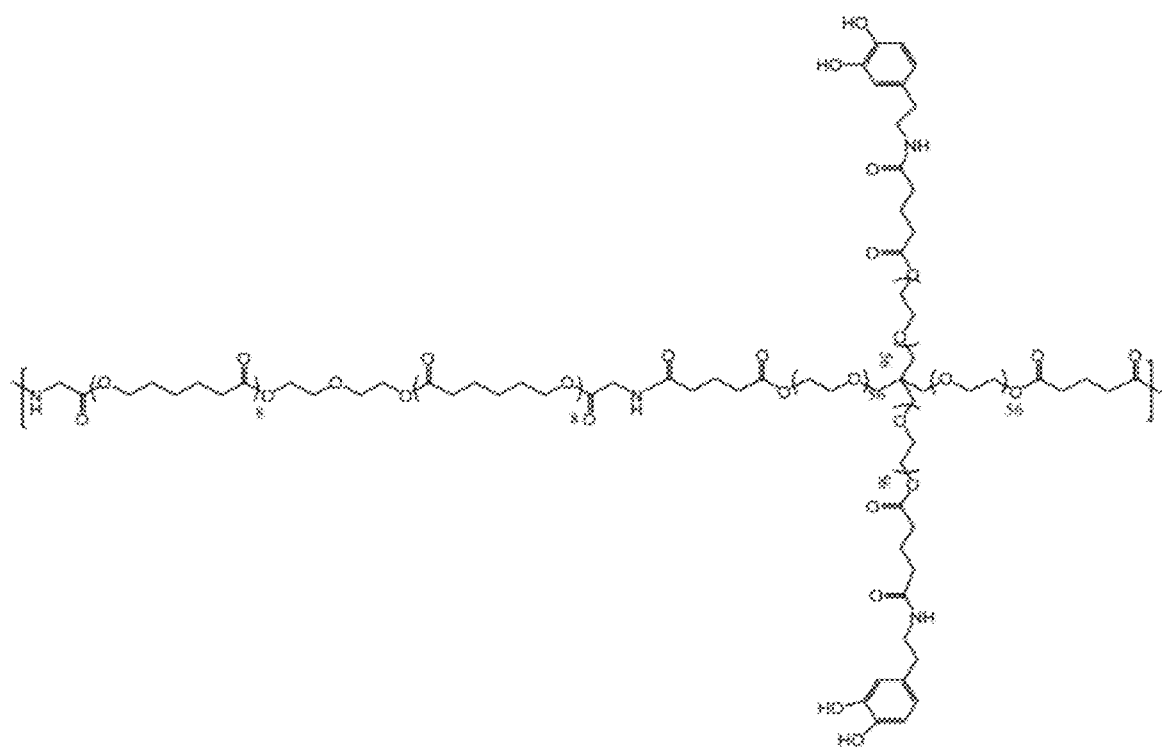
Figure 150:
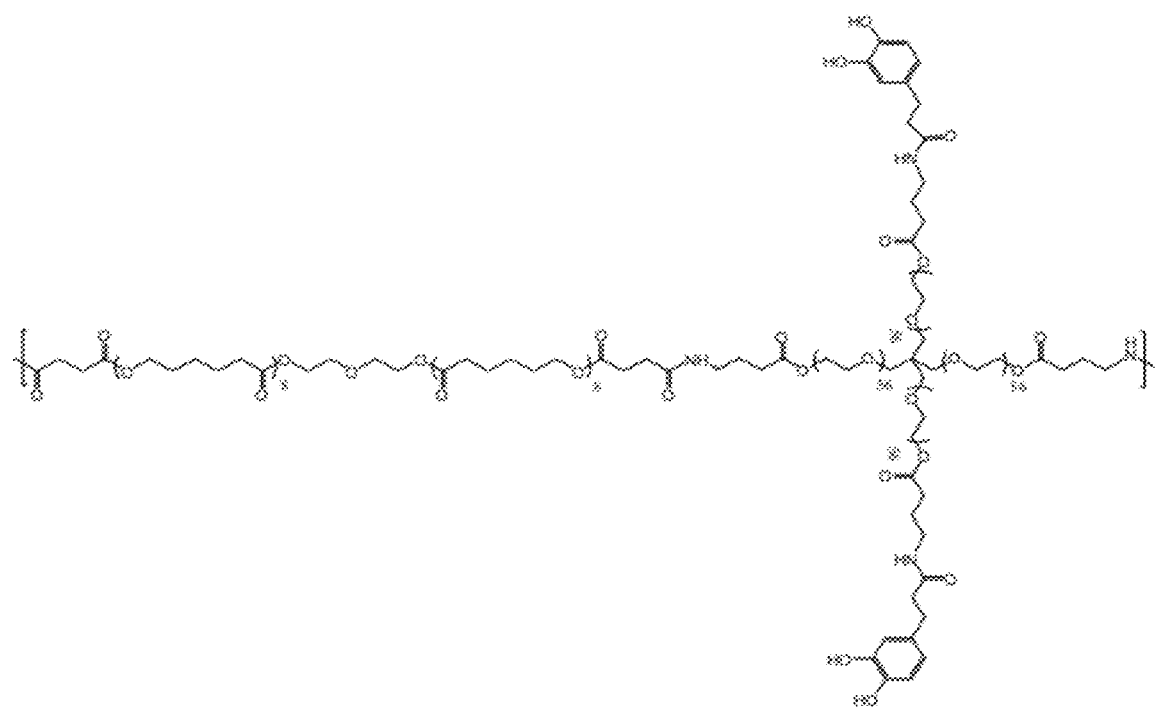
Figure 151:
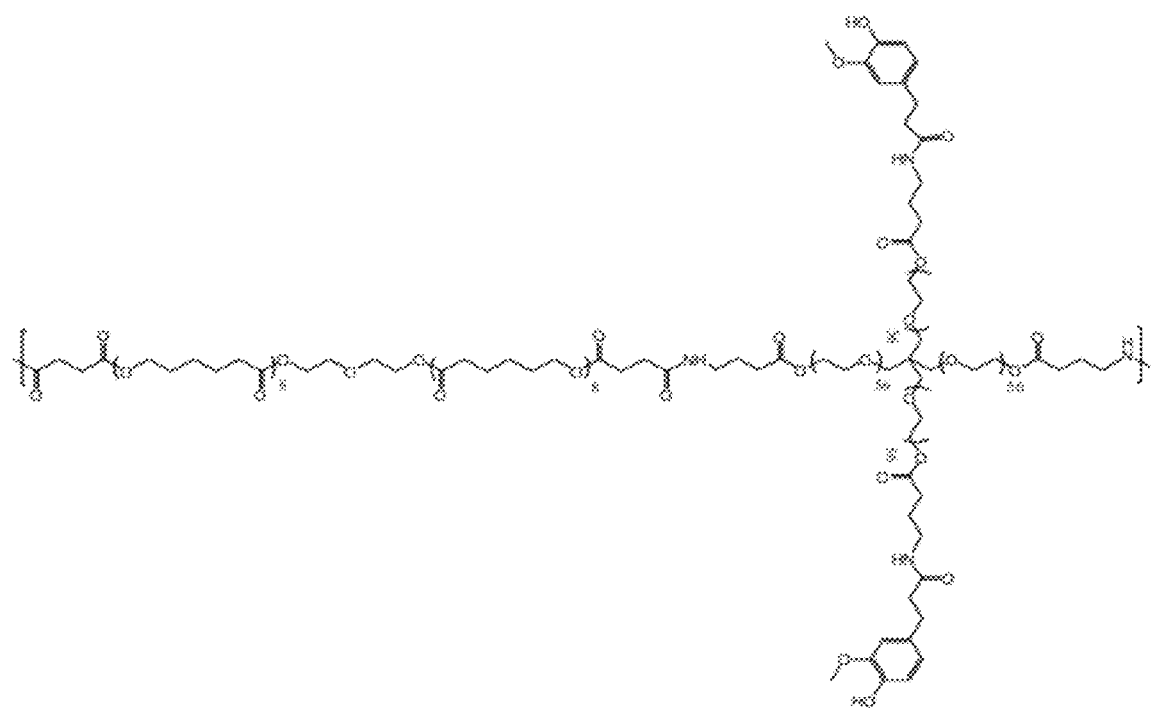
Figure 152:
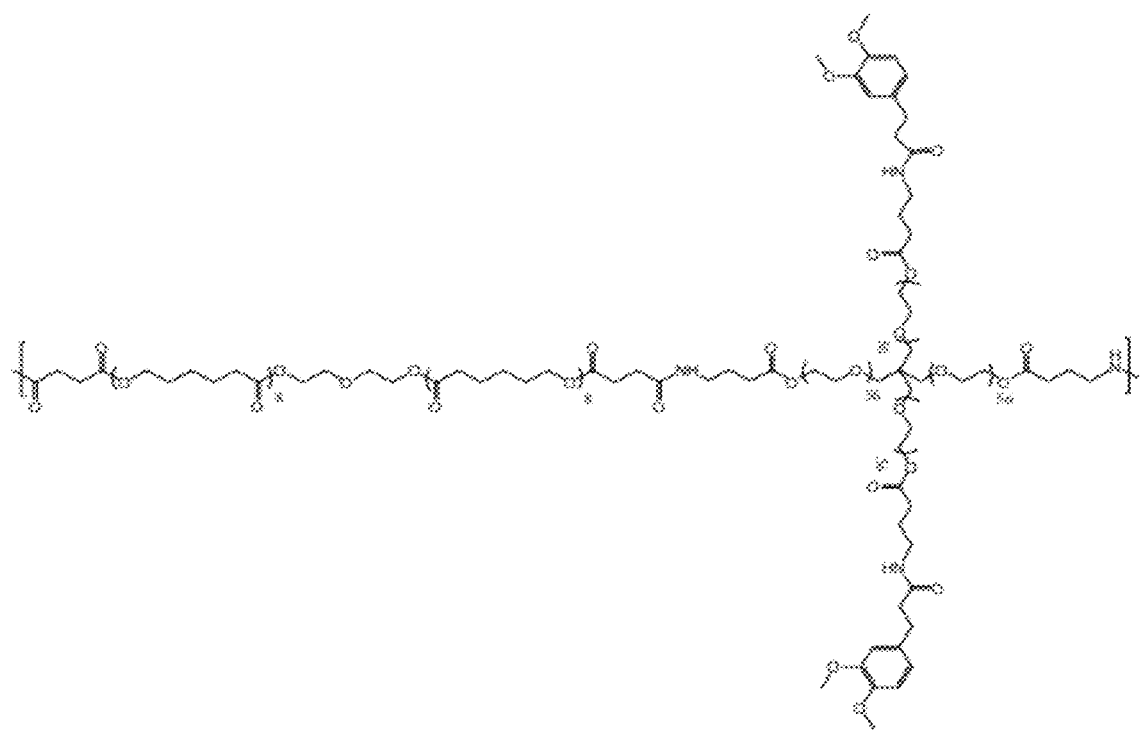
Figure 153:
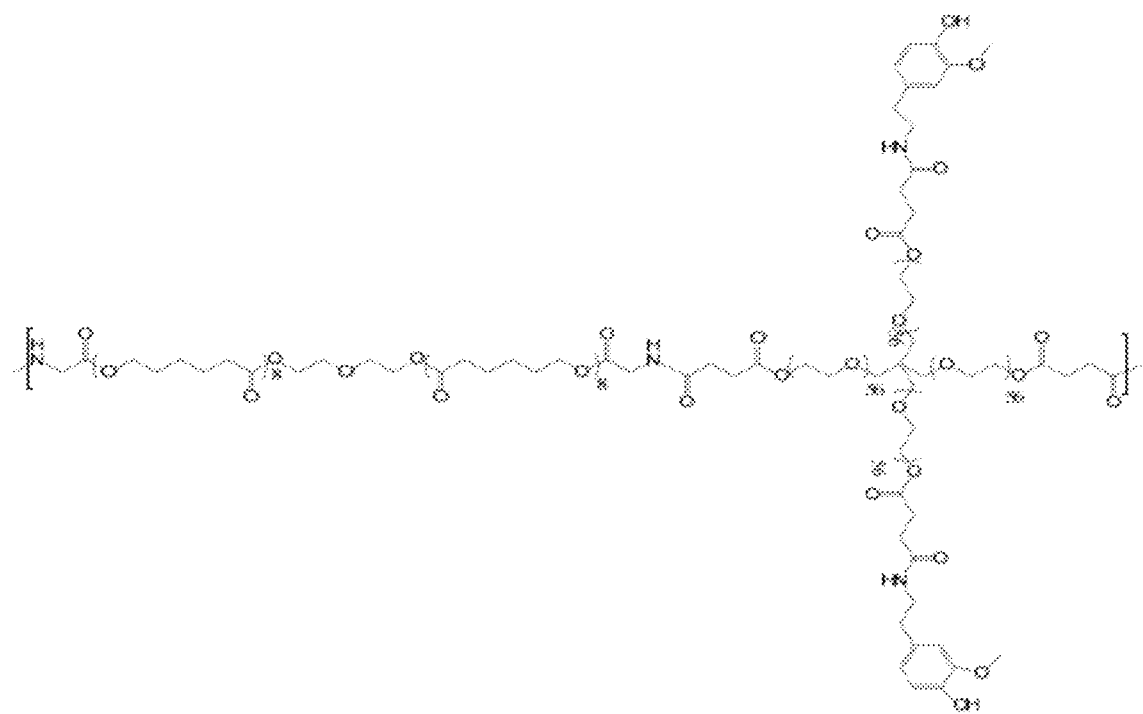
Figure 154:
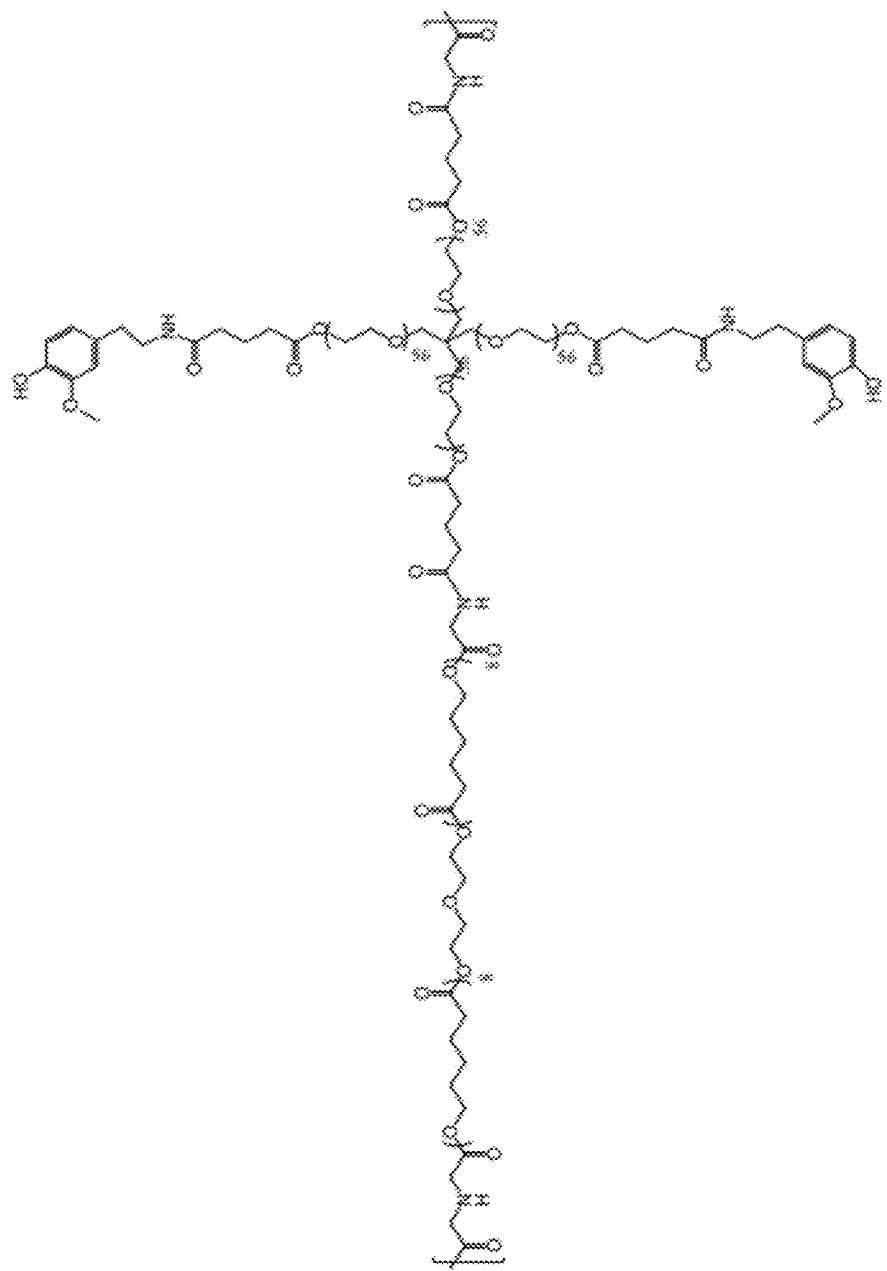
Figure 155:
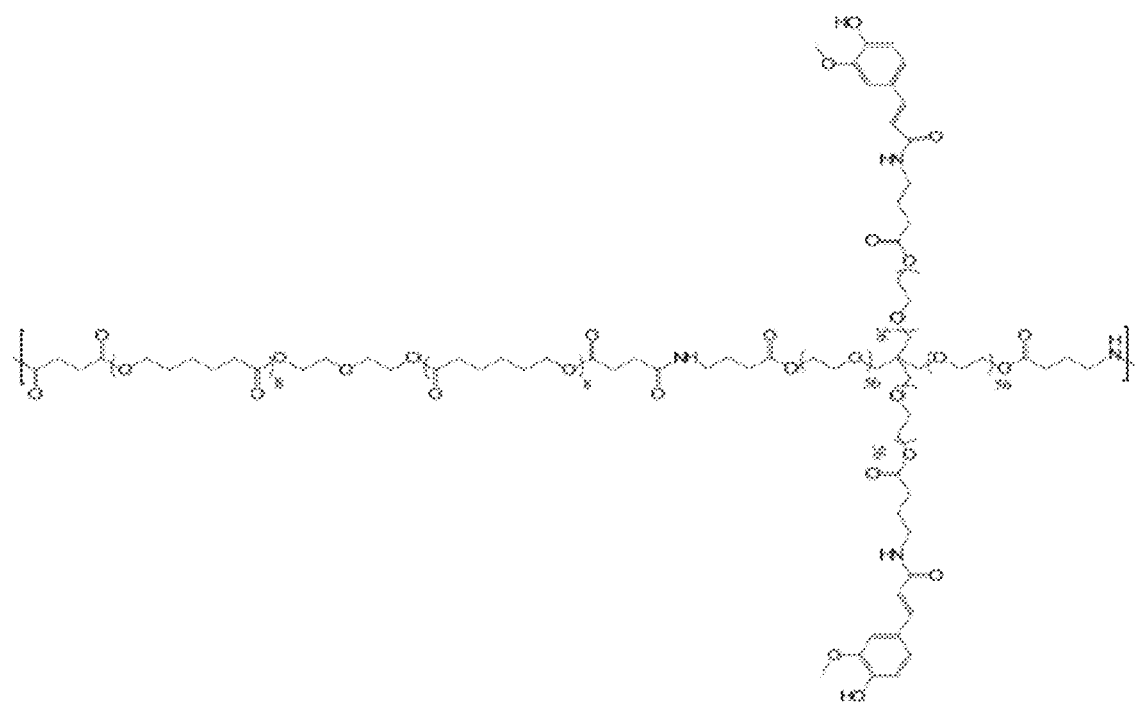
Figure 156:
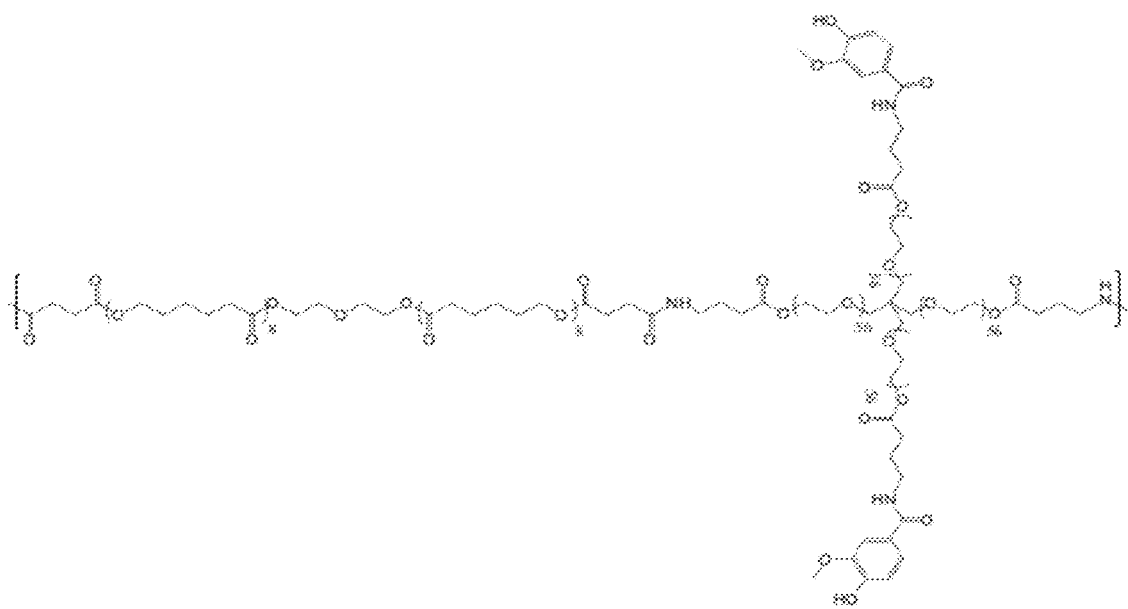
Figure 157:
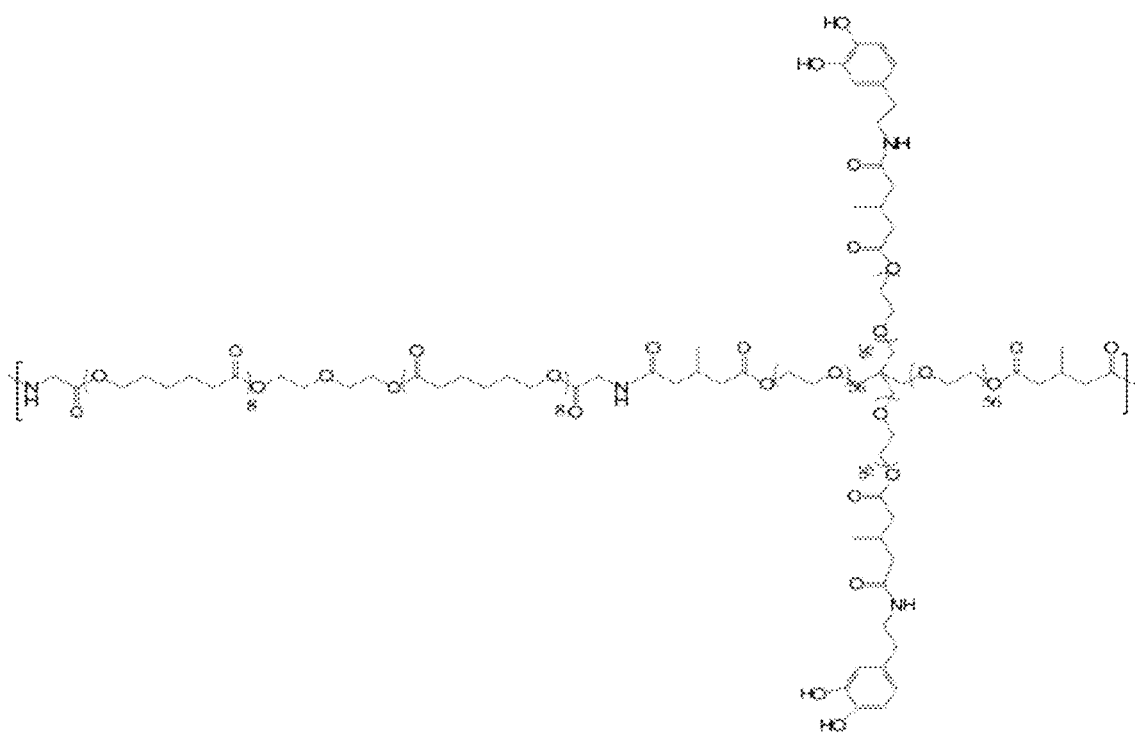
Figure 158:
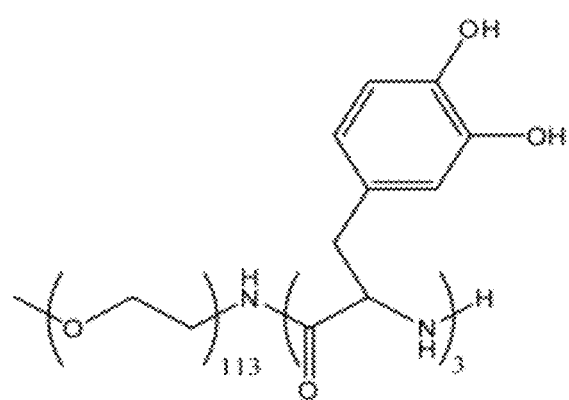
Figure 159:
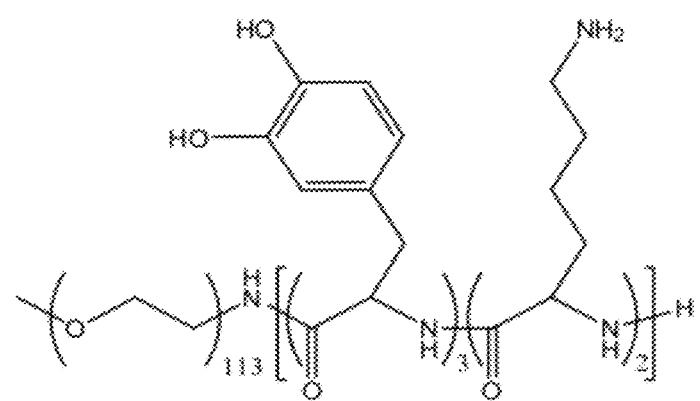
Figure 160:
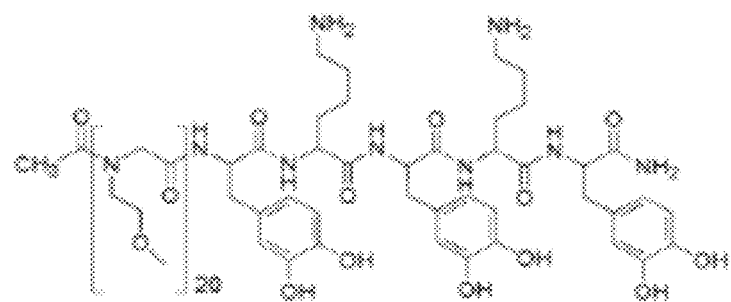
Figure 161:
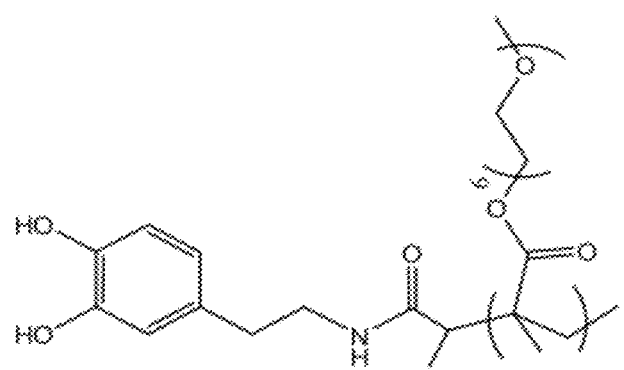
Figure 162:
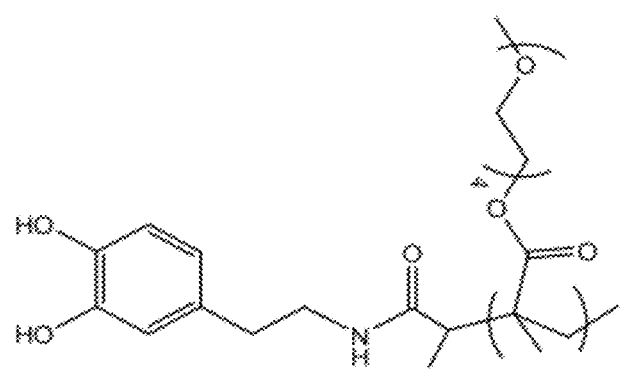
Figure 163:
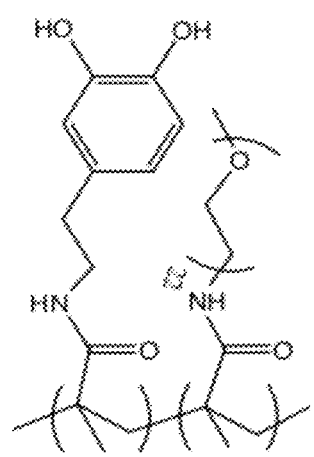
Figure 164:
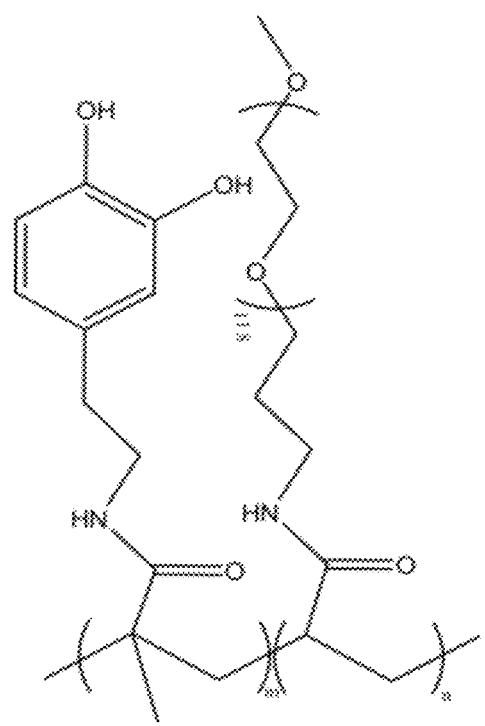
Figure 165:
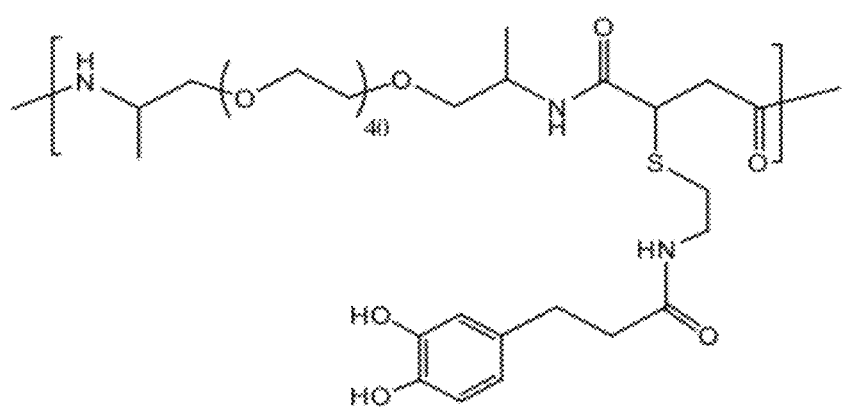
Figure 166:
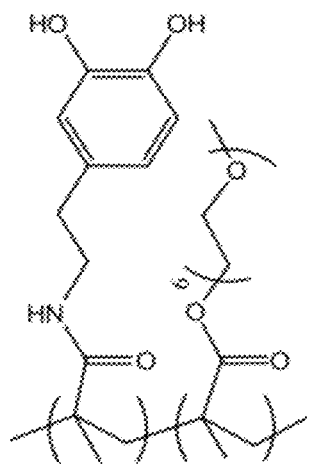
Figure 167:
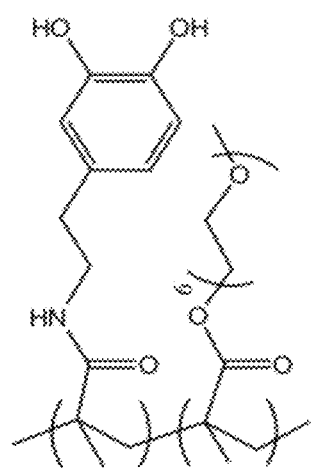

| Name | R&D Name | Description | FIG. No. |
|---|---|---|---|
| Medhesive-138 | p(CL2kEG10kb-g-DMPAu2) | Multi-branched polymer constructed from PCL-(Gly)2 2k and 4-arm PEG-OH 10k (1:1 feed ratio) modified with 3,4-dimethoxyphenylamine. Urethane linkages. | FIG. 148 |
| Medhesive-139 | p(CL2kEG10k(GA)b-g-DMe2) | Multi-branched polymer constructed from PCL-(Gly)2 2k and 4-arm PEG-GA 10k (1:1 feed ratio) modified with Dopamine. | FIG. 149 |
| Medhesive-140 | p(CL2kEG10k(GABA)b-g-DHe2) | Multi-branched polymer constructed from PCL-(SA)2 2k and 4-arm PEG-GABA 10k (1:1 feed ratio) modified with DOHA | FIG. 150 |
| Medhesive-141 | p(CL2kEG10k(GABA)b-g-HFe2) | Multi-branched polymer constructed from PCL-(SA)2 2k and 4-arm PEG-GABA 10k (1:1 feed ratio) modified with Hydroferulic Acid. | FIG. 151 |
| Medhesive-142 | p(CL2kEG10k(GABA)b-g-DMHCAe2) | Multi-branched polymer constructed from PCL-(SA)2 2k and 4-arm PEG-GABA 10k (1:1 feed ratio) modified with 3,4-Dimethoxyhydrocinnamic Acid. | FIG. 152 |
| Medhesive-143 | | Multi-branched polymer constructed from PCL-(Gly)2 2k and 4-arm PEG-SA 10k (1:1 feed ratio) modified with 3-Methoxytyramine. | FIG. 153 |
| Medhesive-144 | p(CL2kEG10k(GA)b-g-MTe2) | Multi-branched polymer constructed from PCL-(Gly)2 2k and 4-arm PEG-GA 10k (1:1 feed ratio) modified with 3-Methoxytyramine. | FIG. 154 |
| Medhesive-145 | | Multi-branched polymer constructed from PCL-(SA)2 2k and 4-arm PEG-GABA 10k (1:1 feed ratio) modified with Ferulic Acid. | FIG. 155 |
| Medhesive-146 | | Multi-branched polymer constructed from PCL-(SA)2 2k and 4-arm PEG-GABA 10k (1:1 feed ratio) modified with Vanillic Acid. | FIG. 156 |
| Medhesive-147 | | Multi-branched polymer constructed from PCL-(Gly)2 2k and 4-arm PEG-MGA 10k (1:1 feed ratio) modified with Dopamine. | FIG. 157 |
| Surphys-001 | mPEG-DOPA3 | 5000 MW mPEG modified with a short peptide consists of 3 DOPA residues. | FIG. 158 |
| Surphys-002 | mPEG-DOPA-Lys | 5000 MW mPEG modified with a short, random peptide consists of 3 DOPA and 2 Lysine residues. | FIG. 159 |
| Surphys-003 | PMP1 | 2000 MW peptoid modified with alternating DOPA-Lys-DOPA-Lys-DOPA peptide | FIG. 160 |
| Surphys-004 | SIATRP-EG9ME | Surface-Initiated ATRP polymerization of EG9ME. | FIG. 161 |
| Surphys-005 | SIATRP-EG4ME | Surface-Initiated ATRP polymerization of EG4ME. | FIG. 162 |
| Surphys-006 | p(DMA3-EG1kMA) | Polymerized DMA3 and EG1kMA. Amide linkage between PEG and methacrylate group. | FIG. 163 |
| Surphys-007 | p(DMA3-EG12AA) | Polymerized from DMA3 and EG12AA (mPEG acrylamide 550 MW PEG). DMA3 accounts for 5-10 wt %. | FIG. 164 |
| Surphys-008 | p(ED2k-g-DOHA) | Linear, repeating Jeffamine ED2001 (1.9k MW) grafted with DOHA. Chain extension achieved with Fumaryl Chloride. | FIG. 165 |
| Surphys-009 | p(EG9ME-DMA3) 4% | Polymerized from DMA3 and EG9ME. DMA3 accounts for 4 wt % | FIG. 166 |
| Surphys-010 | p(EG9ME-DMA3) 22% | Polymerized from DMA3 and EG9ME. DMA3 accounts for 20 wt % | FIG. 167 |

TABLE 1-continued

Figure 168:
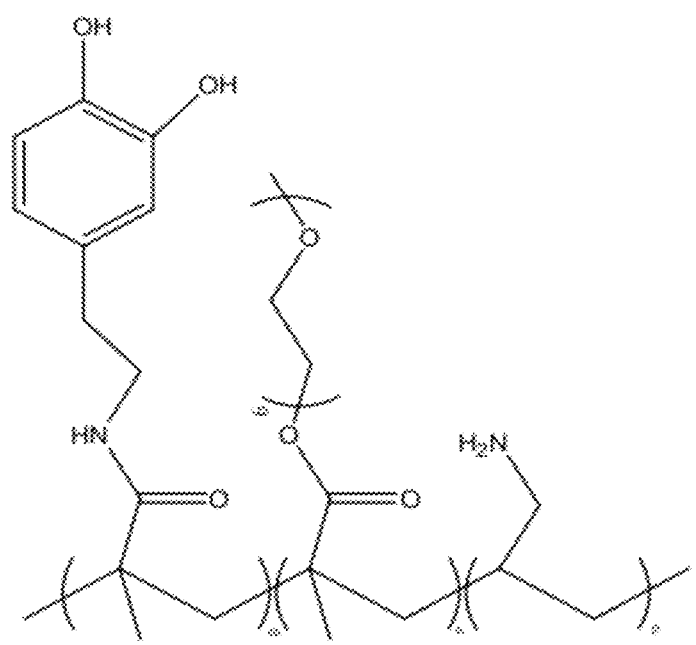
Figure 169:
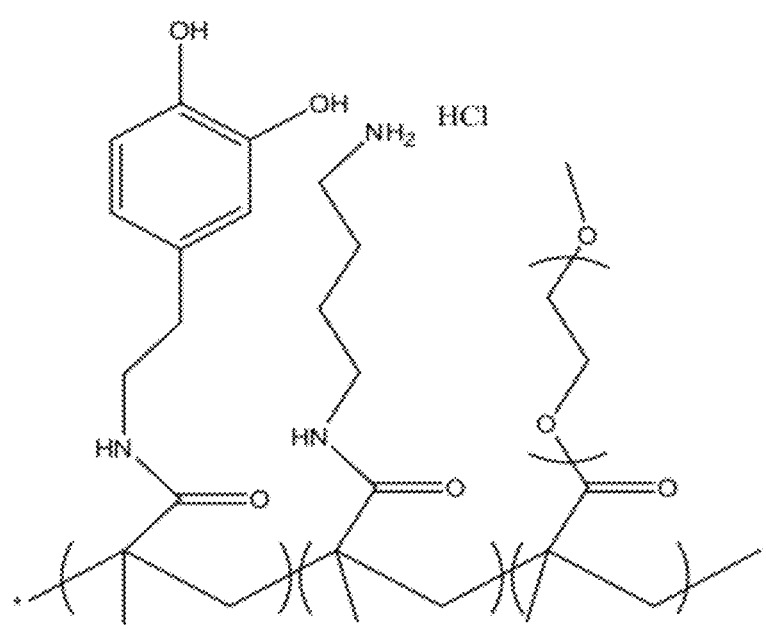
Figure 170:
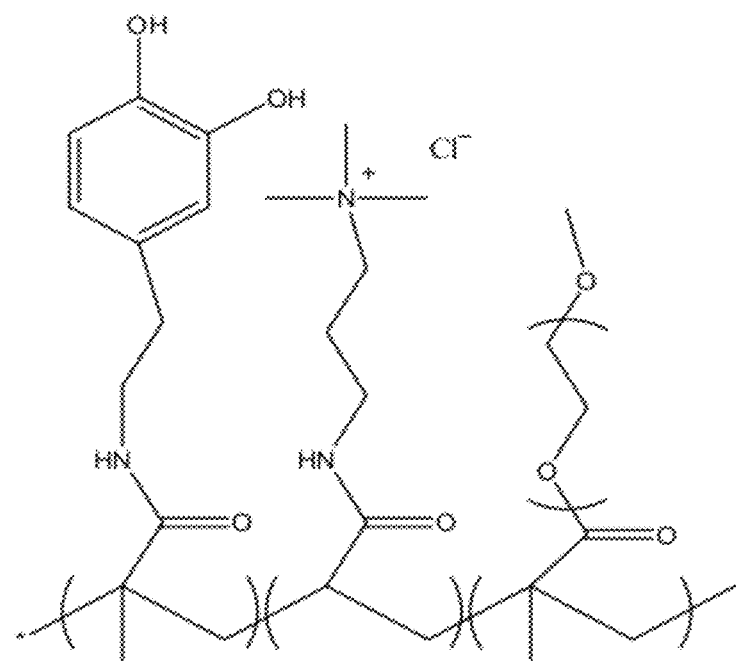
Figure 171:
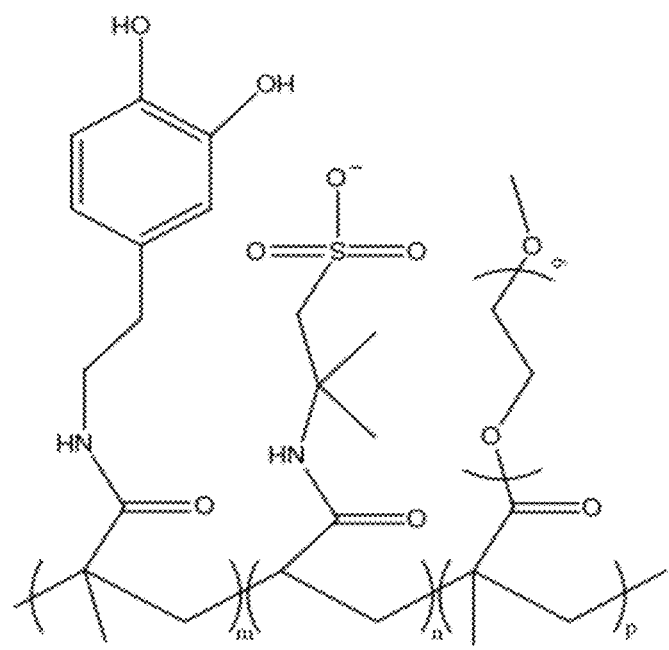
Figure 172:
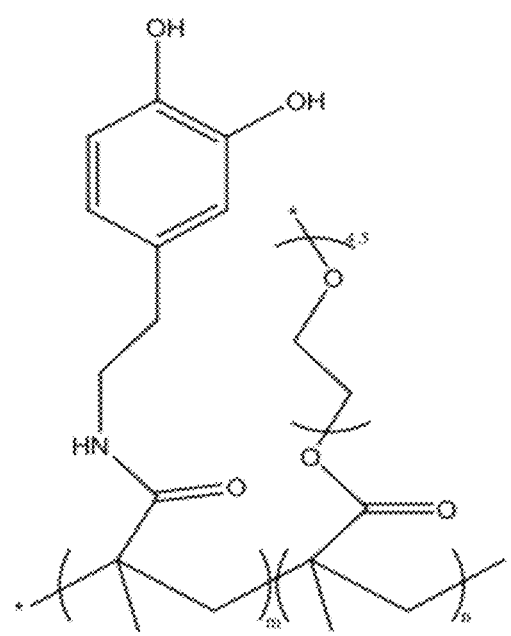
Figure 173:
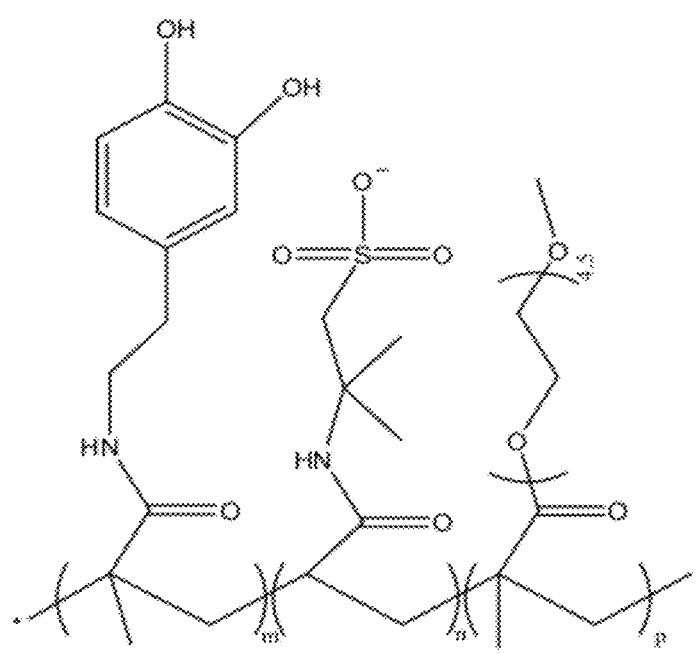
Figure 174:
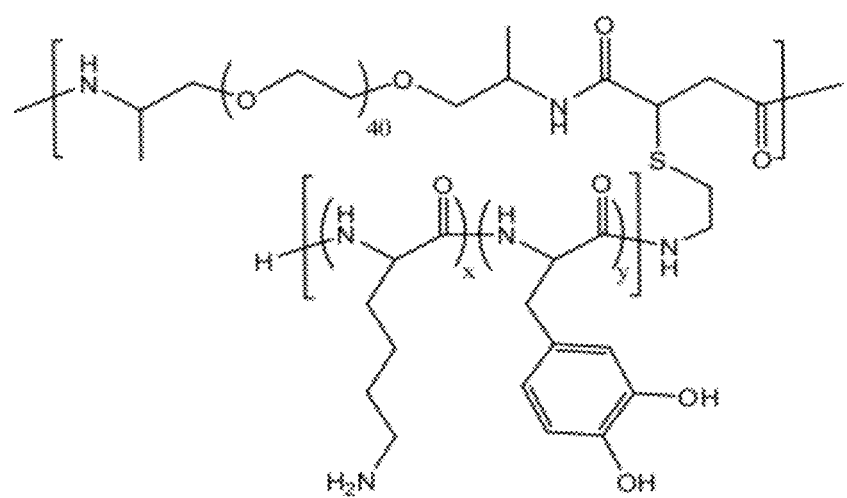
Figure 175:
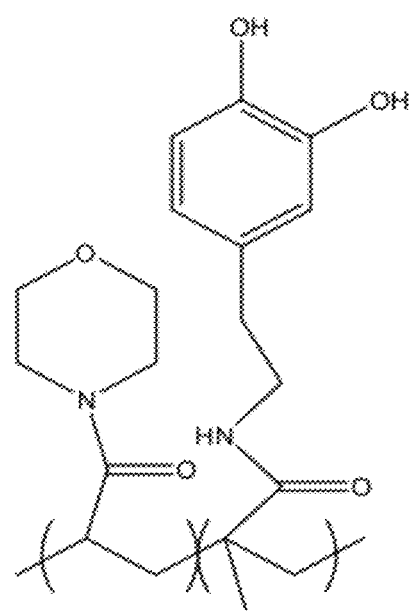
Figure 176:
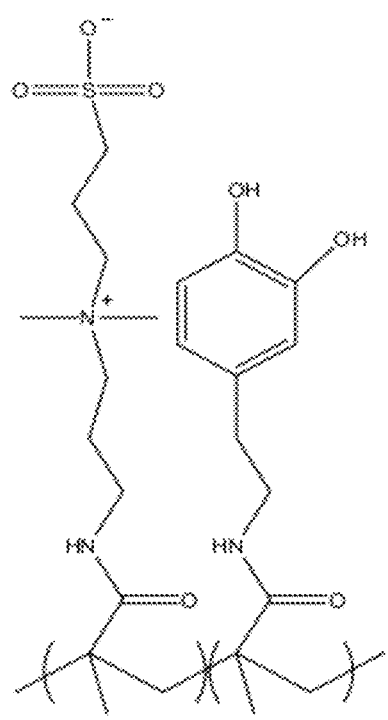
Figure 177:
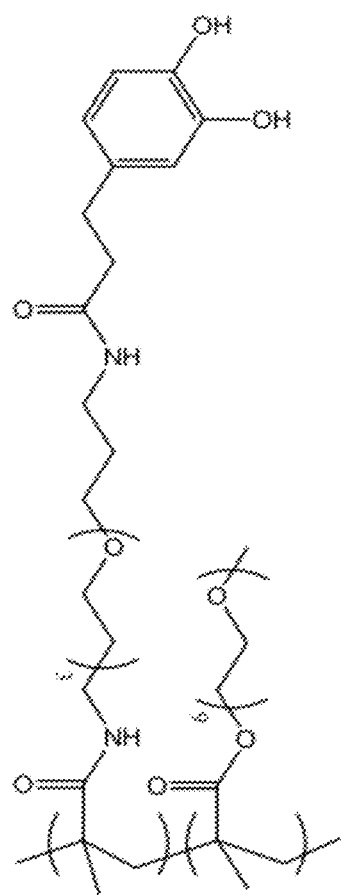
Figure 178:
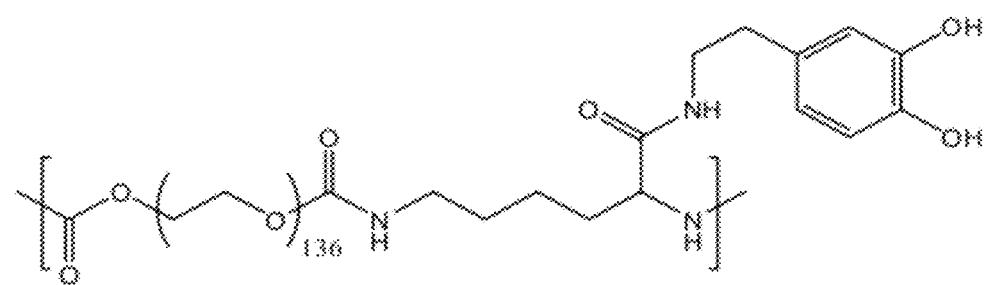
Figure 179:
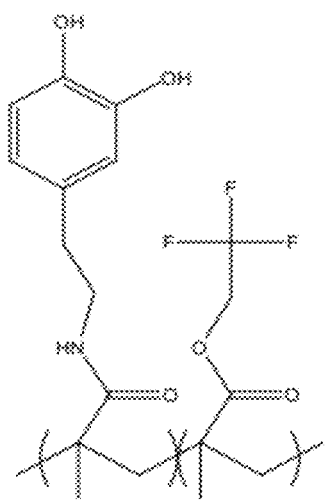
Figure 180:
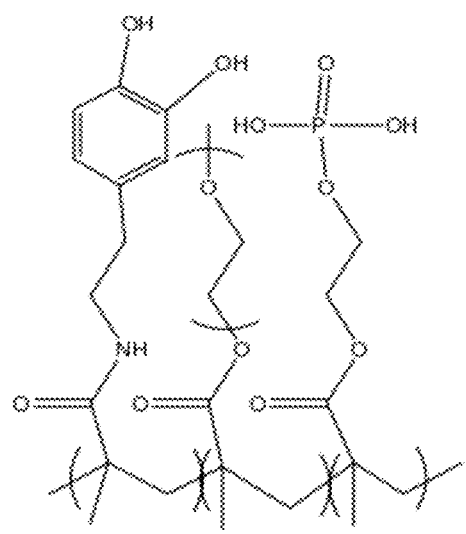
Figure 181:
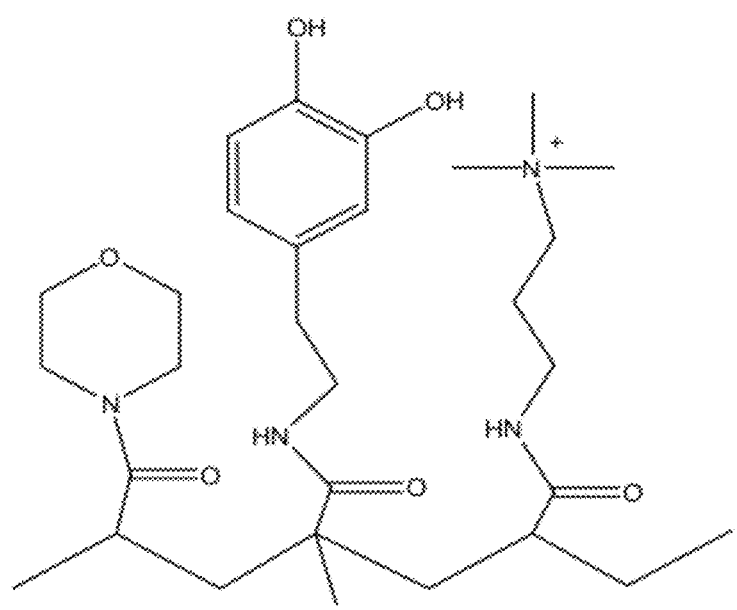
Figure 182:
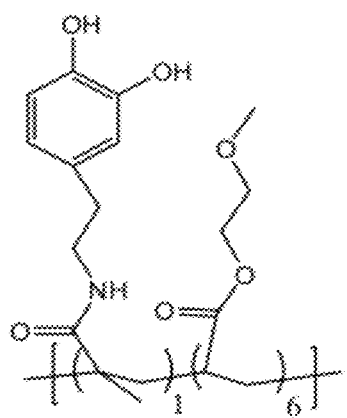
Figure 183:
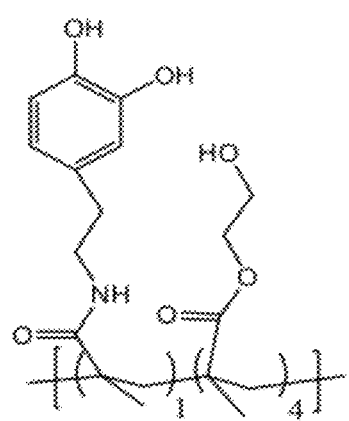
Figure 184:
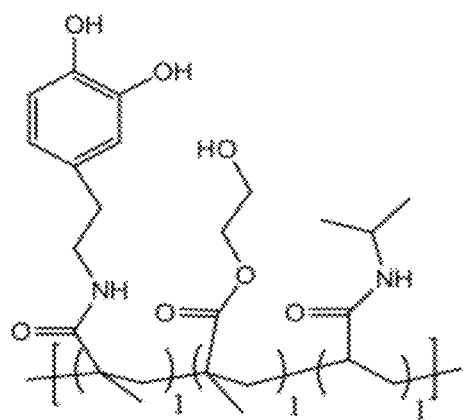
Figure 185:
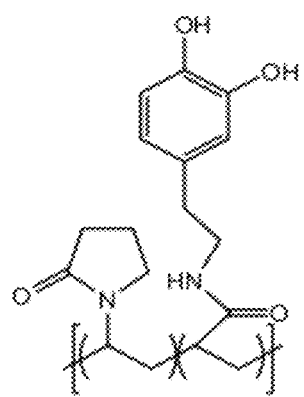
Figure 186:
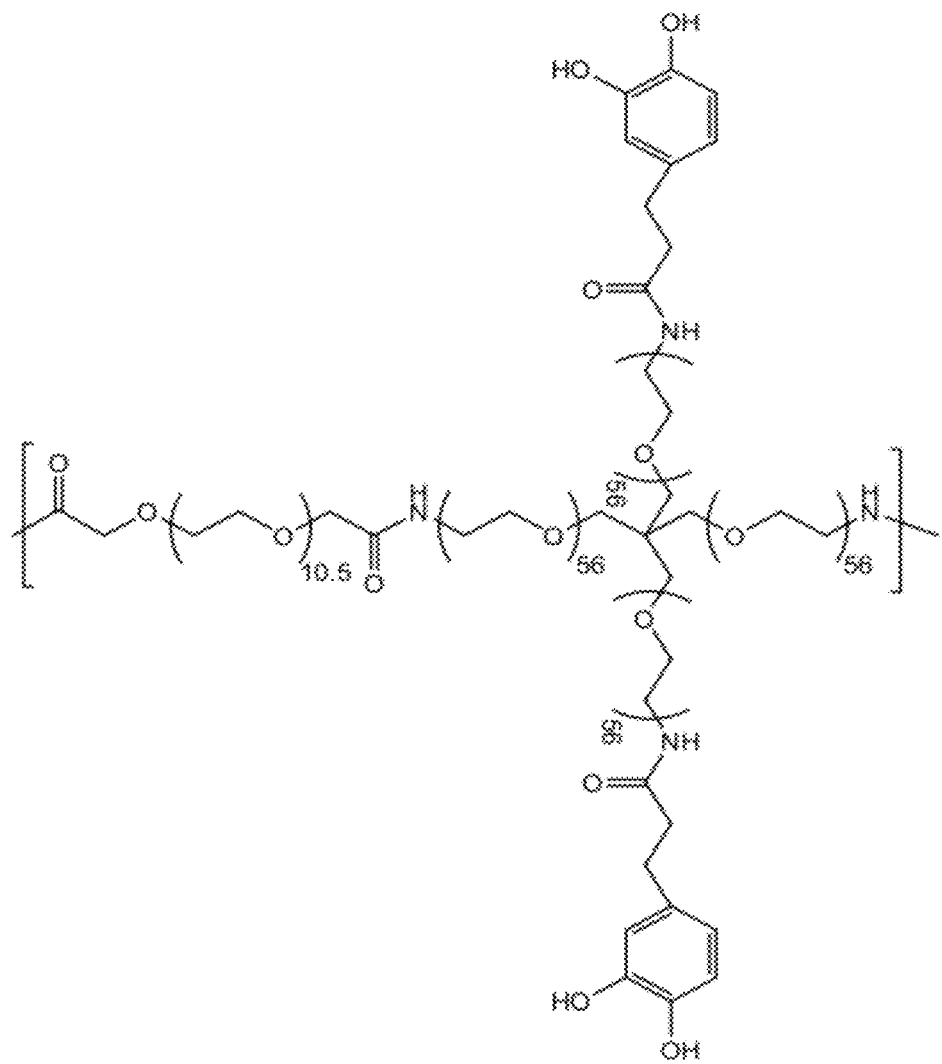
Figure 187:
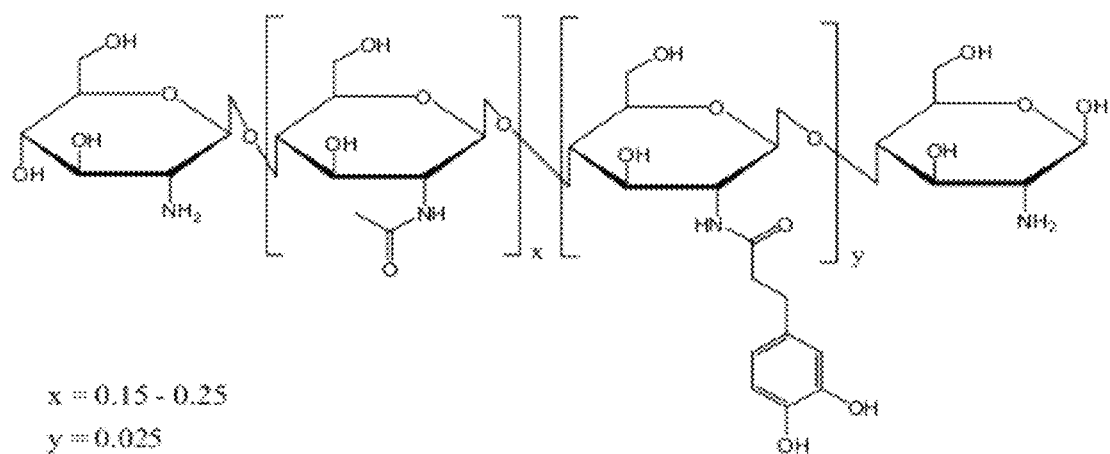
Figure 188:
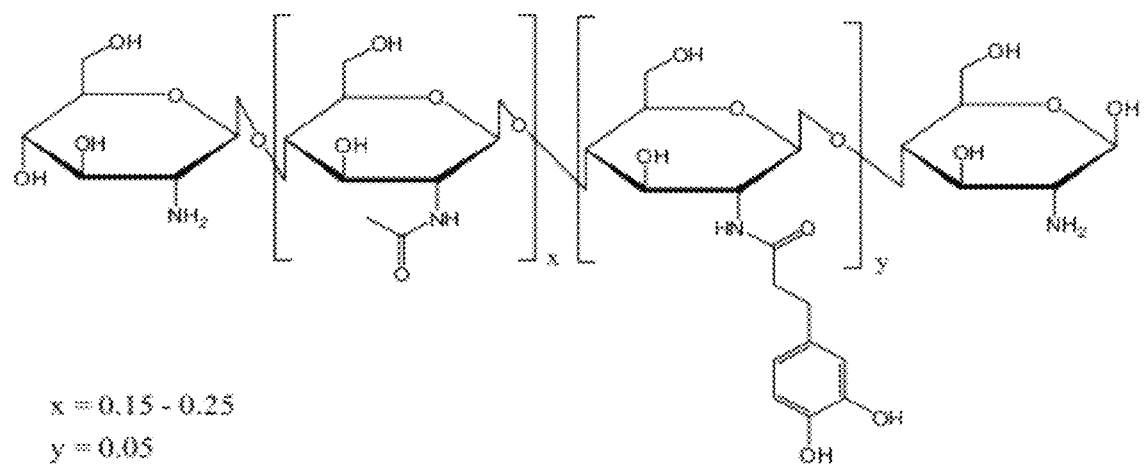
Figure 189:
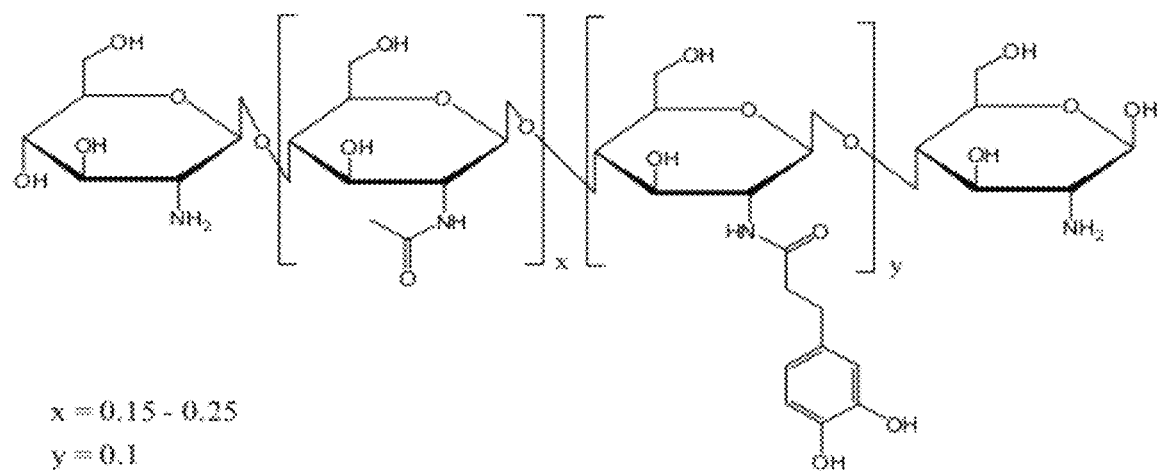
Figure 190:
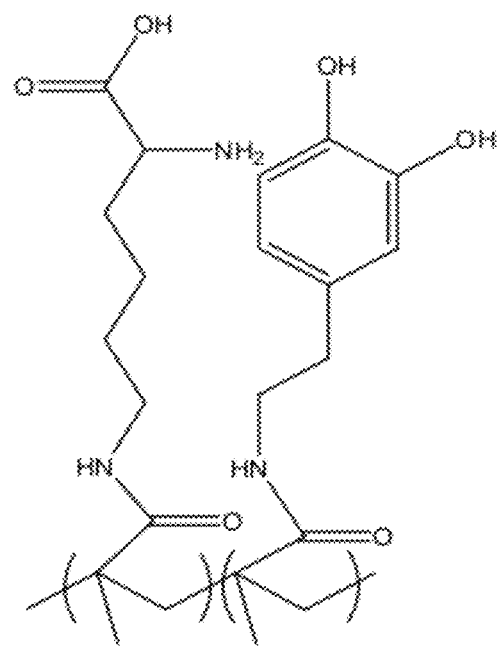

| Name | R&D Name | Description | FIG. NO. |
|---|---|---|---|
| Surphys-011 | p(DMA3-EG9ME-Allylamine) | Polymerized from DMA3, EG9ME and Allylamine with a DMA content of ~10 wt % and Allylamine content of ~5 wt % | FIG. 168 |
| Surphys-012 | p(DMA3-EG9ME-DABMA) | Polymerized from DMA3, EG9ME and DABMA, with a DMA content of ~13 wt % | FIG. 169 |
| Surphys-013 | p(DMA3-EG9ME-APTP) | Polymerized from DMA3, EG9ME and quaternary amine APTP, with a DMA content of 18 wt % and APTP content of 24 wt % | FIG. 170 |
| Surphys-014 | p(DMA3-EG9ME-AMPS) | Polymerized from DMA3, EG9ME and AMPS, with a DMA content of 16 wt % and AMPS content of 21 wt %. | FIG. 171 |
| Surphys-015 | p(DMA3-EG4ME) | Polymerized from equal DMA3 and OEG4ME. DMA3 accounts for 32 wt %. | FIG. 172 |
| Surphys-016 | p(DMA-EG4ME-AMPS) | Polymerized from DMA3, EG4ME and AMPS, with a DMA content of 13 wt %. | FIG. 173 |
| Surphys-017 | p(ED2k-g-DL) | Linear, repeating Jeffamine ED2001 (1.9k MW) grafted with short, random peptide of DOPA and Lys. Chain extension achieved with Fumaryl Chloride. | FIG. 174 |
| Surphys-018 | p(DMA3-NAM) | Polymerized from DMA3 and N-Acryloylmorpholine. DMA3 accounts for 5-10 wt %. | FIG. 175 |
| Surphys-019 | p(DMA3-SBMA) | Polymerized from DMA3 and sulfobetaine methacrylate with stable amide linkage. DMA3 accounts for 5-10 wt %. | FIG. 176 |
| Surphys-020 | p(DMA4-EG9ME) | Polymerized from DMA4 and EG9ME. | FIG. 177 |
| Surphys-021 | p(EG6kLu-g-DH) | Polyether urethane of repeating PEG (6k MW) and Lysine grafted with DOHA). | FIG. 178 |
| Surphys-022 | p(DMA3-TFEMA) | Fluorinated polymer containing 5 wt % DMA3 and trifluoroethyl methacrylate. | FIG. 179 |
| Surphys-023 | p(DMA3-EG9ME-HEMAP) | Polymerized from DMA3, EG9ME and hydroxyethyl methacrylate phosphoric acid. DMA3 accounts for ~5-10 wt % and HEMAP accounts for ~5 wt %. | FIG. 180 |
| Surphys-024 | p(DMA3-NAM-APTP) | Polymerized from DMA3, APTP and N-Acryloylmorpholine. DMA3 accounts for 5-10 wt %. | FIG. 181 |
| Surphys-025 | p(DMA3-MEA) | Polymerized from DMA3 and MEA. DMA3 accounts for 15 wt %. | FIG. 182 |
| Surphys-026 | p(DMA3-HEMA) | Polymerized from DMA3 and HEMA. DMA3 accounts for 27 wt %. | FIG. 183 |
| Surphys-027 | p(DMA3-HEMA-NIPAM) | Polymerized from DMA3 and HEMA and NIPAM. Feed ratio of DMA3:HEMA:NIPAM = 1:1:1 | FIG. 184 |
| Surphys-028 | p(VP-co-DM) | Polymerized VP and activated ester (NAS), then coupled DM. Feed ratio of VP:NAS = 20:1 | FIG. 185 |
| Surphys-029 | p(EG600EG10kb-g-DH2) | Branched polymer constructed from PEG600-diacid and 4-arm PEG-NH2 10k (1:1 feed ratio) modified with DOHA. | FIG. 186 |
| Surphys-030 | Chitosan-1-DOHA | ~2.5% DOHA content attached to the amine group on a 75-85% deacylated, low molecular wieght chitosan structure | FIG. 187 |
| Surphys-031 | Chitosan-2-DOHA | ~5% DOHA content attached to the amine group on a 75-85% deacylated, low molecular wieght chitosan structure | FIG. 188 |
| Surphys-032 | Chitosan-3-DOHA | ~10% DOHA content attached to the amine group on a 75-85% deacylated, low molecular wieght chitosan structure | FIG. 189 |
| Surphys-033 | p(DMA3-KMA1) | Polymerized from DMA3 and eN-Methacryloyl-Lysine (KMA1). | FIG. 190 |

TABLE 1-continued

Figure 191:
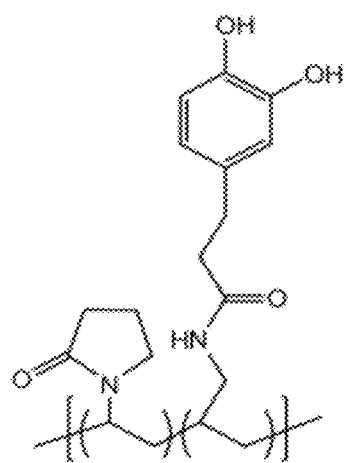
Figure 192:
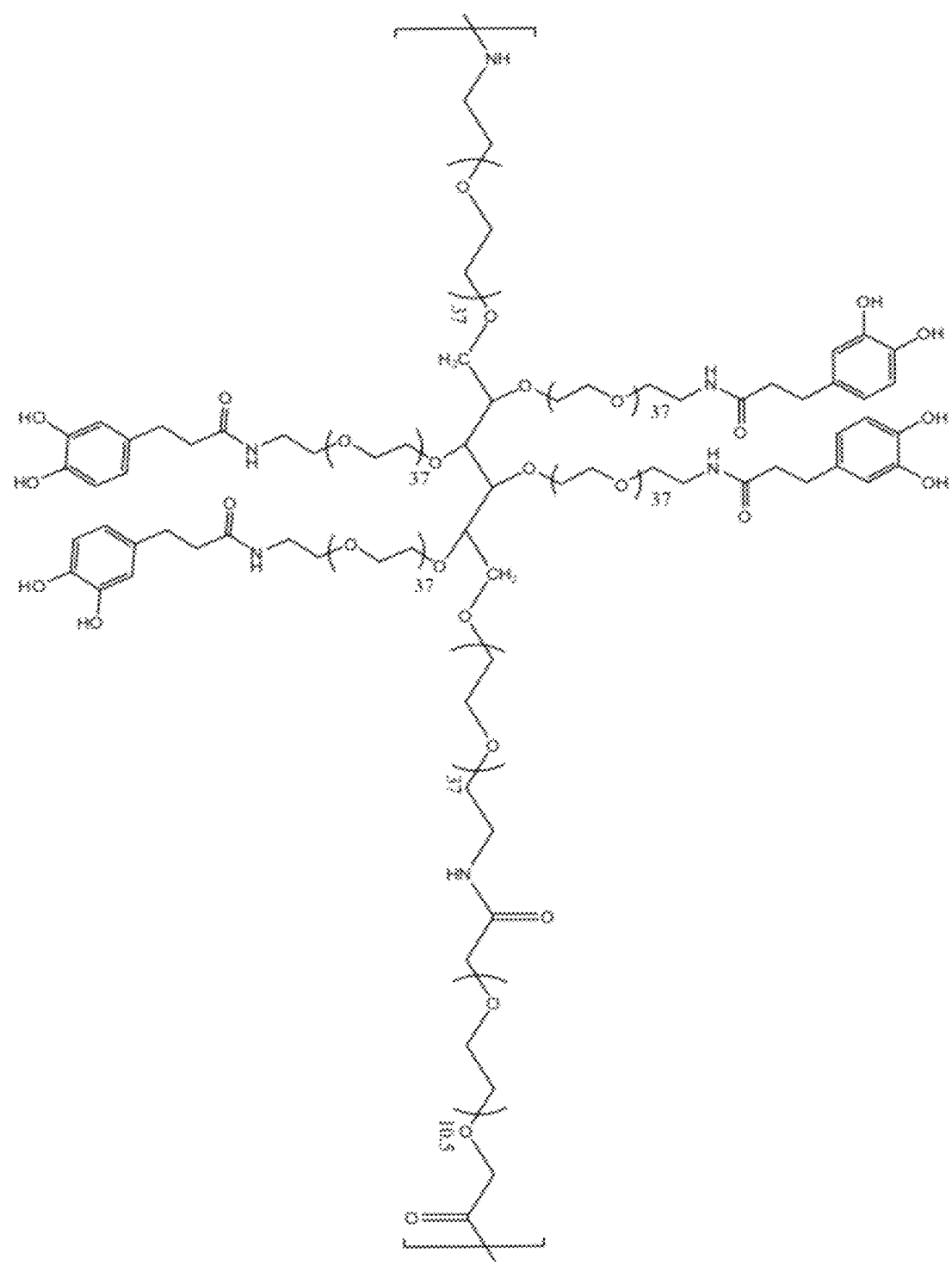
Figure 193:
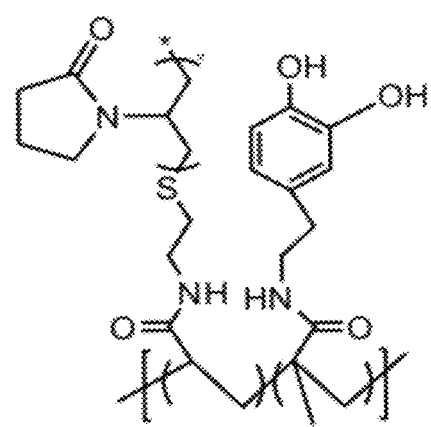
Figure 194:
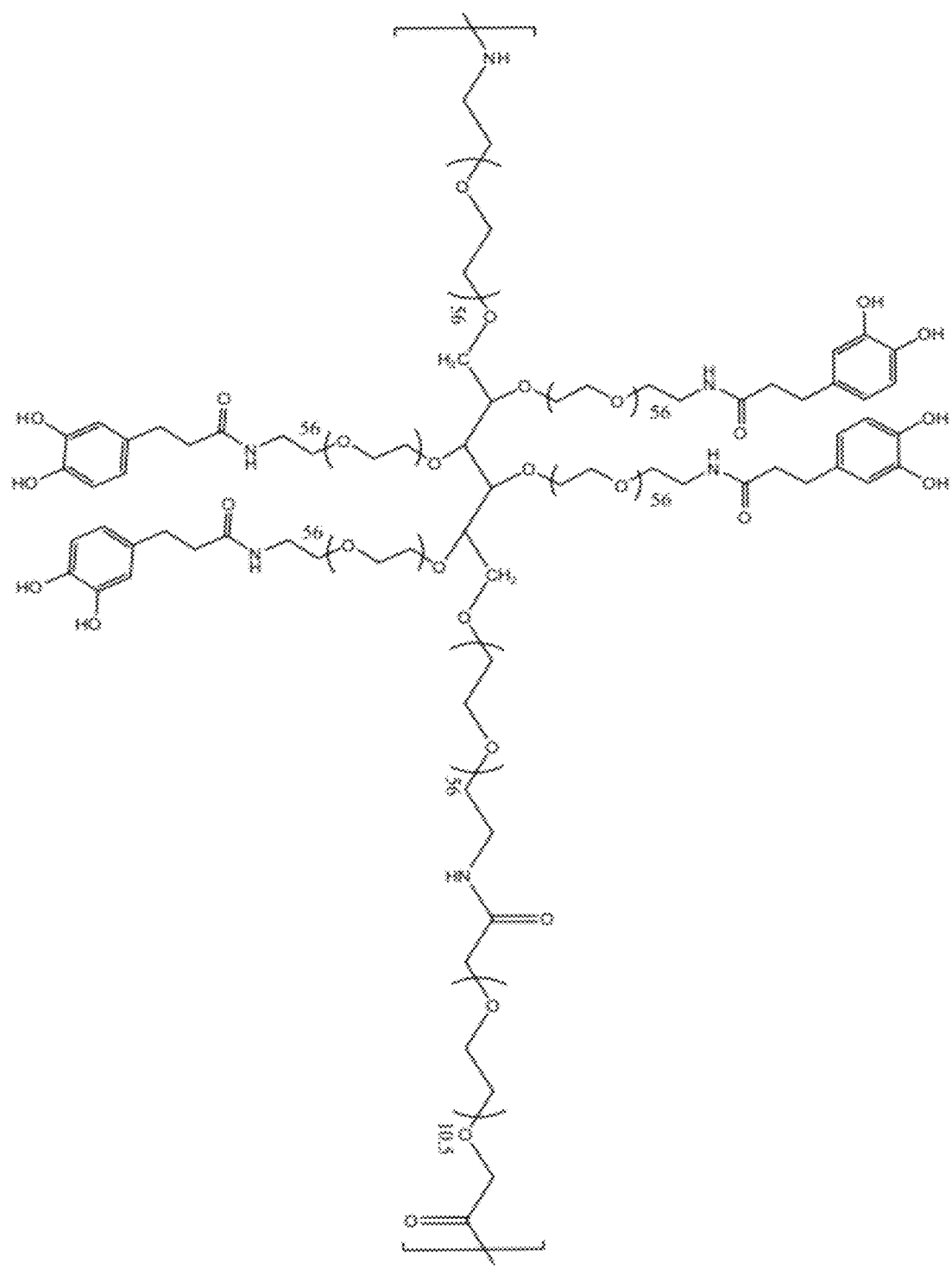
Figure 195:
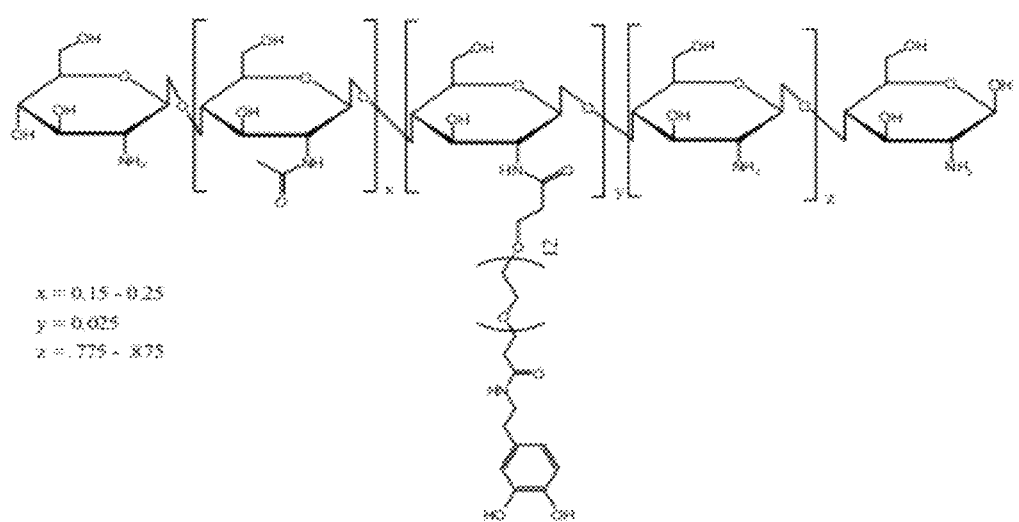
Figure 196:
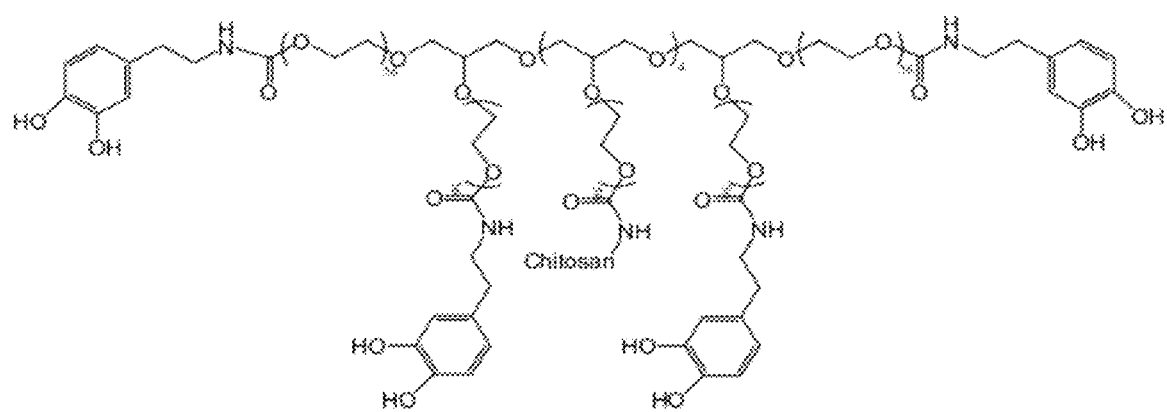
Figure 197:
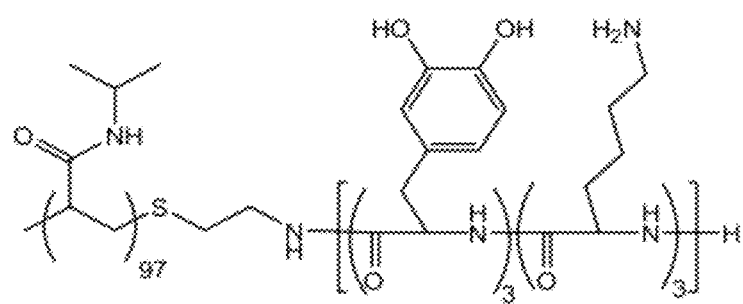
Figure 198:
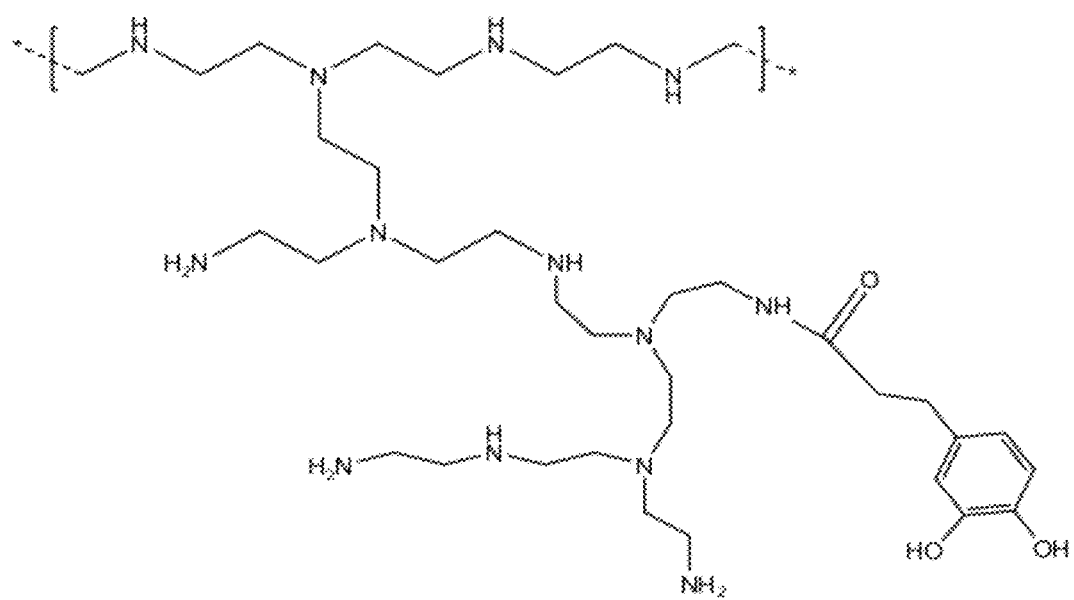
Figure 199:
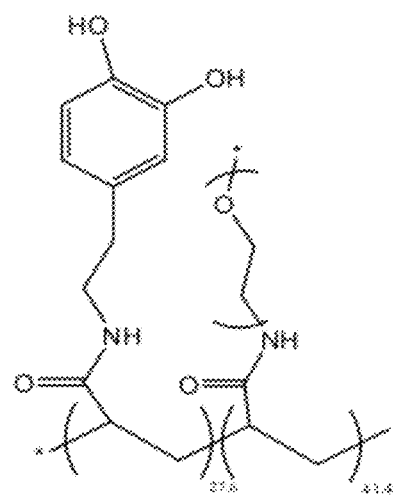
Figure 200:
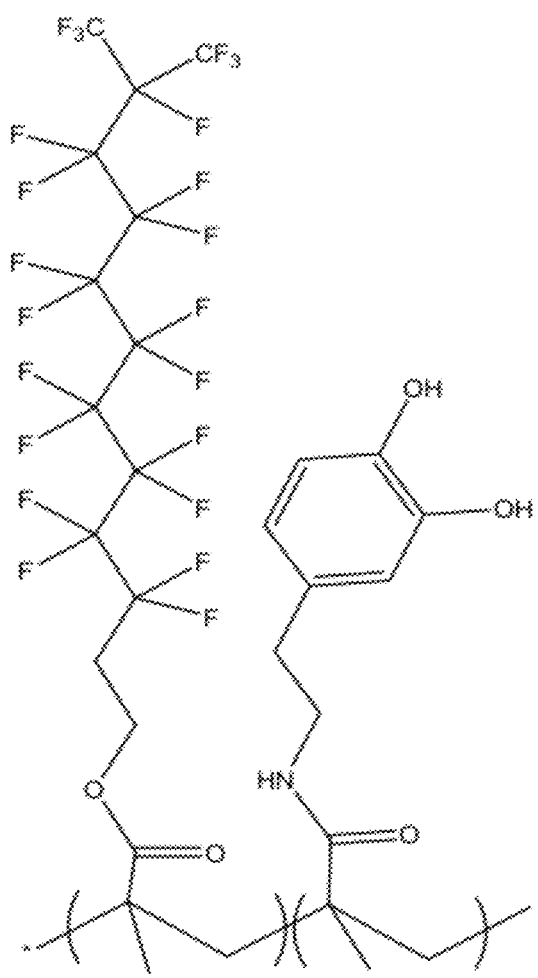
Figure 201:
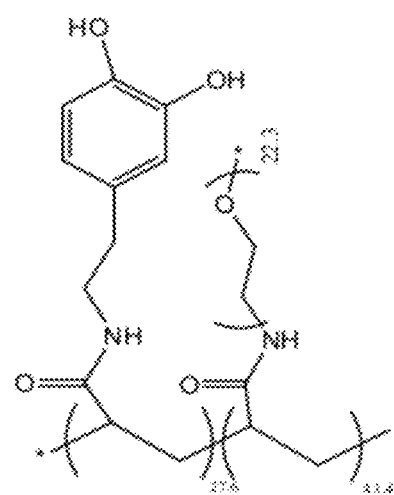
Figure 202:
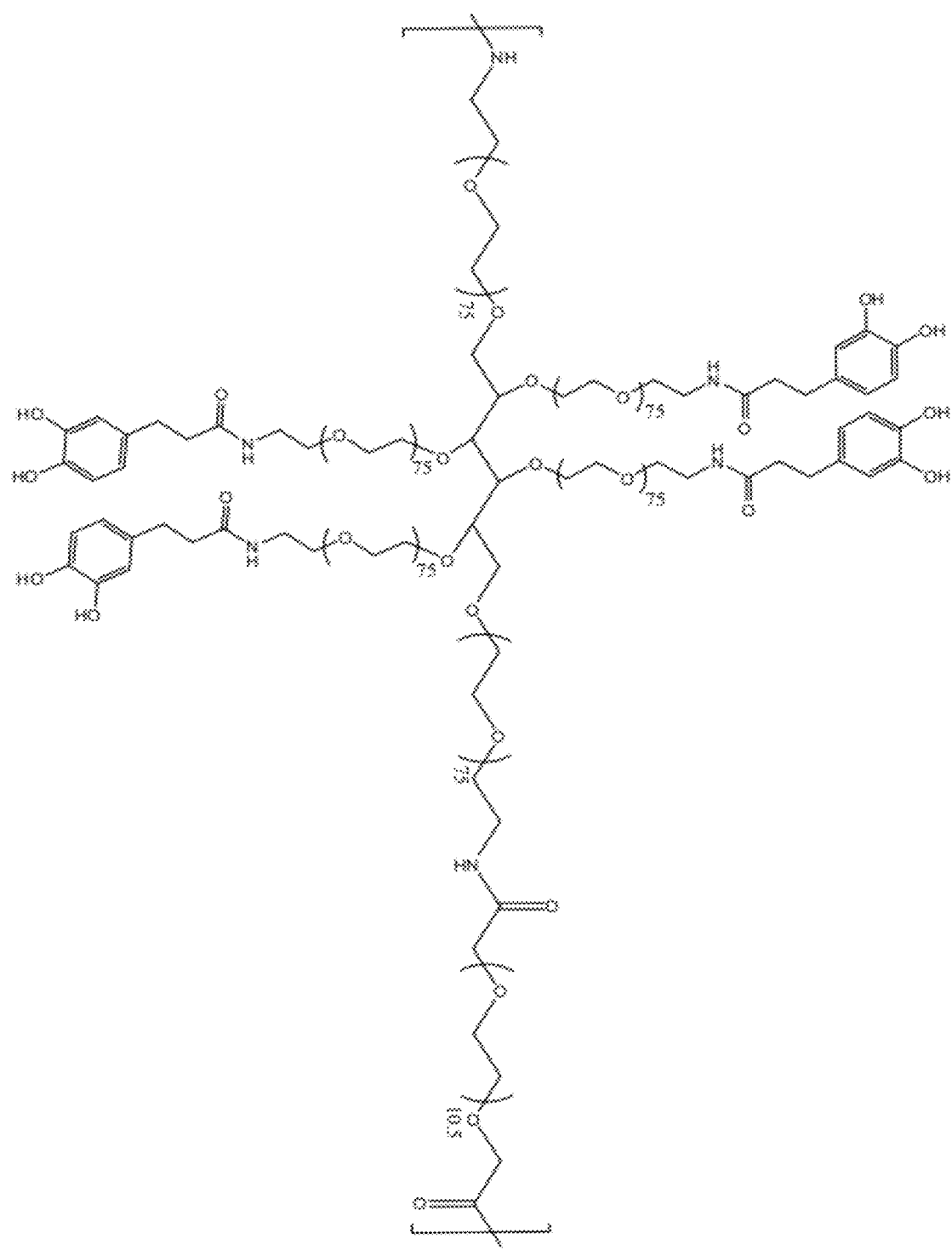
Figure 203:
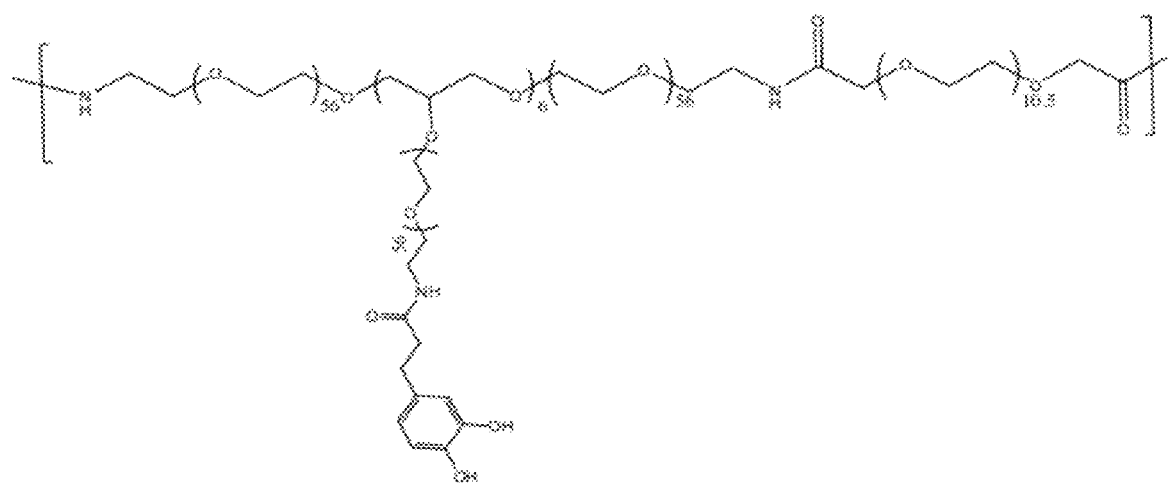
Figure 204:
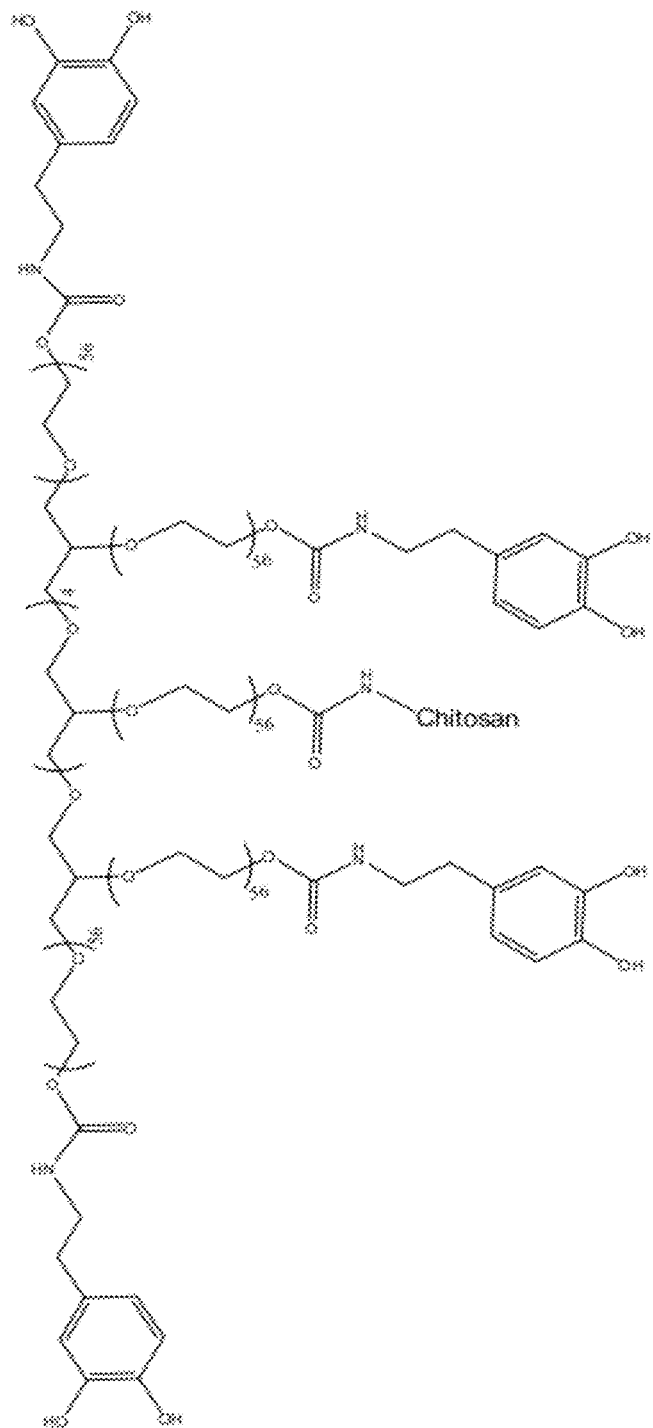
Figure 205:
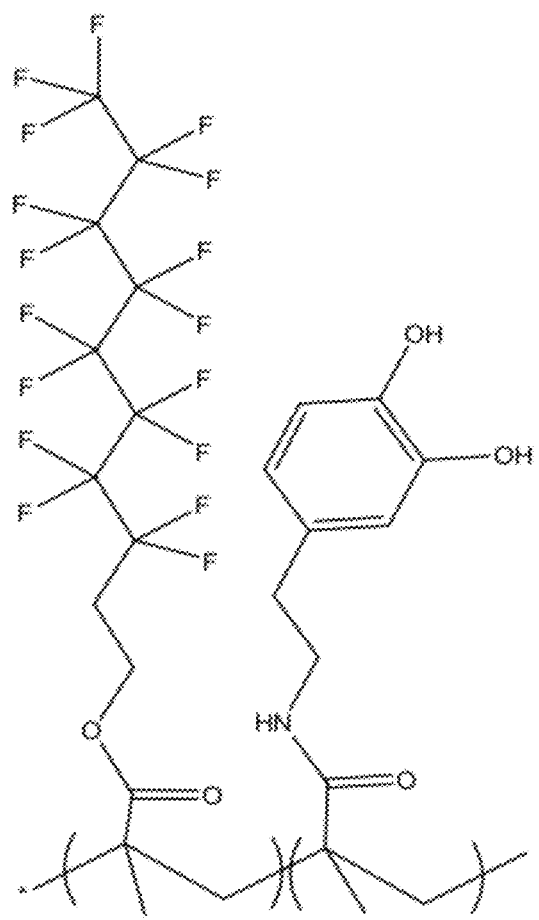
Figure 206:
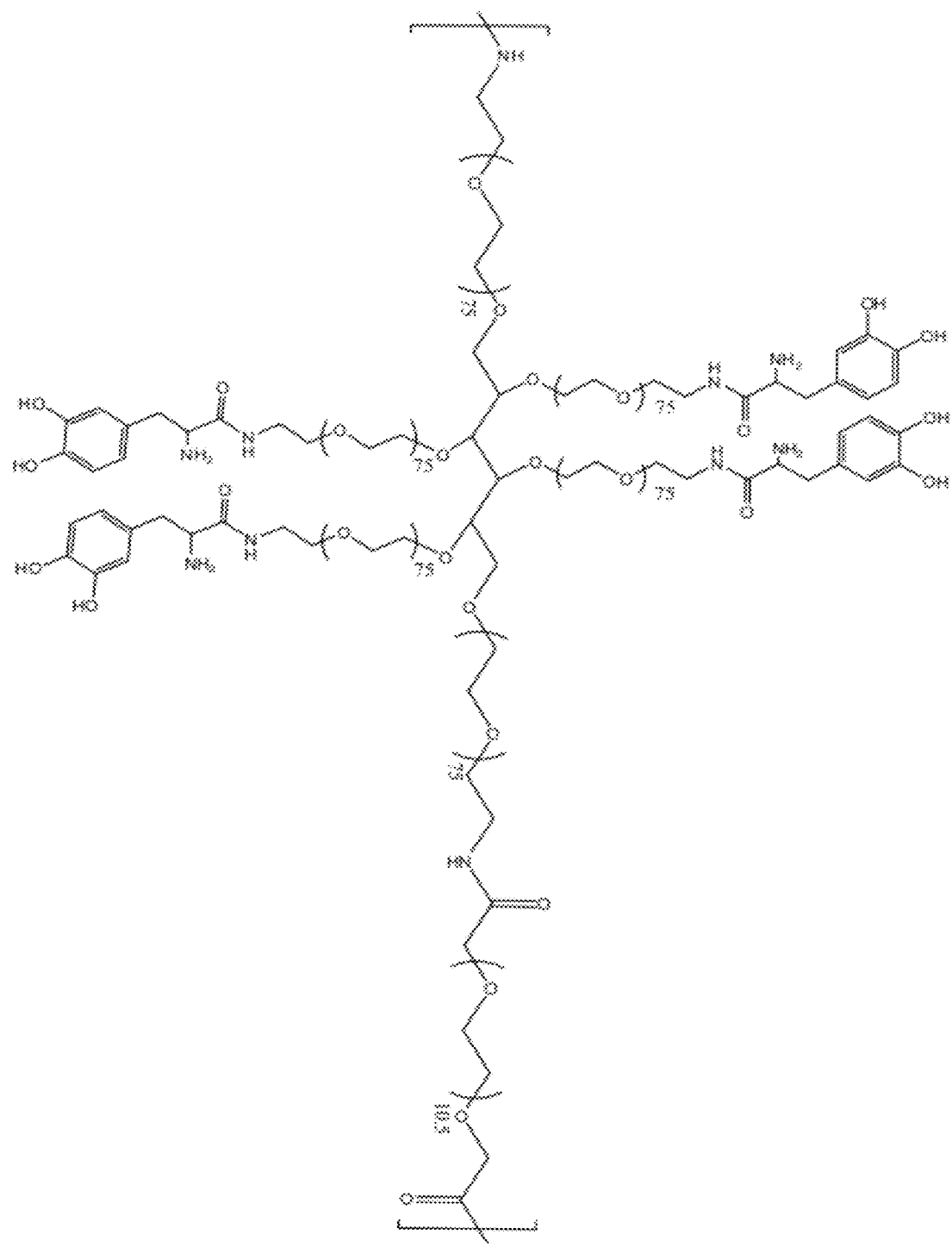
Figure 207:
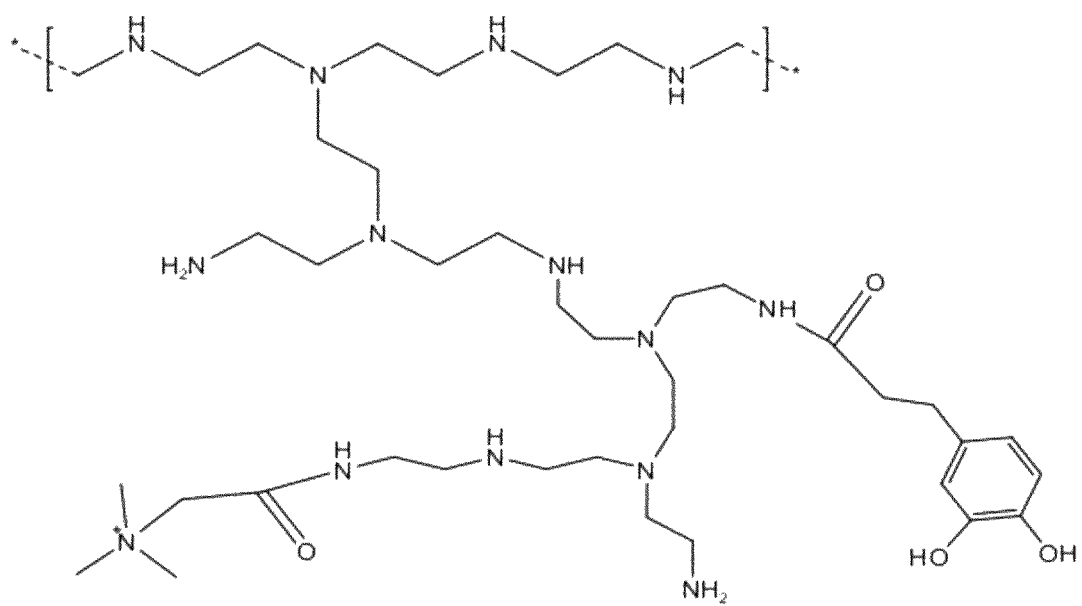
Figure 208:
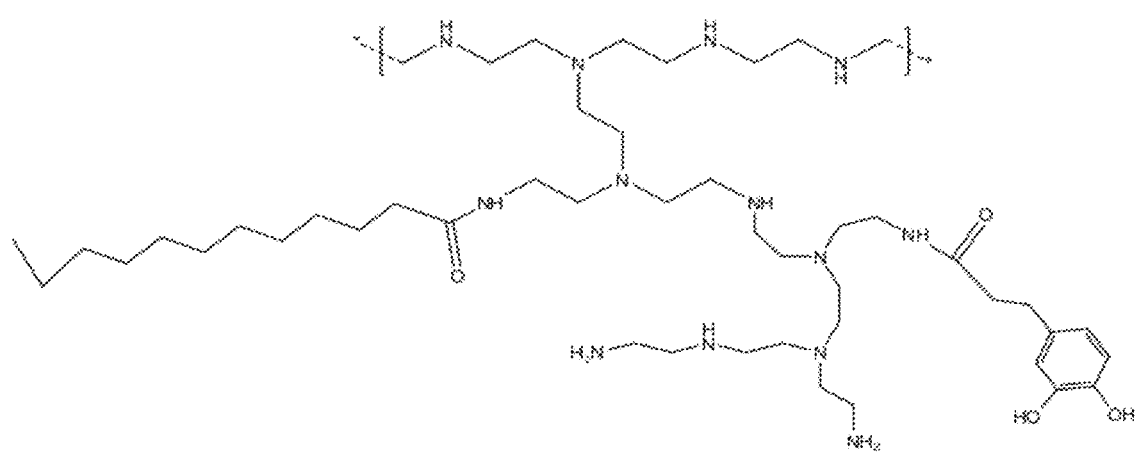
Figure 209:
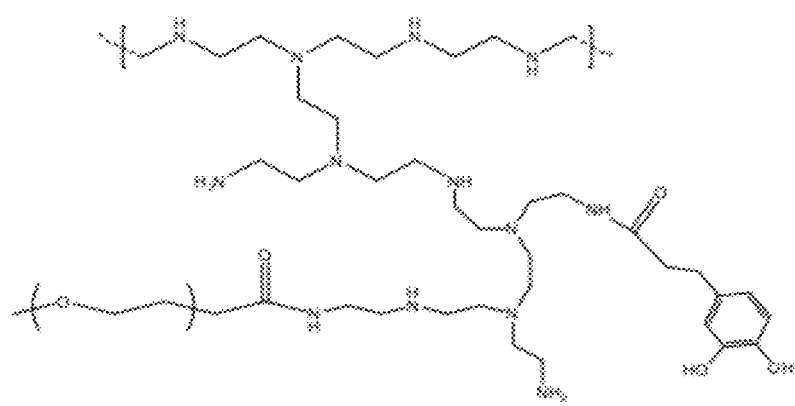
Figure 210:
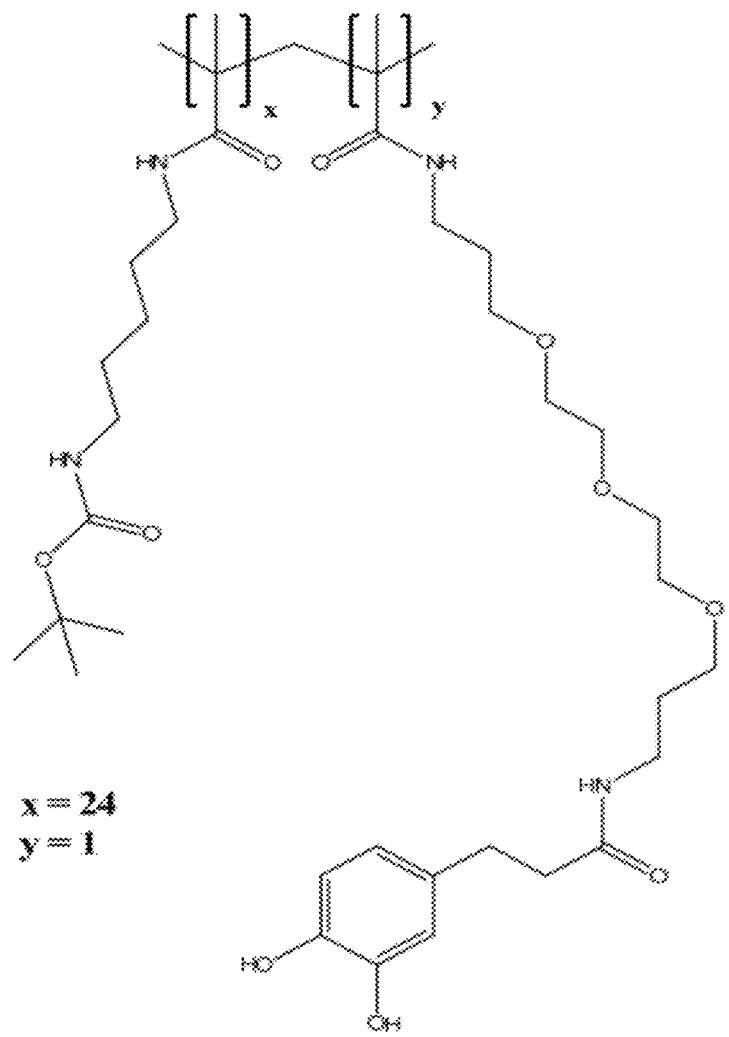

| Name | R&D Name | Description | FIG. NO. |
|---|---|---|---|
| Surphys-034 | p(VP-co-AADH) | Polymerized VP and allylamine, then coupled with DOHA using carbodiimide chemistry. Feed ratio of VP:allylamine = 20:1 | FIG. 191 |
| Surphys-035 | p(EG600EG10kb-g-DH4) | Branched polymer constructed from PEG600-diacid and 6-arm PEG-NH2 10k (1:1 feed ratio) modified with DOHA. | FIG. 192 |
| Surphys-036 | p[DMA3-(ACA-p(VP))] | Polymerized from DMA3 and acrylated Cysteamine-p(VP) with an expected DMA3 content of 5.4 wt %. Monomer:initiator molar ratio = 75:1 | FIG. 193 |
| Surphys-037 | p(EG600EG15kb-g-DH4) | Branched polymer constructed from PEG600-diacid and 6-arm PEG-NH2 15k (1:1 feed ratio) modified with DOHA. | FIG. 194 |
| Surphys-038 | Chitosan-2.5PEGDOHA | ~2.5% DOHA content attached to 600 MW PEG attached to the amine group on a 75-85% deacylated, low molecular wieght chitosan structure | FIG. 195 |
| Surphys-039 | 4Chitosan:4DMu-20KPEG | 8-arm branched PEG capped with 4 DOHA groups and 4 75-85% deacylated, low moleaul weight chitosan substituents. | FIG. 196 |
| Surphys-040 | PNIPAAm-DL | Poly(NIPAAm)-CA terminated with a oligomeric DOPA-Lys peptide. | FIG. 197 |
| Surphys-041 | PEI-DH | Polyethyleneimine 25k, branched coupled with DOHA (molar ratio 10:1 DOHA:PEI). Theoretical wt % DH = 6.8 | FIG. 198 |
| Surphys-042 | p(mPEG2k-DH) | 5000 MW poly(acrylic acid) modified with mPEG-amine (2k) and dopamine. Theoretical wt % of catechol = 5.6% | FIG. 199 |
| Surphys-043 | p(DMA3-ETMDMA) | Polymerized DMA3 and Eicosafluoro-11-(trifluoromethyl)dodecyl methacrylate. | FIG. 200 |
| Surphys-044 | p(mPEG1k-DH) | 5000 MW poly(acrylic acid) modified with mPEG-amine (1k) and dopamine. | FIG. 201 |
| Surphys-045 | p(EG600EG20kb-g-DH4) | Branched polymer constructed from PEG600-diacid and 6-arm PEG-NH2 20k (1:1 feed ratio) modified with DOHA. | FIG. 202 |
| Surphys-046 | p(EG600EG20kb-g-DH3) | Branched polymer constructed from PEG600-diacid and 8-arm PEG-NH2 20k (1:1 feed ratio) modified with DOHA. | FIG. 203 |
| Surphys-047 | 5KChitosan:PEG DMe | 8-arm branched PEG capped with Dopamine groups and 5000 molecular weight chitosan substituents. | FIG. 204 |
| Surphys-048 | p(DMA3-HDFDMA) | Polymerized DMA3 and Heptadecafluorodecylmethacrylate using AIBN as the initiator. | FIG. 205 |
| Surphys-049 | p(EG600EG20kb-g-DOPA4) | Branched polymer constructed from PEG600-diacid and 6-arm PEG-NH2 20k (1:1 feed ratio) modified with N-Boc-DOPA. | FIG. 206 |
| Surphys-050 | PEI-DH-BH | Branched Polyethyleneimine 25k, coupled with DOHA and Betaine Hydrochloride (molar ratio 15:75:1 DOHA:BH:PEI). Theoretical wt % DH = 6.96%, BH = 29.3% | FIG. 207 |
| Surphys-051 | PEI-DH-LA | Branched Polyethyleneimine 25k, coupled with DOHA and Lauric Acid (molar ratio 15:60:1 DOHA:LA:PEI). Theoretical wt % DH = 6.87%, LA = 30.2% | FIG. 208 |
| Surphys-052 | PEI-PEG-DH | Branched Polyethyleneimine 25k, coupled with DOHA and mPEG. | FIG. 209 |
| Surphys-053 | p(Lys-MA-Boc-DMA-3) | Polymerized Methacrylic H-(Lys)-Boc and 5 Wt % DMA-3 | FIG. 210 |

TABLE 1-continued

Figure 211:
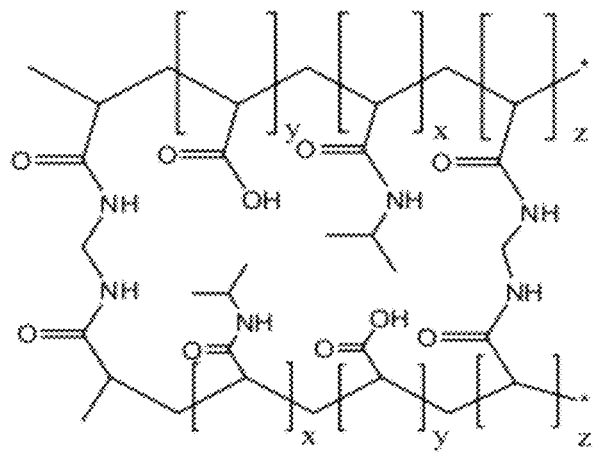
Figure 212:
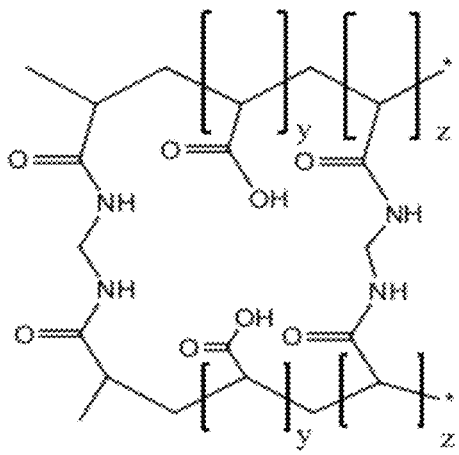
Figure 213:
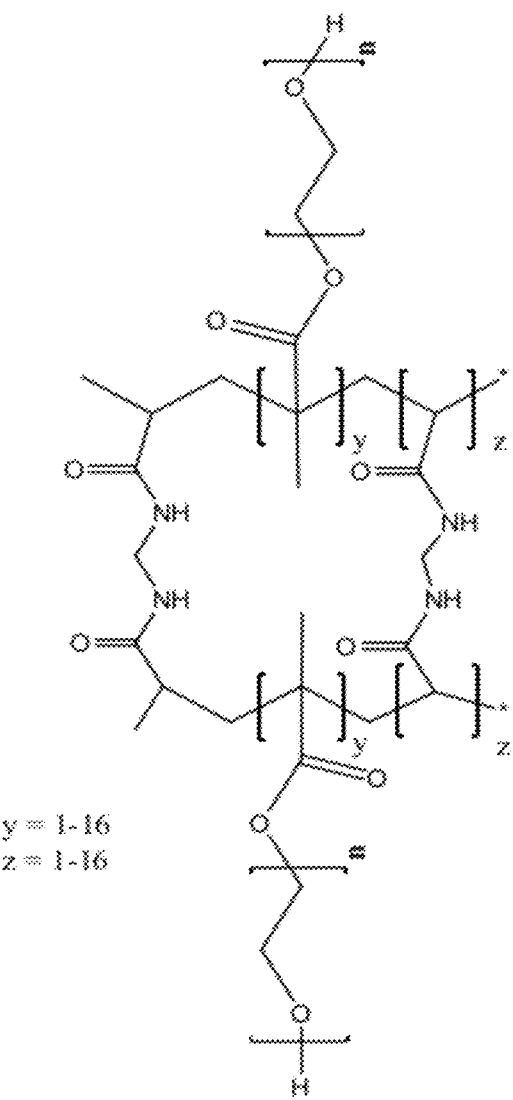
Figure 214:
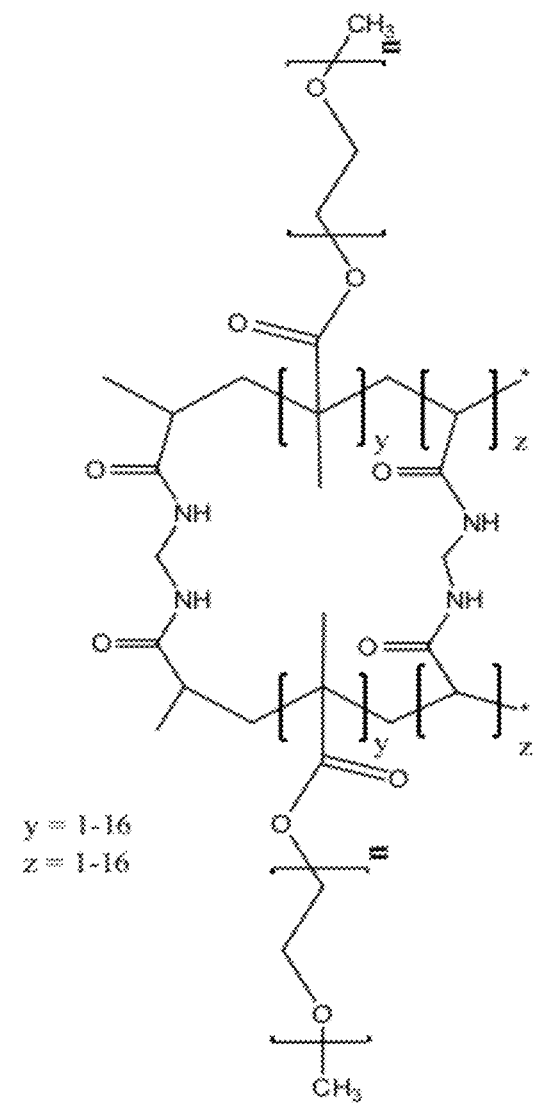
Figure 215:
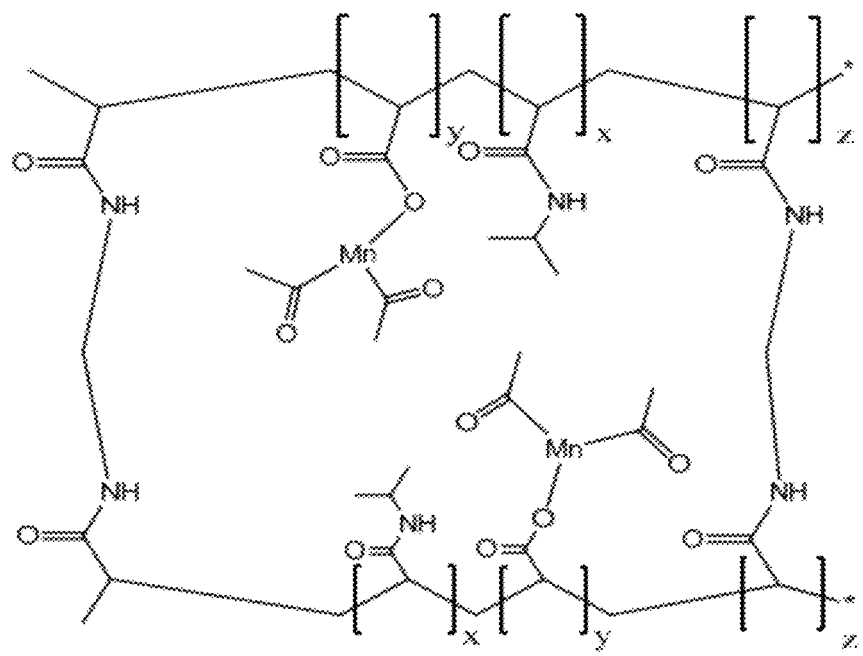
Figure 216:
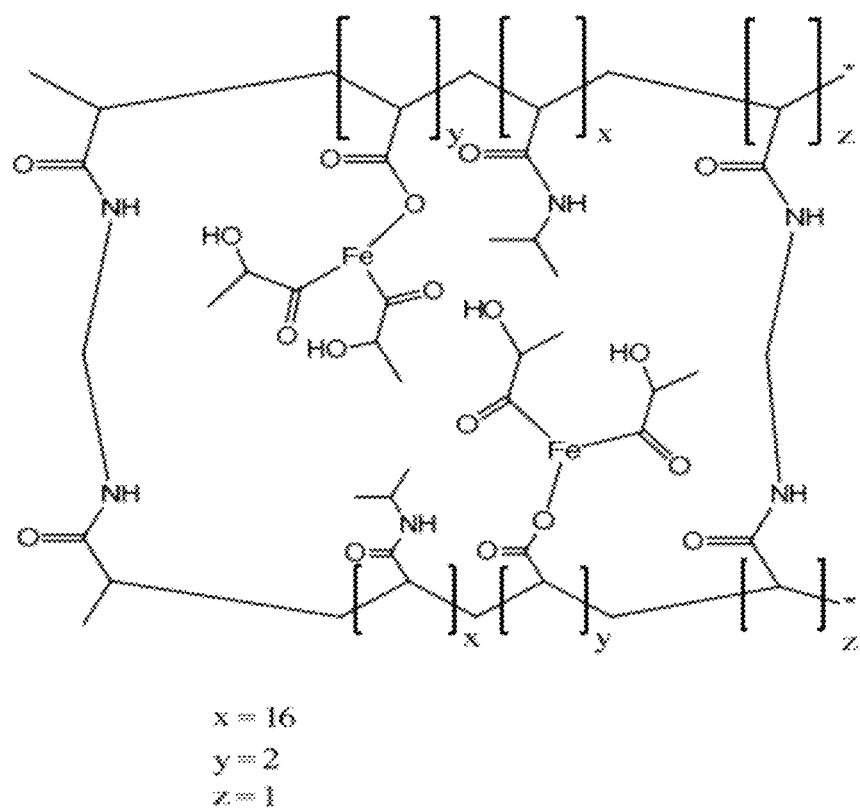
Figure 217:
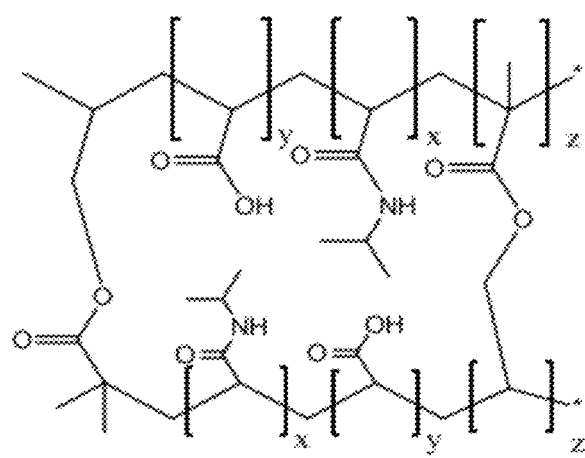
Figure 218:
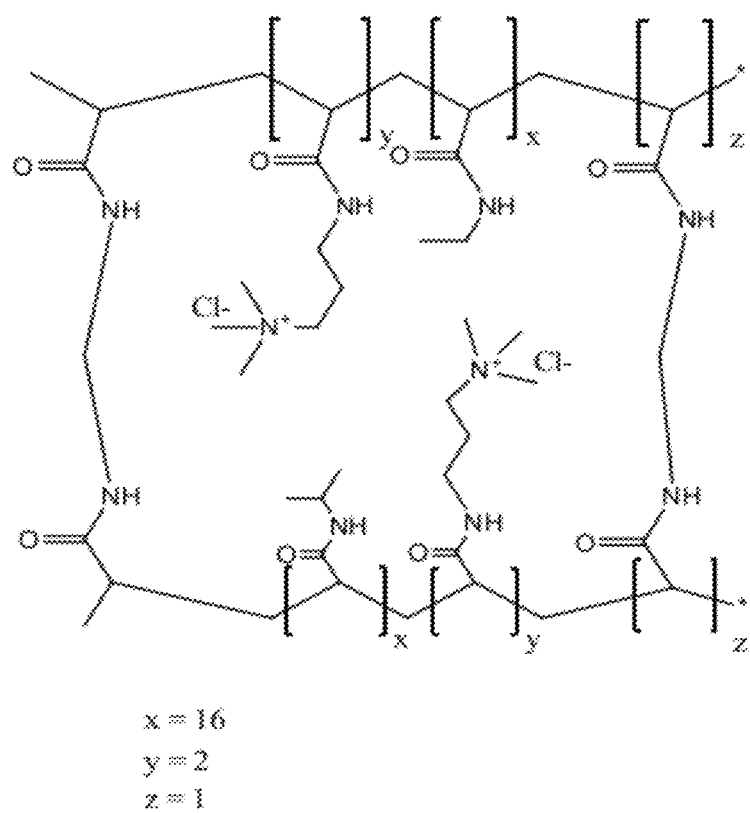
Figure 219:
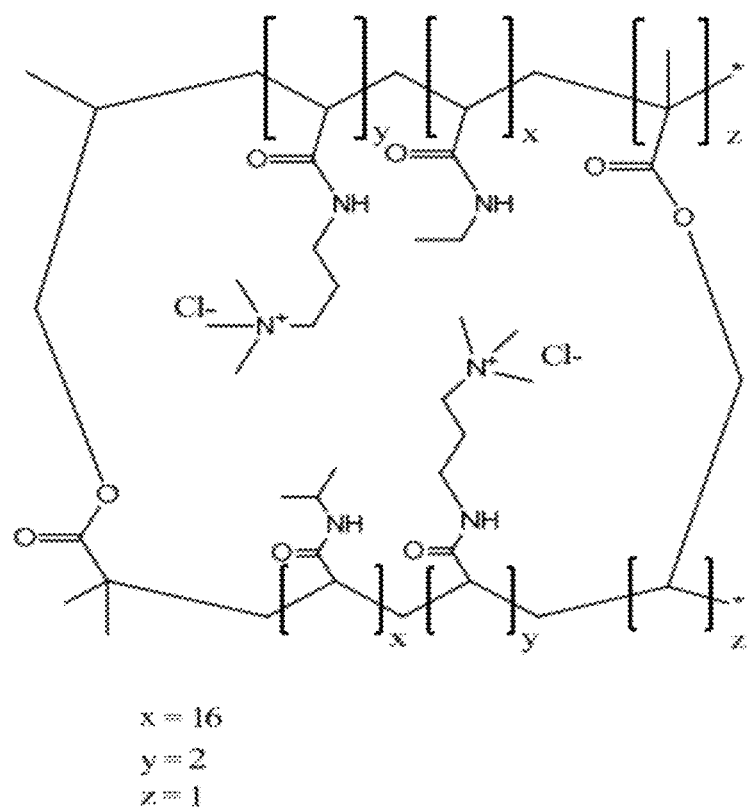
Figure 220:
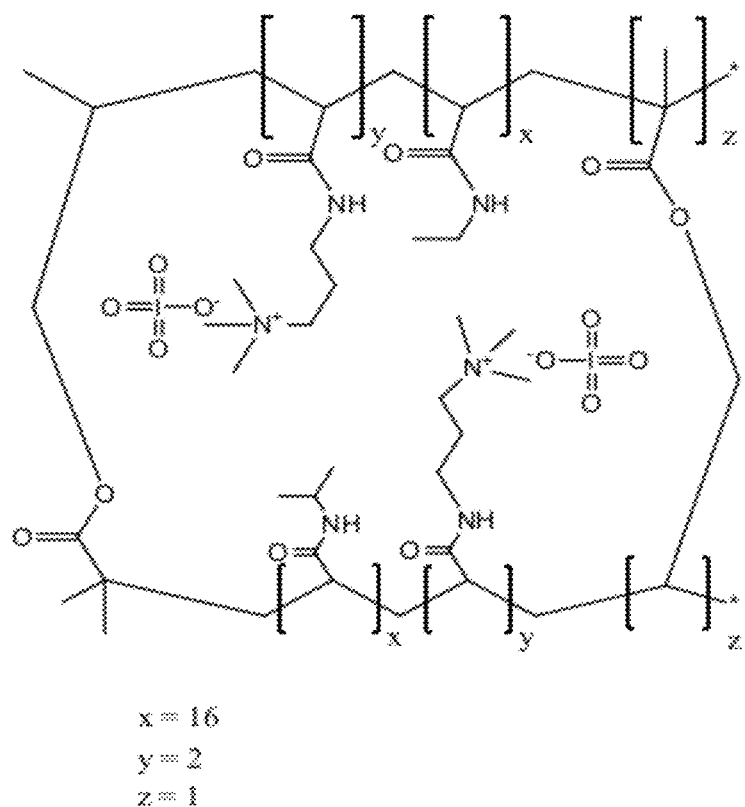
Figure 221:
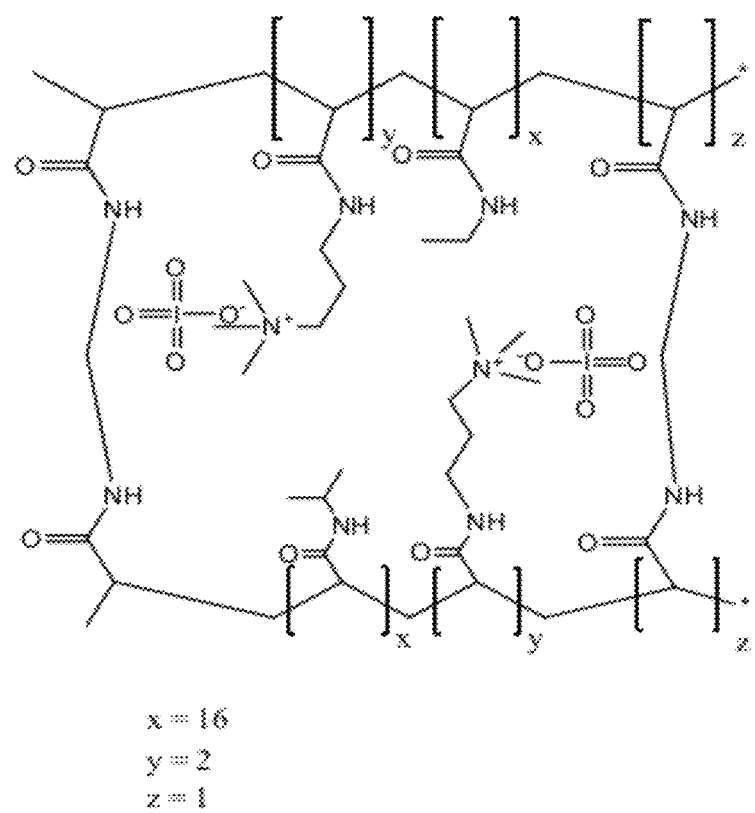

| Name | R&D Name | Description | FIG. No. |
|---|---|---|---|
| Microgel-001 | NIPAAM:AAc:BIS | Polymerized N-isopropylacrylamide, Acrylic Acid, and N,N'-methylenebisacrylamide. Surfactant is Triton X-100 and initiator is Ammonium Persulfate. | FIG. 211 |
| Microgel-002 | AAc:BIS | Polymerized Acrylic Acid and N,N'-methylenebisacrylamide. Surfactant is Triton X-100 and initiator is Ammonium Persulfate. | FIG. 212 |
| Microgel-003 | p(EG)-MA:BIS | Polymerized poly(ethylene glycol) methacrylate with N,N'-methylenebisacrylamide in the presence of Triton X-100 and ammonium persulfate. | FIG. 213 |
| Microgel-004 | p(EG-OMe)-MA:BIS | Polymerized poly(ethylene glycol)methyl ether methacrylate with N,N'-methylenebisacrylamide in the presence of Triton X-100 and ammonium persulfate. | FIG. 214 |
| Microgel-005 | NIPAM:AAC-$Mn^{3+}(AC)_2$:BIS | Polymerized N-isopropylacrylamide, Acrylic Acid, and N,N'-methylenebisacrylamide with Manganese(II) Acetate oxidized to acrylic acid to form an M(III) complex. Surfactant is Triton X-100 and initiator is Ammonium Persulfate. | FIG. 215 |
| Microgel-006 | NIPAM:AAC-$Fe^{3+}(La)_2$:BIS | Polymerized N-isopropylacrylamide, Acrylic Acid, and N,N'-methylenebisacrylamide with Ferrous(II) Lactate oxidized to acrylic acid to form an Fe(III) complex. Surfactant is Triton X-100 and initiator is Ammonium Persulfate. | FIG. 216 |
| Microgel-007 | NIPAM:AAc:VMA | Polymerized N-isopropylacrylamide, Acrylic Acid, and Vinyl Methacrylate. Surfactant is Triton X-100 and initiator is Ammonium Persulfate. | FIG. 217 |
| Microgel-008 | NIPAM:3AAPTAC:BIS | Polymerized N-isopropylacrylamide, (3-Acrylamidopropyl)triethyl-ammonium chloride, and N,N'-methylenebisacrylamide. Surfactant is Triton X-100 and initiator is Ammonium Persulfate | FIG. 218 |
| Microgel-009 | NIPAM:3AAPTAC:VMA | Polymerized N-isopropylacrylamide, (3-Acrylamidopropyl)triethyl-ammonium chloride, and Vinyl Methacrylate. Surfactant is Triton X-100 and initiator is Ammonium Persulfate | FIG. 219 |
| Microgel-010 | NIPAM:3AAPTAC(—$IO_4$):VMA | Polymerized N-isopropylacrylamide, (3-Acrylamidopropyl)triethyl-ammonium chloride, and Vinyl Methacrylate with ion exchange of chlorine for periodate. Surfactant is Triton X-100 and initiator is Ammonium Persulfate. | FIG. 220 |
| Microgel-011 | NIPAM:3AAPTAC(—$IO_4$):BIS | Polymerized N-isopropylacrylamide, (3-Acrylamidopropyl)triethyl-ammonium chloride, and N,N'-methylenebisacrylamide with ion exchange of chlorine for periodate. Surfactant is Triton X-100 and initiator is Ammonium Persulfate. | FIG. 221 |

In the specification and in the claims, the terms "including" and "comprising" are open-ended terms and should be interpreted to mean "including, but not limited to . . . ." These terms encompass the more restrictive terms "consisting essentially of" and "consisting of."

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

"Alkyl," by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl(allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. Preferably, an alkyl group comprises from 1 to 15 carbon atoms ($C_1$-$C_{15}$ alkyl), more preferably from 1 to 10 carbon atoms ($C_1$-$C_{10}$ alkyl) and even more preferably from 1 to 6 carbon atoms ($C_1$-$C_6$ alkyl or lower alkyl).

"Alkanyl," by itself or as part of another substituent, refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl(isopropyl), cyclopropan-1-yl, etc.; butanyls such as butan-1-yl, butan-2-yl(sec-butyl), 2-methyl-propan-1-yl(isobutyl), 2-methyl-propan-2-yl(t-butyl), cyclobutan-1-yl, etc.; and the like.

"Alkenyl," by itself or as part of another substituent, refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl(allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkyldiyl" by itself or as part of another substituent refers to a saturated or unsaturated, branched, straight-chain or cyclic divalent hydrocarbon group derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Where it is specifically intended that the two valencies are on the same carbon atom, the nomenclature "alkylidene" is used. In preferred embodiments, the alkyldiyl group comprises from 1 to 6 carbon atoms (C1-C6 alkyldiyl). Also preferred are saturated acyclic alkanyldiyl groups in which the radical centers are at the terminal carbons, e.g., methandiyl(methano); ethan-1,2-diyl(ethano); propan-1,3-diyl(propano); butan-1,4-diyl (butano); and the like (also referred to as alkylenos, defined infra).

"Alkyleno," by itself or as part of another substituent, refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The locant of a double bond or triple bond, if present, in a particular alkyleno is indicated in square brackets. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In preferred embodiments, the alkyleno group is (C1-C6) or (C1-C3)alkyleno. Also preferred are straight-chain saturated alkano groups, e.g., methano, ethano, propano, butano, and the like.

"Alkylene" by itself or as part of another substituent refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The locant of a double bond or triple bond, if present, in a particular alkylene is indicated in square brackets. Typical alkylene groups include, but are not limited to, methylene (methano); ethylenes such as ethano, etheno, ethyno; propylenes such as propano, prop[1]eno, propa[1,2]dieno, prop[1]yno, etc.; butylenes such as butano, but[1]eno, but[2]eno, buta[1,3]dieno, but[1]yno, but[2]yno, buta[1,3] diyno, etc.; and the like. Where specific levels of saturation are intended, the nomenclature alkano, alkeno and/or alkyno is used. In preferred embodiments, the alkylene group is (C1-C6) or (C1-C3) alkylene. Also preferred are straight-chain saturated alkano groups, e.g., methano, ethano, propano, butano, and the like.

"Substituted," when used to modify a specified group or radical, means that one or more hydrogen atoms of the specified group or radical are each, independently of one another, replaced with the same or different substituent(s). Substituent groups useful for substituting saturated carbon atoms in the specified group or radical include, but are not limited to —$R^a$, halo, —$O^-$, =O, —$OR^b$, —$SR^b$, —$S^-$, =S, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —OC(O)$R^b$, —OC(S)$R^b$, —OC(O)$O^-$, —OC(O)$OR^b$, —OC(S)$OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$ is selected from the group consisting of alkyl, cycloalkyl, heteroalkyl, cycloheteroalkyl, aryl, arylalkyl, heteroaryl and heteroarylalkyl; each $R^b$ is independently hydrogen or $R^a$; and each $R^c$ is independently $R^b$ or alternatively, the two $R^c$s are taken together with the nitrogen atom to which they are bonded form a 5-, 6- or 7-membered cycloheteroalkyl which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl.

Similarly, substituent groups useful for substituting unsaturated carbon atoms in the specified group or radical include, but are not limited to, —$R^a$, halo, —$O^-$, —$OR^b$, —$SR^b$, —$S^-$, —$NR^cR^c$, trihalomethyl, —$CF_3$, —CN, —OCN, —SCN, —NO, —$NO_2$, —$N_3$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —OC(O)$R^b$, —OC(S)$R^b$, —OC(O)$O^-$, —OC(O)$OR^b$, —OC(S)$OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups useful for substituting nitrogen atoms in heteroalkyl and cycloheteroalkyl groups include, but are not limited to, —$R^a$, —$O^-$, —$OR^b$, —$SR^b$, —$S^-$, —$NR^cR^c$, trihalomethyl, —$CF_3$, —CN, —NO, —$NO_2$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)OR^b$, —$C(S)OR^b$, —$C(O)NR^cR^c$, —$C(NR^b)NR^cR^c$, —OC(O)$R^b$, —OC(S)$R^b$, —OC(O)$OR^b$, —OC(S)$OR^b$, —$NR^bC(O)R^b$, —$NR^bC(S)R^b$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups from the above lists useful for substituting other specified groups or atoms will be apparent to those of skill in the art.

The substituents used to substitute a specified group can be further substituted, typically with one or more of the same or different groups selected from the various groups specified above.

The identifier "PA" refers to a poly(alkylene oxide) or substantially poly(alkylene oxide) and means predominantly or mostly alkyloxide or alkyl ether in composition. This definition contemplates the presence of heteroatoms e.g., N, O, S, P, etc. and of functional groups e.g., —COOH, —$NH_2$, —SH, or —OH as well as ethylenic or vinylic unsaturation. It is to be understood any such non-alkyleneoxide structures will only be present in such relative abundance as not to materially reduce, for example, the overall surfactant, non-toxicity, or immune response characteristics, as appropriate, of this polymer. It should also be understood that PAs can include terminal end groups such as PA-O—$CH_2$—$CH_2$—$NH_2$, e.g., PEG-O—$CH_2$—$CH_2$—$NH_2$ (as a common form of amine terminated PA). PA-O—$CH_2$—$CH_2$—$CH_2$—$NH_2$, e.g., PEG-O—$CH_2$—$CH_2$—$CH_2$—$NH_2$ is also available as well as PA-O—$(CH_2$—$CH(CH_3)$—$O)_{xx}$—$CH_2$—$CH(CH_3)$—$NH_2$, where xx is 0 to about 3, e.g., PEG-O—$(CH_2$—CH$(CH_3)$—$O)_{xx}$—$CH_2$—$CH(CH_3)$—$NH_2$ and a PA with an acid end-group typically has a structure of PA-O—$CH_2$—COOH, e.g., PEG-O—$CH_2$—COOH or PA-O—$CH_2$—$CH_2$—COOH, e.g., PEG-O—$CH_2$—$CH_2$—COOH. These can be considered "derivatives" of the PA. These are all contemplated as being within the scope of the invention and should not be considered limiting.

Suitable PAs (polyalkylene oxides) include polyethylene oxides (PEOs), polypropylene oxides (PPOs), polyethylene glycols (PEGs) and combinations thereof that are commercially available from SunBio Corporation, JenKem Technology USA, NOF America Corporation or Creative PEGWorks. It should be understood that, for example, polyethylene oxide can be produced by ring opening polymerization of ethylene oxide as is known in the art.

In one embodiment, the PA can be a block copolymer of a PEO and PPO or a PEG or a triblock copolymer of PEO/PPO/PEO.

Suitable MW ranges of the PA's are from about 300 to about 8,000 daltons, 400 to about 5,000 daltons or from about 450 to about 3,500 daltons.

It should be understood that the PA terminal end groups can be functionalized. Typically the end groups are OH, $NH_2$, COOH, or SH. However, these groups can be converted into a halide (Cl, Br, I), an activated leaving group, such as a tosylate or mesylate, an ester, an acyl halide, N-succinimidyl carbonate, 4-nitrophenyl carbonate, and chloroformate with the leaving group being N-hydroxy succinimide, 4-nitrophenol, and Cl, respectively. etc.

The notation of "L" refers to either a linker or a linking group. A "linker" refers to a moiety that has two points of attachment on either end of the moiety. For example, an alkyl dicarboxylic acid HOOC-alkyl-COOH (e.g., succinic acid) would "link" a terminal end group of a PA (such as a hydroxyl or an amine to form an ester or an amide respectively) with a reactive group of the DHPD (such as an $NH_2$, OH, or COOH). Suitable linkers include an acyclic hydrocarbon bridge (e.g., a saturated or unsaturated alkyleno such as methano, ethano, etheno, propano, prop[1]eno, butano, but[1]eno, but[2]eno, buta[1,3]dieno, and the like), a monocyclic or polycyclic hydrocarbon bridge (e.g., [1,2]benzeno, [2,3]naphthaleno, and the like), a monocyclic or polycyclic heteroaryl bridge (e.g., [3,4]furano [2,3]furano, pyridino, thiopheno, piperidino, piperazino, pyrazidino, pyrrolidino, and the like) or combinations of such bridges, dicarbonyl alkylenes, etc. Suitable dicarbonyl alkylenes include, C2 through C15 dicarbonyl alkylenes such as malonic acid, succinic acid, etc. Additionally, the anhydrides, acid halides and esters of such materials can be used to effect the linking when appropriate and can be considered "activated" dicarbonyl compounds.

Other suitable linkers include moieties that have two different functional groups that can react and link with an end group of a PA. These include groups such as amino acids (glycine, lysine, aspartic acid, etc.), PA's as described herein, poly(ethyleneglycol) bis(carboxymethyl)ethers, polyesters such as polylactides, lactones, polylactones such as polycaprolactone, lactams, polylactams such as polycaprolactam, polyglycolic acid (PGLA), moieties such as tyramine or dopamine and random or block copolymers of 2 or more types of polyesters.

Linkers further include compounds comprising the formula $Y_4$—$R_{17}$—$C(=O)$—$Y_6$, wherein $Y_4$ is OH, NHR, a halide, or an activated derivative of OH or NHR; $R_{17}$ is a branched or unbranched C1-C15 alkyl group; and $Y_6$ is NHR, a halide, or OR, wherein R is defined above. The term "activated derivative" refers to moieties that make the hydroxyl or amine more susceptible to nucleophilic displacement or for condensation to occur. For example, a hydroxyl group can be esterified by various reagents to provide a more active site for reaction to occur.

A linking group refers to the reaction product of the terminal end moieties of the PA and DHPD (the situation where "b" is 0; no linker present) condense to form an amide, ether, ester, urea, carbonate or urethane linkage depending on the reactive sites on the PA and DHPD. In other words, a direct bond is formed between the PA and DH portion of the molecule and no linker is present.

The term "residue" is used to mean that a portion of a first molecule reacts (e.g., condenses or is an addition product via a displacement reaction) with a portion of a second molecule to form, for example, a linking group, such an amide, ether, ester, urea, carbonate or urethane linkage depending on the reactive sites on the PA and DHPD. This can be referred to as "linkage".

The denotation "DHPD" refers to a multihydroxy phenyl derivative, such as a dihydroxy phenyl derivative, for example, a 3,4 dihydroxy phenyl moiety. The denotation "PD" refers to a phenyl derivative. Suitable DHPD derivatives include the formula:

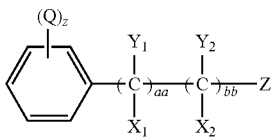

wherein Q is an OH or $OCH_3$;
"z" is 1 to 5;
each $X_1$, independently, is H, $NH_2$, OH, or COOH;
each $Y_1$, independently, is H, $NH_2$, OH, or COOH;
each $X_2$, independently, is H, $NH_2$, OH, or COOH;
each $Y_2$, independently, is H, $NH_2$, OH, or COOH;
Z is COOH, $NH_2$, OH or SH;
aa is a value of 0 to about 4;
bb is a value of 0 to about 4; and
optionally provided that when one of the combinations of $X_1$ and $X_2$, $Y_1$ and $Y_2$, $X_1$ and $Y_2$ or $Y_1$ and $X_2$ are absent, then a double bond is formed between the $C_{aa}$ and $C_{bb}$, further provided that aa and bb are each at least 1.

In one aspect, z is 3.
In particular, "z" is 2 and the hydroxyls are located at the 3 and 4 positions of the phenyl ring.
In particular, "z" is 2 and the hydroxyl group is located at the 4 position and the methoxy group is located at the 3 position of the phenyl ring.

In one embodiment, each $X_1$, $X_2$, $Y_1$ and $Y_2$ are hydrogen atoms, aa is 1, bb is 1 and Z is either COOH or $NH_2$.

In another embodiment, $X_1$ and $Y_2$ are both hydrogen atoms, $X_2$ is a hydrogen atom, aa is 1, bb is 1, $Y_1$ is $NH_2$ and Z is COOH.

In still another embodiment, $X_1$ and $Y_2$ are both hydrogen atoms, aa is 1, bb is 0, and Z is COOH or $NH_2$.

In still another embodiment, aa is 0, bb is 0 and Z is COOH or $NH_2$.

In still yet another embodiment, z is 3, aa is 0, bb is 0 and Z is COOH or $NH_2$.

It should be understood that where aa is 0 or bb is 0, then $X_1$ and $Y_1$ or $X_2$ and $Y_2$, respectively, are not present.

It should be understood, that upon condensation of the DHPD molecule with the PA that a molecule of water, for example, is generated such that a bond is formed as described above (amide, ether, ester, urea, carbonate or urethane).

In particular, DHPD molecules include 3,4-dihydroxyphenethylamine (dopamine), 3,4-dihydroxy phenylalanine (DOPA), 3,4-dihydroxyhydrocinnamic acid (DOHA), 3,4-dihydroxyphenyl ethanol, 3,4 dihydroxyphenylacetic acid, 3,4 dihydroxyphenylamine, 3,4-dihydroxybenzoic acid, 3-(3,4-dimethoxyphenyl)propionic acid, 3,4-dimethoxyphenylalanine, 2-(3,4-dimethoxyphenyl)ethanol, 3,4-dimethoxyphenethylamine, 3,4-dimethoxybenzylamine, 3,4-dimethoxybenzyl alcohol, 3,4-dimethoxyphenylacetic acid, 3-(3,4-dimethoxyphenyl)-2-hydroxypropanoic acid, 3,4-dimethoxybenzoic acid, 3,4-dimethoxyaniline, 3,4-dimethoxyphenol, 3-(4-Hydroxy-3-methoxyphenyl)propionic acid, homovanillyl alcohol, 3-methoxytyramine, 3-methoxy-L-tyrosine, homovanillic acid, 4-hydroxy-3-methoxybenzylamine, vanillyl alcohol, vanillic acid, 5-amino-2-methoxyphenol, 2-methoxyhydroquinone, 3-hydroxy-4-methoxyphenethylamine, 3-hydroxy-4-methoxyphenylacetic acid, 3-hydroxy-4-methoxybenzylamine, 3-hydroxy-4-methoxybenzyl alcohol, and isovanillic acid.

It should be understood that a person having ordinary skill in the art would select appropriate combinations of linkers to provide an array of condensation products embodied and described herein.

In certain embodiments an oxidant is included with the bioadhesive film layer. The oxidant can be incorporated into the polymer film or it can be contacted to the film at a later time. A solution could be sprayed or brushed onto either the adhesive surface or the tissue substrate surface. Alternatively, the construct can be dipped or submerged in a solution of oxidant prior to contacting the tissue substrate. In any situation, the oxidant upon activation, can help promote cross-linking of the multihydroxy phenyl groups with each other and/or tissue. Suitable oxidants include periodates and the like.

The invention further provides cross-linked bioadhesive constructs or hydrogels derived from the compositions described herein. For example, two DHDP moieties from two separate polymer chains can be reacted to form a bond between the two DHDP moieties. Typically, this is an oxidative/radical initiated cross-linking reaction wherein oxidants/initiators such as $NaIO_3$, $NaIO_4$, Fe III salts, ($FeCl_3$), Mn III salts ($MnCl_3$), $H_2O_2$, oxygen, an inorganic base, an organic base or an enzymatic oxidase can be used. Typically, a ratio of oxidant/initiator to DHDP containing material is between about 0.1 to about 10.0 (on a molar basis) (oxidant:DHDP). In one particular embodiment, the ratio is between about 0.5 to about 5.0 and more particularly between about 1.0 to about 3.0 (e.g., 3.0). It has been found that periodate is very effective in the preparation of cross-linked hydrogels of the invention. Additionally, it is possible that oxidation "activates" the DHPD(s) which allow it to form interfacial cross-linking with appropriate surfaces with functional group (i.e. biological tissues with —NH2, —SH, etc.)

The compositions of the invention can be utilized by themselves or in combination with polymers to form a blend. Suitable polymers include, for example, polyesters, PPG, linear PCL-diols (MW 600-2000), branched PCL-triols (MW 900), wherein PCL can be replaced with PLA, PGA, PLGA, and other polyesters, amphiphilic block (di, tri, or multiblock) copolymers of PEG and polyester or PPG, tri-block copolymers of PCL-PEG-PCL (PCL MW=500-3000, PEG MW=500-3000), tri-block copolymers of PLA-PEG-PLA (PCL MW=500-3000, PEG MW=500-3000), wherein PCL and PLA can be replaced with PGA, PLGA, and other polyesters. Pluronic polymers (triblock, diblock of various MW) and other PEG, PPG block copolymers are also suitable. Hydrophilic polymers with multiple functional groups (—OH, —NH2, —COOH) contained within the polymeric backbone such as PVA (MW 10,000-100,000), poly acrylates and poly methacrylates, polyvinylpyrrolidone, and polyethylene imines are also suitable. Biopolymers such as polysaccharides (e.g., dextran), hyaluronic acid, chitosan, gelatin, cellulose (e.g., carboxymethyl cellulose), proteins, etc. which contain functional groups can also be utilized.

Abbreviations: PCL=polycaprolactone, PLA=polylactic acid, PGA=Polyglycolic acid, PLGA=a random copolymer of lactic and glycolic acid, PPG=polypropyl glycol, and PVA=polyvinyl alcohol.

Typically, blends of the invention include from about 0 to about 99.9% percent (by weight) of polymer to composition(s) of the invention, more particularly from about 1 to about 50 and even more particularly from about 1 to about 30.

The compositions of the invention, either a blend or a compound of the invention per se, can be applied to suitable substrates using conventional techniques. Coating, dipping, spraying, spreading and solvent casting are possible approaches.

In one embodiment, adhesive compounds of the present invention provide a method of adhering a first surface to a second surface in a subject. In some embodiments, the first and second surfaces are tissue surfaces, for example, a natural tissue, a transplant tissue, or an engineered tissue. In further embodiments, at least one of the first and second surfaces is an artificial surface. In some embodiments, the artificial surface is an artificial tissue. In other embodiments, the artificial surface is a device or an instrument. In some embodiments, adhesive compounds of the present invention seal a defect between a first and second surface in a subject. In other embodiments, adhesive compounds of the present invention provide a barrier to, for example, microbial contamination, infection, chemical or drug exposure, inflammation, or metastasis. In further embodiments, adhesive compounds of the present invention stabilize the physical orientation of a first surface with respect to a second surface. In still further embodiments, adhesive compounds of the present invention reinforce the integrity of a first and second surface achieved by, for example, sutures, staples, mechanical fixators, or mesh. In some embodiments, adhesive compounds of the present invention provide control of bleeding. In other embodiments, adhesive compounds of the present invention provide delivery of drugs including, for example, drugs to control bleeding, treat infection or malignancy, or promote tissue regeneration.

The present invention surprisingly provides unique bioadhesive constructs that are suitable to repair or reinforce damaged tissue.

The present invention also surprisingly provides unique antifouling coatings/constructs that are suitable for application in, for example, urinary applications. The coatings could be used anywhere that a reduction in bacterial attachment is desired: dental unit waterlines, implantable orthopedic devices, cardiovascular devices, wound dressings, percutaneous devices, surgical instruments, marine applications, food preparation surfaces and utensils.

The constructs include a suitable support that can be formed from a natural material, such as collagen, pericardium, dermal tissues, small intestinal submucosa or man-made materials such as polypropylene, polyethylene, polybutylene, polyesters, PTFE, PVC, polyurethanes and the like. The support can be a film, a membrane, a mesh, a non-woven and the like. The support need only help provide a surface for the bioadhesive to adhere. The support should also help facilitate physiological reformation of the tissue at the damaged site. Thus the constructs of the invention provide a site for remodeling via fibroblast migration, followed by subsequent native collagen deposition. For biodegradable support of either biological or synthetic origins, degradation of the support and the adhesive can result in the replacement of the bioadhesive construct by the natural tissues of the patient.

The constructs of the invention can include a compound of the invention or mixtures thereof or a blend of a polymer with one or more of the compounds of the invention. In one embodiment, the construct is a combination of a substrate, to which a blend is applied, followed by a layer(s) of one or more compounds of the invention.

In another embodiment, two or more layers can be applied to a substrate wherein the layering can be combinations of one or more blends or one or more compositions of the invention. The layering can alternate between a blend and a composition layer or can be a series of blends followed by a composition layer or vice versa.

Not to be limited by theory, it is believe that to improve the overall adhesive strength of the present adhesives, two separate properties require consideration: 1) interfacial binding ability or "adhesion" to a substrate and 2) bulk mechanical properties or "cohesion". It is possible that some polymers may generally fail cohesively, meaning that their adhesive properties are better than their cohesive properties. That is one basis why blending with a hydrophobic polymer increases the bulk cohesive properties.

It has interestingly been found that use of a blend advantageously has improved adhesion to the substrate surface. For example, a blend of a hydrophobic polymer with a composition of the invention may improve the overall cohesive properties and thus the overall strength of the adhesive joint. Subsequent application of a composition of the present invention to the blend layer then provides improved interfacial adhesion between the blend and provides for improved adhesive properties to the tissue to be adhered to as the hydrophobic polymer is not in the outermost layer.

Typically the loading density of the coating layer is from about $0.001$ $g/m^2$ to about $500$ $g/m^2$, more particularly from about $10$ $g/m^2$ to about $360$ $g/m^2$, and more particularly from about $90$ $g/m^2$ to about $250$ $g/m^2$. Thus, typically a coating has a thickness of from about 1 to about 1000 nm. More typically for an adhesive, the thickness of the film is from about 1 to about 1000 microns.

As used herein, "Tisseel" refers to a two component fibrin sealant that consists of human fibrinogen and human thrombin. As used herein, "CoSeal" refers to CoSeal Surgical Sealant, a hydrogel that is formed when two synthetic derivatized polyethylene glycol (PEG) polymers are mixed together and applied to tissue. As used herein, "Dermabond" refers to a sterile, liquid tissue adhesive comprising a monomeric (2-octyl cyanoacrylate) formulation and colorants. As used herein, "Duraseal" refers to a sealant comprising two solutions, a polyethylene glycol (PEG) ester solution and a trilysine amine solution that, when mixed together, cross-link to form a hydrogel sealant. As used herein, "Collamend" referres to a sterile, solid, sheet of lyophilized, acellular porcine dermal collagen and its constituent elastin fibers. As used herein, "Quadraseal" refers to Medhesive compounds with a 4-ARMPG10k backbone.

The following paragraphs enumerated consecutively from 1 through 91 provide for various aspects of the present invention. In one embodiment, in a first paragraph (1), the present invention provides a method for adhering a first surface to a second surface in a subject, comprising:
 a) providing a subject;
 b providing a phenyl derivative polymer;
 c) applying an effective amount of said phenyl derivative polymer to at least one of said first and said second surface in said subject; and
 d) approximating said first surface and said second surface such that said phenyl derivative polymer adheres said first surface to said second surface in said subject.

2. The method of paragraph 1, wherein said phenyl derivative polymer is a multi-hydroxy phenyl derivative, a multi-methoxy phenyl derivative, or a combination thereof.

3. The method of paragraph 1, wherein said phenyl derivative polymer is a polyethylene glycol (PEG) polymer, a polycaprolactone (PCL) polymer, a polylactic acid (PLA) polymer, a polyester polymer, a methacrylate polymer, an acrylate-based polymer, or a combination thereof.

4. The method of paragraph 1, wherein said subject is a subject having or recovering from bariatric surgery, cardiac surgery, thoracic surgery, colon and rectal surgery, dermatologic surgery, general surgery, gynecologic surgery, maxillofacial surgery, neurosurgery, obstetric surgery, oncologic surgery, ophthalmologic surgery, oral surgery, orthopedic surgery, otolaryngologic surgery, pediatric surgery, plastic surgery, cosmetic and reconstructive surgery, podiatric surgery, spine surgery, transplant surgery, trauma surgery, vascular surgery, urologic surgery, dental surgery, veterinary surgery, endoscopic surgery, anesthesiology, an interventional radiologic procedure, an emergency medicine procedure, a battlefield procedure, a deep or superficial laceration repair, a cardiologic procedure, an internal medicine procedure, an intensive care procedure, an endocrinologic procedure, a gastroenterologic procedure, a hematologic procedure, a hepatologic procedure, a diagnostic radiologic procedure, an infectious disease procedure, a nephrologic procedure, an oncologic procedure, a proctologic procedure, a pulmonary medicine procedure, a rheumatologic procedure, a pediatric procedure, a physical medicine or rehabilitation medicine procedure, a geriatric procedure, a palliative care procedure, a medical genetic procedure, a fetal procedure, or a combination thereof.

5. The method of paragraph 4, wherein said subject having or recovering from said neurosurgery or said spine surgery is having or is recovering from a dural repair, an osseous repair, a nerve anastomosis, an endoscopic procedure, a skull base repair, a discectomy procedure, a fibrosis prevention after lumbar discectomy procedure, a scar formation prevention procedure, a posterior fossa procedure, an aneurysm repair, an arteriovenous malformation repair, a cerebrospinal fluid rhinorrhea prevention or repair procedure, a fusion procedure, a procedure to prevent fracture of weakened vertebral bodies, a procedure to repair disc herniation or to prevent the progression of disc herniation, a procedure to provide growth factors in spine surgery, a procedure to prevent or to manage dead space or seroma in spine surgery, an endoscopic neurosurgery or spine surgery procedure, or a procedure to repair an entrance portal in nucleoplasty.

6. The method of paragraph 4, wherein said subject having or recovering from said general surgery is having or is recovering from an inguinal hernia, a ventral hernia, an incisional hernia, an umbilical hernia, a seroma after hernia repair, a laparoscopic procedure, a hematoma, a subcutaneous flap, a mastectomy, an abdominopasty, a bowel resection, a bowel anastomosis, a thyroidectomy, an anastomotic leak after a gastric bypass procedure, a peritoneal adhesion prevention procedure, a burn injury, a fistula in ano, a pancreatic leak, a seroma after axial dissection, an intralesional support for tumor removal procedure, a spleen injury, an appendectomy, a cholecystectomy, a peptic or gastric ulcer repair procedure, closure of dead space to prevent a seroma in a general surgical procedure, fixation and sealing of the insertion site of a transcutaneous device, or a colostomy or other stoma procedure.

7. The method of paragraph 4, wherein said subject having or recovering from said otolaryngologic surgery is having or is recovering from a neck dissection, a tonsillectomy, an adenoidectomy, a tumor removal procedure, a frontal sinus repair, an endoscopic otolaryngologic procedure, or nasal septal surgery.

8. The method of paragraph 4, wherein said subject having or recovering from said vascular surgery is having or is recovering from a neck dissection, a vascular graft procedure, an anastomotic bleeding repair procedure, a primary anastomosis, a percutaneous endovascular procedure, a prosthetic vascular graft procedure, a femoral artery repair, a carotid artery repair, attachment of endothelial cells to prosthetic grafts to create new endothelial lining, an endoscopic vascular surgery procedure, or an aortic reconstruction.

9. The method of paragraph 4, wherein said subject having or recovering from said orthopedic surgery is having or is recovering from a joint replacement, a rotator cuff repair, a ligament repair, a tendon repair, a cartilage repair, attachment of cartilage cells and scaffold to a repair site, a meniscus repair, a labrum repair, a repair of lacerated or traumatized muscle tissue, treatment of a tendon or muscle strain, treatment of ligament sprain or overuse injury, an arthroscopic procedure, a tumor removal, a joint replacement revision, insertion and removal of an external fixator, a comminuted fracture stabilization procedure, a transcutaneous implant procedure (sealing of a pin insertion site to prevent entrance of bacteria), implantation of a bone stimulator, a bone graft procedure, a sports injury, a trauma procedure, a bone tumor removal procedure, a pubis symphysis separation repair, a slipped rib repair, closure of dead space to prevent a seroma in an orthopedic procedure, a fusion procedure, an open fracture repair, a closed fracture repair, treatment of a stress fracture, treatment of growth plate disorders and slipped epiphysis, treatment of a bony defect, treatment of osteoporosis or osteopenia, a bone fixation procedure, fixation of trauma implants to bone, an endoscopic orthopedic procedure, or containment of bone fragments at fracture site with and without internal fixation.

10. The method of paragraph 4, wherein said subject having or recovering from said obstetric surgery is having or is recovering from amniocentesis, premature rupture of amniotic membranes, an endoscopic obstetric procedure, or a cervical occlusion procedure.

11. The method of paragraph 4, wherein said subject having or recovering from said gynecologic surgery is having or is recovering from a Fallopian tube occlusion, a contraceptive procedure, a urinary incontinence procedure, a cystocoele repair, a rectocoele repair, a pelvic floor repair, a vulvovaginal reconstruction procedure, an amniotic membrane graft procedure, an endoscopic gynecologic procedure, or fixation of embryo transfer with in vitro fertilization.

12. The method of paragraph 4, wherein said subject having or recovering from said transplant surgery is having or is recovering from a pancreatic islet cell implantation, liver transplantation, kidney transplantation, pancreas transplantation, an endoscopic transplant procedure, or a combination thereof.

13. The method of paragraph 4, wherein said subject having or recovering from said fetal procedure is having or is recovering from balloon tracheal occlusion, closure of amniotic membranes, or a fetoscopic procedure.

14. The method of paragraph 4, wherein said subject having or recovering from said thoracic surgery is having or is recovering from a pulmonary lobectomy, bi-lobectomy, sleeve lobectomy, bullectomy, segmentectomy, pulmonary wedge resection, an air leak, a tracheoesophageal fistula repair, a neotracheal reconstruction, a pleural leak, a thoracoscopic or bronchoscopic procedure, an endoscopic thoracic surgery procedure, closure of a tracheal or bronchial defect, or repair of a bronchopleural fistula.

15. The method of paragraph 4, wherein said subject having or recovering from said ophthalmologic surgery is having or is recovering from an ocular procedure, a retinal procedure, a retinal detachment procedure, a corneal repair, a glaucoma procedure, a glaucoma drainage device procedure, a laser procedure, a tissue flap procedure after laser surgery, a conjunctival repair, a pterygium repair, cataract surgery, repair of wet or dry macular degeneration, an endoscopic ophthalmologic procedure, or a sclera flap procedure.

16. The method of paragraph 4, wherein said subject having or recovering from said oral surgery is having or is recovering from an oral wound closure, a tongue injury, a cheek injury, a tooth bed injury, a wisdom tooth removal, a root canal procedure, a bridge reconstruction procedure, a canker sore, a gum graft procedure, removal of an oral tumor or other lesion, an endoscopic oral surgery procedure, or periodontal flap surgery.

17. The method of paragraph 4, wherein said subject having or recovering from said plastic surgery is having or is recovering from a browplasty, a flap seroma repair, aesthetic surgery, a ptosis repair, rhytidectomy, a fasciocutaneous flap, body contouring surgery, a seroma after breast, face and body reconstructive surgery, a rhinoplasty, a skin graft to a wound or burn site, a muscle transfer to a wound site, a musculocutaneous flap, a decubitus injury, an ulcerative condition, a diabetic ulcer, a body contouring procedure, a liposuction procedure, a skin graft donor site repair, an endoscopic plastic surgery procedure, or a muscle transfer donor site repair.

18. The method of paragraph 4, wherein said subject having or recovering from said cardiac surgery is having or is recovering from coronary artery anastomotic bleeding, a heart valve placement procedure, placement of a ventricular patch, control of bleeding from adhesions during a re-operative cardiac procedure, bleeding after a congenital heart defect repair, an endoscopic cardiac surgery procedure, or bleeding during and after cardiopulmonary bypass.

19. The method of paragraph 4, wherein said subject having or recovering from said urologic surgery is having or is recovering from an incontinence repair, a hypospadius repair, a fistula after hypospadius repair, a percutaneous nephrostomy, a percutaneous nephrolithotomy, a percutaneous nephrectomy, a vasovasotomy, a urinary fistula, a ureteral reconstruction, a circumcision, prostate surgery, vas deferens surgery, an anastomosis of the urethra, a stoma procedure, an endoscopic urologic procedure, or urologic trauma 20. The method of paragraph 4, wherein said subject is having or is recovering from an amputation, a tissue leak, a tissue perforation, a hematoma, a bleeding control procedure, a repair of luminal tissue, a tissue defect, a skin lesion, a topical wound closure, a microbial colonization or infection barrier procedure, a burn, a mucus membrane lesion, implantation of a pacemaker, implantation of a nerve stimulator, implanation of a pump, implantation of a bone stimulator, fixation of a vascular catheter, fixation of a second tissue to bone, a fistula repair, a skin wound closure, a vascular access procedure, a percutaneous device procedure, or a periosteal flap.

21. The method of paragraph 1, wherein said subject is a mammal.

22. The method of paragraph 21, wherein said mammal is a human.

23. The method of paragraph 1, wherein said phenyl derivative polymer comprises a catechol compound.

24. The method of paragraph 23, wherein said catechol compound is 3,4-dihyroxyphenylalanine (DOPA), dopamine, 3,4-dihydroxyhydrocinnamic acid, a DOPA derivative, a conjugation of DOPA, poly(DOPA), poly(DOPA-Lys), hydroferulic acid, 3-methoxytyramine, homovanillic acid, 3,4-dihydroxybenzylamine, 3,4-dihydroxybenzoic acid, 4-hydroxy-3-methoxybenzylamine, or 3,4 dimethoxyhydrocinnamic acid.

25. The method of paragraph 1, wherein said phenyl derivative polymer further comprises a linker compound.

26. The method of paragraph 25, wherein said linker compound is an amide linker compound, a urethane linker compound, a urea linker compound, a di-acid linker compound, an amine-diol linker compound, an ester linker compound, a gamma-aminobutyric acid linker compound, a 3,4-dihydroxybenzoic acid linker compound, a 4-hydroxy-3-methoxybenzylamine linker compound, a glycine linker compound, an amino acid linker compound, or a lysine linker compound.

27. The method of paragraph 1, wherein said phenyl derivative polymer comprises a branched polymer.

28. The method of paragraph 1, wherein said phenyl derivative polymer comprises at least one compound from Table 1.

29. The method of paragraph 1, wherein at least one of said first surface or said second surface is a tissue.

30. The method of paragraph 29, wherein said tissue is skin tissue, hair tissue, nail tissue, corneal tissue, tongue tissue, oral cavity tissue, esophageal tissue, anal tissue, urethral tissue, vaginal tissue, urinary epithelial tissue, salivary gland tissue, mammary gland tissue, lacrimal gland tissue, sweat gland tissue, prostate gland tissue, bulbourethral gland tissue, Bartholin's gland tissue, uterine tissue, respiratory and gastrointestinal tract goblet cell tissue, gastric mucosal tissue, gastric gland tissue, pancreatic tissue, pulmonary tissue, pituitary gland tissue, thyroid gland tissue, parathyroid gland tissue, testicular tissue, ovarian tissue, respiratory gland tissue, gastrointestinal gland tissue, adrenal gland tissue, renal tissue, liver tissue, adipose tissue, duct cell tissue, gall bladder tissue, epidydimal tissue, vas deferens tissue, blood vessel tissue, lymph gland tissue, lymphatic duct tissue, synovial tissue, serosal tissue, squamous tissue, cochlear tissue, choroid plexus tissue, ependymal tissue, dural tissue, pia-arachnoid tissue, sclera tissue, retinal tissue, iris tissue, ciliary tissue, dental tissue, otic tissue, ligament tissue, tendon tissue, elastic cartilage tissue, fibrocartilage tissue, hyaline cartilage tissue, bone marrow tissue, intervertebral disc tissue, compact bone tissue, cancellous bone tissue, skeletal muscle tissue, cardiac muscle tissue, smooth muscle tissue, cardiac valve tissue, pericardial tissue, pleural tissue, peritoneal tissue, blood cell tissue, neuronal tissue, glial tissue, sensory transducer cell tissue, pain sensitive tissue, autonomic neuron tissue, peripheral nervous system tissue, cranial nerve tissue, ocular lens tissue, germ cell tissue, thymus tissue, placental tissue, fetal membrane tissue, umbilical tissue, stem cell tissue, mesodermal tissue, ectodermal tissue, endodermal tissue, autologous tissue, allograft tissue or a combination thereof.

31. The method of paragraph 29, wherein said first surface and said second surface are the same tissue.

32. The method of paragraph 29, wherein said first surface and said second surface are different tissue.

33. The method of paragraph 29, wherein said first surface is a living tissue and said second surface is a tissue implant.

34. The method of paragraph 1, wherein said first surface is a tissue and said second surface is device.

35. The method of paragraph 1, wherein said applying is manual applying, applicator applying, instrument applying, manual spray applying, aerosol spray applying, syringe applying, airless tip applying, gas-assist tip applying, percutaneous applying, surface applying, topical applying, internal applying, enteral applying, parenteral applying, protective applying, catheter applying, endoscopic applying, arthroscopic applying, encapsulation scaffold applying, stent applying, wound dressing applying, vascular patch applying, vascular graft applying, image-guided applying, radiologic applying, brush applying, wrap applying, or drip applying.

36. The method of paragraph 1, wherein said approximating is manual approximating, mechanical approximating, suture approximating, staple approximating, synthetic mesh approximating, biologic mesh approximating, transverse approximating, longitudinal approximating, end-to-end approximating, or overlapping approximating.

37. The method paragraph 1, wherein said phenyl derivative polymer further comprises an anti-microbial compound, an antibiotic compound, a growth factor compound, a gene therapy vector, stem cell tissue, undifferentiated progenitor cells, differentiated cells, an analgesic compound, an anesthetic compound, an RNAi compound, a morphogenetic protein, a sustained release compound, endothelialized graft tissue, bone graft tissue, autograft tissue, allograft tissue, xenograft tissue, a bone graft substitute, a coagulation factor compound, a hormone compound, a steroid hormone compound, a bioactive compound, or a chemotherapeutic agent.

38. The method of paragraph 1, wherein said phenyl derivative polymer is configured to degrade at a predetermined rate.

39. The method of paragraph 1, wherein said phenyl derivative polymer comprises a predetermined strength.

40. The method of paragraph 1, wherein said phenyl derivative polymer comprises a predetermined tensility.

41. The method of paragraph 1, wherein said phenyl derivative polymer is a film polymer.

42. The method of paragraph 41, wherein said film polymer is a single layer film polymer.

43. The method of paragraph 41, wherein said film polymer is a multi-layer film polymer.

44. The method of paragraph 41, wherein said film polymer comprises an oxidant.

45. The method of paragraph 41, wherein said phenyl derivative polymer is applied on at least one side of a mesh.

46. The method of paragraph 45, wherein said mesh is a biologic mesh or a synthetic mesh.

47. The method of paragraph 41, wherein said film polymer is a stand-alone film polymer.

48. The method of paragraph 41, wherein at least one surface of said film polymer is adhesive.

49. In a further embodiment, in a $49^{th}$ paragraph (49) the present invention provides a method for sealing a surface in a subject, comprising:
 a) providing a subject;
 b providing a phenyl derivative polymer; and
 c) applying an effective amount of said phenyl derivative polymer to said surface in said subject.

50. The method of paragraph 49, wherein said phenyl derivative polymer is a multi-hydroxy phenyl derivative, a multi-methoxy phenyl derivative, or a combination thereof.

51. The method of paragraph 49, wherein said phenyl derivative polymer is a polyethylene glycol (PEG) polymer, a polycaprolactone (PCL) polymer, a polylactic acid (PLA) polymer, a polyester polymer, a methacrylate polymer, an acrylate-based polymer, or a combination thereof.

52. The method of paragraph 49, wherein said subject is a subject having or recovering from bariatric surgery, cardiac surgery, thoracic surgery, colon and rectal surgery, dermatologic surgery, general surgery, gynecologic surgery, maxillofacial surgery, neurosurgery, obstetric surgery, oncologic surgery, ophthalmologic surgery, oral surgery, orthopedic surgery, otolaryngologic surgery, pediatric surgery, plastic surgery, cosmetic and reconstructive surgery, podiatric surgery, spine surgery, transplant surgery, trauma surgery, vascular surgery, urologic surgery, dental surgery, veterinary surgery, endoscopic surgery, anesthesiology, an interventional radiologic procedure, an emergency medicine procedure, a battlefield procedure, a deep or superficial laceration repair, a cardiologic procedure, an internal medicine procedure, an intensive care procedure, an endocrinologic procedure, a gastroenterologic procedure, a hematologic procedure, a hepatologic procedure, a diagnostic radiologic procedure, an infectious disease procedure, a nephrologic procedure, an oncologic procedure, a proctologic procedure, a pulmonary medicine procedure, a rheumatologic procedure, a pediatric procedure, a physical medicine or rehabilitation medicine procedure, a geriatric procedure, a palliative care procedure, a medical genetic procedure, a fetal procedure, or a combination thereof.

53. The method of paragraph 52, wherein said subject having or recovering from said neurosurgery or said spine surgery is having or is recovering from a dural repair, an osseous repair, a nerve anastomosis, an endoscopic procedure, a skull base repair, a discectomy procedure, a fibrosis prevention after lumbar discectomy procedure, a scar formation prevention procedure, a posterior fossa procedure, an aneurysm repair, an arteriovenous malformation repair, a cerebrospinal fluid rhinorrhea prevention or repair procedure, a fusion procedure, a procedure to prevent fracture of weakened vertebral bodies, a procedure to repair disc herniation or to prevent the progression of disc herniation, a procedure to provide growth factors in spine surgery, a procedure to prevent or to manage dead space or seroma in spine surgery, an endoscopic neurosurgery or spine surgery procedure, or a procedure to repair an entrance portal in nucleoplasty.

54. The method of paragraph 52, wherein said subject having or recovering from said general surgery is having or is recovering from an inguinal hernia, a ventral hernia, an incisional hernia, an umbilical hernia, a seroma after hernia repair, a laparoscopic procedure, a hematoma, a subcutaneous flap, a mastectomy, an abdominopasty, a bowel resection, a bowel anastomosis, a thyroidectomy, an anastomotic leak after a gastric bypass procedure, a peritoneal adhesion prevention procedure, a burn injury, a fistula in ano, a pancreatic leak, a seroma after axial dissection, an intralesional support for tumor removal procedure, a spleen injury, an appendectomy, a cholecystectomy, a peptic or gastric ulcer repair procedure, closure of dead space to prevent a seroma in a general surgical procedure, fixation and sealing of the insertion site of a transcutaneous device, or a colostomy or other stoma procedure.

55. The method of paragraph 52, wherein said subject having or recovering from said otolaryngologic surgery is having or is recovering from a neck dissection, a tonsillectomy, an adenoidectomy, a tumor removal procedure, a frontal sinus repair, an endoscopic otolaryngologic procedure, or nasal septal surgery.

56. The method of paragraph 52, wherein said subject having or recovering from said vascular surgery is having or is recovering from a neck dissection, a vascular graft procedure, an anastomotic bleeding repair procedure, a primary anastomosis, a percutaneous endovascular procedure, a prosthetic vascular graft procedure, a femoral artery repair, a carotid artery repair, attachment of endothelial cells to prosthetic grafts to create new endothelial lining, an endoscopic vascular surgery procedure, or an aortic reconstruction.

57. The method of paragraph 52, wherein said subject having or recovering from said orthopedic surgery is having or is recovering from a joint replacement, a rotator cuff repair, a ligament repair, a tendon repair, a cartilage repair, attachment of cartilage cells and scaffold to a repair site, a meniscus repair, a labrum repair, a repair of lacerated or traumatized muscle tissue, treatment of a tendon or muscle strain, treatment of ligament sprain or overuse injury, an arthroscopic procedure, a tumor removal, a joint replacement revision, insertion and removal of an external fixator, a comminuted fracture stabilization procedure, a transcutaneous implant procedure (sealing of a pin insertion site to prevent entrance of bacteria), implantation of a bone stimulator, a bone graft procedure, a sports injury, a trauma procedure, a bone tumor removal procedure, a pubis symphysis separation repair, a slipped rib repair, closure of dead space to prevent a seroma in an orthopedic procedure, a fusion procedure, an open fracture repair, a closed fracture repair, treatment of a stress fracture, treatment of growth plate disorders and slipped epiphysis, treatment of a bony defect, treatment of osteoporosis or osteopenia, a bone fixation procedure, fixation of trauma implants to bone, an endoscopic orthopedic procedure, or containment of bone fragments at fracture site with and without internal fixation.

58. The method of paragraph 52, wherein said subject having or recovering from said obstetric surgery is having or is recovering from amniocentesis, premature rupture of amniotic membranes, an endoscopic obstetric procedure, or a cervical occlusion procedure.

59. The method of paragraph 52, wherein said subject having or recovering from said gynecologic surgery is having or is recovering from a Fallopian tube occlusion, a contraceptive procedure, a urinary incontinence procedure, a cystocoele repair, a rectocoele repair, a pelvic floor repair, a vulvovaginal reconstruction procedure, an amniotic membrane graft procedure, an endoscopic gynecologic procedure, fixation of embryo transfer with in vitro fertilization, an adhesion prevention procedure in a laparoscopic pelvic procedure, an adhesion prevention procedure in an open pelvic procedure, an adhesion prevention procedure after ovarian surgery, or an adhesion prevention procedure after uterine myomectomy.

60. The method of paragraph 52, wherein said subject having or recovering from said transplant surgery is having or is recovering from a pancreatic islet cell implantation, liver transplantation, kidney transplantation, pancreas transplantation, an endoscopic transplant procedure, or a combination thereof.

61. The method of paragraph 52, wherein said subject having or recovering from said fetal procedure is having or is recovering from balloon tracheal occlusion, closure of amniotic membranes, or a fetoscopic procedure.

62. The method of paragraph 52, wherein said subject having or recovering from said thoracic surgery is having or is recovering from a pulmonary lobectomy, bi-lobectomy, sleeve lobectomy, bullectomy, segmentectomy, pulmonary wedge resection, an air leak, a tracheoesophageal fistula repair, a neotracheal reconstruction, a pleural leak, a thoracoscopic or bonchoscopic procedure, an endoscopic thoracic surgery procedure, closure of a tracheal or bronchial defect, or repair of a bronchopleural fistula.

63. The method of paragraph 52, wherein said subject having or recovering from said ophthalmologic surgery is having or is recovering from an ocular procedure, a retinal procedure, a retinal detachment procedure, a corneal repair, a glaucoma procedure, a glaucoma drainage device procedure, a laser procedure, a tissue flap procedure after laser surgery, a conjunctival repair, a pterygium repair, cataract surgery, repair of wet or dry macular degeneration, an endoscopic ophthalmologic procedure, or a sclera flap procedure.

64. The method of paragraph 52, wherein said subject having or recovering from said oral surgery is having or is recovering from an oral wound closure, a tongue injury, a cheek injury, a tooth bed injury, a wisdom tooth removal, a root canal procedure, a bridge reconstruction procedure, a canker sore, a gum graft procedure, removal of an oral tumor or other lesion, an endoscopic oral surgery procedure, or periodontal flap surgery.

65. The method of paragraph 52, wherein said subject having or recovering from said plastic surgery is having or is recovering from a browplasty, a flap seroma repair, aesthetic surgery, a ptosis repair, rhytidectomy, a fasciocutaneous flap, body contouring surgery, a seroma after breast, face and body reconstructive surgery, a rhinoplasty, a skin graft to a wound or burn site, a muscle transfer to a wound site, a musculocutaneous flap, a decubitus injury, an ulcerative condition, a diabetic ulcer, a body contouring procedure, a liposuction procedure, a skin graft donor site repair, an endoscopic plastic surgery procedure, or a muscle transfer donor site repair.

66. The method of paragraph 52, wherein said subject having or recovering from said cardiac surgery is having or is recovering from coronary artery anastomotic bleeding, a heart valve placement procedure, placement of a ventricular patch, control of bleeding from adhesions during a re-operative cardiac procedure, bleeding after a congenital heart defect repair, an endoscopic cardiac surgery procedure, a pericardial adhesion prevention procedure, a retrosternal adhesion prevention procedure, or bleeding during and after cardiopulmonary bypass.

67. The method of paragraph 52, wherein said subject having or recovering from said urologic surgery is having or is recovering from an incontinence repair, a hypospadius repair, a fistula after hypospadius repair, a percutaneous nephrostomy, a percutaneous nephrolithotomy, a percutaneous nephrectomy, a vasovasotomy, a urinary fistula, a ureteral reconstruction, a circumcision, prostate surgery, vas deferens surgery, an anastomosis of the urethra, a stoma procedure, an endoscopic urologic procedure, or urologic trauma 68. The method of paragraph 52, wherein said subject is having or is recovering from an amputation, a tissue leak, a tissue perforation, a hematoma, a bleeding control procedure, a repair of luminal tissue, a tissue defect, a skin lesion, a topical wound closure, a microbial colonization or infection barrier procedure, a burn, a mucus membrane lesion, implantation of a pacemaker, implantation of a nerve stimulator, implantation of a pump, implantation of a bone stimulator, fixation of a vascular catheter, fixation of a second tissue to bone, a fistula repair, a skin wound closure, a vascular access procedure, a percutaneous device procedure, or a periosteal flap.

69. The method of paragraph 49, wherein said subject is a mammal.

70. The method of paragraph 49, wherein said mammal is a human.

71. The method of paragraph 49, wherein said phenyl derivative polymer comprises a catechol compound.

72. The method of paragraph 71, wherein said catechol compound is 3,4-dihydroxyphenylalanine (DOPA), dopamine, 3,4-dihydroxyhydrocinnamic acid, a DOPA derivative, a conjugation of DOPA, poly(DOPA), poly(DOPA-Lys), hydroferulic acid, 3-methoxytyramine, homovanillic acid, 3,4-dihydroxybenzylamine, 3,4-dihydroxybenzoic acid, 4-hydroxy-3-methoxybenzylamine, or 3,4 dimethoxyhydrocinnamic acid.

73. The method of paragraph 49, wherein said phenyl derivative polymer further comprises a linker compound.

74. The method of paragraph 73, wherein said linker compound is an amide linker compound, a urethane linker compound, a urea linker compound, a di-acid linker compound, an amine-diol linker compound, an ester linker compound, a gamma-aminobutyric acid linker compound, a 3,4-dihydroxybenzoic acid linker compound, a 4-hydroxy-3-methoxybenzylamine linker compound, a glycine linker compound, an amino acid linker compound, or a lysine linker compound.

75. The method of paragraph 49, wherein said phenyl derivative polymer comprises a branched polymer.

76. The method of paragraph 49, wherein said phenyl derivative polymer comprises at least one compound from Table 1.

77. The method of paragraph 49, wherein said surface is a tissue.

78. The method of paragraph 77, wherein said tissue is skin tissue, hair tissue, nail tissue, corneal tissue, tongue tissue, oral cavity tissue, esophageal tissue, anal tissue, urethral tissue, vaginal tissue, urinary epithelial tissue, salivary gland tissue, mammary gland tissue, lacrimal gland tissue, sweat gland tissue, prostate gland tissue, bulbourethral gland tissue, Bartholin's gland tissue, uterine tissue, respiratory and gastrointestinal tract goblet cell tissue, gastric mucosal tissue, gastric gland tissue, pancreatic tissue, pulmonary tissue, pituitary gland tissue, thyroid gland tissue, parathyroid gland tissue, testicular tissue, ovarian tissue, respiratory gland tissue, gastrointestinal gland tissue, adrenal gland tissue, renal tissue, liver tissue, adipose tissue, duct cell tissue, gall bladder tissue, epidydimal tissue, vas deferens tissue, blood vessel tissue, lymph gland tissue, lymphatic duct tissue, synovial tissue, serosal tissue, squamous tissue, cochlear tissue, choroid plexus tissue, ependymal tissue, dural tissue, pia-arachnoid tissue, sclera tissue, retinal tissue, iris tissue, ciliary tissue, dental tissue, otic tissue, ligament tissue, tendon tissue, elastic cartilage tissue, fibrocartilage tissue, hyaline cartilage tissue, bone marrow tissue, intervertebral disc tissue, compact bone tissue, cancellous bone tissue, skeletal muscle tissue, cardiac muscle tissue, smooth muscle tissue, cardiac valve tissue, pericardial tissue, pleural tissue, peritoneal tissue, blood cell tissue, neuronal tissue, glial tissue, sensory transducer cell tissue, pain sensitive tissue, autonomic neuron tissue, peripheral nervous system tissue, cranial nerve tissue, ocular lens tissue, germ cell tissue, thymus tissue, placental tissue, fetal membrane tissue, umbilical tissue, stem cell tissue, mesodermal tissue, ectodermal tissue, endodermal tissue, autologous tissue, allograft tissue or a combination thereof.

79. The method of paragraph 49, wherein said applying is manual applying, applicator applying, instrument applying, manual spray applying, aerosol spray applying, syringe applying, airless tip applying, gas-assist tip applying, percutaneous applying, surface applying, topical applying, internal applying, enteral applying, parenteral applying, protective applying, catheter applying, endoscopic applying, arthroscopic applying, encapsulation scaffold applying, stent applying, wound dressing applying, vascular patch applying, vascular graft applying, image-guided applying, radiologic applying, brush applying, wrap applying, or drip applying.

80. The method paragraph 49, wherein said phenyl derivative polymer further comprises an anti-microbial compound, an antibiotic compound, a growth factor compound, a gene therapy vector, stem cell tissue, undifferentiated progenitor cells, differentiated cells, an analgesic compound, an anesthetic compound, an RNAi compound, a morphogenetic protein, a sustained release compound, endothelialized graft tissue, bone graft tissue, autograft tissue, allograft tissue, xenograft tissue, a bone graft substitute, a coagulation factor compound, a hormone compound, a steroid hormone compound, a bioactive compound, or a chemotherapeutic agent.

81. The method of paragraph 49, wherein said phenyl derivative polymer is configured to degrade at a predetermined rate.

82. The method of paragraph 49, wherein said phenyl derivative polymer comprises a predetermined strength.

83. The method of paragraph 49, wherein said phenyl derivative polymer comprises a predetermined tensility.

84. The method of paragraph 49, wherein said phenyl derivative polymer is a film polymer.

85. The method of paragraph 84, wherein said film polymer is a single layer film polymer.

86. The method of paragraph 84, wherein said film polymer is a multi-layer film polymer.

87. The method of paragraph 84, wherein said film polymer comprises an oxidant.

88. The method of paragraph 84, wherein said phenyl derivative polymer is applied on at least one side of a mesh.

89. The method of paragraph 88, wherein said mesh is a biologic mesh or a synthetic mesh.

90. The method of paragraph 84, wherein said film polymer is a stand-alone film polymer.

91. The method of paragraph 84, wherein at least one surface of said film polymer is adhesive.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight.

EXAMPLES

Experimental Example 1

Topical Wound Closure in the Rat

Using a "bilateral" incision wound model on the dorsal surface of the rat (Oxlund et al, J Surg Res, 1996; 66:25-30, Jorgensen et al., J Surg Res, 1995; 58:295-301) healing across an incision site whose ends are opposed with a bioadhesive was investigated by measuring the tensile failure properties of incision sites treated with two formulations of a bioadhesive, and comparing this with the failure properties of incisions repaired with a representative commercially available cyanoacrylate adhesive (Dermabond), and with suture alone. Wound site healing was also qualitatively assessed using histology.

Experimental Design:

48 Sprague-Dawley rats (350-399 g) were tested. The dorsal skin was shaved, and the skin prepped for surgery. Two 5-cm long incision wounds were made 15 mm from and parallel to the dorsal midline, and centered on the thoracolumbar junction. The incisions were made perpendicular to the skin surface, and through the epidermis, dermis and subcutaneous muscle layers, but leaving the deep fascia intact. Hemostasis was obtained by direct pressure using sterile gauze. The wounds were repaired by 1 of the 4 following treatments: 1. Formulation QuadraSeal-DH 15%; 2. Formulation QuadraSeal-DH 30%; 3. Dermabond (2-octyl cyanoacrylate adhesive); and 4. Interrupted 5-0 polypropylene sutures only (placed 5 mm apart and 3-4 mm from the wound line).

The repaired wounds were dressed with gauze and tape, appropriate antibiotic was administered, and the animals were allowed to recover. Twelve animals were euthanized at each of 4 hours, and 3, 7, and 21 days. The treatments were applied to the groups of 12 animals at each of the 4 time points according to the following design (numbers represent the 4 treatments defined above, pairs of numbers represent treatments for the 2 incisions in each of 12 animals): (1-2, 2-1, 3-1, 4-1, 1-3, 2-3, 3-2, 4-2, 1-4, 2-4, 3-4, and 4-3) providing 6 5-cm incision samples for each treatment at each of 4 time points, with each treatment paired with all others twice at each time point. Treatments 3 and 4 served as comparative controls. The skin from the incision wound test area on both sides of the spine was harvested from each animal. The subcutaneous muscle fascia was separated from the undersurface of the skin. Three uniform 30 mm×10 mm test strips of skin were cut at equally spaced intervals from the skin samples from both sides of the spine. Two of the samples from each incision were stored in a zip-lock plastic bag and transported to a biomechanics lab for mechanical testing within two hours from sample harvest. The third strip from each incision was fixed in formalin and prepared for histology as described below. The test strips of skin for mechanical testing were mounted in a materials test machine by means of grips with serrated surfaces to minimize slippage during testing. The test strips were loaded to failure in tension at a rate of 10 mm/min, and the tensile failure strength was recorded and the character of the tissue failure noted. In the specimens from the 3, 7 and 21-day groups where the wound was closed with sutures, one of the two specimens from the incision was tested with the sutures cut, and the other specimen with the sutures intact. Descriptive histology was performed on one of the three 30 mm×10 mm test strips from the 6 animals at each of 4 time points for each of the 4 treatments, for a total of 96 sections for this histologic assessment. The harvested skin samples were immediately fixed in 10% formalin, processed and embedded in paraffin. Histologic specimens (5 μm thick) were sectioned perpendicular to the wound surface and stained with hematoxylin and eosin.

Results—Mechanical Testing

Figure 222:
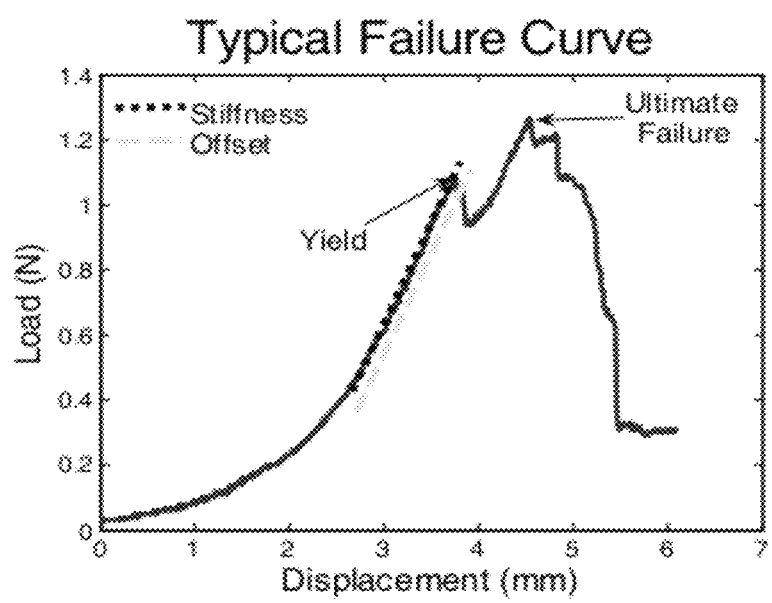
FIG. 222 shows a mechanical failure adhesive testing curve.

Referring to FIG. 222, yield and ultimate failure were calculated from load-displacement curves. Curves were shifted such that the first point at which 0.05 N was exceeded was considered a displacement of 0.0 mm. The ultimate load or peak load was selected as the highest value on the curve, and the displacement at this point was recorded. A secondary, linear stiffness region was chosen graphically, and a stiffness line was fit to this region using a least-squares approach. This line was shifted by 2% of the displacement at peak load, and intersected with the load-displacement curve to determine the yield load and displacement. This point corresponded to the first perturbation in the curve where failure of the incision site began, and was the same as the peak load in the absence of a distinct yield point. The two yield and ultimate loads were averaged within each rat incision. Analysis of variance with pair-wise comparisons was performed on the log-transformed data to provide normality and equal variance conditions. The incisions in several animals broke open early in the postoperative period, and the animals were euthanized. This occurred in the animals that had been designated for 21 days. The incisions in several test samples from animals at early time points were fragile and broke open during/after harvest and before mechanical testing. These samples are tallied in Tables 2. and 3. During testing the intact fascia of some specimens dominated the wound strength during and after failure of the wound.

TABLE 2

Number of test samples that broke before testing (fragile wounds)

| | Dermabond | Cmpnd 1 | Cmpnd 2 | Suture (Intact) | Suture (Removed) |
|---|---|---|---|---|---|
| 4 Hours | 1 | 3 | 4 | 0 | NA |
| 3 Days | 2 | 6 | 0 | 0 | 3 |
| 7 Days | 0 | 2 | 2 | 0 | 0 |
| 21 Days | 0 | 0 | 0 | 0 | 0 |

TABLE 3

Number of animal incisions represented in the final statistics at each time point

| | Dermabond | Cmpnd 1 | Cmpnd2 | Suture |
|---|---|---|---|---|
| 4 Hours | 6 | 4 | 4 | 6 |
| 3 Days | 6 | 3 | 5 | 6 |
| 7 Days | 6 | 4 | 4 | 6 |
| 21 Days | 5 | 2 | 5 | 4 |

Figure 223:
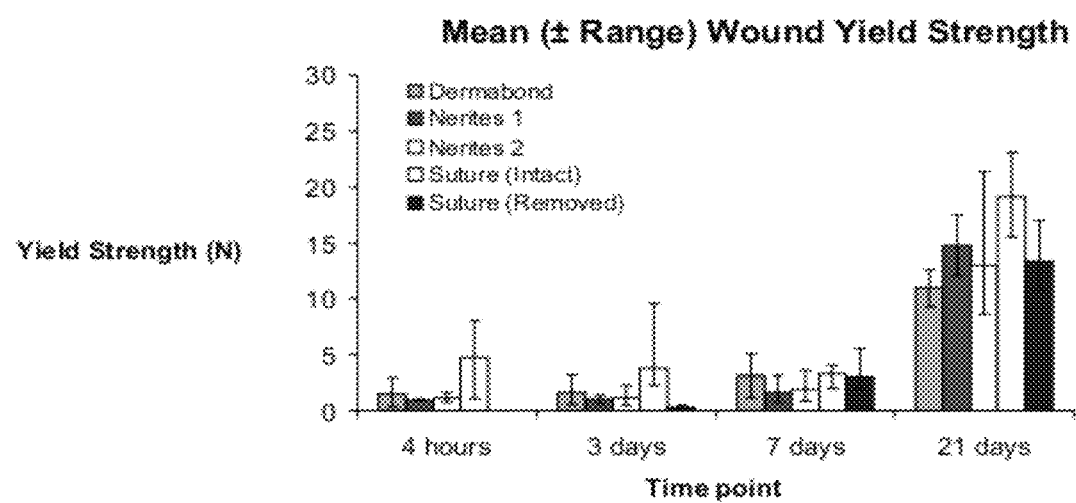
FIG. 223 shows mean wound yield strength.
Figure 224:
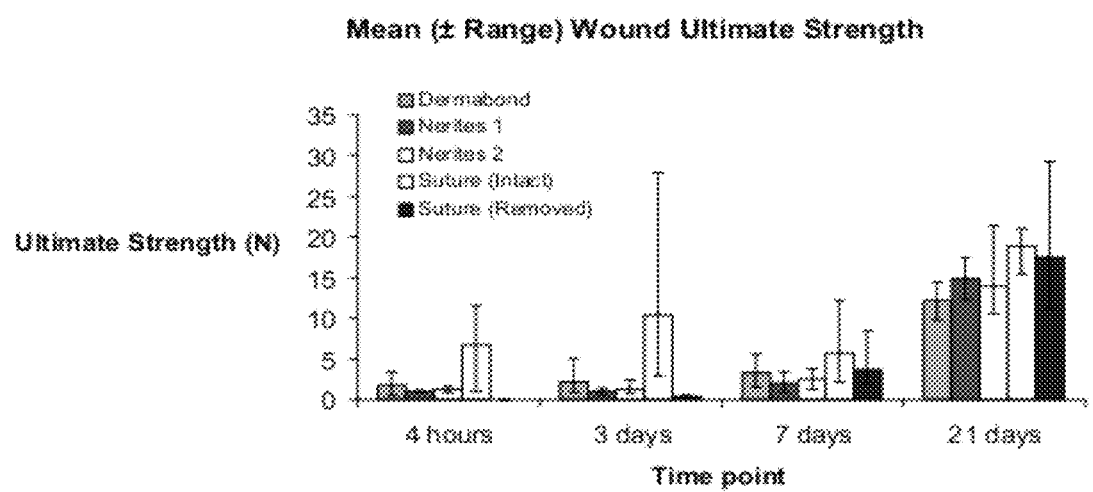
FIG. 224 shows mean wound ultimate strength.
Figure 225:
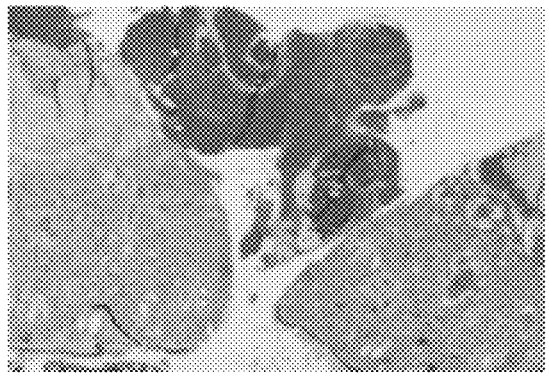
FIG. 225 shows histological micrographs at 4-hours.
Figure 225:
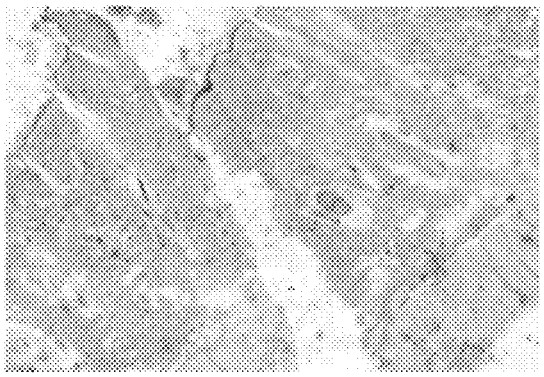
Figure 225:
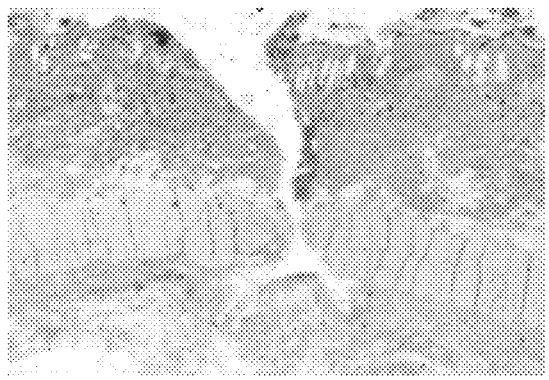
Figure 225:
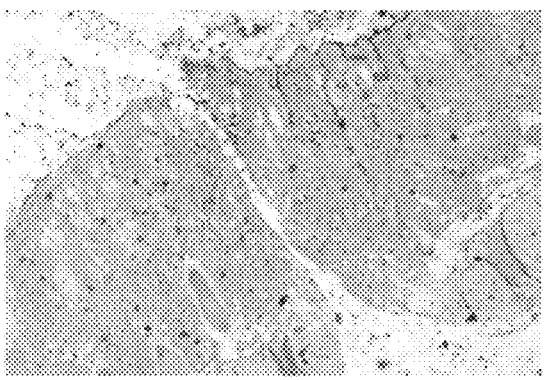
Figure 226:
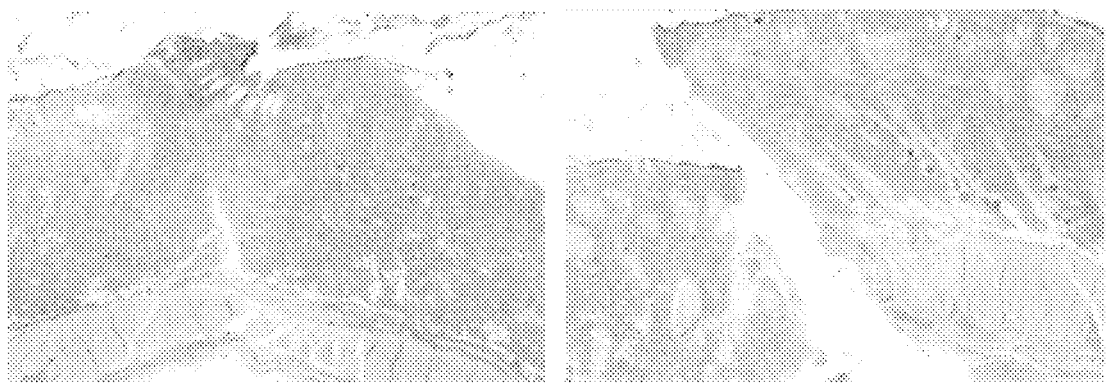
FIG. 226 shows histological micrographs at 3 days.
Figure 226:
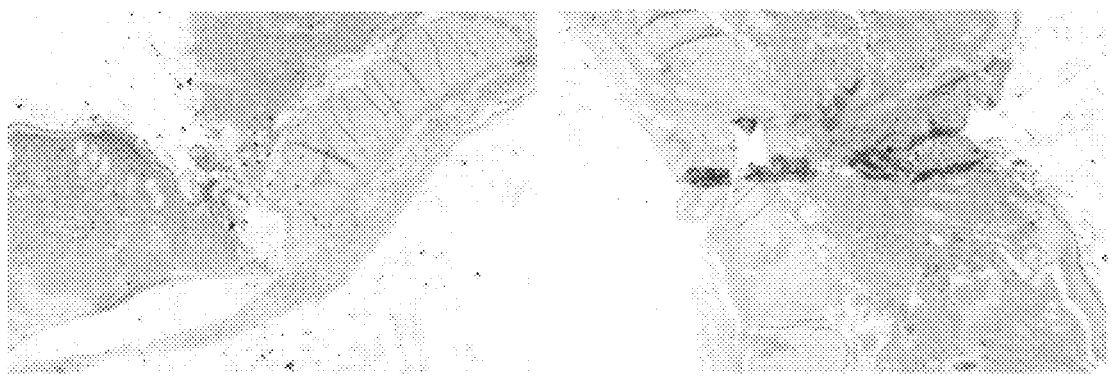
Figure 227:
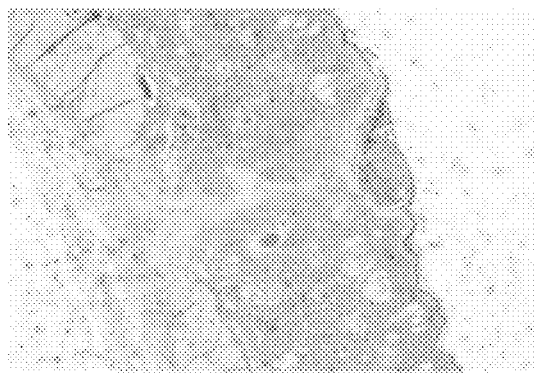
FIG. 227 shows histological micrographs at 7 days.
Figure 227:
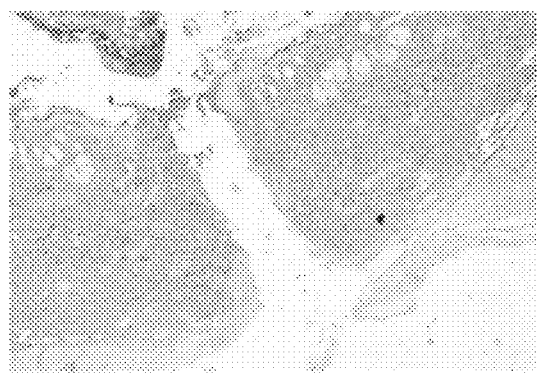
Figure 227:
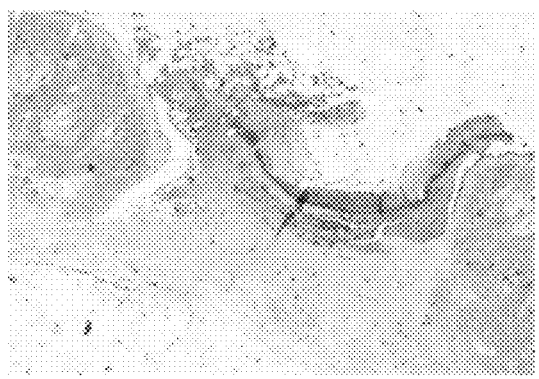
Figure 227:
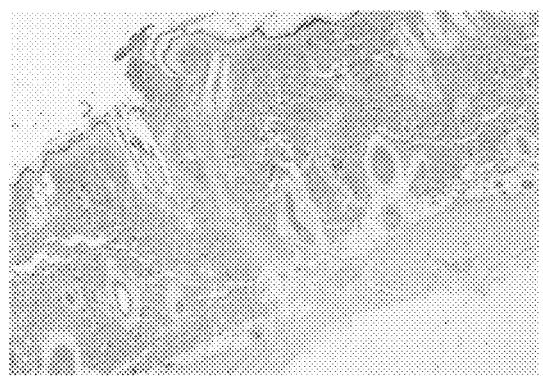

The yield and ultimate failure results are summarized in the FIGS. 223 and 224. At the 4-hour and 3-day time points, wounds closed by suture (intact) were significantly stronger (yield and ultimate) than the wounds closed by the 2 test compound ("Cmpnd") adhesives, Dermabond, and sutures that we cut at testing (see statistics results in Appendix). At 7 days, there were no significant differences between any of the treatments in terms of yield and ultimate strengths. All wounds that were mechanically tested appeared to be healed at 21 days. Again, at 21 days, there were no significant differences between any of the treatments except Dermabond and suture intact (p=0.018), for yield and ultimate strengths. The 2 test adhesives work as well as suture and Dermabond in terms of failure strength at 21 days.

Results—Histology:

4-Hour:

There were no consistent differences among the 4 treatments in the 4-hour histology. There was no evidence of healing at this early time point. With all treatments, histology showed the initial signs of an inflammatory response. There was no presence of fibroblasts.

3-Day:

There were no consistent differences among the 4 treatments in the 3-day histology. The inflammatory response was much greater than at 4 hours for all treatments as reflected by the large number of neutrophils that had accumulated at the wound site. There was evidence of the initiation of wound repair as revealed by the presence of some fibroblasts. The sides of the wounds remained un-united in all treatments. Although the ends of the wounds appear to be tightly opposed in the 3-day images of the QuadraSeal-DH 15% and suture specimens, there was no evidence of significant wound healing with reparative fibrous tissue in these 2 specimens.

7-Day:

Differences between the treatments became more evident at this time point. There was a reduction in the number of inflammatory cells by 7 days, although they were still present at the wound site. There were a large number of fibroblasts with varying levels of associated reparative scar tissue in all specimens depending upon the treatment. In most cases, wound repair seemed to begin in the deep dermal layer and then progressed up toward the epidermis. This reparative process, although present, was less organized and insufficient to provide full-thickness healing of wounds treated with Dermabond at the 7-day time point. The repair process was even less intense with treatment with QuadraSeal-DH 30%. However, the repair process was much more organized and led to 3 of 5 suture-treated specimens and 3 of 6 QuadraSeal-DH 15% treated specimens to exhibit full-thickness wound healing at 7 days.

21-Day:

All specimens exhibited full-thickness wound healing by 21 days: 2 of 2 with QuadraSeal-DH 15%, 6 of 6 with QuadraSeal-DH 30%, 4 of 4 with Dermabond, and 4 of 4 with suture. The reparative tissue in the wound site exhibited a large number of fibroblasts and collagen fibers. Re-epithelization was evident with all treatments.

Experimental Example 2

Suture Line Sealing on a PTFE Vascular Graft

The purpose of this study was to evaluate the biocompatibility of the test articles, as well as the ability of the test articles to prevent blood loss in vascular applications in the canine model. The performance of the test articles were compared to CoSeal™.

TABLE 4

| ARTICLE | LOT NUMBER | EXPIRATION DATE |
| --- | --- | --- |
| CoSeal | 060842 | July 2008 |
| Medhesive CV SLOWGEL | 90843 | Dec. 05, 2008 |
| Medhesive CV FASTGEL | 91352 | Dec. 05, 2008 |

8 adult mixed breed dogs, weighing an average of 28.6±1.7 kg were purchased from Covance Research Products, Kalamazoo, Mich. The study design is shown in Table 5.

TABLE 5

| Animal Number | METHOD OF ACHIEVING VASCULAR REPAIR HEMOSTASIS | | NECROPSY |
| --- | --- | --- | --- |
| | Left femoral artery | Right femoral artery | |
| 1 | CoSeal | Medhesive CV SLOWGEL | Day 14 |
| 2 | CoSeal | Medhesive CV FASTGEL | Day 14 |

TABLE 5-continued

| Animal Number | METHOD OF ACHIEVING VASCULAR REPAIR HEMOSTASIS | | NECROPSY |
| --- | --- | --- | --- |
| | Left femoral artery | Right femoral artery | |
| 3 | Medhesive CV SLOWGEL | Medhesive CV FASTGEL | Day 14 |
| 4 | Medhesive CV FASTGEL | Medhesive CV SLOWGEL | Day 14 |
| 5 | Medhesive CV SLOWGEL | CoSeal | Day 14 |
| 6 | Medhesive CV FASTGEL | CoSeal | Day 14 |
| 7 | Medhesive CV FASTGEL | Medhesive CV SLOWGEL | Day 14 |
| 8 | Medhesive CV SLOWGEL | Medhesive CV FASTGEL | Day 14 |

Surgical Procedure

To avoid differences in blood pressure and bleeding parameters, two surgeons were used to perform simultaneous bilateral femoral patch implantations. Following clipping and scrubbing of both hind legs the animals were placed in dorsal recumbency on the operating table, and then aseptically prepped and draped. Indirect blood pressure was monitored during the procedure, and pressures were recorded every 2 minutes during the hemostasis evaluation period. An incision was made over both femoral arteries and the arteries were exposed by sharp and blunt dissection. Lidocaine was applied topically to the femoral arteries to prevent vasospasm during dissection. Once the femoral arteries were isolated, heparin was given as needed to achieve and maintain an activated clotting time (ACT) of approximately 300 seconds. The ACT was recorded approximately 1 to 10 minutes after the initial bolus of heparin and approximately every 30 minutes throughout the surgical procedure and hemostasis evaluations. To occlude blood flow, atraumatic clamps were placed on the femoral arteries proximal and distal to the arteriotomy site. An approximate 1.5 cm longitudinal arteriotomy was made into the ventral surface of each vessel. An elliptical ePTFE patch, approximately 1.5 cm long and 0.5 cm wide was cut to size and sewn into place with 6-0 Prolene on a taper needle in a continuous suture pattern. When the ePTFE patches were implanted, the distal and proximal vessel clamps were released for 1-3 seconds to expand the vessel and to document suture line bleeding. The clamps were re-applied and the vessel blotted dry with sterile gauze. The gauze was discarded. A uniform layer of test or control sealant was applied to the suture line and to the ePTFE patch surface. If required, a second application was applied as an overlay or touch-up to the first application. The test and control sealants were allowed to gel for at least 60 seconds.

Hemostasis Evaluation

After the sealant was allowed to completely gel the surgeons simultaneously removed the distal and proximal clamps from each artery. Close observation of the treatment site determined oozing or bleeding, which was recorded. If hemostasis was not achieved, direct pressure with gauze sponges was employed for 5 minutes. The time of hemostasis, if achieved within 5 minutes, was noted. The gauze sponges were weighed to assess blood loss. After hemostasis was established, the defect was observed for an additional 5 minute period. Any recurrence of bleeding or oozing, re-bleeding, runoff or sloughing of the sealant was recorded. Blood was wiped from the vessel and the pads were weighed to calculate blood loss. If the contralateral vessel achieved hemostasis, it was also monitored for the 5 minute period. Following the time to hemostasis evaluations, the muscle, subcutaneous and subcuticular tissues were closed with 3-0 PDS suture and the skin was closed with cyanoacrylate glue.

The dogs were recovered from anesthesia and returned to the study room where postoperative monitoring continued. Long term postoperative monitoring included twice-daily inspections of the surgical site for signs of bleeding, or infection.

Necropsy and Postmortem Evaluations

Prior to necropsy the animals were sedated and angiography of both femoral arteries was performed to demonstrate vessel patency. The animals were euthanized with intravenous sodium pentobarbital solution, followed by exsanguination. The vascular implant sites were exposed and inspected for evidence of chronic bleeding, inflammation, or infection. Both femoral arteries to include the patched segment and at least 1 cm of native vessel proximal and distal to the patch were excised and longitudinally slit open on the side opposite the patch. Each vessel was pinned flat on a piece of cork, gently rinsed with saline to remove any residual blood, and grossly examined for evidence of sealant on the luminal surface of the patch or vessel, as well as adhered thrombus. The vessels were fixed in 10% neutral buffered formalin, sectioned, stained with H &E stain, and read by a board-certified pathologist.

Results

Pre-operative clinical examinations and CBC and serum chemistry evaluations confirmed that the animals were in good health at the time of implantation. In all cases, clamp release following implantation demonstrated suture line bleeding. Immediate hemostasis after one application of sealant was observed in 1 of 4 CoSeal applications, and 5 of 6 Medhesive CV FG and Medhesive CV SG applications, respectively. Re-bleeding during the 5-minute observation period resulted in 1 CoSeal re-bleed, 2 Medhesive CV SG re-bleeds and 3 Medhesive CV FG re-bleeds. Blood lost during the 5-minute observation period were: Medhesive CV SG, 1.8±1.8 mL; Medhesive CV FG, 4.9±5.9 mL; and CoSeal 4.1±4.2 mL. Each group had one instance where no blood loss occurred.

Experimental Example 3

Adjunctive Sealing of Gastrointestinal Tissues

Figure 228:
FIG. 228 shows the small intestine burst test apparatus
Figure 229:
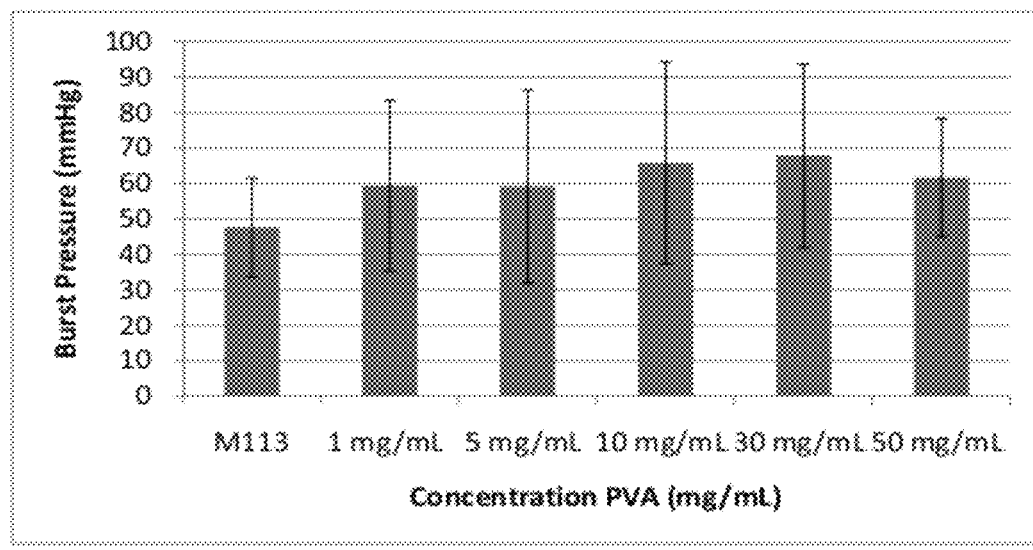
FIG. 229 shows burst testing results for M113 (30 wt %)+PVA (89-98 kDa) applied to sutured defect in porcine small intestine.
Figure 230:
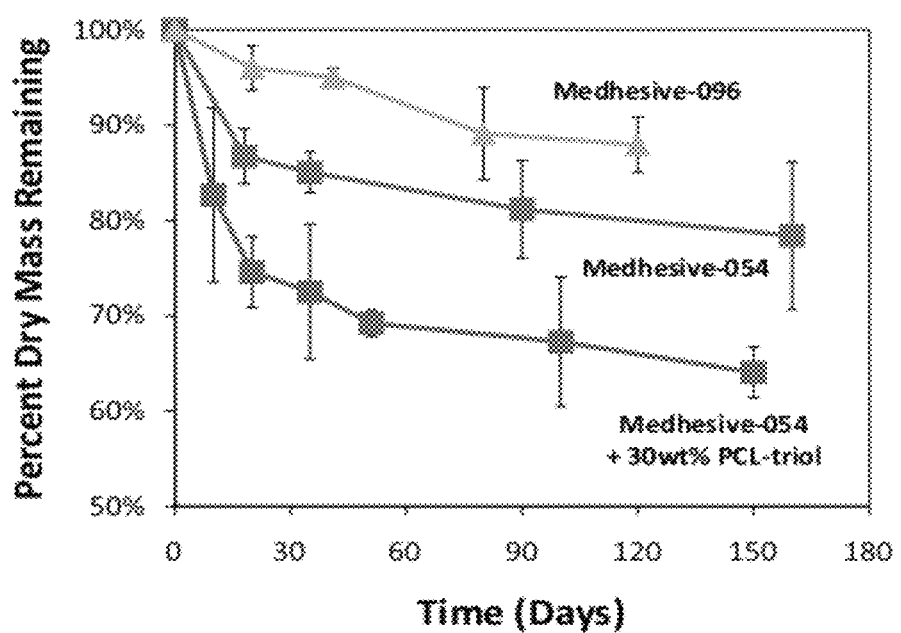
FIG. 230 shows the in vitro degradation profile of adhesive films incubated at 37° C. in PBS (pH 7.4).

Medhesive-113 was formulated at varying concentrations with varying amounts of poly vinyl alcohol (PVA) added. The formulations used applied over a ~3 mm defect in a segment of porcine small intestine secured with a single suture. The formulation was allowed to cure for 10 minutes under ambient conditions. The tissue/adhesive test assembly was conditioned in a saline bath for 1 h. After the conditioning period the segment was pressurized with air (FIG. 228) and the maximum pressure withstood was recorded (FIG. 229). The addition of PVA to the formulation made the resulting adhesive surprisingly elastic and the formulations containing higher amounts of PVA were more extensible and resisted higher pressures than those with less of no PVA added.

Experimental Example 4

Tendon Repair

Figure 231:
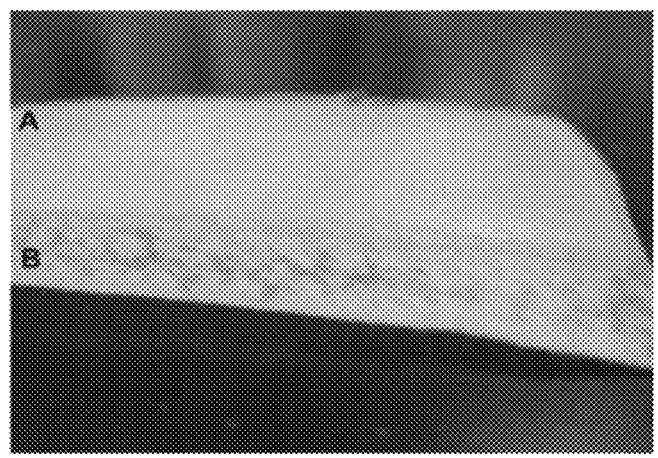
FIG. 231 shows a photograph of adhesive film (4 cm×8 cm, (A)) coated onto a 6 cm×8 cm segment of BioTape (B).
Figure 232:
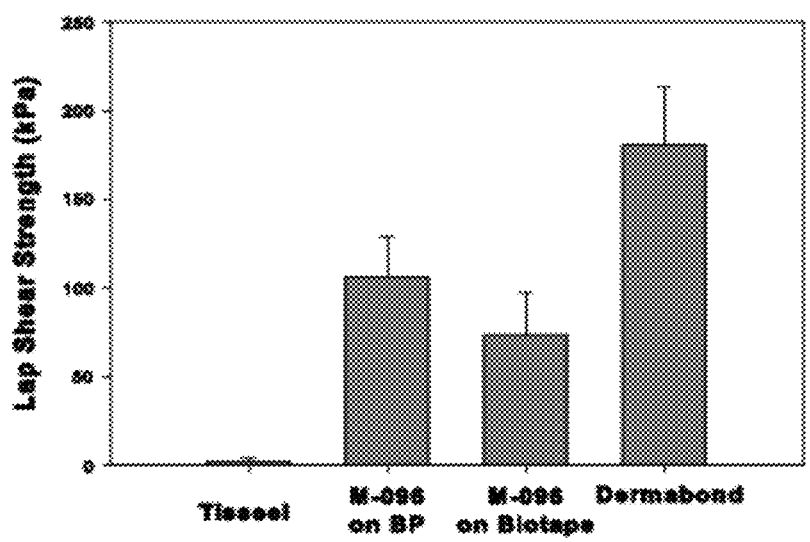
FIG. 232 shows lap shear adhesion testing using bovine pericardium as test substrate; BP=bovine pericardium, N≥6.

To test use of adhesives of the present invention for tendon repair, the adhesive properties of an adhesive-coated biologic mesh using lap shear adhesion tests (ASTM F2255) was evaluated. Medhesive-096 (FIG. 106) was solvent cast onto either bovine pericardium or a commercially available porcine dermal tissue (Biotape XM™, Wright Medical Technology) to form the bioadhesive construct (FIG. 231). Bovine pericardium was chosen as a backing because it is an inexpensive and readily abundant extracellular matrix with suitable material properties (tensile strength of 41±9.8 N/cm). Additionally, several acellular bovine pericardium-based products (e.g., Veritas®, Synovis Surgical Innovations; Tutomesh®, RTI Biologics) have been approved by the FDA for soft tissue reconstruction. Biotape is a porcine dermal tissue that has been evaluated for tendon repair. To perform the lap shear tests, adhesive coated-constructs were activated with a solution of $NaIO_4$ (40 uL) prior to bringing the adhesive into contact with the test substrate (also bovine pericardium). The adhesive joints were weighted down (100 g) for 10 minutes and incubated at 37° C. in PBS (pH 7.4) for an hour prior to testing. Dermabond® (Ethicon Inc.) and Tisseel™ (Baxter Healthcare Corporation), commercially available tissue adhesives, were included in the testing as controls. The adhesives were applied in situ according to the instructions of the manufacturer. The minimum sample size was 6 in each test condition. Statistical assessment was performed using an analysis of variance (ANOVA), with pair-wise comparisons made with the Tukey test and a significance level of 0.05. As demonstrated in FIG. 232, strong moisture resistance adhesive strength was imparted to both biologic meshes. The adhesive constructs demonstrated adhesive strengths that were 28-40 times greater than that of fibrin glue. While Dermabond exhibited the highest adhesive strength among all adhesives tested, meshes fixed with cyanoacrylates have been reported to have reduced tissue integration combined with a pronounced inflammatory response. Due to the release of toxic degradation products (formaldehyde), cyanoacrylates are not approved for general internal applications in the US. Both Medhesive-096-coated bovine pericardium and Biotape were used in subsequent mechanical testing of repaired tendons.

Figure 233:
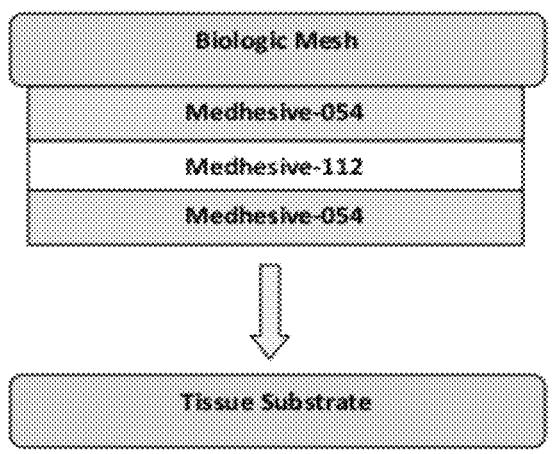
FIG. 233 shows A) a schematic of tri-layer adhesive film coated onto a biologic mesh, and B) lap shear adhesion strength (left y-axis) of adhesive-coated bovine pericardium, and tensile elastic modulus (right y-axis) of polymer films.
Figure 233:
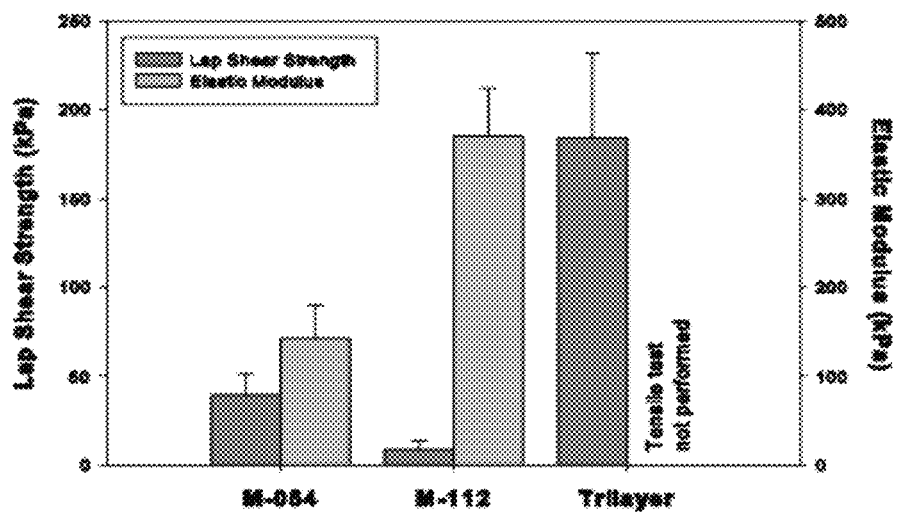

In addition to a single layered adhesive coating, the present invention provides a tri-layered coating consisting of a layer of Medhesive-112 sandwiched between two layers of Medhesive-054, as illustrated in FIG. 233. The tri-layered construct demonstrated significantly higher lap shear adhesive strength (185±47.4 kPa) compared to its individual components; Medhesive-054 (39.0±12.5 kPa) and Medhesive-112 (8.48±4.64 kPa). Medhesive-054 is the most hydrophilic polymer of those synthesized, which may be most suitable for interfacial binding. Medhesive-112 has elevated polyester content (25 wt %), and the Medhesive-112 films may exhibit poor adhesive strength (poor interfacial binding properties) despite having a tensile modulus that is 2.6 times greater than that of Medhesive-054. The tri-layered-construct combines the interfacial binding properties of Medhesive-054 with the strong bulk mechanical properties of Medhesive-112 in creating an adhesive film that exhibited adhesive strength that is equivalent to that of Dermabond (181±33.4 kPa, FIG. 232). Currently, a step-by-step solvent casting method is used to provide the tri-layer. Alternatively, a computer-controlled spraying machine (Prism 300, Ultrasonic Systems, Inc.) may be used to fabricate multilayered-coatings more easily and quickly. Adhesive constructs produced by this spray method exhibited adhesive strengths (91.1±6.23 kPa) that are equivalent to those with the solvent casting method (105±22.9 kPa). The coefficient of variation (CV), a measure of variance in the data computed by the ratio of the standard deviation to the mean, was lower with the spray method (CV=6.8%) compared with the solvent casting method (CV=22%), which may be attributed to a more evenly coated film. Additionally, the spray method may be used to control the thickness as well as the pattern of films coated onto the mesh.

Mechanical Properties of Repair Tendons

Figure 234:
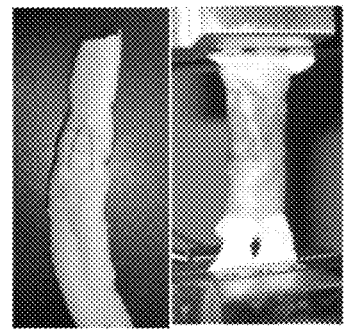
FIG. 234 shows photographs of sutured tendon (left), and sutured tendon augmented with adhesive-coated bovine pericardium wrap (right).

The mechanical properties of tendons repaired by suture combined with the bioadhesive constructs of the present invention, were compared with the standard of care-tendons repaired by sutures alone. As demonstrated in FIG. 234 (left), transected porcine tendons (rear leg deep flexor) were sutured with both parallel (Polysorb™ braided lactomer™ 4-0, Covidien) and 3-loop pulley (Maxon™ monofilament polyglyconate, 0, Covidien) suture patterns. The parallel sutures were used to keep the two ends of the transected tendon in intimate contact in order to minimize gap formation, while the 3-loop pulley was intended to be the main structural component that held the severed tendon together. For construct-repaired groups, the sutured tendons were further reinforced by wrapping either bovine pericardium or Biotape coated with Medhesive-096 around the tendon (FIG. 234 (right)). The bioadhesive construct was first secured to the tendon with three stay sutures, and then a solution of $NaIO_4$ (20 mg/mL) was sprayed onto the adhesive prior to wrapping it around the tendon. The wrapped tendons were held tightly for 10 min and incubated at 37° C. (PBS, pH 7.4) for 1 hr prior to testing. Both sutured tendons and adhesive-wrapped tendons were loaded to failure at a rate of 25 mm/min, and load/displacement (strain) data were recorded. For each test group, 10 samples were included, and statistical analysis was performed as previously described.

TABLE 6

Tensile structural properties of repaired tendons

| | | | |
|---|---|---|---|
| Linear Stiffness (N) | 1045 ± 305 | 1451 ± 254* | 1305 ± 340# |
| Failure Load (N) | 105 ± 25.1 | 151 ± 37.4* | 130 ± 45.5# |
| Strain @ Failure Load | 0.158 ± 0.0208 | 0.159 ± 0.0318 | 0.159 ± 0.0298 |
| Energy to Failure (J) | 0.386 ± 0.131 | 0.630 ± 0.194* | 0.492 ± 0.236 |
| Peak Load (N) | 217 ± 45.7 | 231 ± 35.6 | 245 ± 35.8 |
| Strain @ Peak Load | 0.356 ± 0.0602 | 0.370 ± 0.0612 | 0.380 ± 0.0606 |

*$p < 0.05$ compared to suture only;
$p < 0.15$ compared to suture only.
BP = *bovine pericardium*.
N = 10 replicates per treatment.

Figure 235:
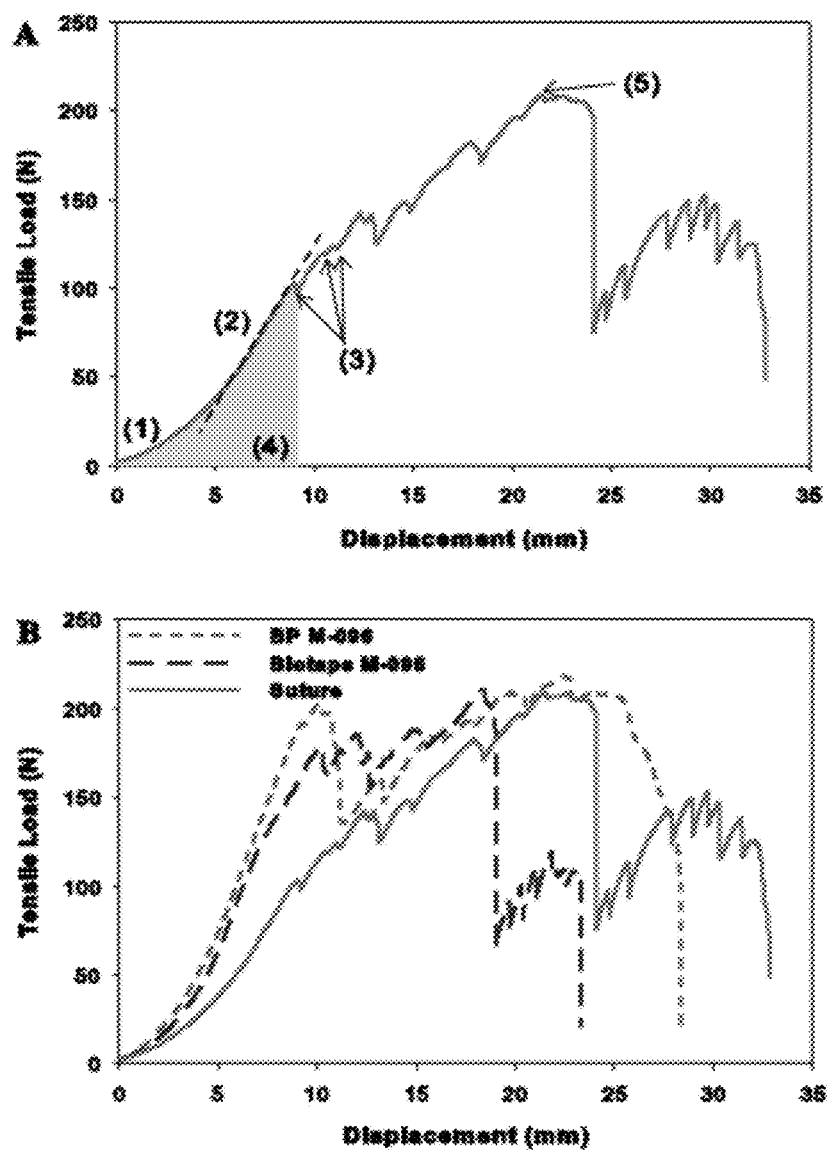
FIG. 235 shows a tensile failure test of a tendon repaired with suture alone (top panel), and representative curves for each type of repaired tendon (bottom panel). (1) Toe region, (2) dashed line indicating the slope or the linear stiffness of the repaired tendon, (3) arrows indicating the first parallel suture being pulled off, which is considered failure of the repair (failure load), (4) energy to failure as calculated by the area under the curve up to the failure load, and (5) peak load where 3-loop suture begins to fail.
Figure 236:
FIG. 236 shows a thin film adhesive and a thin film adhesive coated onto a synthetic mesh (pre-coated mesh adhesive).
Figure 236:
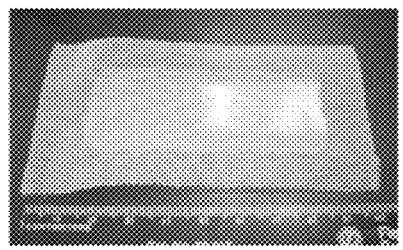
Figure 237:
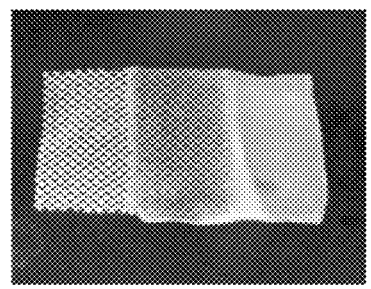
FIG. 237 shows a pre-coated mesh adhesive attached to bovine pericardium.

FIG. 235A demonstrates a representative load vs. strain curve for a sutured tendon, which contains typical features that were evident in all test groups (FIG. 235B); (1) non-linear toe region where the fibers are being recruited as the tendon is stretched, (2) linear region representing the linear stiffness of the repaired tendon, (3) arrows pointing to reduction in the load corresponding with the parallel sutures being pulled off the tendon, with the first of these instances being considered as the irreversible failure of the repair (failure load), (4) the area under the load-strain curve up to the failure load, used to calculate energy to failure, and (5) peak load where the 3-loop pulley began to fail, as it is pulled through the tendon. As shown in Table 6, adhesive wrapped tendons increased the stiffness of the repair by 25-40% over the controls, indicating more force was required to stretch these tendons. While sutured tendons readily formed a gap at the transected site at loads as low as 10 N, no visible gap was formed in bovine pericardium-wrapped tendons until failure as determined by ultrasound images. Gap formation has been attributed to inflammation and inadequate healing as a result of poorly aligned collagen fibers. Adhesive-wrapped tendons also exhibited increased failure load and energy to failure (24-44% and 27-63%, respectively), compared with suture-only controls. Thus, patients with adhesive-wrapped tendons could initiate a rehabilitation program at an earlier time point or perform a more aggressive rehabilitation regimen. Tension applied to the tendon during healing improves the orientation of collagen fibers and calf muscle strength. The strains to failure for all test groups were not statistically different, indicating that the parallel sutures begin to fail when tendons were being pulled to the same strain, regardless of treatment. Similarly, both peak load and strain corresponding to failure of the 3-loop sutures were not statistically different between the three test groups. While the 3-loop suture is the primary structural component that holds the tendon together, irreversible failure had already occurred when the parallel sutures were pulled out of the tendons. Initial failure load, and not peak failure load, is the more important failure metric when considering repeated loading of a healing tendon.

Experimental Example 5

Pelvic Floor Collapse Repair

This Example demonstrate the ability of thin film adhesives of the present invention to be incorporated into NovaSilk polypropylene mesh used for cystocele repair, showing that adhesive-coated NovaSilk resists 4 pounds of load without fail. Thin film adhesives may be coated onto synthetic mesh, including polypropylene, then referred to as "pre-coated mesh adhesives". Pre-coated mesh adhesives do not become "sticky" until a cross-linking agent is introduced to the film. It can be brushed onto the tissue surface before laying the pre-coated mesh on top; it can be brushed onto the pre-coated mesh itself; or the pre-coated mesh can be dipped into the cross-linker before application, or the cross-linker may be embedded within the film, so that the adhesive will become activated only in situ without the additional step of cross-linker delivery.

Methods

Adhesive Polymers

Two polymers comprising the dihydroxyphenol (DHP) adhesive endgroup were synthesized for evaluation as a pre-coated mesh adhesive. Both Medhesive-054 and Medhesive-096 are copolymers of polycaprolactone (PCL) and branched polyethylene glycol (PEG) which was end-functionalized with DHP. The difference between the two polymers is the molecular weight of PCL segments; Medhesive-054 has a shorter PCL segment making it a more hydrophilic polymer.

Medhesive-096 Film Formation and Mesh Incorporation

Figure 238:
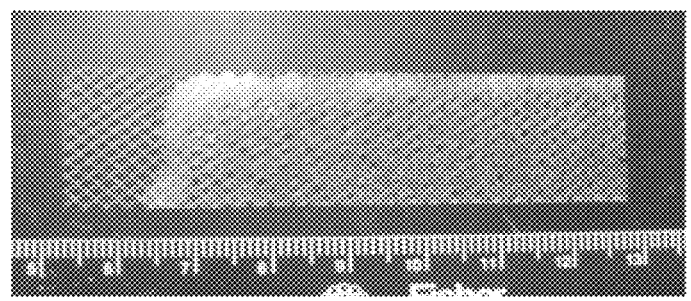
FIG. 238 shows a pre-coated adhesive mesh.

Medhesive-096 polymer films were cast from 10 wt % solutions in chloroform. Alternative formulations substituted a branched PEG-polylactic acid copolymer (PEG-PLA) for 20% of the total polymer content. Polymer solutions were poured into 80 mm×40 mm Teflon® molds and were incubated at 37° C. for 1 hour to facilitate solvent evaporation. Medhesive-096 films were then thoroughly dried under vacuum overnight. After removal of the films from the molds, each film was trimmed and placed on a glass plate covered with a release liner material (3M). The NovaSilk mesh was placed over the polymer film and the assembly was covered with another piece of release liner and glass plate. The glass plates were pressed together and maintained at 55° C. for 1 hour. Pre-coated adhesive meshes were cut into 2 cm strips each possessing ~6 cm of their length coated with adhesive (FIG. 238).

Medhesive-054 Film Formation and Mesh Incorporation

Medhesive-054 polymer films were cast in the same manner as Medhesive-096 films, except that partially dried films containing Medhesive-054 were removed from the molds and placed on sheet of release liner directly beneath the NovaSilk mesh. The assembly was covered with another piece of release liner and glass plate. The glass plates were pressed together and maintained at 55° C. for 1 hour. The resulting pre-coated adhesive mesh was further dried under vacuum overnight.

Adhesive Activation and Adhesion Testing

Figure 239:
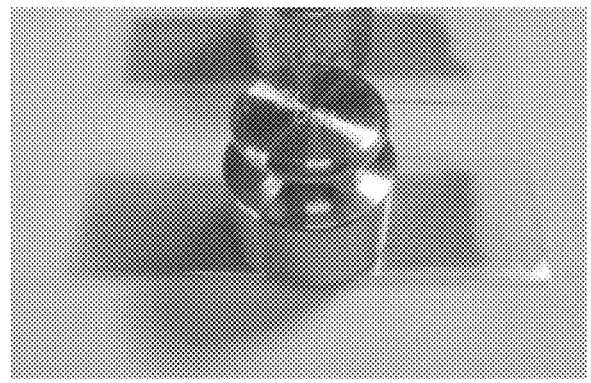
FIG. 239 shows an adhesive test assembly.

Fresh bovine pericardium was cut into 2.5 cm×7.5 cm strips and stored in phosphate buffered saline until use. To activate the adhesive, pre-coated meshes were sprayed with a fine mist of $NaIO_4$ cross-linker (20 mg/ml) from a refillable aerosol sprayer (Preval). Strips were immediately approximated to the adventitial side of the pericardium and covered with a glass microscope slide and a 100 gram weight (FIG. 239). The tissue-mesh assemblies were allowed to cure for 10 minutes under ambient conditions. The test assemblies were subsequently covered with PBS-soaked gauze pads and incubated at 37° C. for 1 hour.

Figure 240:
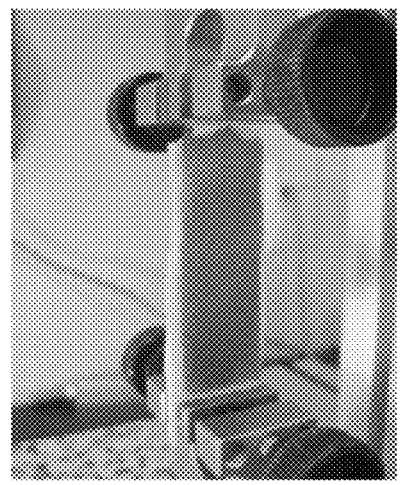
FIG. 240 shows a mounted test assembly.

To evaluate the lap shear strength of the adhesive joint, the ends of test assemblies were mounted in the grips of a universal tensile tester (ADMET, Inc.), as illustrated FIG. 240. The adhesive joint was strained using a crosshead speed of 10 mm/min. The peak load prior to failure was recorded and the adhesive failure mode was noted for each sample.

Results

Film Preparation

Medhesive-054 and Medhesive-096 required slightly different procedures for casting the adhesive films and incorporation into the synthetic meshes. Unsupported Medhesive-054 films were prone to cracking during the drying process. The process was subsequently altered to allow the film to dry partially followed by incorporation into the synthetic mesh. Further drying under vacuum produced few physical defects in the films.

Adhesive Strength

Figure 241:
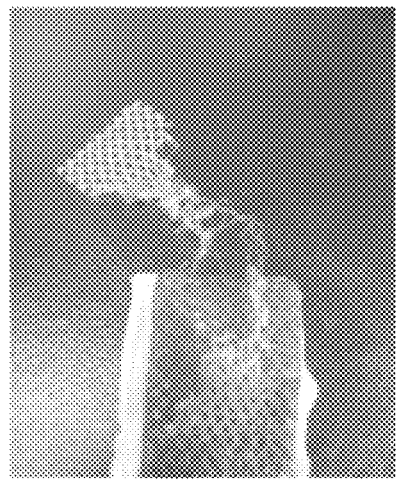
FIG. 241 shows that failure observed with Mehesive-054+ 20% PEG-PLA arose from failure of the synthetic mesh material.
Figure 242:
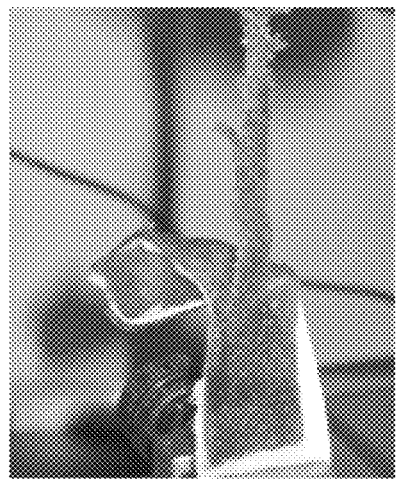
FIG. 242 shows Medhesive-054 during tensile testing. Transverse deformation of the mesh contributes to failure of the adhesive joint.

The results of lap shear adhesion testing are shown in Tables 7-10. Based on the failure modes for each of the formulations, the lap shear adhesion testing suggests that the Medhesive-096 formulations generally have a weaker interaction with the tissue substrate, where failure was predominantly characterized by the adhesive film being released from the tissue surface. The strongest formulation evaluated was Medhesive-054+20% PEG-PLA which resisted 5.5±0.8 pounds of force prior to complete rupture of the adhesive joint. In most cases, this formulation resulted in failure of the synthetic mesh material prior to failure for the adhesive (FIG. 241). It was observed across all formulations that the mesh material significantly narrowed in the direction transverse to loading. While this behavior is not surprising for this type of material, it does contribute additional forces on the adhesive. As shown in FIG. 242, in the case of Medhesive-054 formulations these transverse forces from the individual mesh fibers appear to "slice" though the adhesive and contribute to the failure of the adhesive joint. In the case Medhesive-096, where that adhesive interaction is somewhat weaker, the transverse force causes the adhesive to release from the tissue surface. Thin film polymer Medhesive-054, when formulated with PEG-PLA, is capable of resisting in excess of 4 pounds of shear loading, and in most cases the adhesive is stronger than the mesh into which it was incorporated.

TABLE 7

Lap Shear Adhesion Test Results for Medhesive-096

| Sample no. | Peak Load (N) | Peak Load (lb) | Length (mm) | Width (mm) | Shear Stress (kPa) | Failure Mode |
|---|---|---|---|---|---|---|
| 1 | 17.24 | 3.86 | 70 | 20 | 12.3 | Adhesive @ tissue surface |
| 2 | 14.61 | 3.27 | 70 | 20 | 10.4 | Adhesive @ tissue surface |
| 3 | NO TEST | | | | | slipped out of grip |
| 4 | 16.69 | 3.74 | 70 | 20 | 11.9 | adhesive/cohesive |
| 5 | 15.68 | 3.51 | 65 | 20 | 12.1 | adhesive/cohesive |
| 6 | 20.22 | 4.53 | 65 | 20 | 15.6 | adhesive/cohesive |
| 7 | 13.08 | 2.93 | 63 | 20 | 10.4 | adhesive/cohesive |
| 8 | 16.2 | 3.63 | 65 | 20 | 12.5 | adhesive/cohesive |
| 9 | 9.62 | 2.15 | 66 | 20 | 7.3 | Adhesive @ tissue surface |
| 10 | 16.07 | 3.60 | 66 | 20 | 12.2 | Adhesive @ tissue surface |
| Mean +/− | | 3.5 0.7 | | Mean +/− | 11.6 2.2 | |

TABLE 8

Lap Shear Adhesion Test Results for Medhesive-096 + 20% PEG-PLA

| Sample no. | Peak Load (N) | Peak Load (lb) | Length (mm) | Width (mm) | Shear Stress (kPa) | Failure Mode |
|---|---|---|---|---|---|---|
| 1 | 10.77 | 2.41 | 68 | 20 | 7.9 | Adhesive @ tissue surface |
| 2 | 12.04 | 2.70 | 62 | 20 | 9.7 | Adhesive @ tissue surface |
| 3 | 5.86 | 1.31 | 63 | 20 | 4.7 | Adhesive @ tissue surface |
| 4 | 13.59 | 3.04 | 63 | 20 | 10.8 | Adhesive @ tissue surface |
| 5 | 5.66 | 1.27 | 63 | 20 | 4.5 | Adhesive @ tissue surface |
| 6 | 11.64 | 2.61 | 64 | 20 | 9.1 | Adhesive @ tissue surface |
| 7 | 10.86 | 2.43 | 65 | 20 | 8.4 | Adhesive @ tissue surface |
| 8 | 6.53 | 1.46 | 65 | 20 | 5.0 | Adhesive @ tissue surface |
| Mean +/− | | 2.2 0.7 | | Mean +/− | 7.5 2.5 | |

TABLE 9

Lap Shear Adhesion Test Results for Medhesive-054

| Sample no. | Peak Load (N) | Peak Load (lb) | Length (mm) | Width (mm) | Shear Stress (kPa) | Failure Mode |
|---|---|---|---|---|---|---|
| 1 | 11.77 | 2.64 | 65 | 20 | 9.1 | Mesh sheared through adhesive due to deformation of the mesh |
| 2 | 19.33 | 4.33 | 65 | 20 | 14.9 | Mesh sheared through adhesive due to deformation of the mesh |

TABLE 9-continued

Lap Shear Adhesion Test Results for Medhesive-054

| Sample no. | Peak Load (N) | Peak Load (lb) | Length (mm) | Width (mm) | Shear Stress (kPa) | Failure Mode |
|---|---|---|---|---|---|---|
| 3 | 13.55 | 3.04 | 60 | 20 | 11.3 | Mesh sheared through adhesive due to deformation of the mesh |
| 4 | 12.66 | 2.84 | 61 | 20 | 10.4 | Mesh sheared through adhesive due to deformation of the mesh |
| 5 | 15.53 | 3.48 | 62 | 20 | 12.5 | Mesh sheared through adhesive due to deformation of the mesh |
| 6 | 11.01 | 2.47 | 63 | 20 | 8.7 | Mesh sheared through adhesive due to deformation of the mesh |
| 7 | 12.63 | 2.83 | 62 | 20 | 10.2 | Mesh sheared through adhesive due to deformation of the mesh |
| 8 | 14.5 | 3.25 | 63 | 20 | 11.5 | Mesh sheared through adhesive due to deformation of the mesh |
| 9 | 17.35 | 3.89 | 64 | 20 | 13.6 | Mesh sheared through adhesive due to deformation of the mesh |
| 10 | 16.9 | 3.79 | 62 | 20 | 13.6 | Mesh sheared through adhesive due to deformation of the mesh |
|  | Mean +/- | 3.3 0.6 |  | Mean +/- | 11.6 2.0 |  |

TABLE 10

Lap Shear Adhesion Test Results for Medhesive-054 + 20% PEG-PLA

| Sample no. | Peak Load (N) | Peak Load (lb) | Length (mm) | Width (mm) | Shear Stress (kPa) | Failure Mode |
|---|---|---|---|---|---|---|
| 1 | 28.73 | 6.44 | 60 | 20 | 23.9 | Mesh tore |
| 2 | 30.13 | 6.75 | 64 | 20 | 23.5 | Mesh sheared through the adhesive; |
| 3 | 24.86 | 5.57 | 65 | 20 | 19.1 | Mesh tore |
| 4 | 23.56 | 5.28 | 63 | 20 | 18.7 | Mesh tore; adhesive was strong enough to make the tissue curl |
| 5 | 20.81 | 4.66 | 64 | 20 | 16.3 | Mesh tore; adhesive was strong enough to make the tissue curl |
| 6 | 20.29 | 4.54 | 65 | 20 | 15.6 | Mesh tore; adhesive was strong enough to make the tissue curl |
| 7 | 24.26 | 5.43 | 68 | 20 | 17.8 | Mesh tore; adhesive was strong enough to make the tissue curl |
| 8 | 28.19 | 6.31 | 62 | 20 | 22.7 | Mesh tore; adhesive was strong enough to make the tissue curl |
| 9 | 21.88 | 4.90 | 63 | 20 | 17.4 | Mesh tore |
| 10 | 23.96 | 5.37 | 62 | 20 | 19.3 |  |
|  | Mean +/- | 5.5 0.8 |  | Mean +/- | 19.4 3.0 |  |

Experimental Example 6

Vascular Access Closure

Figure 243:
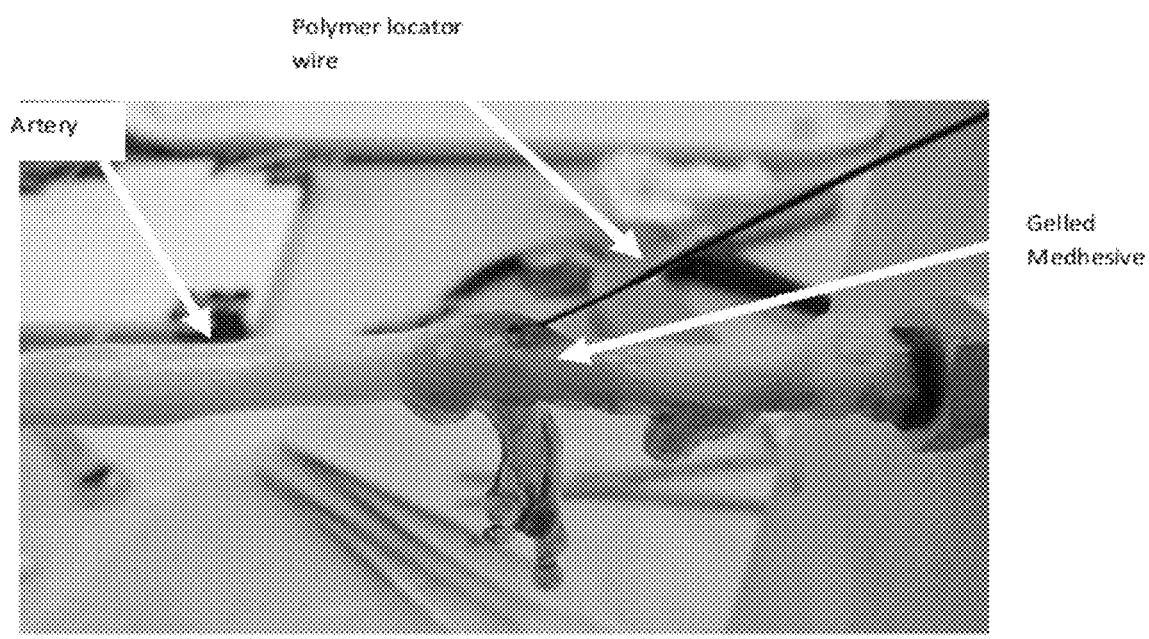
FIG. 243 shows metal locator wires which had been inserted into the lumen of an artery.

The capacity of adhesives of the present invention to seal vascular access sites was assessed using porcine carotid arteries. Medhesive-061 was applied over one of two different metal locator wires which had been inserted into the lumen of the artery (FIG. 243). After allowing the sealant to cure for 1 minute, the artery was pressurized and the peak pressure prior to rupture was recorded. The results of this burst testing are shown in Table 11. During the application of the adhesive, no material entered the lumen of the artery.

TABLE 11

Results of burst testing Medhesive-061 applied to exterior of carotid artery.

|  | Test 1 | Test 2 | Test 3 | Test 4 | Test 5 | Test 6 |
|---|---|---|---|---|---|---|
| Artery type | Porcine carotid | Porcine carotid | Porcine carotid | Porcine carotid | Canine carotid | Canine carotid |
| Medhesive formulation | 061 (6-arm) | 061 (6-arm) | 061 (8-arm) | 061 (8-arm) | 061 (8-arm) | 061 (8-arm) |
| Locator wire | Metal w/disc | Metal w/disc | Polymer w/balloon | Polymer w/balloon | Polymer w/balloon | Polymer w/balloon |
| Locator wire removal/ impact on | Cohesive failure (some | Cohesive failure (some | Clean | Clean | Clean | Clean |

TABLE 11-continued

Results of burst testing Medhesive-061 applied to exterior of carotid artery.

|  | Test 1 | Test 2 | Test 3 | Test 4 | Test 5 | Test 6 |
|---|---|---|---|---|---|---|
| Medhesive | Medhesive remained attached to wire) | Medhesive remained attached to wire) | | | | |
| Second coat Medhesive | Yes | Some (syringe failed) | Yes | Very little | Yes | No |
| Burst pressure | 13.38 psi | 2.40 psi | Vessel dissection | 0.63 psi | Vessel leaking | Vessel leaking |
| Failure mode | Cohesive | Cohesive | n/a | | n/a | n/a |

Experimental Example 7

Seroma Prevention

This project demonstrates that adhesives of the present invention reduce or prevent seroma formation in a well characterized rat mastectomy model. This model requires the removal of the pectoralis musculature, partial axillary lymph node dissection and the disruption of dermal lymphatics. Animals were placed in 1 of 9 test groups where the mastectomy dead space was closed with either 1 of 8 formulations of liquid adhesives, or with normal saline (control). In the event of seroma formation, fluid was collected from the affected area at postoperative days 5, 10 and 14, and the volumes were recorded. After 14 days, the animals were euthanized and the mastectomy sites were excised, examined and prepared for histology.

Study Design

Eight adhesive formulations were selected that exhibit a range of relevant adhesive strengths and degradation rates, and were included in this animal study to demonstrate how each of these two variables might affect the reduction in seroma formation. The formulations/treatment groups are were:

Treatments (n=3 animals per treatment)
1. Medhesive-068 (fastest degradation): 15% wt
2. Medhesive-068: 20% wt
3. Medhesive-068: 30% wt
4. Medhesive-102 (slowest degradation): 10% wt
5. Medhesive-061 (strongest formulation): 15% wt
6. Medhesive-061: 30% wt
7. QuadraSeal DME or equivalent (high swelling)
8. Medhesive-069 (link to U of M study): 15%
9. Saline-only control After closure of the tissue dead space using the adhesives, serous fluid was aspirated at days 5, 10 and 14. This outcome measure reflects the existence and extent of the seroma formation. Additionally, visual analysis of aspirated fluids and presence of adhesive remnants in the seroma site, and visual and histological assessment of inflammation and tissue healing were determined as secondary outcome measures.

Surgical Procedure

All surgical procedures were performed using sterile technique. Animals were anesthetized with an intramuscular injection of xylazine (4-9 mg/kg) and ketamine (40-90 mg/kg). After sedation, the animals were ventilated via a nose cone with a mixture of oxygen and isofluorane. An incision was made from the jugular notch to the xiphoid process. The skin lateral to the incision was elevated and dissected free from its muscular attachments allowing for easy removal of the pectoralis muscle. In order to prevent hemorrhage, the axillary artery and vein (that supply the muscle) were first carefully exposed and ligated. The pectoralis was then removed leaving as little of a stump as possible attached to the humerus so that the effect of muscle necrosis would be minimized. Hemostasis was maintained throughout the procedure by careful dissection without the use of electrocautery. Next, axillary lymph node excisions were carefully performed with the aid of magnification. To ensure consistent seroma formation, the subcutaneous lymphovasculature was traumatized by scraping the inner surface of the elevated skin flap with a #15 blade approximately 20 times. The wound was then inspected carefully for hemostasis. In 2 of the 3 animals for each of the 8 adhesive treatments, the adhesive was sprayed onto the chest wall, and the skin flap was immediately placed on top of the adhesive and chest wall, and held in place with moderate pressure for 2 minutes. In the remaining third animal in each treatment, the adhesive was sprayed onto both the chest wall and skin flap surfaces, and the skin flap was then similarly placed on the chest wall and held for 2 minutes. The wounds were then carefully closed using staples in order not to disturb the adhered tissue planes. In the negative control animals, a fine mist of saline (0.2 mL) was applied to the skin flap and chest wall by a spray applicator. The animals were removed from the ventilator and given pain medication (buprenorphine 0.05-0.1 mg/kg subcutaneously) postoperatively and every 12 hours for up to 3 days as needed.

Assessments

On postoperative days 5, 10 and 14, animals were anesthetized (intramuscular injection of ketamine (40-90 mg/kg) and xylazine (4-9 mg/kg)), and the fluid that had accumulated at the seroma site, if present, was aspirated under sterile conditions with a 15-gauge needle and syringe, and its volume quantified. On postoperative day 14, the animals were then euthanized by an intravenous overdose of pentobarbital (100 mg/kg). The original midline incision was opened, paying careful attention to the degree of healing between the skin flap and chest wall. Full-thickness biopsies of skin flap and the chest wall were harvested and grossly evaluated to determine if any remnants of polymer were present at the site. Harvested tissues were then sent for histological preparation with hematoxylin and eosin staining. Histological sections were assessed in blinded fashion by a board-certified pathologist, with particular attention being paid to descriptions of tissue healing and consolidation at the seroma site, and evidence of potential infection and inflammation.

TABLE 12

| Treatment | Animal ID | Aspirations (ml) 5-day | 10-day | 14-day | Total |
|---|---|---|---|---|---|
| M-068 (15 wt %) (fastest degradation) | 09V64 | 0 | 0 | 0 | 0 |
|  | 09V71 | 0 | 0 | 0 | 0 |
|  | 09V72 | 0 | 0 | 0 | 0 |
| M-068 (20 wt %) | 09V65 | 1.9 ss | 0 | 0 | 1.9 |
|  | 09V70 | 1.2 ss | 0 | 0 | 1.2 |
|  | 09V73 | 5.4 ss | 4.5 ss | 6.8 ss | 16.7 ss |
| M-068 (30 wt %) | 09V66 | 1.2 ss | 0 | 0 | 1.2 |
|  | 09V69 | 0 | 0 | 0 | 0 |
|  | 09V74 | 5.5 ss | 5.2 ss | 4.8 ss | 15.5 |
| M-102 (10 wt %) (slowest degradation) | 09V52 | 0 | 0 | 0 | 0 |
|  | 09V56 | 0 | 0 | 0 | 0 |
|  | 09V61 | 0 | 0 | 0 | 0 |
| M-061 (15 wt %) (strongest formulation) | 09V51 | 0 | 0 | 0 | 0 |
|  | 09V57 | 0 | 0 | 0 | 0 |
|  | 09V60 | 0 | 1.1 ss | 0.5 ss | 1.6 |
| M-061 (30 wt %) | 09V53 | 0 | 0.9 ss | 0 | 0.9 |
|  | 09V55 | 0 | 5.2 ss | 0 | 5.2 |
|  | 09V62 | 0 | 3.8 ss | 2.5 ss | 6.3 |
| QuadraSeal DME (15 wt %) | 09V67 | 0 | 0 | 0 | 0 |
|  | 09V68 | 0 | 0 | 0 | 0 |
|  | 09V75 | 2.2 ss | 3.4 ss | 2.0 s | 7.6 |
| M-069 (15 wt %) (link to U of M study) | 09V50 | 0 | 0 | 0 | 0 |
|  | 09V58 | 0 | 0 | 0 | 0 |
|  | 09V59 | 0 | 0 | 0 | 0 |
| Saline only (Integra) | 09V49 | 0 | 0 | 0 | 0 |
|  | 09V54 | 0 | 0 | 0 | 0 |
|  | 09V63 | 0.5 | 0 | 0 | 0.5 |
|  | 09V76 | 0 | 0 | 0 | 0 |
| U of M saline controls | — | — | — | — | 2 |
|  | — | — | — | — | 5 |
|  | — | — | — | — | 4 |
|  | — | — | — | — | 5 |

Results

No fluids were aspirated from the mastectomy sites that were treated with M-068 (15 wt %), M-102 (15 wt %) and M-069 (15 wt %). Fluid was aspirated when surgical sites were treated with M-068 (20 wt % and 30 wt %), M-061 (15 wt % and 30 wt %) and QuadraSeal DME (15 wt %). The skin flap healed to the chest wall over the majority of the surgical site in all 3 animals when M-068 (15 wt %), the rapidly degrading polymer, was used. However, there were several very small pockets of non-healing close to the midline incision in each animal. Several large and swollen lymph nodes were present in each of the animals reflecting an immune response. Histological assessment indicated minimal to mild inflammation in 2 of the 3 animals. There was no evidence adhesive in the surgery sites, either macroscopically and histologically, so the polymer degraded in the 2-week time frame. Although no fluids were aspirated when the surgical sites were treated with M-102 (15 wt %), the slowly degrading polymer, large portions of the skin flap did not heal down to the chest wall in all 3 animals. The pockets between the skin flap and chest wall were very noticeable but did not contain fluid. Small amounts of adhesive were present in the surgical site in 2 of the 3 animals, and there was minimal foreign body reaction associated with this material. This is not surprising since M-102 (15 wt %) is a more slowly degrading polymer than M-068 (15 wt %). There were mild to moderate numbers of macrophages and lymphocytes present in all animals. This finding implies that a slower degrading polymer may prevent healing of tissue planes in this model, but this doesn't necessarily lead to seroma formation. Adhesives of the present invention (different weight percents of M-069) were used to close mastectomy sites in several further animals. This study was done with adhesives that had been stored for several months before surgery. The surgical sites in these animals exhibited large seroma formation. One of these formulations, M-069 (15 wt %), was used in the present study. The polymer was made several days before implantation, and the bioburden was reduced to acceptable levels in this polymer. M-069 (15 wt %) did not result in seroma formation. The skin flap healed to the chest wall in 2 of the 3 animals. The inflammatory response was variable with minimal to marked numbers of neutrophils, macrophages and lymphocytes. The first 2 of 3 animals treated with M-068 (20 wt % and 30 wt %) and QuadraSeal DME (15 wt %) resulted in minimal to no aspirated fluid (0 to 1.9 ml) from the surgical sites. The third animal with these treatments was operated on 10 days later, and exhibited large amounts of aspirated fluid (7.6 to 16.7 ml). Surgeries were the same at both time points, and controls at both times resulted in no aspirated fluid indicating that there was no confounding variable associated with repeatability of the surgical procedure. As with M-068 (15 wt %), several large and swollen lymph nodes were present in the surgical sites of each of the animals treated with M-068 (20 wt % and 30 wt %) and QuadraSeal DME (15 wt %). No adhesive remnants were present in any of the animals, reflecting the faster degradation rate even with the higher weight-percent formulations. Similar to M-068 (15 wt %), the skin flap healed down to the chest wall in the 2 animals of each treatment that did not have the large seroma formation referred to in the previous bullet-point. In the animals with the large seroma, there was no healing in the pocket where the fluid had accumulated, but the skin flap was adhered to the chest wall everywhere else. M-061 (15 wt % and 30 wt %) were the strongest polymer formulations used in this study. Very little fluid was aspirated (0 to 1.6 ml) in animals treated with M-061 (15 wt %), and in 2 of these 3 animals, multiple moveable rice-sized segments of adhesive were present in the surgical site. The skin flap healed down to the chest wall in 2 of the 3 animals, but did not in the third. Large masses of adhesive were present in the surgical sites of all 3 animals treated with M-061 (30 wt %).

Experimental Example 8

Ostomy Sealing

Figure 244:
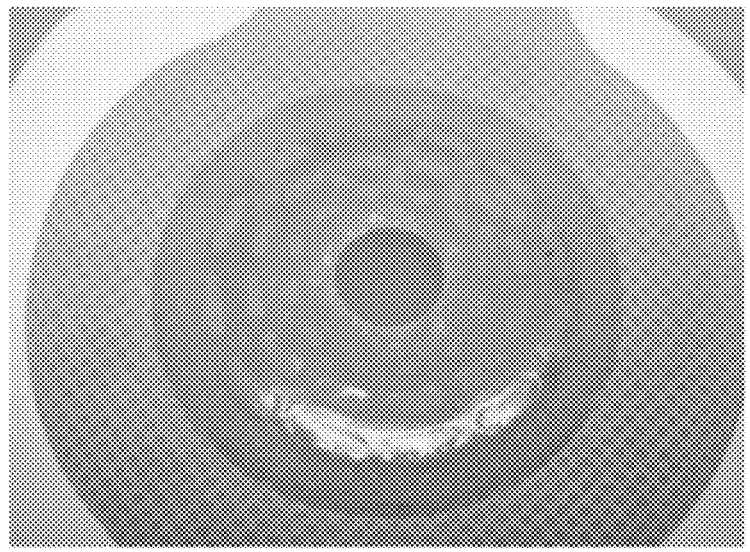
FIG. 244 shows Medhesive-096 applied to the annulus of fabric surrounding a colostomy bag collection port.
Figure 245:
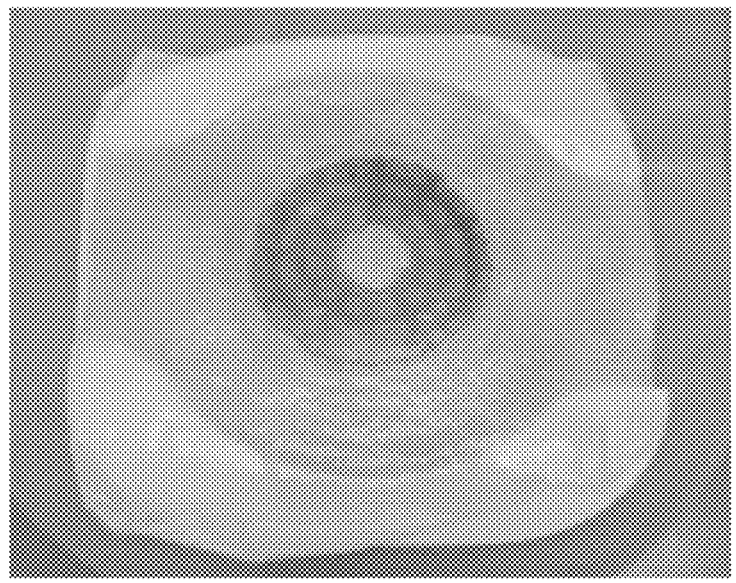
FIG. 245 shows translucent bovine pericardium adhered to a Medhesive-coated ostomy collection port.
Figure 246:
FIG. 246 shows a that a Medhesive-coated ostomy collection port creates a water tight seal with soft tissue.

To demonstrate that adhesives of the present invention may be used to attach ostomy collection bags to soft tissue to create a water-tight seal, Medhesive-096 was cast into a 240-g/m$^2$ film. The polymer film was pressed into the fabric material surrounding the collection bag port using light pressure and mild heat (55° C.) as shown in FIG. 244. The film was allowed to cool and was subsequently actived by spraying with a solution of 10 mg/mL NaIO$_4$. The adhesive coated fabric was immediately approximated on bovine pericardium (to simulate the soft tissue of the stoma) as shown in FIG. 245. The tissue fabric assembly was allowed to cure 10 minutes under ambient conditions. The collection bag was connected and filled with 500 mL water containing blue dye. The bag was inverted; no leaks were detected (FIG. 246).

Experimental Example 9

Hernia Repair Using a Patterned Adhesive-Coated Mesh (2.5-cm Discs) in a Porcine Model Methods A 2.5-cm diameter discs of polyester mesh coated with 5-mm stripes of Medhesive-141 (240 g/m$^2$) films were implanted between peritoneum and abdominal muscle of a pig. 20 mg/mL of NaIO$_4$ solution brushed onto both sides of the adhesive-coated mesh and sample was placed on top of the peritoneum with pressure applied from the surgeon by placement of hands over the abdominal muscle layer. After mesh implantation, the abdominal wall fascia, subcutaneous tissue, and skin were closed with a running suture. The pig was euthanized on Day 14 and the implant site was harvested for histologic evaluation.

Results

Figure 247:
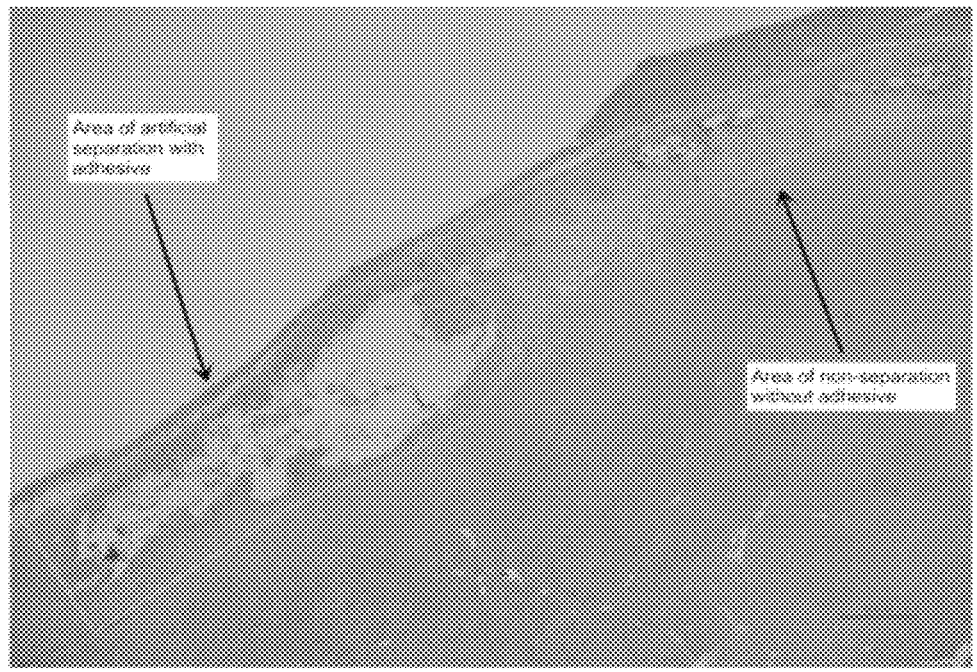
FIG. 247 shows a histologic section showing adhesive-coated (Left box) and non-coated (Right box) regions.
Figure 248:
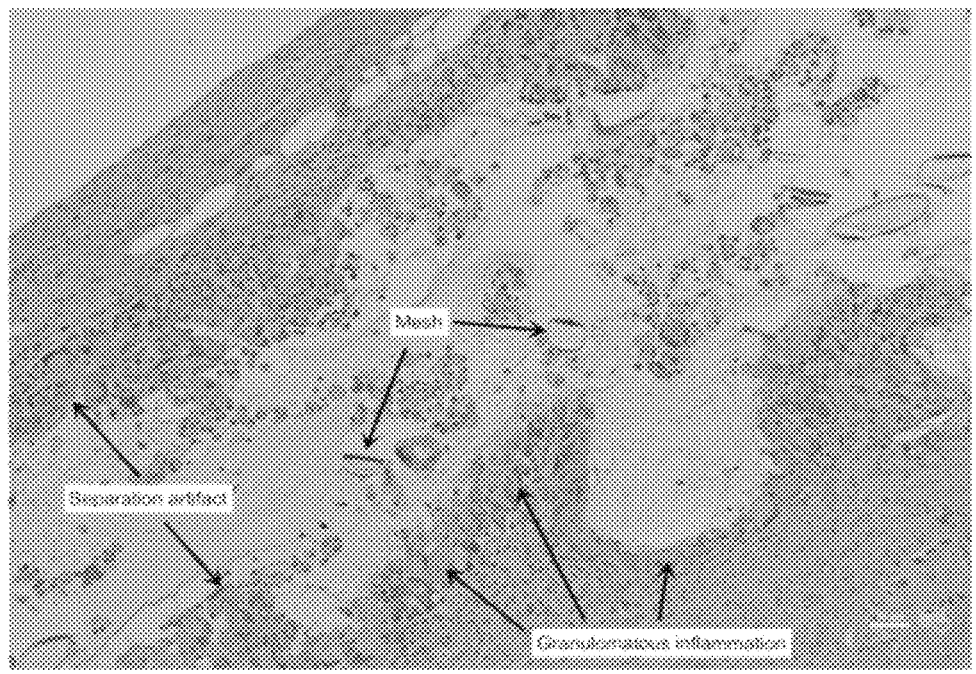
FIG. 248 shows a magnified region of mesh coated with adhesive showing signs of tissue in-growth into the mesh.
Figure 249:
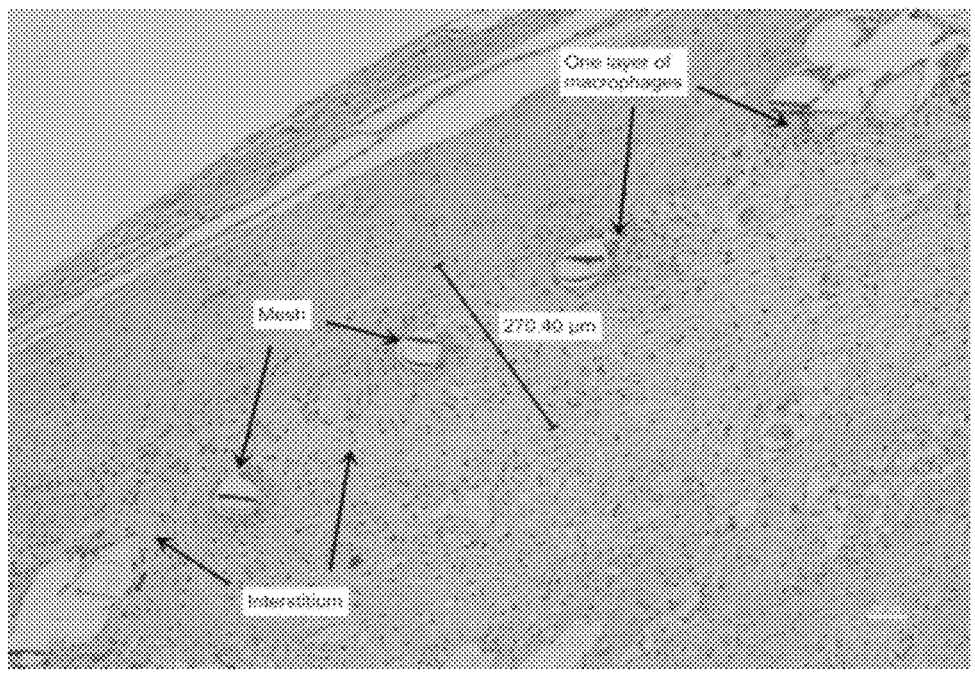
FIG. 249 shows a region of mesh not coated with adhesive with scar plate encapsulating the mesh fibers.

The mesh with adhesive was completely adhered bilaterally throughout its length. The mesh uniformly alternated between areas of artificial separation (adhesive-coated region) to areas with no separation (mesh with no coating). By 14 days, regions with no adhesive coating demonstrated significant scar plate formation, ingrowth of fibroplasia with collagen deposition, and a foreign body response to the prosthetic surface of the mesh, whereas the adhesive-coated region was start to show signs of ingrowth (FIGS. 247-249). The patterning strategy allow adhesive to secure the mesh in place immediately after surgery, while allowing cellular infiltration to occur in the region not coated with the adhesive. With time, tissue ingrowth into the uncoated region of mesh secures the mesh in place as the adhesive degrades and loses its strength.

Experimental Example 10

Thin Film Adhesives Coated on Biotape

Addhesive-coated BioTape was observed using a high resolution scanning electron microscope (SEM) (LEO 1530) which uses a Schottly-type field-emission electron source. No fixation procedures were applied to the specimens. Small, square pieces (about 1×1 cm) were affixed to aluminum mounts with double sided carbon tape, stored in a desiccator and gold coated (60/40 gold/palladium alloy approx. 10-20 nm) in a SeeVac Auto conductavac IV sputter coater. SEM was used to collect profile and surface images of Medhesive-096-coated BioTape.

Figure 250:
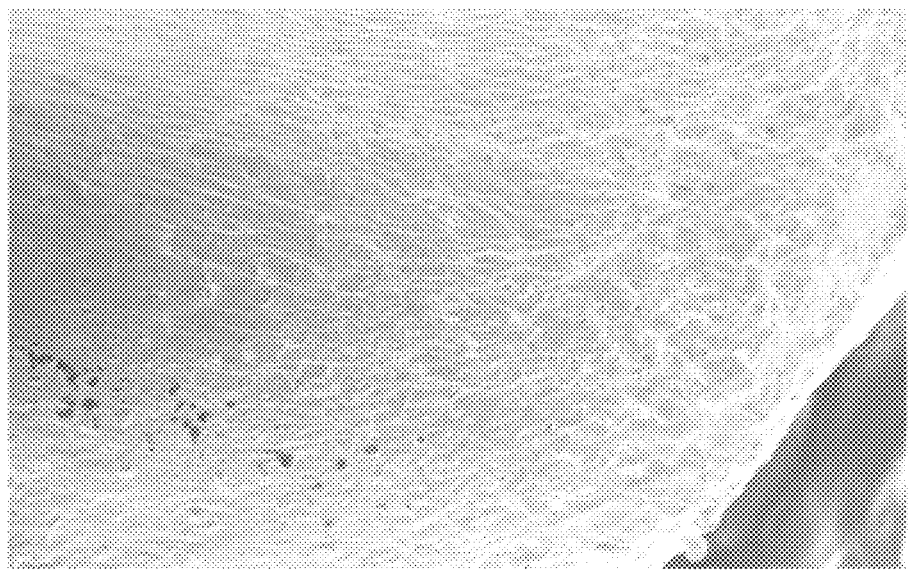
FIG. 250 shows a low magnification scanning electron microscopy (SEM) image showing the top adhesive surface of Medhesive-096 coated BioTape.
Figure 251:
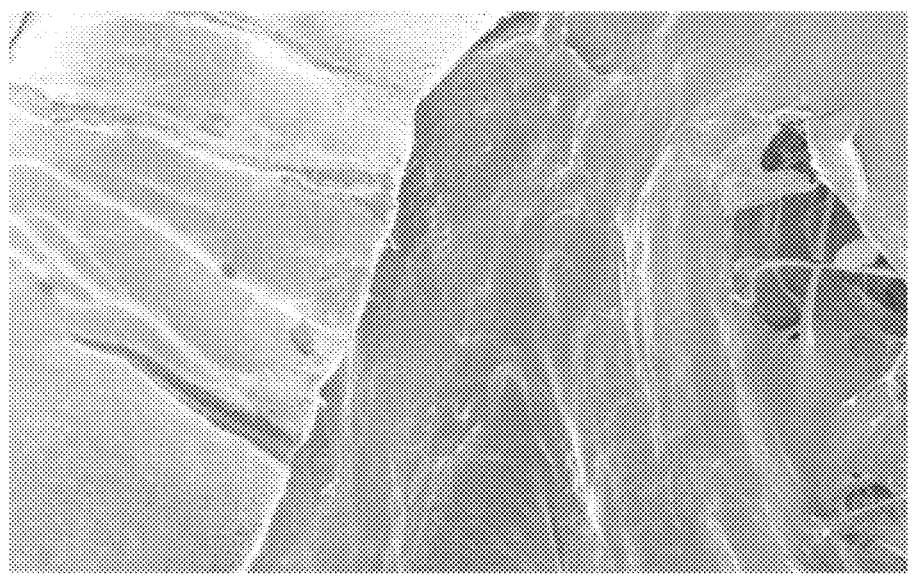
FIG. 251 shows a low magnification SEM image showing the edge of the adhesive surface against BioTape.
Figure 252:
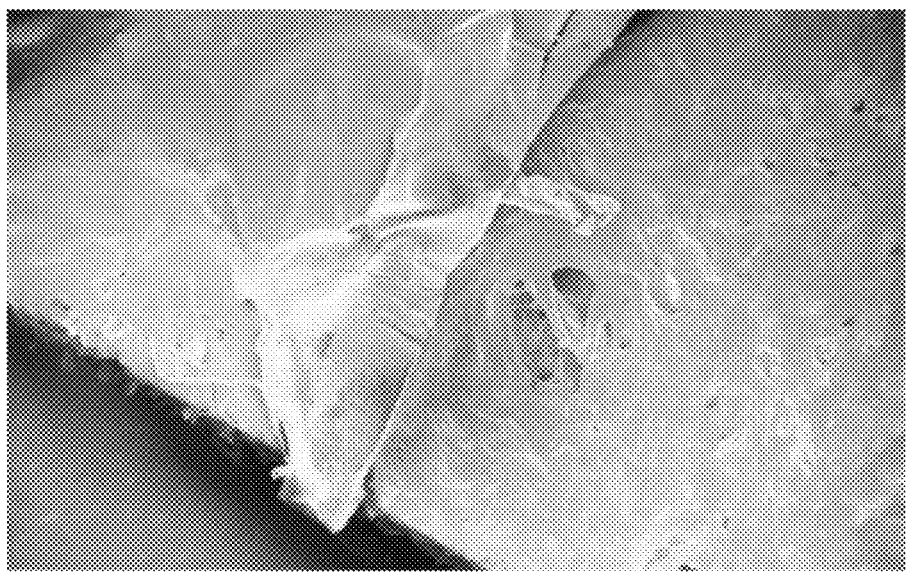
FIG. 252 shows a low magnification SEM image showing the edge of the adhesive surface against BioTape.
Figure 253:
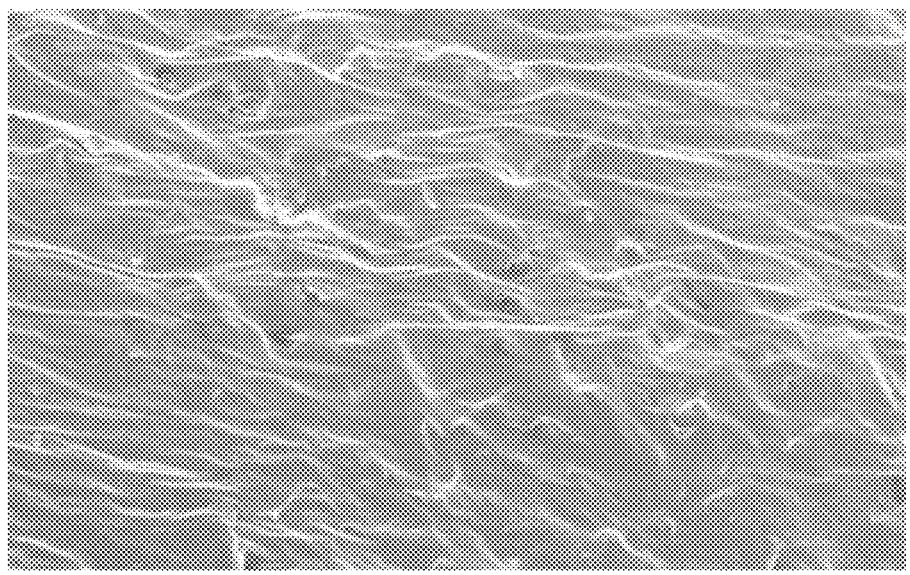
FIG. 253 shows a SEM image of the adhesive surface at increasing magnification.
Figure 254:
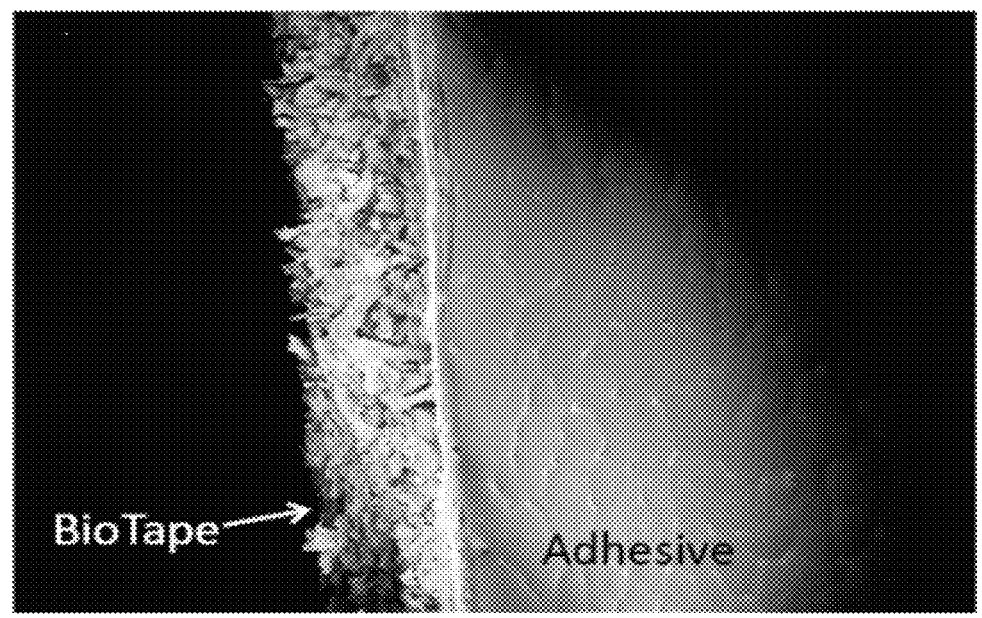
FIG. 254 shows a SEM image showing the adhesive/BioTape interface in cross-section at increasing magnification.
Figure 255:
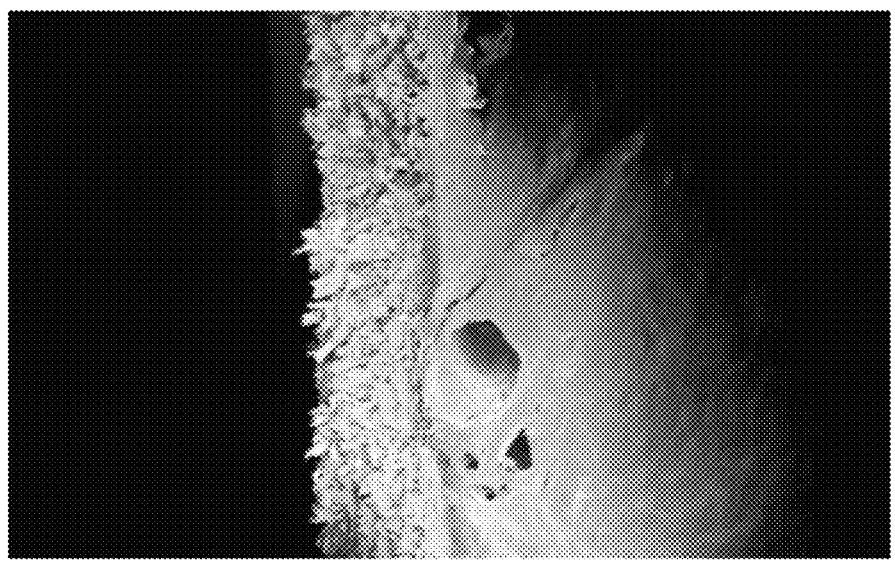
FIG. 255 shows a SEM image showing the adhesive/BioTape interface in cross-section at increasing magnification.
Figure 256:
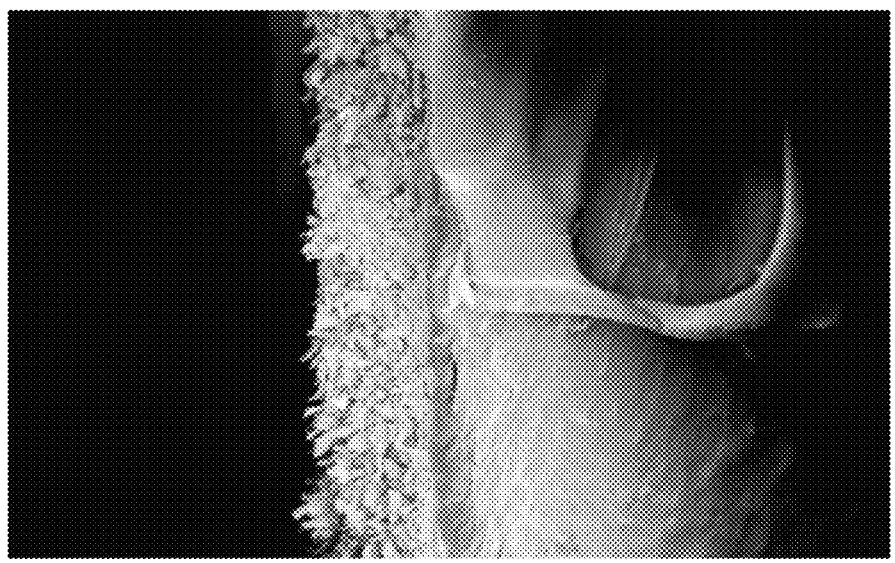
FIG. 256 shows a SEM image showing the adhesive/BioTape interface in cross-section at increasing magnification.
Figure 257:
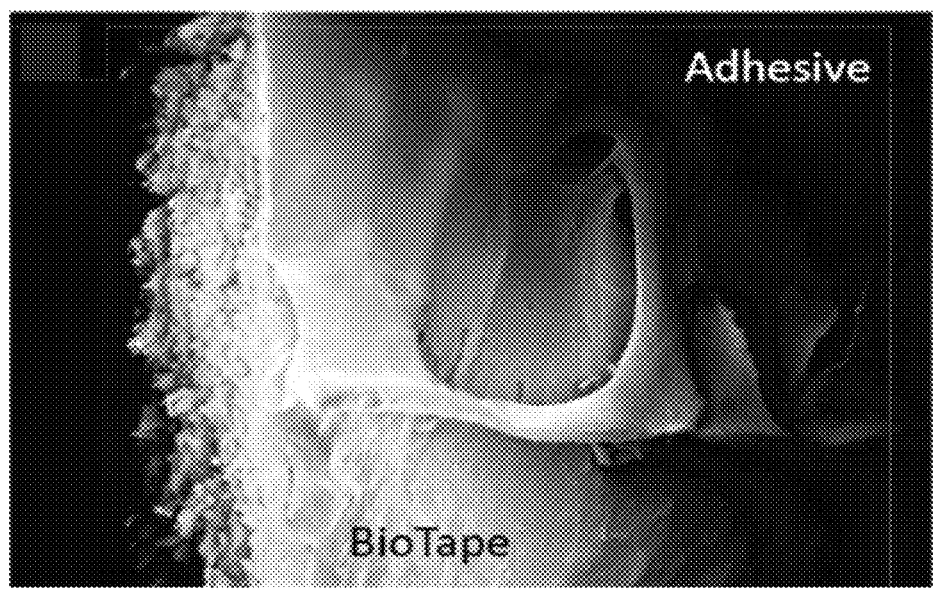
FIG. 257 shows a SEM image showing the adhesive/BioTape interface in cross-section at increasing magnification.

FIGS. 250-257 show SEM images of the Medhesive-096-coated BioTape. FIG. 250 shows a low magnification image showing the top adhesive surface of Medhesive-096. FIGS. 251 and 252 show a low magnification image showing the edge of the adhesive surface against BioTape. FIG. 253 shows a SEM image of the adhesive surface at increasing magnification. This section exhibits the smooth layer of adhesive conforming to the rough texture of BioTape. FIGS. 254-257 show SEM images showing the adhesive/BioTape interface in cross-section at increasing magnification. Nanoscale fiber orientation of BioTape is observed. Porosity is observed in FIG. 255.

Experimental Example 13

Synthesis of PCL1.25k-diSA 10 g of polycaprolactone-diol (PCL-diol, MW=1,250, 8 mmol), were added to 8 g of succinic anhydride (SA, 80 mmol), 6.4 mL of pyridine (80 mmol), and 100 mL of chloroform in a round bottom flask (250 mL). The solution was refluxed in a 75-85° C. oil bath with Ar purging for overnight. The reaction mixture was allowed to cool to room temperature and 100 mL of chloroform was added. The mixture was washed successively with 100 mL each of 12.1 mM HCl, saturated NaCl, and deionized water. The organic layer was dried over magnesium sulfate and then the volume of the mixture was reduced by half by rotary evaporator. After pouring the mixture into 800 mL of a 1:1 hexane and diethyl ether, the polymer was allowed to precipitate at 4° C. for overnight. The polymer was collected and dried under vacuum to yield 8.1 g of PCL1.25k-diSA. $^1$H NMR (400 MHz, DMSO/TMS): δ 12.2 (s, 1H, COOH—), 4.1 (s, 2H, PCL-CO—$CH_2$—$CH_2$—COOH—) 4.0 (s, 12H, O—(CO—$CH_2$—$(CH_2)_4$—O)$_6$ CO—$CH_2$—$CH_2$—COOH), 3.6 (s, 2H, PCL-CO—$CH_2$—$CH_2$—COOH—) 3.3 (s, 2H, —$CH_2$—PCL$_6$-SA), 2.3 (t, 12H, O—(CO—$CH_2$—$(CH_2)_3$—$CH_2$—O)$_6$CO—$CH_2$—$CH_2$—COOH), 1.5 (m, 24H, O—(CO—$CH_2$—$CH_2$—$CH_2$—$CH_2$—$CH_2$—O)$_6$CO—$CH_2$—$CH_2$—COOH), 1.3 (m, 12H, O—(CO—$CH_2$—$CH_2$—$CH_2$—$CH_2$—$CH_2$—O)$_6$ CO—$CH_2$—$CH_2$—COOH). Similarly, PCL2k-diSA was synthesized using the procedure with 2,000 MW PCL-diol.

Experimental Example 14

Synthesis of PCL2k-diGly 10 g of polycaprolactone-diol (5 mmole, MW 2000) with 2.63 g of Boc-Gly-OH (15 mmole) was dissolved in 60 mL chloroform and purged with argon for 30 minutes. 3.10 g of DCC (15 mmole) and 61.1 mg of DMAP (0.5 mmole) were added to the reaction mixture and the reaction was allowed to proceed overnight with argon purging. The solution was filtered into 400 mL of diethyl ether along with 40 mL of chloroform. The precipitate was collected through filtration and dried under vacuum to yield 4.30 g of PCL2k-di-BocGly. A Boc protecting group on PCL2k-di-BocGly was removed by reacting the polymer in 14.3 mL of chloroform and 14.3 mL of trifluoroacetic acid for 30 minutes. After precipitation twice in ethyl ether, the polymer was dried under vacuum to yield 3.13 g of PCL2k-diGly. $^1$H NMR (400 MHz, CDCl3/TMS): δ 4.2 (m, 4H, $CH_2NH_2$—) 4.0 (t, 16H, O—(CO—$CH_2$—$(CH_2)_3CH_2$—O)$_8$CO—$CH_2$—$CH_2$—COOH), 3.8 (t, 2H, O—$CH_2CH_2$—O—CO-PCL), 3.6 (t, 2H, O—$CH_2CH_2$—O—CO-PCL), 2.3 (t, 16H, O—$CH_2CH_2$—O—CO—$CH_2(CH_2)_4$—OCO), 1.7 (m, 32H, O—$CH_2CH_2$—O—CO—$CH_2CH_2CH_2CH_2CH_2$—OCO), 1.3 (m, 16H, O—$CH_2CH_2$—O—CO—$CH_2CH_2CH_2CH_2CH_2$—OCO). PCL1.25k-diGly was synthesized using the similar procedure while using 1,250 MW PCL-diol.

Experimental Example 15

Synthesis of PEG10k-(SA)$_4$ 100 g of 4-armed PEG-OH (10,000 MW); 40 mmol —OH), and 20 g of succinic anhydride (200 mmol) were dissolved with 1 L chloroform in a round bottom flask equipped with a condensation column. 16 mL of pyridine were added and refluxed the mixture in a 75° C. oil bath with Ar purging for overnight. The polymer solution was cooled to room temperature, and washed successively with equal volume of 12 mM HCl, nanopure water, and saturated NaCl solution. The organic layer was then dried over $MgSO_4$ and filtered. The polymer was precipitated from diethyl ether and the collected. The precipitate was dried under vacuum to yield 75 g PEG10k-(SA)$_4$. $^1$H NMR (400 MHz, $D_2O$): δ 4.28 (s, 2H, PEG-$CH_2$—O—C(O)—$CH_2$), 3.73-3.63 (m, PEG), 2.58 (s, 4H, PEG-$CH_2$—O—C(O)—$C_2H_4$—COOH). PEG10k-(GA)$_4$ was synthesized using the similar procedure while using glutaric anhydride instead of succinic anhydride.

Experimental Example 16

Synthesis of Medhesive-132

50 grams of PEG10k-(SA)$_4$ were dissolved in 200 mL of DMF with 10.35 grams of PCL2k-diglycine, and 1.83 g of Dopamine-HCl in a round bottom flask. HOBt (3.24 g), HBTU (9.125 g), and Triethylamine (4.65 mL) were dissolved in 200 mL of chloroform and 300 mL of DMF. The HOBt/HBTU/Triethylamine solution was added dropwise to the PEG/PCL/Dopamine reaction over a period of 30-60 minutes. The reaction was stirred for 24 hours. 1.11 g of Dopamine and 1.01 mL Triethylamine were added to the reaction and stirred for 4 hours. The solution was filtered into diethyl ether and placed at 4° C. for 4-24 hours. The precipitate was vacuum-filtrated and dried under vacuum for 4-24 hours. The polymer was dissolved in 400 mL of 50 mM HCl and 400 mL of methanol. This was then filtered using coarse filter paper and dialyzed in 10 L of water at pH 3.5 for 2 days with changing of the water at least 12 times. The solution was then freeze dried and placed under a vacuum for 4-24 hours. $^1$H NMR (400 MHz, DMSO/TMS): δ 8.7-8.5 (s, 1H, $C_6H_3$(OH)$_2$—), 7.9 (d, 2H, $C_6H_3$(OH)$_2$—), 6.5 (dd, 1H, $C_6H_3$(OH)$_2$—), (dd, 1H, $C_6H_3$(OH)$_2$—$CH_2$—$CH_2$—CONH—$CH_2$—$CH_2$—O—), 4.1 (s, 2H, PCL-CO—$CH_2$—$CH_2$—COOH—), 4.0 (s, 16H, O—(CO—$CH_2$—$(CH_2)_4$—O)$_6$CO—$CH_2$—$CH_2$—COOH), 3.6 (s, 2H, PCL-CO—$CH_2$—$CH_2$—COOH—) 3.3 (s, 2H, —$CH_2$-$PCL_6$—), 2.3 (t, 16H, O—(CO—$CH_2$—$(CH_2)_3$—$CH_2$—O)$_6$CO—$CH_2$—$CH_2$—COOH), 1.5 (m, 32H, O—(CO—$CH_2$—$CH_2$—$CH_2$—$CH_2$—$CH_2$—O)$_6$CO—$CH_2$—$CH_2$—COOH), 1.3 (m, 16H, O—(CO—$CH_2$—$CH_2$—$CH_2$—$CH_2$—$CH_2$—O)$_6$CO—$CH_2$—$CH_2$—COOH). UV-vis spectroscopy: 0.165±0.024 μmole Dopmaine/mg polymer (2.50±0.35 wt % Dopamine).

Experimental Example 17

Synthesis of Medhesive-0136

20.02 grams of PEG10k-$(SA)_4$ were dissolved in 80 mL of DMF with 2.71 grams of PCL1.25k-diglycine, and 0.73 g of Dopamine-HCl in a round bottom flask. HOBt (1.30 g), HBTU (3.65 g), and Triethylamine (1.86 mL) were dissolved in 80 mL of chloroform and 120 mL of DMF. The HOBt/HBTU/Triethylamine solution was added dropwise to the PEG/PCL/Dopamine reaction over a period of 30-60 minutes. The reaction was stirred for 24 hours. 0.445 g of Dopamine and 0.403 mL Triethylamine were added to the reaction and stirred for 4 hours. This solution was filtered into diethyl ether and place at 4° C. for 4-24 hours. The precipitate was vacuum filtrated and dried under vacuum for 4-24 hours. The polymer was dissolved in 160 mL of 50 mM HCl and 160 mL of methanol. This was then filtered using coarse filter paper and dialyzed in 10 L of water at pH 3.5 for 2 days with changing of the water at least 12 times. The solution was then freeze dried and placed under a vacuum for 4-24 hours. After drying, $^1$H NMR and UV-VIS were used to determine purity and coupling efficiency of the catechol. $^1$H NMR (400 MHz, DMSO/TMS): δ 8.7-8.6 (s, 1H, $C_6H_3$(OH)$_2$—), 7.9 (d, 2H, $C_6H_3$(OH)$_2$—), 6.5-6.6 (dd, 1H, $C_6H_3$(OH)$_2$—), (dd, 1H, $C_6H_3$(OH)$_2$—$CH_2$—$CH_2$—CONH—$CH_2$—$CH_2$—O—), 4.1 (s, 2H, PCL-CO—$CH_2$—$CH_2$—COOH—) 4.0 (s, 12H, O—(CO—$CH_2$—$(CH_2)_4$—O)$_6$CO—$CH_2$—$CH_2$—COOH), 3.6 (s, 2H, PCL-CO—$CH_2$—$CH_2$—COOH—) 3.3 (s, 2H, —$CH_2$-$PCL_6$-SA), 2.3 (t, 12H, O—(CO—$CH_2$—$(CH_2)_3$—$CH_2$—O)$_6$CO—$CH_2$—$CH_2$—COOH), 1.5 (m, 24H, O—(CO—$CH_2$—$CH_2$—$CH_2$—$CH_2$—$CH_2$—O)$_6$CO—$CH_2$—$CH_2$—COOH), 1.3 (m, 12H, O—(CO—$CH_2$—$CH_2$—$CH_2$—$CH_2$—$CH_2$—O)$_6$CO—$CH_2$—$CH_2$—COOH). UV-vis spectroscopy: 0.254±0.030 μmole Dopamine/mg polymer (3.86±0.45 wt % Dopamine).

Experimental Example 18

Synthesis of Medhesive-137

50 g of 10K, 4-arm PEG-OH (5 mmole) were combined with toluene (300 mL) in a 2000 mL round bottom flask equipped with a condenser, Dean-Stark Apparatus and Argon inlet. While purging with argon, the mixture was stirred in a 140-150° C. oil bath until 150 mL of toluene was removed. The reaction was cooled to room temperature and 53 mL (100 mmole) of the 20% phosgene solution in toluene was added. The mixture was further stirred at 50-60° C. for 4 hours while purged with argon while using a 20 Wt % NaOH in a 50/50 water/methanol trap. Toluene was removed via rotary evaporation with a 20 Wt % NaOH solution in 50/50 water/methanol in the collection trap. The polymer was dried under vacuum for overnight. 3.46 g (30 mmole) of NHS and 375 mL of chloroform were added to PEG and the mixture was purge with argon for 30 minutes. 4.2 ml (30 mmole) of triethylamine in 50 mL chloroform were added dropwise and the reaction mixture was stir with argon purging for 4 hours. After which, 2.3 g (11 mmole) of 3-methoxytyramine hydrochloride (MT) in 100 mL of DMF and 1.54 μl (11 mmole) of triethylamine was added and the mixture was stirred for 4 hours. 12 g (5 mmole) of PCL2k-diGly were added and then another 800 mL of DMF and 1.4 mL of triethylamine were added to the mixture, which was further stirred for overnight. 0.72 g (3.5 mmole) of 3-methoxytyramine hydrochloride was added to cap the reaction along with 0.49 ml of triethylamine. The mixture was precipitated in ethyl 9 L of 50:50 ethyl ether and hexane, and the collected precipitated was dried under vacuum. The crude polymer was dissolved in 700 mL of methanol and dialyzed (15000 MWCO) in 10 L of water at pH 3.5 for 2 days. Lyophilization yielded the 45 g of Medhesive-137. $^1$H NMR (400 MHz, DMSO/TMS): δ 8.7 (s, 1H, $C_6H_3$(OH)—), 7.6 (t, 1H, -PCL-O—$CH_2$—$CH_2$—NHCOO—$CH_2$—$CH_2$—O—)), 7.2 (t, 1H, —$CH_2$—$CH_2$—NHCOO—$CH_2$—$CH_2$—O—)), 6.7 (d, 1H, $C_6H_3$—), 6.6 (s, 1H, $C_6H_3$—), 6.5 (s, 1H, $C_6H_3$—), 4.1-4.0 (m, 32H, OOC$(CH_2)_4$—$CH_2$—O), 3.8 (s, 3H, $C_6H_3$($OCH_3$)), 3.8-3.3 (m, 224H, PEG), 3.1 (m, 2H, $C_6H_3CH_2CH_2$), 2.6 (t, 2H, $C_6H_3CH_2CH_2$), 2.3 (t, 32H, OOC$CH_2$$(CH_2)_4$—), 1.5 (m, 64H, —OOC$CH_2CH_2CH_2CH_2CH_2$—), 1.3 (m, 32H, OOC$CH_2CH_2CH_2CH_2CH_2$—). MT Wt %=2.97%; PCL Wt %=15.6%. UV-vis spectroscopy: 0.171±0.002 μmole MT/mg polymer (3.1±0.03 wt % MT).

Experimental Example 19

Synthesis of Medhesive-138

The procedure for synthesizing Medhesive-137 was used in the preparation of Medhesive-138 while using 3,4-dimethoxyphenylamine (DMPA) instead of 3-methoxytyramine hydrochloride. UV-vis spectroscopy: 0.215±0.005 μmole DMPA/mg polymer (3.9±0.09 wt % DMPA).

Experimental Example 20

Synthesis of Medhesive-139

The procedure for Medhesive-132 was used in the synthesis of Medhesive-139 while using PEG10k-$(GA)_4$ instead of PEG10k-$(SA)_4$. $^1$H NMR (400 MHz, DMSO/TMS): δ 8.7-8.6 (s, 1H, $C_6H_3$(OH)$_2$—), 7.9 (dd, 1H, $C_6H_3$(OH)$_2$—$CH_2$—$CH_2$—CONH—$CH_2$—$CH_2$—O—), 6.5-6.6 (dd, 1H, $C_6H_3$(OH)$_2$—), 4.1 (s, 2H, PCL-CO—$CH_2$—$CH_2$—COOH—)

4.0 (s, 16H, O—(CO—CH$_2$—(CH$_2$)$_4$—O)$_8$CO—CH$_2$—CH$_2$—COOH), 3.6 (s, 2H, PCL-CO—CH$_2$—CH$_2$—COOH—), 2.3 (t, 16H, O—(CO—CH$_2$—(CH$_2$)$_3$—CH$_2$—O)$_8$ CO—CH$_2$—CH$_2$—COOH), 1.5 (m, 32H, O—(CO—CH$_2$—CH$_2$—CH$_2$—CH$_2$—CH$_2$—O)$_8$CO—CH$_2$—CH$_2$—COOH), 1.2-1.4 (m, 16H, O—(CO—CH$_2$—CH$_2$—CH$_2$—CH$_2$—CH$_2$—O)$_8$CO—CH$_2$—CH$_2$—COOH). UV-vis spectroscopy: 0.155±0.005 µmole Dopamine/mg polymer (2.36±0.08 wt % Dopamine).

Experimental Example 21

Synthesis of Medhesive-140

26.25 grams of PEG10k-(GABA)$_4$ were dissolved in 100 mL of DMF with 5.54 grams of PCL2k-diSA, and 1.14 g of DOHA in a round bottom flask. HBTU (4.74 g) and Triethylamine (2.42 mL) were dissolved in 100 mL of chloroform and 150 mL of DMF. The HBTU/Triethylamine solution was added dropwise to the PEG/PCL/DOHA reaction over a period of 30-60 minutes. The reaction was stirred for 24 hours. 0.69 g of DOHA and 0.525 mL Triethylamine were added to the reaction and stirred for 4 hours. This solution was filtered into diethyl ether and place at 4° C. for 4-24 hours. The precipitate was vacuum filtered and dried under vacuum for 4-24 hours. The polymer was dissolved in 400 mL of methanol. This was then filtered using coarse filter paper and dialyzed in 5 L of water at pH 3.5 for 2 days with changing of the water at least 12 times. The solution was then freeze dried and placed under a vacuum for 4-24 hours. After drying, $^1$H NMR and UV-VIS were used to determine purity and coupling efficiency of the catechol. $^1$H NMR (400 MHz, DMSO/TMS): δ 8.7-8.6 (s, 1H, C$_6$H$_3$(OH)$_2$—), 7.9 (dd, 1H, C$_6$H$_3$(OH)$_2$—CH$_2$—CH$_2$—CONH—CH$_2$—CH$_2$—O—), 6.5-6.6 (dd, 1H, C$_6$H$_3$(OH)$_2$—), 4.1 (s, 2H, PCL-CO—CH$_2$—CH$_2$—COOH—) 4.0 (s, 16H, O—(CO—CH$_2$—(CH$_2$)$_4$—O)$_8$ CO—CH$_2$—CH$_2$—COOH), 3.6 (s, 2H, PCL-CO—CH$_2$—CH$_2$—COOH—), 2.3 (t, 16H, O—(CO—CH$_2$—(CH$_2$)$_3$—CH$_2$—O)$_8$CO—CH$_2$—CH$_2$—COOH), 1.5 (m, 32H, O—(CO—CH$_2$—CH$_2$—CH$_2$—CH$_2$—CH$_2$—O)$_8$ CO—CH$_2$—CH$_2$—COOH), 1.2-1.4 (m, 16H, O—(CO—CH$_2$—CH$_2$—CH$_2$—CH$_2$—CH$_2$—O)$_8$CO—CH$_2$—CH$_2$—COOH). UV-vis spectroscopy: 0.237±0.023 µmole DOHA/mg polymer (39.1±0.38 wt % DOHA).

Experimental Example 22

Synthesis of PEG10k-(GABA)$_4$ 150 g of PEG-OH (10,000 MW, 15 mmol) were combined with 300 mL of toluene in a 1 L round bottom flask equipped with a Dean-Stark apparatus, condensation column, and an Argon inlet. The mixture was stirred in a 160° C. in an oil bath with Argon purging until 70-80% of the toluene had been evaporated and collected. The reaction mixture was cooled to room temperature. 350 mL of chloroform along with 36.6 g (180 mmol) of N-Boc-gamma-aminobutyric acid (Boc-GABA-OH) dissolved in 325 mL of chloroform were added to the reaction mixture. 37.1 g (180 mmol) of DCC and 733 mg (6 mmol) of DMAP were added to the reaction mixture. The reaction was stirred under Argon for overnight. The insoluble urea was filtered through vacuum filtration and the resulting mixture was filtered into 3.75 L of ether and the precipitate was collected through vacuum filtration and dried under vacuum for 22 hours. A total of 145.5 g of material was collected and was dissolved in 290 mL of chloroform. 290 mL of trifluoroacetic acid were added slowly to the reaction mixture and the reaction mixture was allowed to stir for 30 minutes. The polymer solution was reduced to half through rotary evaporation. The solution was then added to 3 L of ether and placed at 3-5 C for 20 hours. The precipitate was dried under vacuum for 48 hours. A total of 156 g of material was obtained and dissolved in 1560 mL of nanopure water. The solution was then suction filtered and dialyzed (2000 MWCO) against 10 L of nanopure water for 4 hours followed by acidified water (pH 3.5) for 44 hours. The solution was then dialyzed against nanopure water for 4 hours. The solution was filtered and lyophilized to yield 83.5 g of PEG10k-(GABA)$_4$. $^1$H NMR (400 MHz, D$_2$O): δ 4.2 (m, 2H, PEG-CH$_2$—OC(O)—CH$_2$—), 3.8-3.4 (m, 224H, PEG), 3.0 (t, 2H, PEG-OC(O)—CH$_2$CH$_2$CH$_2$—NH$_2$), 2.5 (t, 2H, PEG-OC(O)—CH$_2$CH$_2$CH$_2$—NH$_2$), 1.9 (t, 2H, PEG-OOC—CH$_2$CH$_2$CH$_2$—NH$_2$).

Experimental Example 23

Synthesis of Medhesive-141

26.22 g (2.5 mmol) of PEG10k-(GABA)$_4$, 5.5 g (2.5 mmol) of PCL2k-diSA, and 1.228 g (6.25 mmol) of hydroferulic acid (HF) were dissolved in 100 mL of DMF. 4.74 g (12.5 mmol) of HBTU and 2.42 mL of triethylamine (17.4 mmol) were dissolved in 150 mL of DMF and 100 mL of chloroform. The HBTU and triethylamine solution was added to an addition funnel and was added dropwise to the PEG10k-(GABA)$_4$, PCL2k-diSA, and hydroferulic acid solution over a period of 40 minutes. The reaction was stirred at room temperature for 24 hours. 747 mg (3.8 mmol) of hydroferulic acid were added to the reaction along with 0.525 mL (3.77 mmol) of triethylamine. The reaction was allowed to stir an additional 4 hours. The reaction was gravity filtered into 2.2 L of a 1:1 ether/hexane mix. The solution was then placed at 4° C. for 18 hours. The precipitate was suction filtered and dried under vacuum for 48 hours. The precipitate was then dissolved in 400 mL of methanol and placed in 15000 MWCO dialysis tubing. The mixture was dialyzed against 5 L of acidified nanopure water for 44 hours with changing of the dialysate 10 times. The solution was then dialyzed against 5 L of nanopure water for 4 hours with changing of the solution 4 times. The solution was suction filtered, frozen in a lyophilizer flask, and freeze dried. 27.3 g of Medhesive-141 were obtained. $^1$H NMR (400 MHz, DMSO/TMS): δ 8.6 (s, 1H, C$_6$H$_3$(OH)—), 7.9 (t, 1H, -PCL-O—CH$_2$—CH$_2$—NHCO—CH$_2$—CH$_2$—O—)), 7.8 (t, 1H, —CH$_2$—CH$_2$—NHCO—CH$_2$—CH$_2$—O—)), 6.7 (d, 1H, C$_6$H$_3$—), 6.6 (s, 1H, C$_6$—H$_3$—), 6.5 (s, 1H, C$_6$H$_3$—), 4.1 (m, 2H, PEG-CH$_2$—OOC-GABA), 4.0 (m, 2H, PEG-CH$_2$—OOC-GABA), 3.9 (m, 2H, O—CH$_2$(CH$_2$)$_4$—COO—), 3.7 (s, 3H, C$_6$H$_3$(OCH$_3$) 3.4 (m, 224H, PEG), 3.0 (t, 2H, PEG-OC(O)—CH$_2$CH$_2$CH$_2$—NH$_2$), 2.7 (t, 2H C$_6$H$_3$CH$_2$CH$_2$), 2.5 (t, 2H, PEG-OC(O)—CH$_2$CH$_2$CH$_2$—NH$_2$), 2.3 (m, 4H, NHOC—CH$_2$CH$_2$COO-PCL), 2.3 (m, 32H, —(CH$_2$)$_4$—CH$_2$COO—), 1.6 (m, 2H, PEG-OOC—CH$_2$CH$_2$CH$_2$NH—), 1.6 (m, 64H, —CH$_2$CH$_2$CH$_2$CH$_2$CH$_2$COO—), 1.3 (m, 32H, CH$_2$CH$_2$CH$_2$CH$_2$CH$_2$COO—): HF Wt %=2.63%; PCL Wt %= 17.5%. UV-vis spectroscopy: 0.156±0.011 µmole HF/mg polymer.

Experimental Example 24

Synthesis of Medhesive-142

The same procedure for Medhesive-141 was used except instead of hydroferulic acid, 3,4-dimethoxyhydrocinnamic acid (DMHA) was used. UV-vis spectroscopy: 0.180±0.007 μmole DMHA/mg polymer.

Experimental Example 25

Method for Coating Adhesive onto Mesh Using Solvent Casting

The adhesive polymers were dissolved at 5-15 wt % in chloroform, methanol, or mixture of these solvents. The polymer solutions were solvent casted over a mesh sandwiched between a PTFE mold (80 mm×40 mm or 80 mm×25 mm) and a release liner. The PTFE is sealed with double sided tape or PTFE films with the same dimensions as the mold. Typical polymer coating density is between 60 and 240 g/m$^2$. The solvent was evaporated in air for 30-120 minutes and further dried with vacuum.

Experimental Example 26

Method for Preparing Stand-Alone Thin-Film

A stand alone film was assembled by solvent casting a polymer solution onto a release liner with a PTFE mold using similar parameters and conditions as the solvent casting method above. The solvent was evaporated in air for 30-120 minutes and further dried with vacuum.

Experimental Example 27

Method for Coating Adhesive onto Mesh Using a Heat-Press

A stand-alone thin-film adhesive was pressed against a mesh between two glass plates using clamps. The samples were placed in an oven (55° C.) for 20-120 minutes to yield the adhesive-coated mesh.

Experimental Example 28

Method for Preparing Oxidant Embedded Stand-Alone Thin-Film

A stand-alone thin-film was made by solvent casting a non-reactive polymer (i.e., Medhesive-138, Medhesive-142) solution with oxidant (i.e. NaIO$_4$) onto a release liner with a PTFE mold using similar parameters and conditions as the solvent casting method. The solvent was evaporated at 37° C. for 30-120 minutes and dried under vacuum.

Experimental Example 29

Method for Preparing Multilayered Adhesive-Coated Mesh Embedded with Oxidant

An oxidant embedded stand-alone thin-film is heat pressed over a mesh coated with adhesive in between two clamped glass plates. The samples are placed in the oven at 55° C. for 10-60 minutes and placed in the freezer for 5-30 minutes. The samples are then dried under vacuum.

Experimental Example 30

Method for Lap Shear Adhesion Testing

Lap shear adhesion tests were performed following ASTM procedures (ASTM F2392). Both the adhesive coated-mesh and the test substrates were cut into 2.5 cm×3 cm strips unless stated otherwise. The adhesive was activated through spraying of 20 mg/mL solution of NaIO$_4$ (PBS was added to NaIO$_4$ embedded samples) prior to bringing the adhesive into contact with the test substrate. The adhesive joint was compressed with a 100 g weight for 10 min, and further conditioned in PBS (37° C.) for another hour prior to testing. The adhesives were pulled to failure at 10 mm/min using a universal tester.

Experimental Example 31

Method for In Vitro Degradation

Adhesive coated meshes are cured using 20 mg/mL NaIO$_4$ solution and then incubated in PBS (pH 7.4) at either 37 or 55° C. At a predetermined time point, the samples are dried with vacuum and weighed. The mass loss overtime is then reported.

Experimental Example 32

Degradation Profile of Medhesive-132

Figure 258:
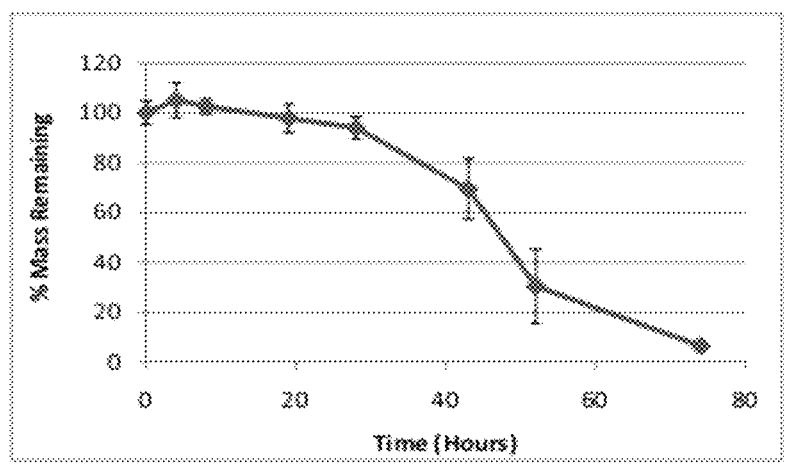
FIG. 258 shows the percent dry mass remaining for 240 $g/m^2$ Medhesive-132 coated on PE mesh incubated in PBS (pH 7.4) at 37° C.

Medhesive-132 coated on a PE mesh completely degraded with 3-4 days of incubation in PBS (pH 7.4) at 37° C. (FIG. 258). When incubated at a higher temperature (55° C.), Medhesive-132 films completely dissolve within 24 hours. Although Medhesive-132 has a similar PCL content (~20 wt %) as Medhesive-096, Medhesive-096 lost only 12% of its original mass over 120 days. This indicates that hydrolysis occurs at a faster rate for the ester bond linking PEG and succinic acid than those within the PCL block. PEG is more hydrophilic than PCL and increased water uptake resulted in faster degradation rate.

Experimental Example 33

Performance of Adhesive-Coated on PTFE Mesh

Figure 259:
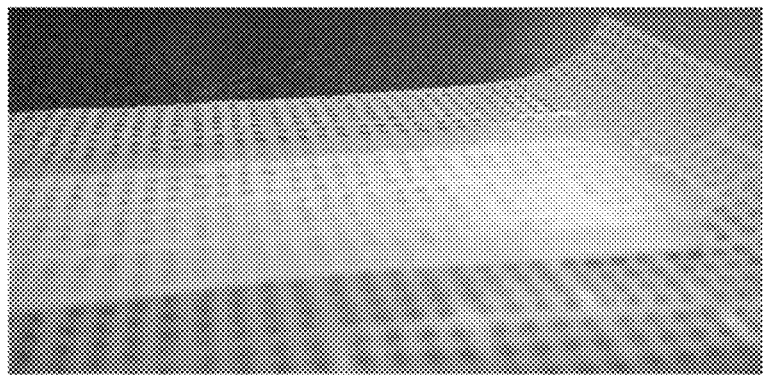
FIG. 259 shows a photograph of adhesive coated on a PTFE (Motif) mesh.
Figure 260:
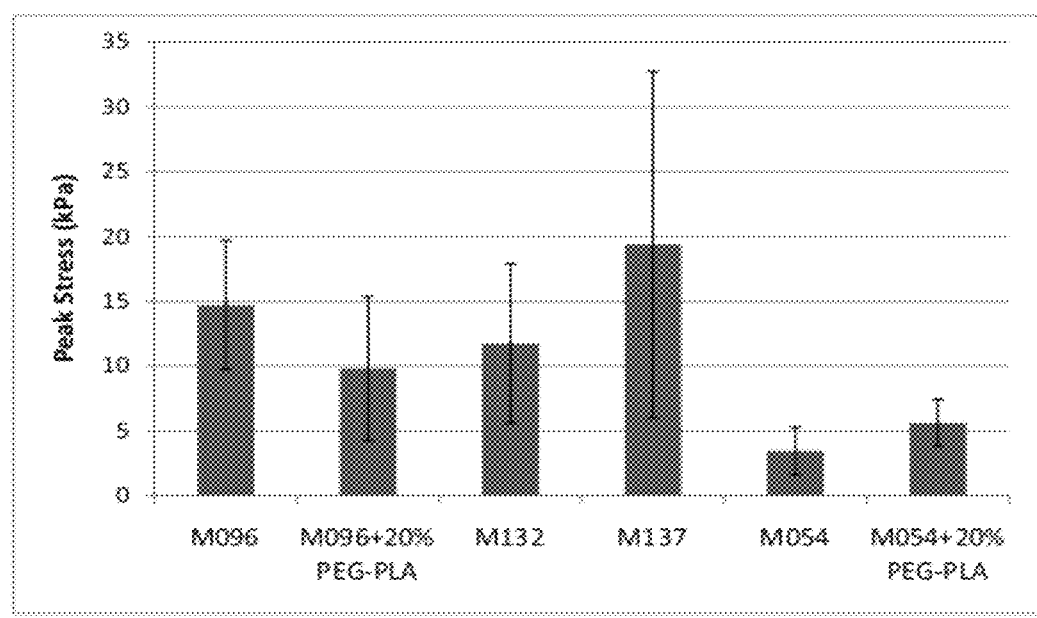
FIG. 260 shows peak lap shear stress of adhesive coated on PTFE mesh. Adhesive coating density is 150 $g/m^2$.
Figure 261:
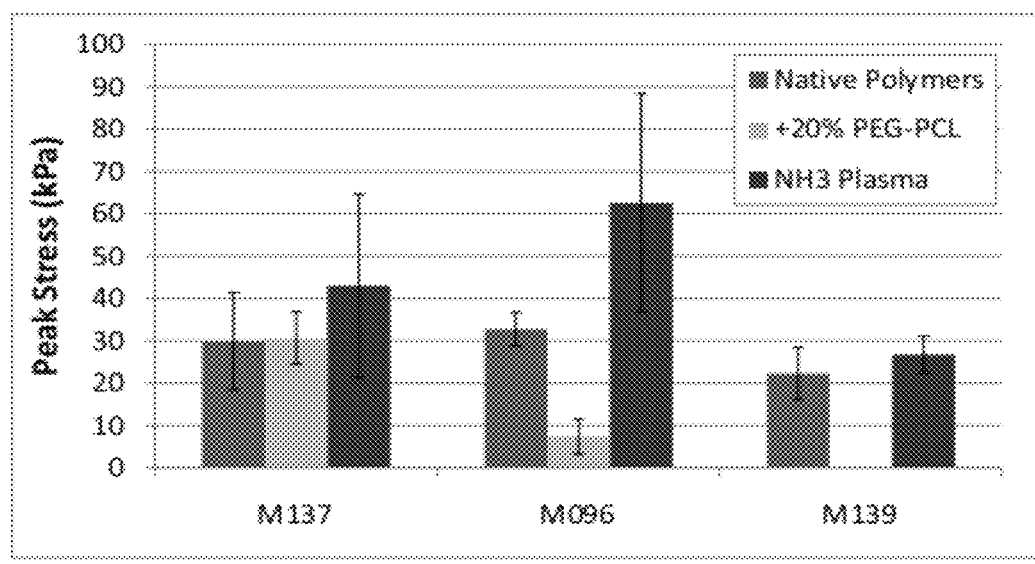
FIG. 261 shows peak lap shear stress of adhesive coated on PTFE mesh at a coating density of 240 $g/m^2$.

Adhesive formulations were coated onto PTFE (Motif) mesh using solvent casting method (FIG. 259) and lap shear adhesion test was performed (FIGS. 260 and 261). Adhesive formulations were blended with either 4-armed PEG-PLA or PEG-PCL up to 20 wt %. PTFE treated with ammonium plasma for 3 min prior to coating resulted in higher peak stress value for Medhesive-096.

Experimental Example 34

Performance of Adhesive Coated on Polyester Mesh

Various adhesives were solvent casted on to PETKM2002 polyester (PE) mesh (0.5 mm pore, 30 g/m$^2$) and a lap shear adhesion test was performed (Table 13). The adhesives demonstrated strong water-resistant adhesive properties to bovine pericardium. The maximum shear strengths measured were between 56 and 78 kPa.

TABLE 13

Lap shear result of adhesive-coated on PETKM2002 PE mesh*

| Adhesive Type | Maximum Strength (pKa) | | Number of repeat |
|---|---|---|---|
| | Average | St. Dev. | |
| Medhesive-139 | 56.2 | 20.9 | 30 |
| Medhesive-140 | 77.7 | 25.9 | 17 |
| Medhesive-141 | 57.4 | 27.3 | 12 |

*240 g/m² coating density

Experimental Example 35

Performance of Adhesive Coated on Polypropylene Mesh

Stand-alone thin-film adhesives were heat-pressed onto NovaSilk polypropylene (PP) mesh at a coating density of 240 g/m² and lap shear adhesion test was performed (Table 14). Medhesive-096 formulations often fail at the adhesive-tissue interface. On the other hand, Medhesive-054+20 wt % PEG-PLA demonstrate a maximum load of 5.5±0.8 pounds of force prior to complete rupture of the adhesive joint. In most cases, this formulation resulted in failure of the synthetic mesh material prior to failure for the adhesive.

TABLE 14

Lap shear result of adhesive-coated on NovaSilk PP mesh*

| Adhesive Type | PEG-PLA (wt %) | Maximum Load (Lbf) | | Maximum Strength (pKa) | |
|---|---|---|---|---|---|
| | | Average | St. Dev. | Average | St. Dev. |
| Medhesive-054 | 0 | 3.3 | 0.6 | 12 | 2.0 |
| Medhesive-054 | 20 | 5.5 | 0.8 | 19 | 3.0 |
| Medhesive-096 | 0 | 3.5 | 0.7 | 12 | 2.2 |
| Medhesive-096 | 20 | 2.2 | 0.7 | 7.5 | 2.5 |

*240 g/m² coating density; contact area = 500-600 mm²; pulled at 5 mm/min.

Experimental Example 36

Performance of Oxidant-Embedded PE Mesh

Oxidant embedded films were tested for adhesion using PETKM2002 PE mesh (Table 15). The adhesive films were coated with 240 g/m² of adhesive film on one side of PE mesh and 120 g/m² of none-reactive film on the other side, which is embedded with $NaIO_4$. The formulations were activated by applying moisture (PBS) to both sides of the mesh while in contact with tissue.

TABLE 15

Lap shear result of adhesive-coated on PE mesh*

| Adhesive Layer | Non-reactive Layer | Maximum Strength (pKa) | |
|---|---|---|---|
| | | Average | St. Dev. |
| Medhesive-137 | Medhesive-138 | 88.0 | 32.2 |
| Medhesive-141 | Medhesive-142 | 104 | 26.4 |

Experimental Example 37

Polymers with Improved Adhesive and Mechanical Properties

TABLE 16

Composition of adhesive polymers

| Adhesive Polymer | Polymer Composition (wt %) | | | | | GPC | |
|---|---|---|---|---|---|---|---|
| | ¹H NMR | | | UV-vis | Catechol Type | Molecular Weight ($M_w$) | PD* |
| | PEG | PCL | Catechol | Catechol | | | |
| Medhesive-054 | 84.0 | 13.4 | 2.6 | 3.1 ± 0.30 | DOHA | | |
| Medhesive-096 | 76.6 | 20.6 | 2.8 | 3.4 ± 0.11 | Dopamine | | |
| Medhesive-105 | 87.8 | 8.9 | 3.3 | 3.9 ± 0.14 | Dopamine | ~ | |
| Medhesive-054 | 84.0 | 13.4 | 2.6 | 3.1 ± 0.30 | DOHA | 217,000 | 3.42 |

TABLE 16-continued

Composition of adhesive polymers

| Adhesive Polymer | Polymer Composition (wt %) | | | UV-vis Catechol | GPC | |
|---|---|---|---|---|---|---|
| | $^1$H NMR | | | | Catechol Type | Molecular Weight ($M_w$) | PD* |
| | PEG | PCL | Catechol | | | | |
| Medhesive-096 | 76.6 | 20.6 | 2.8 | 3.4 ± 0.11 | Dopamine | — | — |
| Medhesive-105 | 87.8 | 8.9 | 3.3 | 3.9 ± 0.14 | Dopamine | — | — |

*Polydispersity (PD) = Weight average molecular weight ($M_w$)/number average molecular weight ($M_n$)

Figure 262:
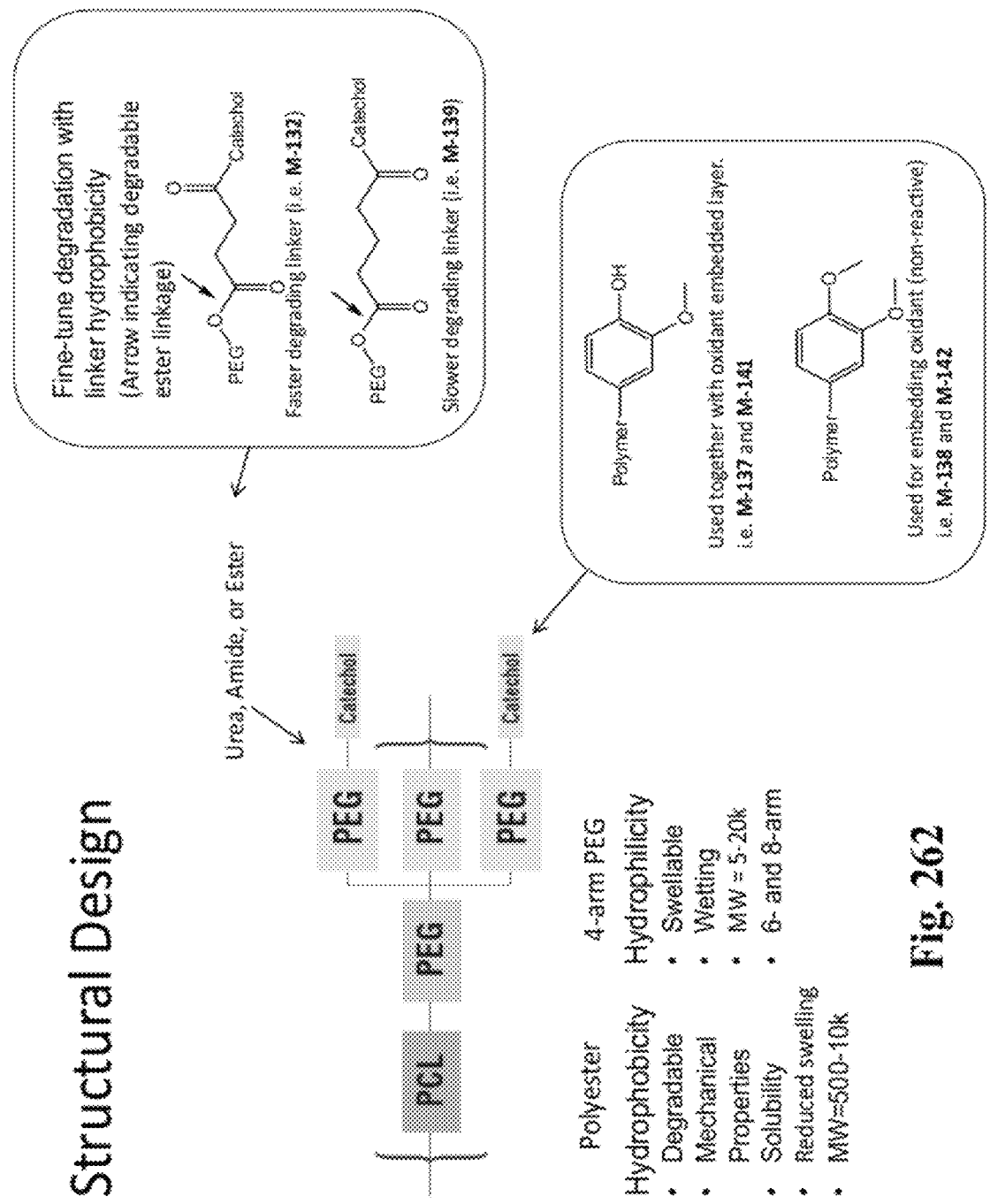
FIG. 262 shows an embodiment of a chemical structure of an adhesive polymer.

Three adhesive polymers were synthesized and their feasibility was assessed as an adhesive coating for biologic meshes. The polymers' representative structure and chemical compositions are shown in FIG. 262 and Table 16, respectively. The adhesive polymers are amphiphilic polymers constructed from hydrophilic polyethylene glycol (PEG) and hydrophobic polycaprolactone (PCL). The presence of PEG allows the adhesive polymer to remain relatively hydrophilic in order to achieve good "wetting" or adhesive contact with a biologic mesh or substrate. The hydrophobic PCL segments increase cohesive strength, prevent rapid dissolution of the film in the presence of water, and reduces the rate of degradation. As the Medhesive polymers degrade, they generate biocompatible degradation products (PEG and 6-hydroxyhexanoic acid). The polymers are modified with DOPA derivatives, dopamine and 3,4-dihydroxyhydrocinnamic acid (DOHA), which serve as the adhesive moiety for interfacial binding, as well as for solidifying the adhesive film when an oxidant is introduced. The catechol accounts for approximately 3-4 wt %.

Experimental Example 38

Characterization of Adhesive Polymer Films

TABLE 17

Equilibrium swelling of the adhesive films

| Adhesive Polymer | Loading Density (g/m$^2$)$^\#$ | Weight % PCL | Swollen Film Thickness (µm)$^\$$ | Extent of Swelling $(W_s-W_i/W_i)$* |
|---|---|---|---|---|
| Medhesive-054 | 23 | 0 | 263 ± 9.64 | 9.8 ± 0.90 |
| | 46 | 0 | 368 ± 4.58 | 7.2 ± 0.61 |
| | 46 | 30 | 260 ± 40.1 | 4.2 ± 0.50 |
| Medhesive-096 | 23 | 0 | 189 ± 4.51 | 7.0 ± 0.20 |
| | 46 | 0 | 261 ± 11.9 | 5.0 ± 0.20 |
| | 46 | 30 | 209 ± 6.66 | 4.2 ± 0.20 |

$^\#$Amount of polymer used to form the dry film in mass per unit area of the mold
$^\$$Measured with micrometer
*For each polymer type, the mean values for each test article are significantly different from each other (p < 0.05)

Adhesive polymers were cast into films by the slow evaporation of methanol or chloroform in a mold. Their percent swelling, tensile mechanical properties, and in vitro degradation profiles were determined. For each test, the films were cured by the addition of a sodium periodate (NaIO$_4$) solution. Additionally, PCL-triol (30 wt %) was formulated into the adhesive film to determine the effect of added PCL content on the physical and mechanical properties of the adhesives. The equilibrium swelling of the adhesive films in phosphate buffered saline (PBS, pH 7.4, 37° C., 24 hours) was calculated by the equation, $(W_s-W_i)/W_i$, where $W_i$ and $W_s$ are the weights of the dry and swollen films measured before and after the swelling experiment, respectively. As shown in Table 17 the degree of swelling is affected by the composition of the adhesive formulation, as well as by the loading density (mass of polymer per unit area of the mold) of the films. For example, higher PCL content in Medhesive-096 (21 wt %) resulted in less swelling compared to Medhesive-054 (13 wt %). When PCL-triol was added to both polymers, the formulations exhibited significantly less swelling. The water uptake is related to the hydrophobicity of the films. In addition to PCL content, the polymer loading density also affected the extent of swelling, with films formed with half the loading density absorbing 1.4 times more water. The loading density affected the cross-linking density of the film, which is inversely proportional to the degree of swelling. (Lee, B. P., J. L. Dalsin, and P. B. Messersmith, *Synthesis and Gelation of DOPA-Modified Poly(ethylene glycol) Hydrogels.* Biomacromol., 2002. 3(5): p. 1038-47.)

Determination of the tensile mechanical properties of the adhesives was based on American Society for Testing and Materials (ASTM) D638 protocols. (ASTM-D638, *ASTM D638-08 Standard Test Method for Tensile Properties of Plastics.* 2008.) Tensile tests on dog-bone shaped films (9.53 mm gauge length, 3.80 mm gauge width, and 12.7 mm fillet radius, swollen in PBS (pH 7.4) for 1 hr) were performed and the maximum tensile strength was measured. Both the Young's modulus and toughness were also determined, based on the initial slope and area under the stress-strain curve, respectively. As shown in Table 18. the mechanical

TABLE 18

Tensile properties of swollen adhesive films

| Adhesive Polymer | Weight % PCL | Young's Modulus (kPa) | Maximum Strength (kPa) | Strain at Failure | Toughness (kJ/m$^3$) |
|---|---|---|---|---|---|
| Medhesive-054 | 0 | 142 ± 37.6 | 168 ± 31.0 | 1.70 ± 0.403 | 168 ± 38.6 |
| | 30 | 103 ± 57.7 | 135 ± 51.6 | 1.95 ± 0.491 | 162 ± 77.3 |
| Medhesive-096 | 0 | 219 ± 40.8 | 251 ± 21.2 | 1.82 ± 0.217 | 266 ± 29.1 |
| | 30 | 235 ± 58.1 | 357 ± 37.5 | 2.73 ± 0.337 | 562 ± 93.1 |

Vertical lines = statistically equivalent; p > 0.05 properties of the film were affected by the PCL content. For example, Medhesive-096 demonstrated significantly higher tensile strength and toughness (251±21.2 kPa, and 266±29.1 kJ/m$^3$, respectively), compared to Medhesive-054 (168±31.0 kPa and 167±38.6 kJ/m$^3$). Strength and toughness values for Medhesive-096 formulated with the addition of 30 wt % of PCL-triol were greater (357±37.5 kPa and 562±93.1 kJ/m$^3$, respectively), indicating that the mechanical properties of these adhesives are modulated by blending them with compounds that impart the desired characteristics. The toughness more than doubled with the addition of PCL-triol to Medhesive-096. Elevated film toughness correlates with high lap shear adhesion strength. (da Silva, L. F. M., T. N. S. S. Rodrigues, M. A. V. Figueiredo, M. F. S. F. de Moura, and J. A. G. Chousal, *Effect of Adhesive Type and Thickness on the Lap Shear Strength* J. Adh., 2006. 82: p. 1091-1115.) The addition of PCL-triol increased the cross-linking density in the film, which resulted in the observed increase in mechanical properties. The increase in cross-linking density did not result in brittle films as shown in the elevated strain values.

Figure 263:
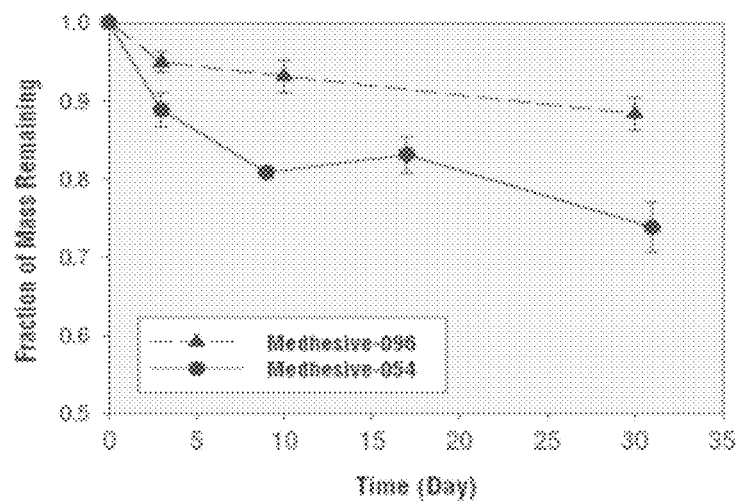
FIG. 263 shows a degradation profile of polymer films performed at 55° C.

In vitro degradation was determined by monitoring the mass loss of the adhesive films incubated in PBS (pH 7.4) over time at 55° C. to accelerate the degradation process (FIG. 263). Medhesive-054 lost over 26±3.2% of its original dry mass over one month, while the more hydrophobic Medhesive-096 demonstrated a slower rate of degradation (12±2.0% mass loss). Hydrolysis was also performed at 37° C. where these films lost over 13±2.9% (Medhesive-054) and 4.0±2.3% (Medhesive-096) after 18 and 20 days of incubation, respectively. Since the adhesive films degrade largely through hydrolysis, more water uptake by Medhesive-054 films (corroborated with elevated swelling) resulted in faster degradation.

These results demonstrate that the chemical architecture and adhesive formulation play a role in the physical and mechanical properties of the adhesive films. The hydrophobicity of the film has a significant impact on the extent of swelling, which is inversely proportional to the mechanical properties and rate of hydrolysis. By designing the adhesive polymers with different compositions, these properties may be tailored and further refined by blending the polymers with PCL-triol.

Experimental Example 39

Adhesive Formulations with Bovine Pericardium Mesh

Figure 264:
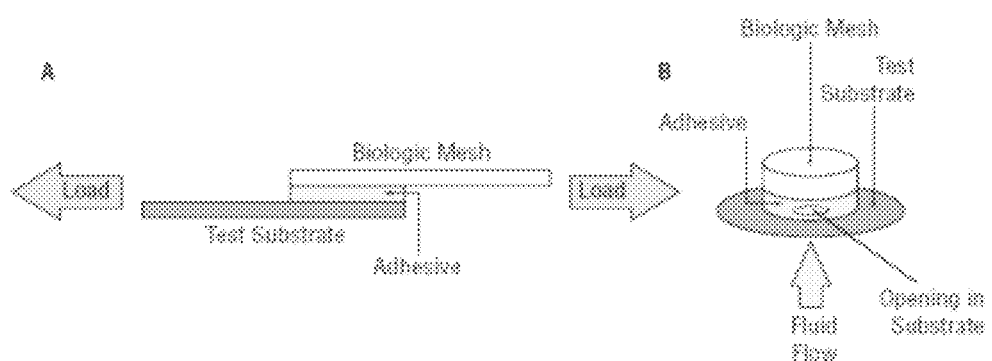
FIG. 264 shows schematic diagrams of A) lap shear and B) burst strength tests.

To test the feasibility of adhesive compounds for hernia repair, an adhesive-coated mesh using bovine pericardium as a support material was evaluated. This biomaterial was chosen because it is an inexpensive and readily abundant extracellular matrix with suitable mechanical properties (tensile strength of 41±9.8 N/cm). Additionally, several acellular bovine pericardium-based products (e.g., Veritas®, Synovis Surgical Innovations; Tutomesh®, RTI Biologics) are approved by the FDA for soft tissue reconstruction. (Santillan-Doherty, P., R. Jasso-Victoria, A. Sotres-Vega, R. Olmos, J. L. Arreola, D. Garcia, B. Vanda, M. GaxHola, A. Santibanez, S. Martin, and R. Cabello, *Thoracoabdominal wall repair with glutaraldehyde-preserved bovine pericardium.* Journal of investigative surgery: the official journal of the Academy of Surgical Research, 1996. 9(1): p. 45-55., Burger, J. W. A., J. A. Halm, A. R. Wijsmuller, S. ten Raa, and J. Jeekel, *Evaluation of new prosthetic meshes for ventral hernia repair.* Surgical endoscopy, 2006. 20(8): p. 1320-5., Lo Menzo, E., J. M. Martinez, S. A. Spector, A. Iglesias, V. Degennaro, and A. Cappellani, *Use of biologic mesh for a complicated paracolostomy hernia.* American journal of surgery, 2008. 196(5): p. 715-9.) To coat the adhesive film onto bovine pericardium, a hydrated segment of pericardium was placed in a template (91 mm×91 mm). A polymer solution in methanol or chloroform was added and allowed to slowly evaporate in a 37° C. oven for at least one hour. The samples were further dried in a vacuum desiccator for at least 24 hours. Procedures from ASTM standards were used to perform lap shear (ASTM F2255) (ASTM-F2255, *Standard Test Method for Strength Properties of Tissue Adhesives in Lap-Shear by Tension Loading.* 2003) and burst strength (ASTM F2392) (ASTM-F2392, *Standard Test Method for Burst Strength of Surgical Sealants* 2004) tests (FIG. 264). The adhesive coated-pericardium segments were cut into either 2.5 cm×5 cm strips for lap shear tests or 15 mm-diameter circular samples for burst strength tests. The samples were hydrated in PBS, and a solution of $NaIO_4$ (40 µL) was added to the adhesive on the coated mesh prior to bringing the adhesive into contact with the test substrate, which was also bovine pericardium. The test substrates were shaped into either 2.5 cm×5 cm strips or 40 mm-diameter circles for lap shear and burst strength testing, respectively. A 3 mm-diameter defect was formed in the center of the test substrate for the burst strength test. The adhesive joint was compressed with a 100 g weight for 2 hours, and further conditioned in PBS (37° C.) for another hour prior to testing. Mechanical test conditions included assessing the effect of varying $NaIO_4$ concentrations, polymer loading density, and contact time between the adhesive construct and test substrate. Due to the innate biologic variability of the bovine pericardium, the same batch of pericardium was used for each series of experiments to minimize the variation in the results due to the tissue. The minimum sample size was 6 in each test condition. Statistical assessment was performed using an analysis of variance (ANOVA), pair-wise comparisons with the Tukey test, and a significant level of 0.05.

TABLE 19

Lap shear test results with varying $NaIO_4$ concentrations[#]

| $NaIO_4$ Concentration (mg/mL) | Maximum strength (kPa) | Work of adhesion $(J/m^2)$[%] | Strain at Failure |
|---|---|---|---|
| 10 | 9.34 ± 2.89* | 22.2 ± 12.3[$] | 0.489 ± 0.439 |
| 20 | 46.6 ± 19.3 | 77.0 ± 26.1[$] | 0.365 ± 0.0698 |
| 30 | 42.3 ± 26.1 | 60.7 ± 34.5 | 0.315 ± 0.0627 |
| 40 | 45.0 ± 20.4 | 60.8 ± 14.6 | 0.168 ± 0.118 |

[#]Performed using Medhesive-054-coated bovine pericardium
[%]Normalized by initial area of contact
*Significantly different from other test articles (p < 0.05)
[$]Significantly different from each other (p < 0.05)

TABLE 20

Adhesion test results with varying polymer loading densities[#]

| Loading Density $(g/m^2)$ | Maximum Strength (kPa) | Work of adhesion $(J/m^2)$ [%] | Strain at failure | Burst Pressure (mm Hg) |
|---|---|---|---|---|
| 15 | 18.9 ± 5.41 | 33.2 ± 5.48 | 0.432 ± 0.201 | — |
| 30 | 31.7 ± 12.5 | 77.9 ± 35.5 | 0.494 ± 0.0997 | 219 ± 116 |
| 60 | 42.5 ± 12.3 | 91.6 ± 24.1 | 0.428 ± 0.0684 | 422 ± 136 |
| 90 | 37.9 ± 11.5 | 94.4 ± 42.2 | 0.422 ± 0.0543 | 495 ± 174 |

[#]Performed using Medhesive-054-coated bovine pericardium
[%] Normalized by initial area contact
Vertical lines = statistically equivalent; p > 0.05

TABLE 21

Lap shear test results performed after varying contact time[#]

| Contact Time (min) | Maximum Strength (kPa) | Work of adhesion $(J/m^2)$[%] | Strain at failure |
|---|---|---|---|
| 10 | 62.0 ± 23.2 | 89.4 ± 42.1 | 0.324 ± 0.137 |
| 70* | 60.6 ± 33.0 | 115 ± 43.6 | 0.479 ± 0.0892 |
| 120* | 55.7 ± 19.4 | 70.0 ± 21.5 | 0.332 ± 0.0361 |
| 180* | 58.2 ± 16.8 | 134 ± 79.9 | 0.518 ± 0.155[$] |

[#]Performed using Medhesive-054-coated bovine pericardium
[%]Normalized by initial area of contact
*Submerged in PBS at 37° C. for the final 60 min before testing
[$]Statistically higher than 10-min contact time ($p < 0.05$)

Using bovine pericardium as the support mesh, $NaIO_4$ concentration and polymer loading density were optimized. As demonstrated in Table 19, both lap shear adhesion strength and work of adhesion, the total amount of energy required to separate the adhesive joint, increased with increasing NaIO4 concentration, but exhibited no further increase when the concentration exceeded 20 mg/mL. Varying the polymer loading density also affected the adhesive properties as shown in Table 20, with higher loading density yielding higher adhesive strengths for both lap shear and burst tests. Additionally, a test was performed to determine the effect of contact time on the strength of the adhesive joints (Table 21). It was found that the adhesive joint had already reached maximum strength after merely 10 min of contact, suggesting that our adhesive is a fast acting adhesive suitable for surgical repair.

Figure 265:
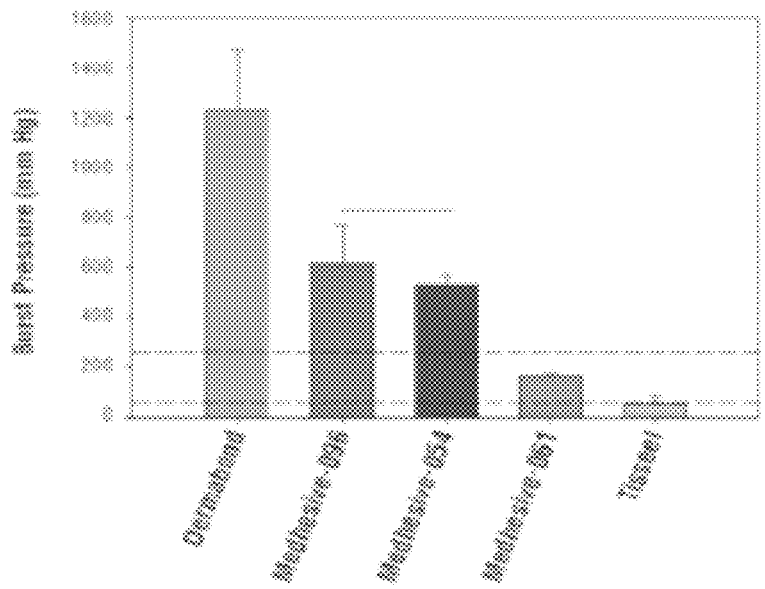
FIG. 265 shows the pressure required to burst through the adhesive joint sealed with adhesive-coated bovine pericardium. Dashed lines represent reported abdominal pressure range. Solid line represents statistical equivalence ($p>0.05$).
Figure 266:
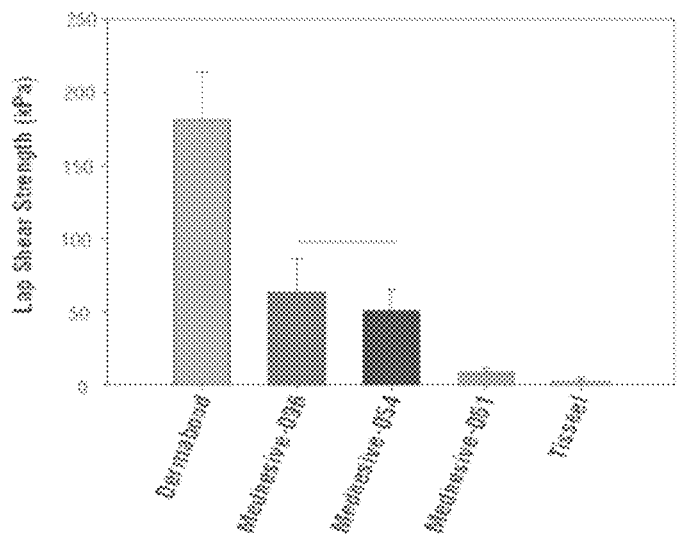
FIG. 266 shows lap shear adhesive strength required to separate an adhesive joint formed using adhesive-coated bovine pericardium. Solid line represents statistical equivalence ($p>0.05$).

Using optimized parameters, the adhesive properties of the bioadhesive constructs were determined and compared to controls: Dermabond®, Tisseel™, and Medhesive-061 (a liquid tissue adhesive). For both burst strength and lap shear adhesion tests (FIGS. 265 and 266, respectively), Dermabond exhibited the highest adhesive strengths, and Medhesive-054 and Medhesive-096 significantly outperformed Medhesive-061 and Tisseel. Additionally, both Medhesive-054 (615±151 mm Hg) and Medhesive-096 (526±49.0 mm Hg), can withstand a pressure that is well above reported physiological intra-abdominal pressures (64-252 mm Hg), (Cobb, W. S., J. M. Burns, K. W. Kercher, B. D. Matthews, N. H. James, and H. B. Todd, *Normal intraabdominal pressure in healthy adults*. The Journal of Surgical Research, 2005. 129(2): p. 231-5) indicating that the bioadhesive constructs are of use in hernia repair.

Experimental Example 40

Adhesive Properties Adhesive Constructs

Figure 267:
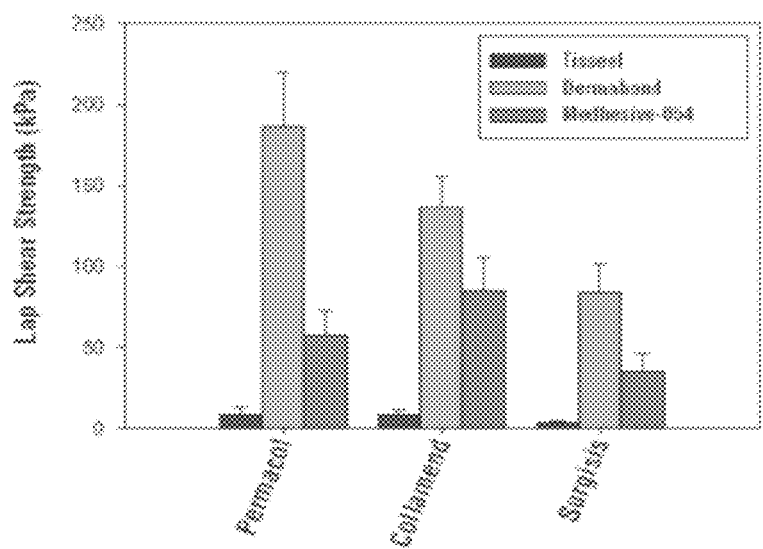
FIG. 267 shows lap shear adhesive strength required to separate an adhesive joint formed using adhesive-coated bovine pericardium.

In addition to bovine pericardium, 3 commercially available biologic meshes, Permacol™, CollaMend™, and Surgisis™, were coated with Medhesive-054, and lap shear adhesion tests were performed using hydrated bovine pericardium as the test substrate. Although Dermabond exhibited the highest shear strength, meshes fixed with cyanoacrylate were reported to have reduced tissue integration combined with pronounced inflammatory response. (Fortelny, R. H., A. H. Petter-Puchner, N. Walder, R. Mittermayr, W. Öhlinger, A. Heinze, and H. Redl, *Cyanoacrylate tissue sealant impairs tissue integration of macroporous mesh in experimental hernia repair* Surgical Endoscopy, 2007. 21(10): p. 1781-1785.) Additionally, cyanoacrylate adhesive significantly reduced the elasticity of the mesh and abdominal wall, and impaired the biomechanical performance of the repair. Due to the release of toxic degradation products (formaldehyde), cyanoacrylates are not approved for general subcutaneous applications in the US. (Sierra, D. and R. Saltz, *Surgical Adhesives and Sealants: Current Technology and Applications*. 1996, Lancaster, Pa.: Technomic Publishing Company, Inc., Ikada, Y., *Tissue adhesives*, in *Wound Closure Biomaterials and Devices*, C. C. Chu, J. A. von Fraunhofer, and H. P. Greisler, Editors. 1997, CRC Press, Inc.: Boca Raton, Fla. p. 317-346.) Medhesive-054 combined with all mesh types outperformed Tisseel by seven- to ten-fold (FIG. 267). Even with weak adhesive strengths, fibrin-based sealants have demonstrated at least some level of success in mesh fixation in vivo, (Topart, P., Vandenbroucke, F., Lozac'h, P., *Tisseel vs tack staples as mesh fixation in totally extraperitoneal laparoscopic repair of groin hernias*. Surg. Endosc., 2005. 19: p. 724-727, Schwab, R., Willms, A., Kroger, A., Becker, H. P., *Less chronic pain following mesh fixation using fibrin sealant in TEP inguinal hernia repair*. Hernia, 2006. 10: p. 272-277, Olivier ten Hailers, E. J., Jansen, J. A., Marres, H. A. M., Rakhorst, G., Verkerke, G. J., *Histological assessment of titanium and polypropylene fiber mesh implantation with and without fibrin tissue glue*. Journal of Biomedical Materials Research Part A, 2006: p. 372-380) which suggests that the adhesive constructs of the present invention have sufficient adhesive properties for hernia repair. While the Medhesive-054 constructs exhibited adhesive strengths that were 30-60% of those of Dermabond, it is possible to further optimize the coating technique or adhesive formulation for each mesh type. As shown in Table 22, the measured coating mass on each mesh type was nearly equivalent. However, the coating thicknesses on both the Permacol and Surgisis meshes were significantly less than that on the CollaMend mesh.

TABLE 22

Coating thickness and weight of Medhesive-054 on each biologic mesh

| Mesh Type | Coating Thickness (μm) | Coating Mass (g/m²) |
|---|---|---|
| Permacol | 22 | 66 |
| CollaMend | 86 | 66 |
| Surgisis | 34 | 73 |

*Difference of averaged values of coated and uncoated meshes ($n \geq 9$)

Experimental Example 41

Sterilization of Adhesive Compounds

To determine the effect of electron-beam (E-beam) irradiation on adhesive polymers a polymer was exposed to 10 kGy E-beam irradiation that did not alter the composition of the adhesive (Table 23). E-beam sterilization had no effect on the catechol, as the catechol $^1H$ NMR spectrum of phenol (6.2-6.7 ppm) and the maximum absorbance wavelength ($\square_{max}$=280 nm, UV-vis) were unchanged. Both the weight average molecular weight ($M_w$) and polydispersity (PD) of the E-beam-treated polymer increased by 29% and 21%, respectively, indicating that this sterilization method likely resulted in intermolecular cross-linking. However, E-beam irradiation did not have a significant impact on the adhesive performance of Medhesive-054.

TABLE 23

Effect of E-beam sterilization on Medhesive-054

| Sterilization Method | Polymer Composition (wt %) [1H NMR] | | | UV-vis | GPC | Lap Shear Adhesion Test [#] | | |
|---|---|---|---|---|---|---|---|---|
| | PEG | PCL | Catechol | Catechol * | Molecular weight (PD) | Maximum Strength (kPa) * | Work of Adhesion (J/m$^2$) * | Strain at failure * |
| Non-sterile | 84.0 | 13.4 | 2.6 | 3.1 ± 0.30 | 217,000 (3.42) | 76.5 ± 21.7 | 172 ± 68.9 | 0.57 ± 0.20 |
| 10 kGy | 83.4 | 13.8 | 2.8 | 3.5 ± 0.31 | 280,000 (4.15) | 70.1 ± 14.0 | 138 ± 59.6 | 0.50 ± 0.32 |

* Non-sterile vs. 10 kGy samples not statistically different based on t-test (p > 0.05).
[#] Bovine pericardium used as both backing and substrate.

Accordingly, at least 3 adhesive polymers were shown to be of use for mesh fixation. The adhesives were cast into films and characterized using a swelling experiment, tensile mechanical test, and in vitro degradation test. Hydrophobicity of a film had the greatest impact on its physical and mechanical properties, which could be tailored by both the composition of the adhesive polymer, and the adhesive formulation through blending the polymer with PCL-triol. Using bovine pericardium as a biologic mesh, a method of coating the adhesives on the mesh was demonstrated. The same coating procedure was used to create bioadhesive constructs with 3 different types of commercially available meshes. Based on the lap shear and burst strength adhesion tests, the bioadhesive constructs demonstrated adhesive properties that are suitable for hernia repair.

Experimental Example 42

In Vitro Degradation of Adhesive Compounds

Figure 268:
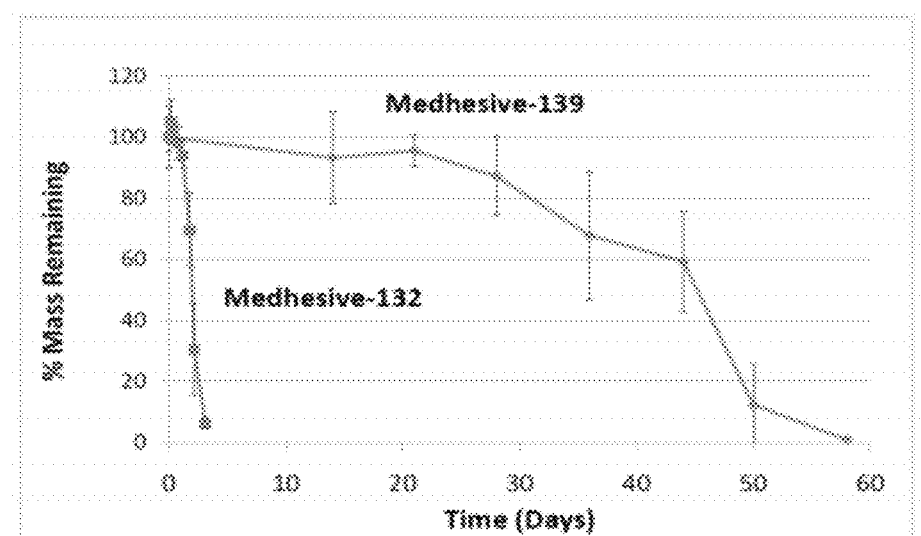
FIG. 268 shows in vitro degradation of adhesive-coated PE meshes incubated in PBS at 37° C.

Adhesive (240 g/m$^2$) coated PE mesh was activated by spraying 20 mg/mL NaIO$_4$ solutions and cut into 10-mm discs. The samples were incubated in 10-mL phosphate buffered saline (PBS) at 37 and 55° C. The amount of time for the adhesive to completely dissolve was recorded (Table 24). At a predetermined time point, the samples were dried and weighed to determine mass of the adhesive remaining (FIG. 268).

TABLE 24

Degradation time of adhesive polymers coated on PE mesh

| Polymer | Temperature (° C.) | Degradation Time (Day) |
|---|---|---|
| Medhesive-132 | 37 | 3 |
| | 55 | <1 |
| Medhesive-139 | 37 | 51-58 |
| | 55 | 10-14 |
| Medhesive-140 | 37 | 49-59 |
| | 55 | 9-11 |
| Medhesive-141 | 37 | 42-49 |
| | 55 | 9-11 |
| Medheisve-141/Medhesive-142 with embedded NaIO$_4$ | 37 | 63 |
| | 55 | 13 |
| Medhesive-144 | 37 | 48 |
| | 55 | 13 |

Experimental Example 43

Cytotoxicity of Adhesive-Coated PE Mesh 15-mm discs of oxidant embedded thin film adhesive (Medhesive-141/Medhesive-142) device were cut and activated by placing over 200 uL EMEM extraction fluid in a glass scintillation vial. Samples were allowed to cure (crosslink) for 10 minutes. The total volume of extraction fluid used was calculated based on a 20 ml/60 cm$^2$ ratio. To simulate patterning, an excess amount of extraction fluid to emulate 50%, 57.1% and 66.7% adhesive coverage was used. Extraction was done at 37° C. for 24 hours and placed over a sub-confluent layer of L929 fibroblasts for 48 hours. Percent viability was then quantified (normalized to negative controls) using the MTT cytotoxicity assay and UV Spectrophotometry at 570 nm wavelength. All samples demonstrated passing grade (>70% cell viability).

TABLE 25

Cytotoxicity of oxidant-embedded films

| M141 (g/m2) | M142 barrier (g/m2) | M142 carrier (g/m2) | NaIO4 (mg/mL) | NaIO4 (g/m2) | % L929 Cell Viability | Pattern |
|---|---|---|---|---|---|---|
| 120 | 0 | 120 | 1.25 | 1.78 | 93 | no |
| 120 | 120 | 120 | 1.25 | 1.78 | 93 | no |
| 120 | 120 | 120 | 2.5 | 3.56 | 90 | no |
| 180 | 0 | 120 | 2.5 | 3.56 | 74 | no |
| 240 | 0 | 0 | 0 | | 98, 77, 78 | no |
| 240 | 0 | 120 | 2.5 | 3.56 | 91, 72, 88 | no |
| 240 | 0 | 120 | 10 | 14.24 | 72 | 50% |
| 240 | 0 | 120 | 7.5 | 10.68 | 83, 78, 81, 71 | 50% |

TABLE 25-continued

Cytotoxicity of oxidant-embedded films

| M141 (g/m2) | M142 barrier (g/m2) | M142 carrier (g/m2) | NaIO4 (mg/mL) | NaIO4 (g/m2) | % L929 Cell Viability | Pattern |
|---|---|---|---|---|---|---|
| 240 | 0 | 120 | 5 | 7.12 | 96, 93, 98, 109, 84 | 50% |
| 240 | 0 | 120 | 5 | 7.12 | 72, 90 | 57% |
| 240 | 0 | 120 | 5 | 7.12 | 76, 90 | 66.70% |

Experimental Example 44

Adhesive-Coating on Synthetic Mesh

Polymer solutions in either chloroform or methanol were solvent cast onto synthetic mesh at different coating densities (90-240 g/m$^2$). Additionally, both PP and PE meshes of different mesh weights and pore sizes were used, and lap shear adhesion tests were performed. The adhesive-coated meshes demonstrated strong adhesive properties to wetted tissue (bovine pericardium) and reproducibility (Table 26).

TABLE 26

Lap shear adhesion test results of adhesive-coated synthetic meshes

| Adhesive Formulation* | Mesh Type | Mesh Weight (g/m$^2$) | Pore Size (mm) | Lap Shear Strength Average (kPa) | St. Dev. (kPa) | CV** | Sample Size |
|---|---|---|---|---|---|---|---|
| Medhesive-132 | PP | 25 | 1.5 × 1.2 | 39.0 | 14.1 | 36.3 | 28 |
| Medhesive-132 | PP | 68 | 1.0 | 36.6 | 12.4 | 33.8 | 12 |
| Medhesive-132 | PE | 30 | 0.5 | 39.7 | 13.9 | 35.0 | 30 |
| Medhesive-139 | PE | 30 | 0.5 | 56.2 | 20.9 | 37.1 | 30 |
| Medhesive-140 | PE | 30 | 0.5 | 79.4 | 28.7 | 36.1 | 30 |
| Medhesive-141 | PE | 30 | 0.5 | 63.6 | 25.3 | 39.8 | 30 |
| Medhesive-144 | PE | 30 | 0.5 | 41.2 | 25.2 | 61.2 | 30 |

*Coating density of 240 g/m
**Coefficient of Variation; CV = St. Dev./Average × 100

Experimental Example 45

Oxidant Embedding

Figure 269:
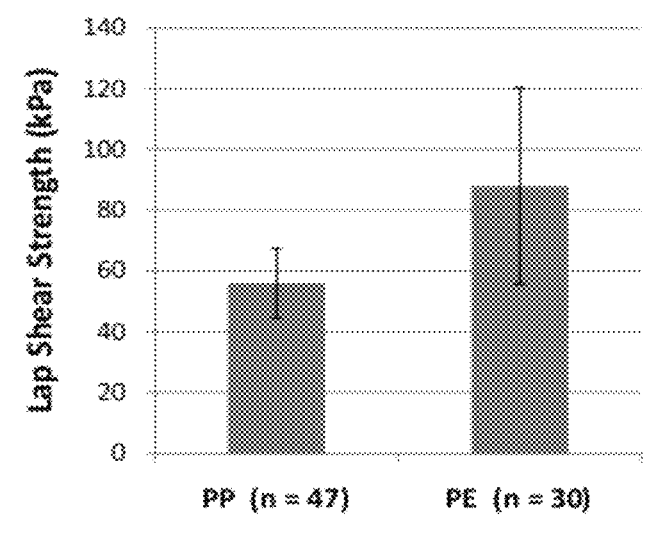
FIG. 269 shows a lap shear test performed on Medhesive-137/Medhesive-138 films embedded with $NaIO_4$. Both meshes had a weight of 30 g/m². The PP and PE had pore sizes of 1.5×1.2 mm and 0.5 mm, respectively.
Figure 270:
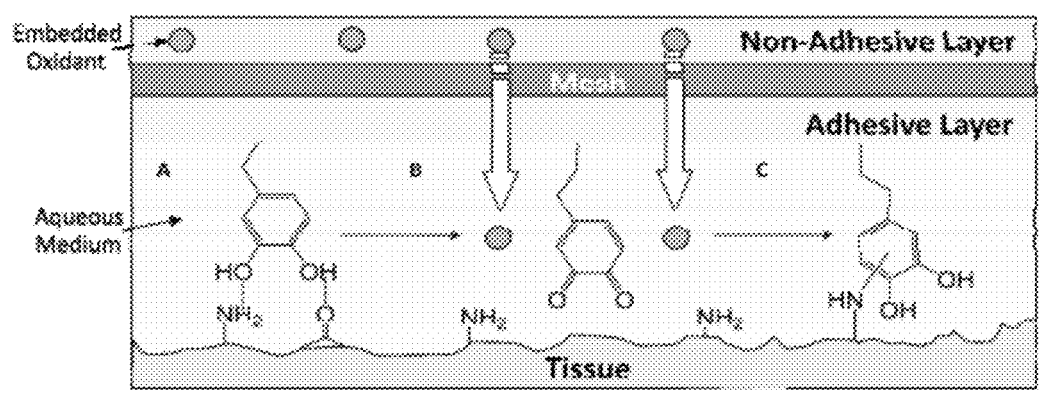
FIG. 270 shows a schematic diagram of multi-layered design for embedding oxidant in a non-adhesive layer. When the adhesive comes into contact with the aqueous medium (A), the films swell and the embedded oxidant dissolves and diffuses to the adhesive layer, which oxidizes the catechol (B), and interfacial binding occurs between the adhesive layer and the tissue surface (C).

The adhesive layer (Medhesive-137 or Medhesive-141) was solvent cast onto either PE or PP meshes. The non-adhesive layer (Medhesive-138 or Medhesive-142) was cast into a film with embedded oxidant (NaIO$_4$) at 7-14 g/m$^2$ and heat-pressed onto the adhesive-coated mesh to make the bilayer construct (FIG. 269). Alternatively, the adhesive layer was casted first into a film and heat pressed onto the mesh with the non-adhesive film either in one step or in two separate steps (i.e. one layer at a time). The bi-layer films were activated by adding water (i.e. PBS), which hydrates the films and dissolves the embedded oxidant to activate the adhesive. (FIG. 270) Lap shear strength of Medhesive-141/Medhesive-142 (240 and 120 g/m$^2$, respectively) embedded with 14 g/m$^2$ of NaIO4 was determined to be 109±20.4 kPa. (Table 27).

TABLE 27

Lap shear results of oxidant embedded film at different Medhesive-141 coating density and NaIO$_4$:hydroferulic acid (HF) molar ratio*

| Med-141 (g/m$^2$) | NaIO$_4$/HF | Maximum Lap Shear Load (CV) |
|---|---|---|
| 240 | ~3:1 | 16.99N (33.72%) |
| 240 | ~0.75 | 3.33N (60.43%) |
| 210 | ~0.85 | 2.47N (53.96%) |
| 180 | ~1 | 7.83N (85.59%) |
| 150 | ~1.19 | 6.72N (75.6%) |
| 120 | ~1.49 | 7.23N (61.95%) |

Experimental Example 46

Preliminary Sterilization and Shelf Life

The effects of 2 sterilization methods, i.e., electron-beam (E-beam) and ethylene oxide (EtO), on the performance of adhesive-coated meshes were determined using lap shear testing on a bovine pericardium substrate (Table 28). A preliminary shelf-life study was performed on E-beam sterilized samples. There were no statistical differences in terms of lap shear results for storage up to 22 and 35 days for E-beam-sterilized Medhesive-132 and oxidant embedded samples, respectively (Table 29).

TABLE 28

Effect of sterilization on lap shear strength of adhesive-coated synthetic meshes

| Adhesive Formulation | Mesh Type | Sterilization Method | Lap Shear Strength Average (kPa) | St. Dev. (kPa) | Sample Size |
|---|---|---|---|---|---|
| Medhesive-137/138 Oxidant Embedded | PE | Non-sterile | 88.0 | 32.3 | 30 |
| | | E-beam | 128 | 18.2 | 6 |
| Medhesive-132 | PE | Non-sterile | 39.7 | 13.9 | 28 |
| | | E-beam | 44.8 | 9.43 | 4 |
| Medhesive-137/138 Oxidant Embedded | PP | Non-sterile | 56.0 | 11.6 | 30 |
| | | EtO | 30.4 | 20.8 | 6 |
| Medhesive-132 | PP | Non-sterile | 39.0 | 14.2 | 28 |
| | | EtO | 38.4 | 16.0 | 6 |

TABLE 29

Effect of storage on the lap shear strength of adhesive-coated PE meshes

| Adhesive Formulation | Days Post Sterilization | Lap Shear Strength | | Sample Size |
|---|---|---|---|---|
| | | Average (kPa) | St. Dev. (kPa) | |
| Medhesive-137/138 Oxidant Embedded | Non-sterile | 88.0 | 32.3 | 30 |
| | 8 | 69.7 | 32.2 | 8 |
| | 35 | 41.9 | 12.2 | 2 |
| Medhesive-132 | Non-sterile | 39.7 | 13.9 | 30 |
| | 2 | 44.8 | 9.43 | 4 |
| | 22 | 69.8 | 43.0 | 4 |

Experimental Example 47

Intraperitoneal Implantation of Adhesive-Coated Mesh in a Rabbit Model

Figure 271:
FIG. 271 shows adhesive-coated mesh attached to the peritoneum after activation.
Figure 272:
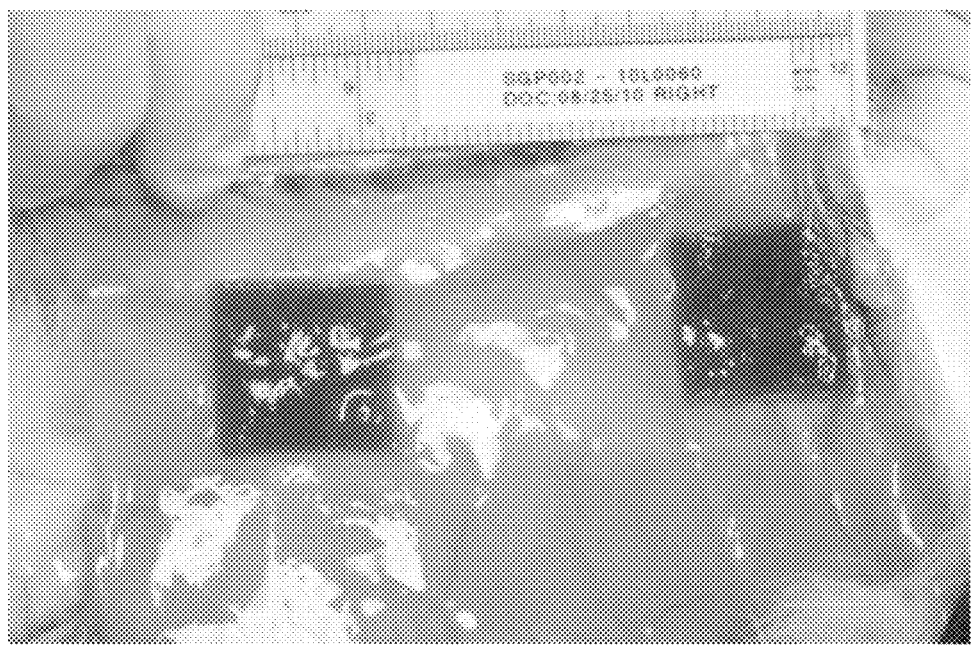
FIG. 272 shows adhesive-coated mesh adhered tightly to peritoneum with no curling, post-surgical adhesion, and shrinkage at day 7.
Figure 273:
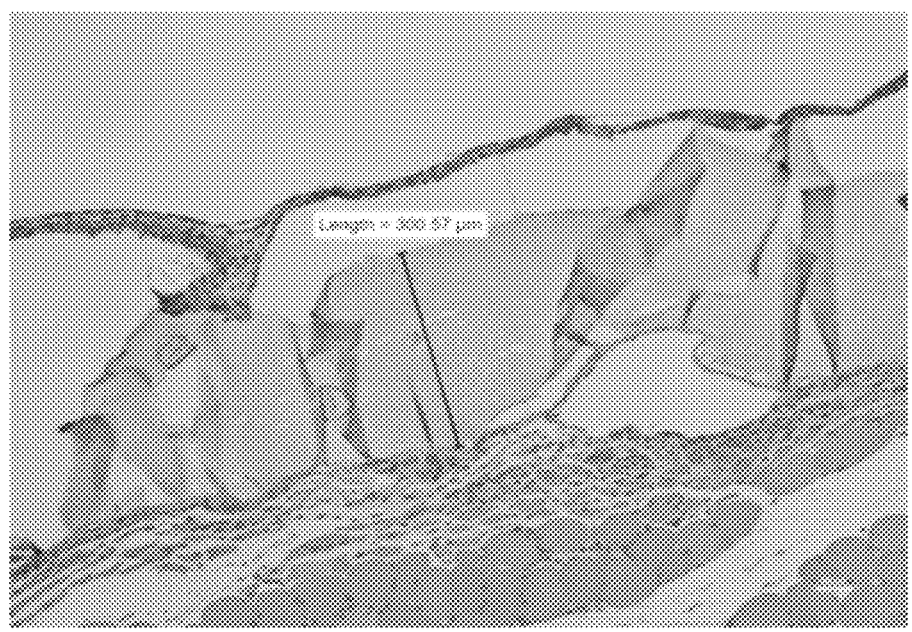
FIG. 273 shows an H&E stain of harvested implant site at 10× objective magnification showing thin scar plate formation. The black line marks the thickness of the adhesive.
Figure 274:
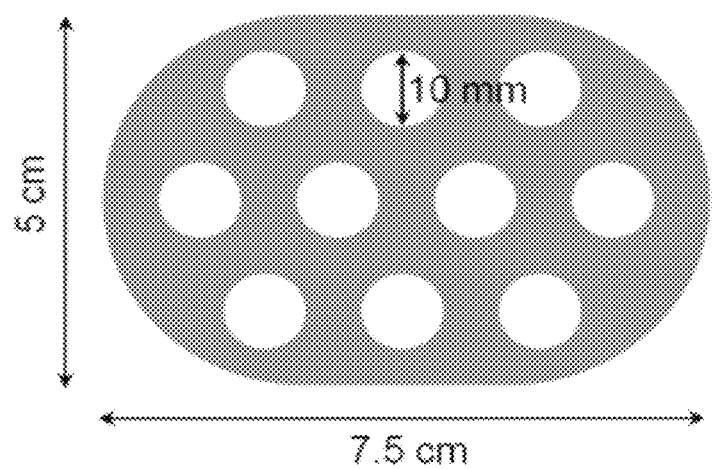
FIG. 274 shows the dimensions of an adhesive-coated mesh with uncoated regions (10-mm diameter circles).
Figure 275:
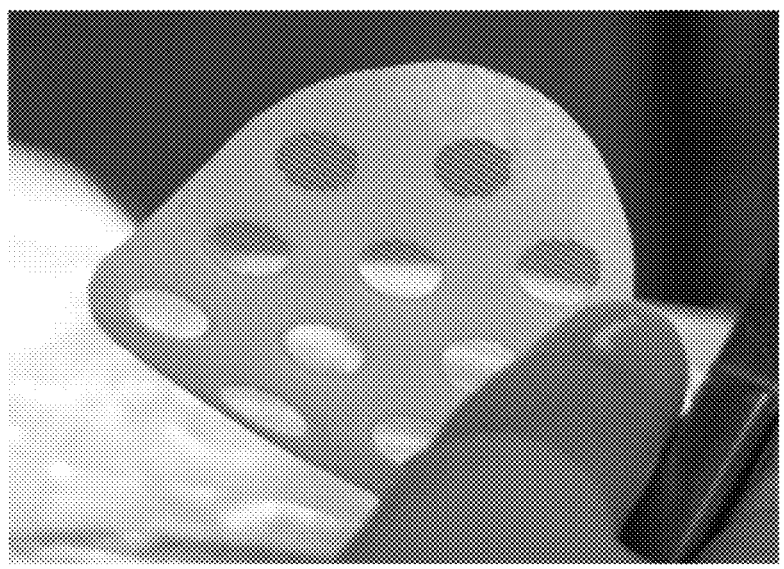
FIG. 275 shows an adhesive coated onto PE mesh in a pattern.
Figure 276:
FIG. 276 shows inserting the patterned adhesive mesh in between the peritoneum and the abdominal muscle wall.
Figure 277:
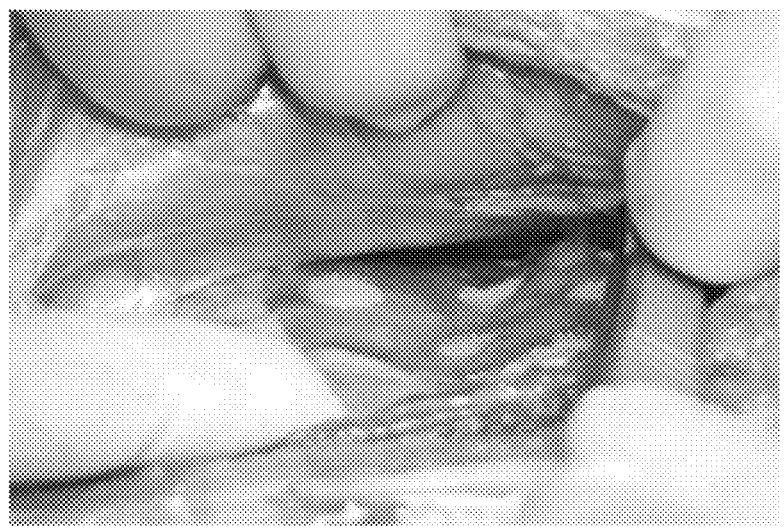
FIG. 277 shows a photograph of in situ activated adhesive-coated mesh with the construct conforming to the shape of the tissue.

Bilateral 2.5×2.5 cm segments of adhesive-coated mesh were implanted into the peritoneum of 3 rabbits (4 samples per animal). Adhesive formulations used were Medhesive-139, Medhesive-140, and Medhesive-141 at a coating density of 240 g/m². A midline abdominal incision was created to expose the peritoneum, and the adhesive-coated meshes were adhered to the peritoneum, activated via brushing of 20 mg/mL of NaIO4 solution. A single stay suture was place on one of the corners to prevent migration. The wound was closed. The rabbits were euthanized on day 7 and the implant site was evaluated for migration, curling, and shrinkage, and then harvested for histologic evaluation. At day 7, all samples remained adhered tightly to the peritoneum with no migration, shrinkage, and curling (FIGS. 271-273). Early scar plate formation was evident. However, the scar plate was immature and would not have been capable of preserving attachment without the presence of the adhesive. Inflammation at the prosthetic surface was driven predominantly by the adhesive with macrophages and foreign body giant cells lining up against the adhesive surface.

Experimental Example 48

Extraperitoneal Implantation of Adhesive Mesh with Embedded Oxidant

Three samples (Table 30) of 5×7.5 cm (oval-shaped) adhesive-coated meshes are implanted extraperitoneally in a porcine model (2 pigs). PE mesh is sandwiched between a layer of Medhesive-141 (240 g/m²) and Medhesive-142 (120 g/m²) embedded with oxidant (NaIO₄). One of the 3 samples showed patterns of 5-mm circles not coated with Medhesive-141 and Medhesive-142 for rapid tissue ingrowth.

TABLE 30

Samples implanted in the porcine model

| Sample | Adhesive | Pattern | NaIO₄ Concentration (g/m²) |
|---|---|---|---|
| Control | No adhesive, Sutured | No | No |
| 25015A | Yes | No | 14 |
| 25016A | Yes | No | 7.1 |
| 25014A | Yes | Yes (75% surface coverage w/ adhesive) | 14 (75% coverage) |

The samples are placed directly on the surgically exposed peritoneal surface of the animal in bilateral rows of 4 each in a discrete tissue pocket between the peritoneum and muscle/fascial layer. (FIGS. 274-277) The medial side of the mesh is marked by placing a surgical staple in the overlying muscle tissue. The dry adhesive-coated meshes are placed in the tissue pocket and held with digital pressure for 5 minutes. The adhesive is activated with the moisture in the tissue, which dissolved and released the oxidant during hydration. Control PE meshes are sutured to peritoneum. The animals are euthanized at days 14 and 28, and the test constructs are subjected to gross, mechanical, and histological evaluation of tissue response and initial tissue ingrowth.

Figure 278:
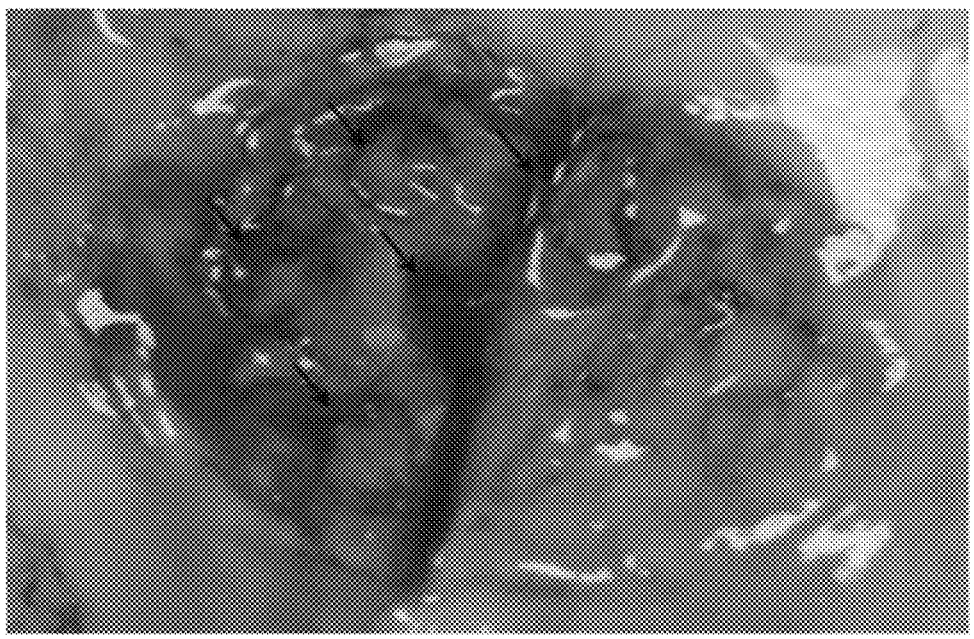
FIG. 278 shows a photograph of a patterned adhesive-coated mesh observed bendath a layer of peritoneum after 14-days of implantation. The arrows point to regions not coated with adhesive, with the adhesive construct conforming to the tissue.
Figure 279:
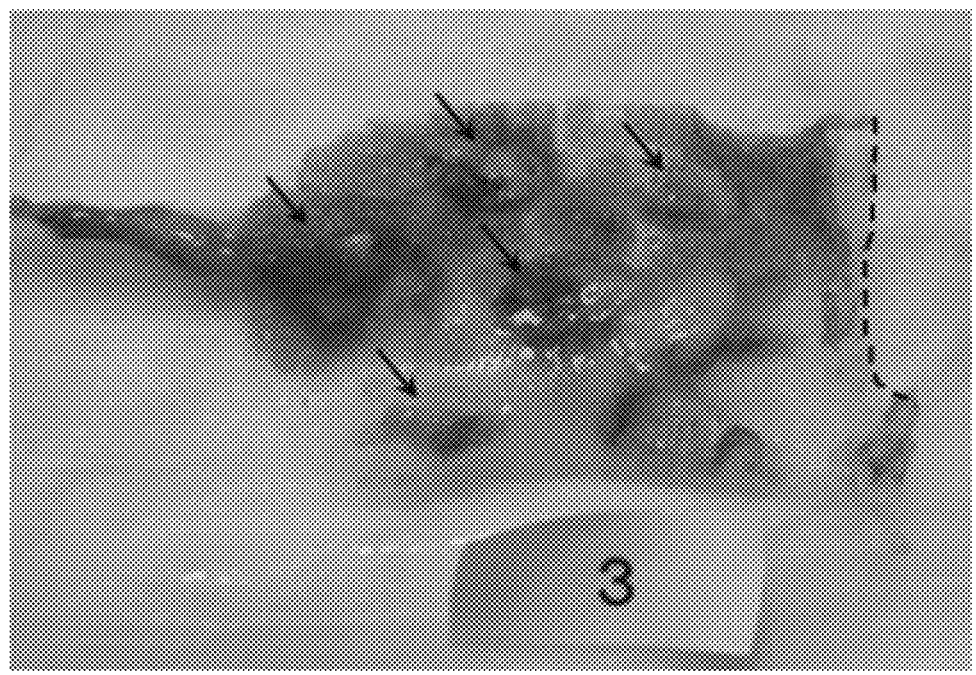
FIG. 279 shows a photograph of a patterned adhesive-coated mesh after subjection to mechanical testing. The arrows point to areas not coated with adhesive demonstrating a significant amount of tissue ingrowth, with tissue remaining attached to the mesh. The dashed line indicate mesh tears during tensile testing.

At day 14, one pig was euthanized and the implant site was explanted (FIG. 278). An edge of the adhesive construct was separated from the tissue and the construct was pulled with a handheld tensile tester until failure. The tensile load required to separate the patterned adhesive coated mesh from the tissue was 54.6 N, which resulted in mesh failure (dashed line in FIG. 279). The portion of the mesh remaining attached to the tissue was subjected to a second tensile testing, requiring 66.7 N to be fully detached. There was a significant amount of ingrowth in the regions not coated with adhesive with the tissue adherent to the detached mesh (arrows in FIG. 279).

Experimental Example 49

Tensile Testing of Adhesive Films

Figure 280:
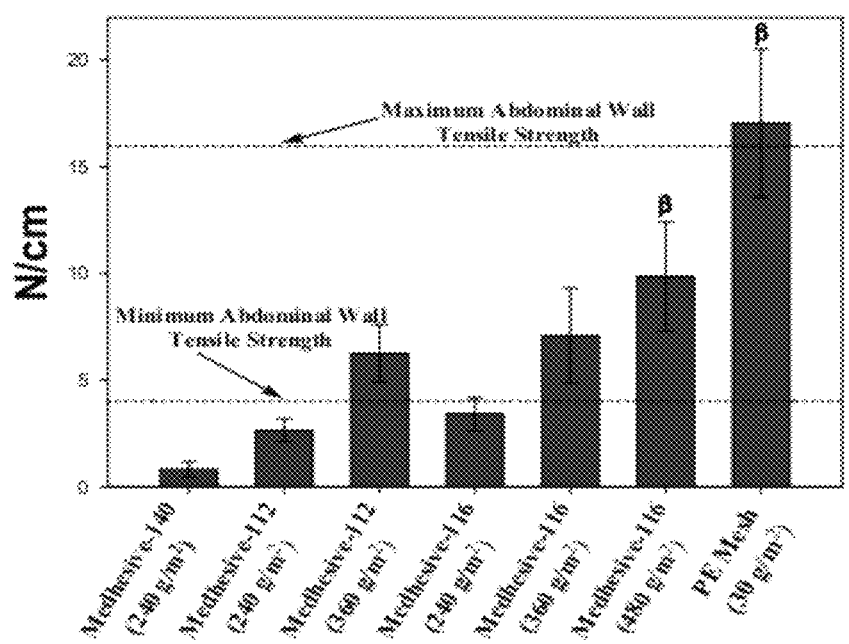
FIG. 280 shows the maximum tensile strength of adhesive films compared to polyester (PE) mesh. The dashed lines indicate tensile strength ranges of the abdominal wall. "β" indicates no statistical difference ($p > 0.05$).

Adhesive polymers were cast into films from chloroform at a coating density of 240-480 g/m². The films were cut into a dog-bone shape, sprayed with 20 mg/mL NaIO₄ solution, and allowed to cure for 10 min. After hydration for one hour in PBS at 37° C., the films were pulled to failure at 10 mm/min using a universal tester. Tensile failure testing revealed increased maximum tensile strength with increased coating density, with values within the range of the mechanical properties of the abdominal wall (FIG. 280).

Each reference (including, but not limited to, journal articles, U.S. and non-U.S. patents, patent application publications, and international patent application publications) cited in the present application is incorporated herein by reference in its entirety.

We claim:
1. A method of hernia repair, comprising
a) providing a subject having a hernia;
b) providing a construct comprising an adhesive compound and a support wherein said adhesive compound is a multi-hydroxyl phenyl derivative polymer, a multi-methoxy phenyl derivative polymer, a combination multi-hydroxyl and multi-methoxy phenyl derivative polymer, a mono-methoxy and mono-hydroxyl phenyl derivative polymer or a combination thereof wherein said adhesive compound is p(CL1.25kEG10kb-g-DH2), p(CL2kGEG10kb-g-DMu2), p(CL1.25kEG10kb-g-

DMu2), p(CL5.6kEG10kb-g-DH2), p(LA4.2kEG10kb-g-DH2), p(CL2kEG10k(SA)b-g-DMe2, p(CL1.25kEG10k(SA)b-g-DMe2), p(CL2kEG10kb-g-MTu2), p(CL2kEG10kb-g-DMPAu2), p(CL2kEG10k(GA)b-g-DMe2), p(CL2kEG10k(GABA)b-g-DHe2), p(CL2kEG10k(GABA)b-g-HFe2), p(CL2kEG10k(GABA)b-g-DMHCAe2), p(CL2kEG10k(GA)b-g-MTe2) or a combination thereof, and c) affixing said construct to said subject to repair said hernia.

2. The method of claim 1, wherein said hernia is a congenital hernia, an acquired hernia, an inguinal hernia, an indirect inguinal hernia, a direct inguinal hernia, a saddle bag hernia, a sliding hernia, an umbilical hernia, a paraumbilical hernia, an incisional hernia, a ventral hernia, a femoral hernia, a Copper's hernia, an epigastric hernia, a Spigelian hernia, a semilunar hernia, a Littre's hernia, a Richter's hernia, a lumbar hernia, a sciatic hernia, a sports hernia, an Amyand's hernia, an anal hernia, a Maydl hernia, a hiatus hernia, a diaphragmatic hernia, a paraesophageal hernia, a perineal hernia, a properitoneal hernia, a mesenteric hernia, an intraparietal hernia, a bilateral hernia, a complicated hernia, an incarcerated hernia, a strangulated hernia, an uncomplicated hernia, a complete hernia, an incomplete hernia, an intracranial hernia, an internal hernia, an external hernia or a combination thereof.

3. The method of claim 1, wherein said subject is a mammal.

4. The method of claim 3, wherein said mammal is a human.

5. The method of claim 1, wherein said adhesive compound is a liquid, a coating or a film.

6. The method of claim 1, wherein said polymer is polyethylene glycol (PEG) polymer, a polycaprolactone (PCL) polymer, a polylactic acid (PLA) polymer, a polyester polymer, a multiblock polymer or combination thereof.

7. The method of claim 1, wherein said adhesive compound is configured to degrade at a predetermined rate.

8. The method of claim 1, wherein said adhesive compound is activated in situ.

9. The method of claim 8, wherein said activated adhesive compound is activated by water, by saline, by at least one bodily fluid, by temperature, by pH, or by pressure.

10. The method of claim 1, wherein said adhesive compound comprises an oxidant.

11. The method of claim 10, wherein said oxidant is embedded within said adhesive compound.

12. The method of claim 10, wherein said oxidant is applied to said adhesive compound by spraying, brushing or dipping or a combination thereof.

13. The method of claim 1, wherein said support is an adhesive compound polymer, a film polymer, a scaffold, a membrane, a graft, an implant, a mesh or a combination thereof.

14. The method of claim 13, wherein said support is a synthetic support or a biologic support.

15. The method of claim 14, wherein said synthetic support comprises a polypropylene support, a polyester support, a condensed polytetrafluoroethylene (cPTFE) support, an expanded polytetrafluoroethylene (cPTFE) support, a polycarbonate polyurethane-urea support, a copolymer of polyglycolide, polyactide and polytrimethylene support, a copolymer polyactide support, a polytrimethylene carbonate support, a polylactic acid (PLA) support, a tyrosine polyarylate support, a polydroxyalkanoate support, a silk-elastin polymer support or a combination thereof.

16. The method or claim 14, wherein said biologic support comprises a dermis support, a human-derived dermis support, a porcine-derived dermis support, a bovine-derived dermis support, a collagen-containing matrix support, an engineered dermis support, a pericardium support, an extracellular matrix support, or a small intestine submucosa support.

17. The method of claim 1, wherein said adhesive compound is coated upon said support in a predetermined pattern.

18. The method of claim 17, wherein said pattern comprises at least one region coated with said adhesive compound and at least one region not coated with said adhesive compound.

19. The method of claim 1, wherein said affixing comprises a tissue adhesive, a suture, a staple, a tack or a combination thereof.

20. The method of claim 1, wherein said construct comprises an adhesive compound on at least one surface of said support, and a non-adhesive compound on at least one surface of said support.

21. The method of claim 20, wherein said non-adhesive compound comprises an anti-adhesive compound.

22. The method of claim 20, wherein said non-adhesive compound comprises an oxidant.

* * * * *